United States Patent
Jang et al.

(10) Patent No.: US 12,029,204 B2
(45) Date of Patent: Jul. 9, 2024

(54) TRANSGENIC ANIMALS AND TRANSGENIC EMBRYOS PRODUCING AN ENGINEERED NUCLEASE

(71) Applicant: Lart Bio Co., LTD, Seoul (KR)

(72) Inventors: Goo Jang, Seoul (KR); Soo Young Yum, Seoul (KR); Gyeong Min Gim, Seoul (KR); Won You Lee, Seoul (KR); Ji Hyun Park, Gyeonggi-do (KR)

(73) Assignee: Lart Bio Co., LTD., Seoul (KR)

( * ) Notice: Subject to any disclaimer, the term of this patent is extended or adjusted under 35 U.S.C. 154(b) by 0 days.

(21) Appl. No.: 16/626,227

(22) PCT Filed: Aug. 14, 2019

(86) PCT No.: PCT/KR2019/010388
§ 371 (c)(1),
(2) Date: Dec. 23, 2019

(87) PCT Pub. No.: WO2020/036445
PCT Pub. Date: Feb. 20, 2020

(65) Prior Publication Data
US 2021/0337776 A1    Nov. 4, 2021

Related U.S. Application Data

(60) Provisional application No. 62/764,905, filed on Aug. 16, 2018.

(30) Foreign Application Priority Data

Jun. 3, 2019   (KR) .................. 10-2019-0065613

(51) Int. Cl.
*A01K 67/0275* (2024.01)
*C12N 9/22* (2006.01)
*C12N 15/11* (2006.01)

(52) U.S. Cl.
CPC ............ *A01K 67/0275* (2013.01); *C12N 9/22* (2013.01); *C12N 15/11* (2013.01); *A01K 2217/05* (2013.01); *A01K 2227/101* (2013.01); *C12N 2310/20* (2017.05); *C12N 2800/80* (2013.01)

(58) Field of Classification Search
CPC ............ A01K 67/0275; A01K 2217/05; A01K 2227/101; A01K 2217/15; A01K 67/0278; A01K 67/0276; A01K 2267/01; A01K 2267/02; A01K 2267/03; C12N 2310/20; C12N 15/8509; C12N 15/8771; C12N 2800/90; C12N 2830/003
See application file for complete search history.

(56) References Cited

U.S. PATENT DOCUMENTS

2021/0337776 A1    11/2021  Jang et al.

FOREIGN PATENT DOCUMENTS

| JP | 2016-502840 | 2/2016 |
|---|---|---|
| JP | 2017/510299 A | 4/2017 |
| KR | 10-2015-0044524 A | 4/2015 |
| KR | 10-2015-0044524 A | 4/2015 |
| KR | 10-2018-0082981 A | 7/2018 |
| KR | 10-2018-0082981 A | 7/2018 |
| KR | 10-2019-0065615 A | 2/2020 |
| KR | 10-2019-0065615 B | 8/2020 |
| WO | WO-2014/093622 A2 | 6/2014 |
| WO | WO-2015/148761 A1 | 10/2015 |
| WO | WO-2015/168125 A1 | 11/2015 |
| WO | WO-2016/186772 A2 | 11/2016 |
| WO | WO-2017/044864 A1 | 3/2017 |
| WO | WO-2017/062723 A9 | 6/2017 |
| WO | WO-2017/218852 A1 | 12/2017 |
| WO | WO-2018/132936 A1 | 7/2018 |

OTHER PUBLICATIONS

Gaj et al. (Genome-Editing Technologies: Principles and Applications. Cold Spring Harbor Perspectives in Biology, vol. 8, issue 12, Dec. 2012) (Year: 2012).*

Eckardt S, McLaughlin KJ, Willenbring H. Mouse chimeras as a system to investigate development, cell and tissue function, disease mechanisms and organ regeneration. Cell Cycle. Jul. 1, 2011;10(13):2091-9. doi: 10.4161/cc.10.13.16360. Epub Jul. 1, 2011. PMID: 21606677; PMCID: PMC3230469. (Year: 2011).*

Tan et al (Gene targeting, genome editing: from Dolly to editors. Transgenic Res., vol. 3, Jun. 2016, cited in IDS dated Dec. 29, 2022) (Year: 2016).*

Petris et al (Hit and go CAS9 delivered through a lentiviral based self-limiting circuit. Nature Communications, vol. 8, May 2017, cited in IDS dated Dec. 29, 2022) (Year: 2017).*

(Continued)

*Primary Examiner* — Valerie E Bertoglio
*Assistant Examiner* — Matasha Dhar
(74) *Attorney, Agent, or Firm* — Foley Hoag LLP; David P. Halstead

(57) ABSTRACT

The present specification relates to a transgenic animal and a transgenic embryo producing components of an engineered nuclease.

According to the disclosure of the present specification, the transgenic animal (or embryo) producing components of an engineered nuclease is a transgenic animal (or embryo) which includes a first cell having a genome including a first toolbox; and a second cell having a genome including a second toolbox, wherein the first toolbox and the second toolbox include at least one of a polynucleotide encoding an RNA-guided endonuclease and a polynucleotide encoding a guide nucleic acid that is able to specifically bind to a target site, respectively, wherein the first toolbox is present in a first locus of the genome of the first cell; the second toolbox is present in a second locus of the genome of the second cell; and the first locus is different from the second locus.

9 Claims, 58 Drawing Sheets

Specification includes a Sequence Listing.

(56) References Cited

OTHER PUBLICATIONS

Hahn et al (Production of Cas9-Expressing Cattle Using DNA Transposon. Reproduction, Fertility and Development, 2016). cited in IDS dated Jun. 15, 2021 (Year: 2016).*
Xu et al (piggyBac mediates efficient in vivo CRISPR library screening for tumorigenesis in mice. PNAS, 2017). cited in IDS dated Jun. 15, 2021 (Year: 2017).*
Office Action for Japanese Patent Application No. 2019-562368, mailed Dec. 22, 2020. 5 pages. With English Translation.
Notice of Allowance for Korean Patent Application No. 10-2020-0045470, mailed Dec. 15, 2020. 6 pages. With English Translation.
Notice of Allowance for Korean Patent Application No. 10-2020-0045471, mailed Dec. 15, 2020. 4 pages. With English Translation.
Kamihira, "Gene Transfer Into Animal Cells", Journal of Biotechnology, Dec. 2017, vol. 95, No. 12, pp. 734-738. With English Translation of Japanese Abstract.
Platt et al., "CRISPR-Cas9 Knockin Mice for Genome Editing and Cancer Modeling", Cell, Oct. 9, 2014, V. 159, pp. 440-455.
Yum et al., "Long-term health and germline transmission in transgenic cattle following transposon-mediated gene transfer", BMC Genomics, 2018, V 19, N 387, pp. 1-12.
Li et al., "One-Step piggyBac Transposon-Based CRISPR/Cas9 Activation of Multiple Genes," Molecular Therapy: Nucleic Acids, 8:64-76 (2017).
Platt et al., "CRISPR-Cas9 Knockin Mice for Genome Editing and Cancer Modeling," Cell, 159:440-455 (2014).
Yum et al., "Efficient generation of transgenic cattle using the DNA transposon and their analysis by next-generation sequencing," Scientific Reports, 6:27185 (2016).
Yum et al., "Long-term health and germline transmission in transgenic cattle following transposon-mediated gene transfer," BMC Genomics, 19:387 (2018).
Notice of Final Rejection Translation for Korean Application No. 10-2019-0065615 dated Jun. 30, 2020.
Notice of Reason for Refusal Translation for Korean Application No. 10-2020-0045470 dated Jun. 30, 2020.
Notice of Reason for Refusal Translation for Korean Application No. 10-2020-0045471 dated Jun. 30, 2020.
Notice of Allowance for Korean Application No. 10-2019-0065613 mailed Jan. 30, 2020.
Notice of Allowance Translation for Korean Application No. 10-2019-0065613 mailed Jan. 30, 2020.
Notice of Allowance for Korean Application No. 10-2019-0065614 mailed Jan. 30, 2020.
Notice of Allowance Translation for Korean Application No. 10-2019-0065614 mailed Jan. 30, 2020.
Office Action for Korean Application No. 10-2019-0065615 mailed Jan. 30, 2020.
Office Action Translation for Korean Application No. 10-2019-0065615 mailed Jan. 30, 2020.
Cebrian-Serrano et al., "Maternal Supply of Cas9 to Zygotes Facilitates the Efficient Generation of Site-Specific Mutant Mouse Models," Plos One, 12(1): e0169887 (2017).
Hahn, S. E., '205 Production Of Cas9-Expressing Cattle Using DNA Transposon', Reproduction Fertility and Development. 2016, vol. 29, pp. 211-211.
Office Action of Australian Patent Application No. 2019275586, Mar. 15, 2021.
Xu, C. et al., 'Piggybac mediates efficient in vivo CRISPR library screening for tumorigenesis in mice', Proceedings of the National Academy of Science USA. 2017, vol. 114, pp. 722-727.
Eckardt et al., "Mouse chimeras as a system to investigate development, cell and tissue function, disease mechanisms and organ regeneration", Cell Cycle, 10(13):2091-2099 (2011).
Gaj et al., "Genome-Editing Technologies: Principles and Applications", Cold Spring Harbor Perspectives in Biology, vol. 8(12): 21 pages (2012).
Lee et al., ""Generation of genetically-engineered animals using engineered endonucleases"" Arch.Pharm.Res, 41:885-897 (2018).

Li et al., "One-step piggyBac transposon-based CRISPR/Cas9 activation of multiple genes" Molecular Therapy Nucleic Acids, 8-64 (2017).
Petris et al., ""Hit and go CAS9 delivered through a lentiviral based self-limiting circuit"" Nature Communications, 8(15334): 1-9 (2017).
Proudfoot et al., "Genome edited sheep and cattle" Transgenic res, 24:147-153 (2015).
Tan et al., "Gene targeting, genome editing: from Dolly to editors" Transgenic Res, 25: 273-287 (2016).
Wei et al., "Cattle with a precise, zygotemediated deletion safely eliminate the major milk allergen betalactoglobulin" Scientific Reports: 8(7661): 13 pages (2018).
Yum et al., "Development of genome engineering technologies in cattle: from random to specific" Journal of Animal Science and Biotechnology, 9(16): 9 pages (2018).
International Search Report received for PCT/KR2019/010388, issued on Dec. 6, 2019.
Office Action received for KR 10-2019-0065613, issued Aug. 16, 2019, with translation.
Written Opinion received for PCT/KR2019/010388, issued on Dec. 6, 2019.
Yum. "Generation and analysis of transgenic cattle with germline transmission via transposon," Thesis, Seoul National University (Jul. 2018).
Brevini et al., "No shortcuts to pig embryonic stem cells Embryonic Stem Cells in Domestic Animals" Theriogenology, 74:544-550 (2010).
Cao et al., "Isolation and Culture of Primary Bovine Embryonic Stem Cell Colonies by a Novel Method" Journal of Experimental Zoology 311 :368-376 (2009).
Dennis. "Welfare Issues of Genetically Modified Animals" ILAR Journal, vol. 43, No. 2 (2002).
Foundations of Genetic Engineering, Saint-Petersburg, SPbGTU editorial house, p. 411-413 2002.
Glick et al., "Molecular Biotechnology Principles and applications of recombinant DNA" Mir, 2nd edition (2002).
Houdebine, "Methods to Generate Transgenic Animals, Genetic Engineering in Livestock" New Applications and Interdisciplinary Perspectives, vol. 14 pp. 31-46 (2009).
Korablev et al., "Manipulations with early mouse embryos for generation of genetically modified animals" Vavilov Journal of Genetics and Breeding, 21. 7 (2017).
Paris et al., "Equine embryos and embryonic stem cells: Defining reliable markers of pluripotency" Theriogenology, 74: 516-524 (2010).
Russian Patent Application No. 2021106372 Office Action issued on Mar. 27, 2023.
Voncken et al., "Transgenic mouse methods and protocols" Methods in Molecular Biology, 693 (2003).
Zhou et al., "Developing tTA Transgenic Rats for Inducible and Reversible Gene Expression" Int.J.Biol.Sci, 5: 171-181 (2009).
Office Action of JP Patent Application No. 2022-063838 issued on Jul. 11, 2023.
Bavequa et al., "Efficient edition of the bovine PRNP prion gene in somatic cells and IVF embryos using the CRISPR Cas9 system" Theriogenology (2016).
Ikeda et al., "Correction of a Disease Mutation using CRISPR Cas9-assisted Genome Editing in Japanese Black Cattle" Scientific Reports, vol. 7 (2017).
Ni et al., "Efficient Gene Knockout in Goats Using CRISPR Cas9 System" Plos One, vol. 9, No. 9 (2014).
Office Action of Australian Patent Application No. 2021232801 issued on Nov. 29, 2023.
Office Action of Australian Patent Application No. 2021232802 issued on Nov. 29, 2023.
Park et al., "Targeted gene knock-in by CRISPR Cas ribonucleoproteins in porcine zygotes" Sci Rep, 7 42458. doi 10.1038 srep42458 (2017).
Wang et al., "Cre-dependent Cas9-expressing pigs enable efficient in vivo genome editing" Genome Research (2017).

* cited by examiner

FIG. 11
140(a)
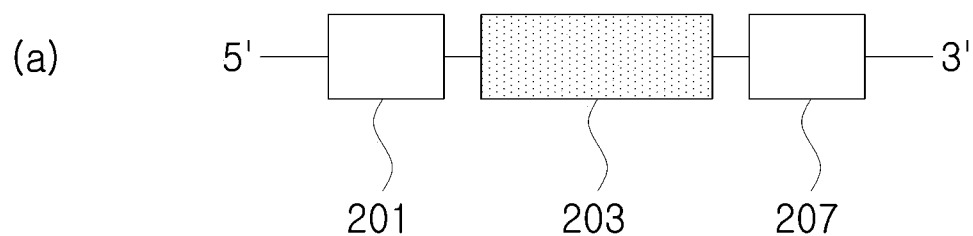
140(b)
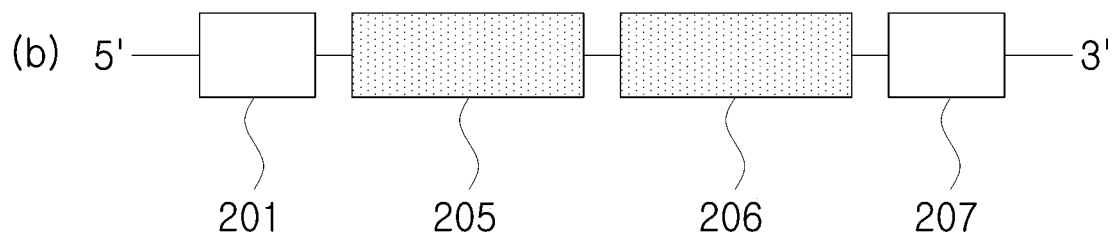
140(c)
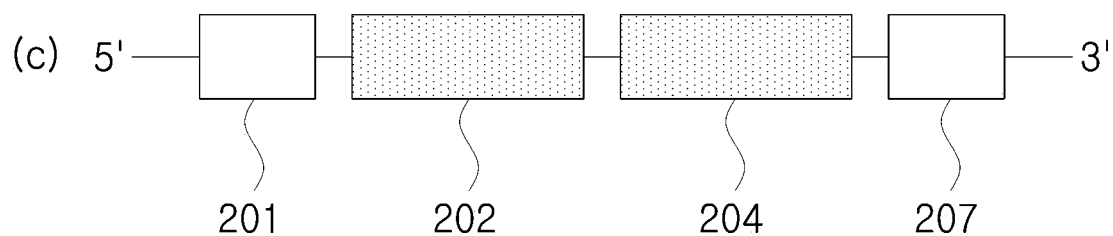

FIG. 12
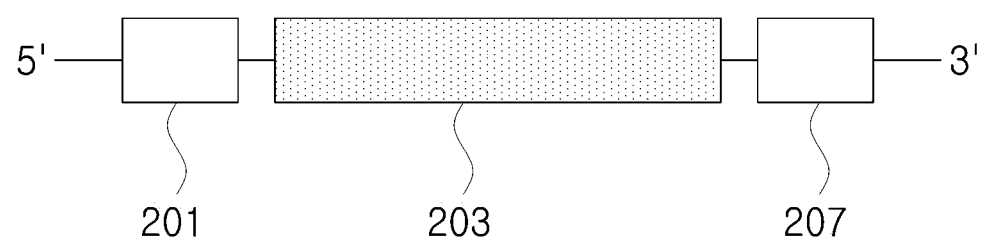
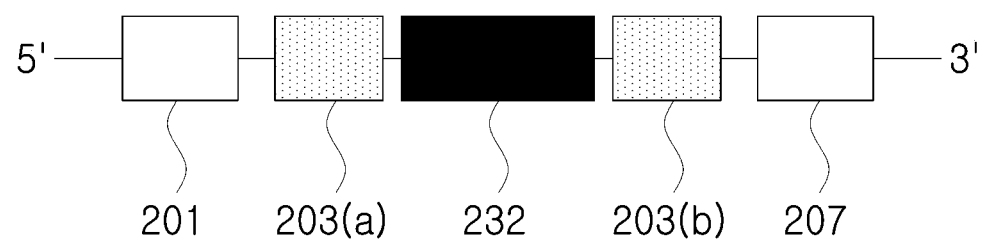

Embryos

FIG. 30
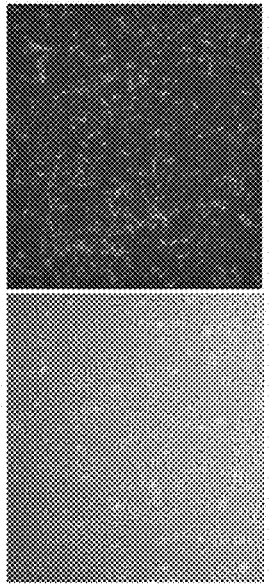
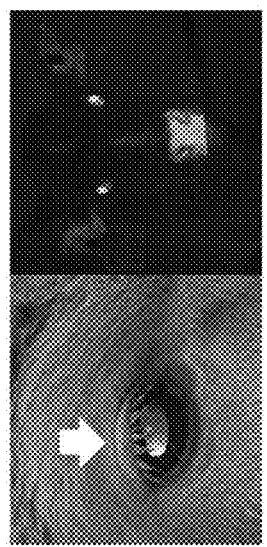
(b)
(a)
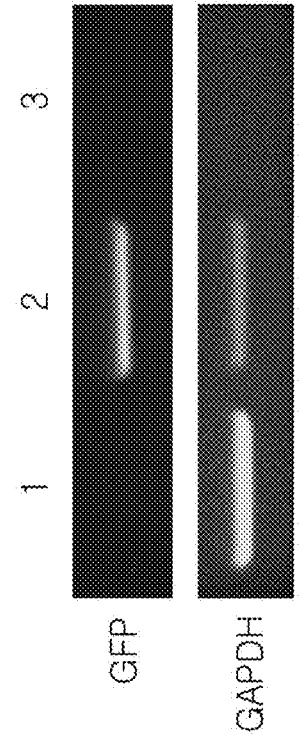
GFP
GAPDH
(d)
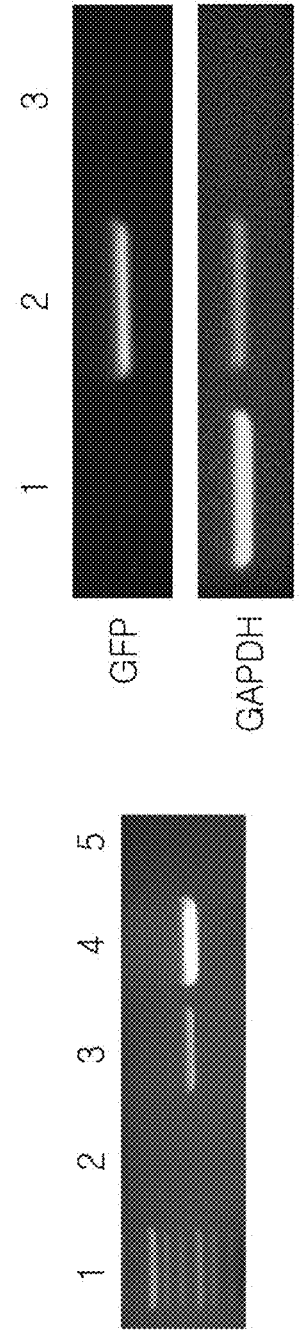
(c)

(a)  (b)

FIG. 33
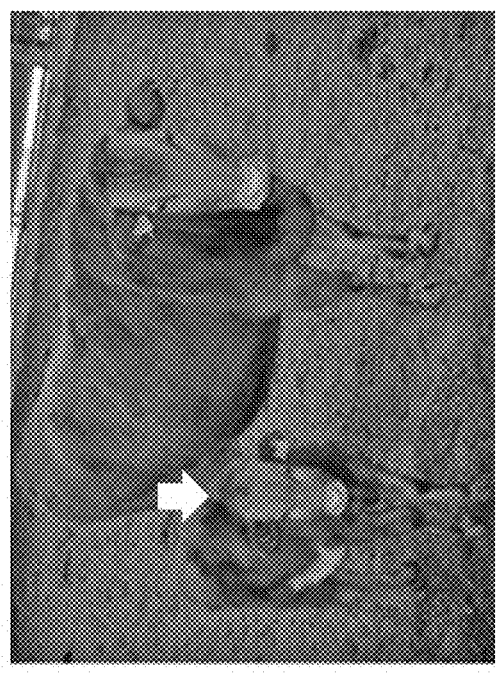 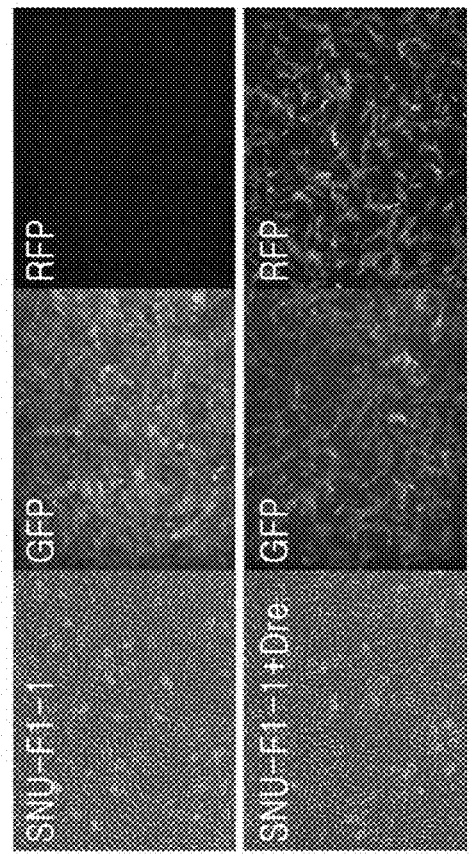
(a) (b)

FIG. 43
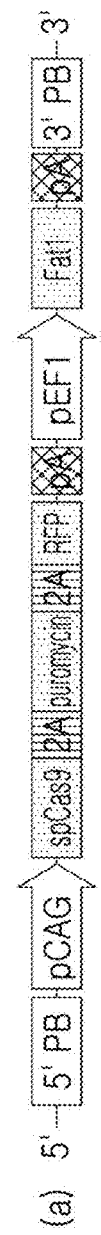
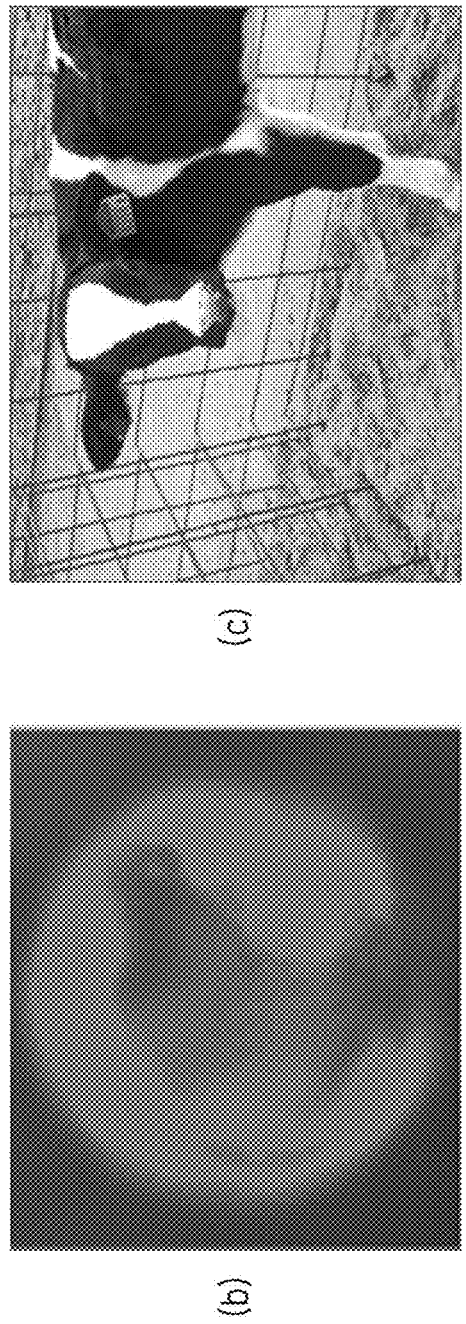

FIG. 44
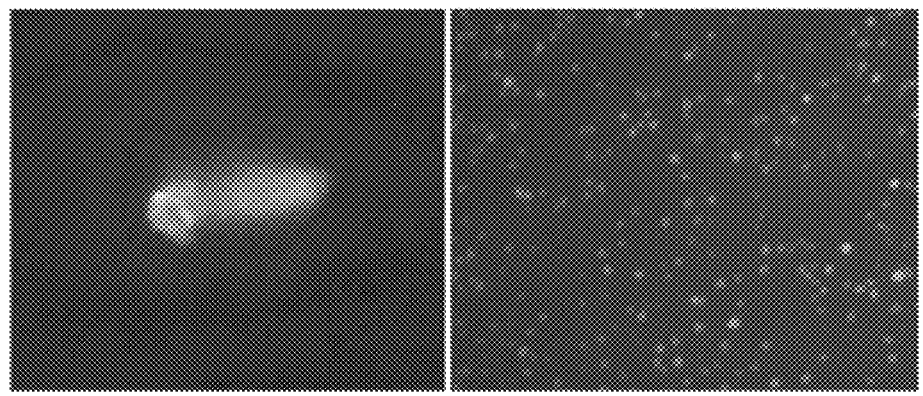
(a)
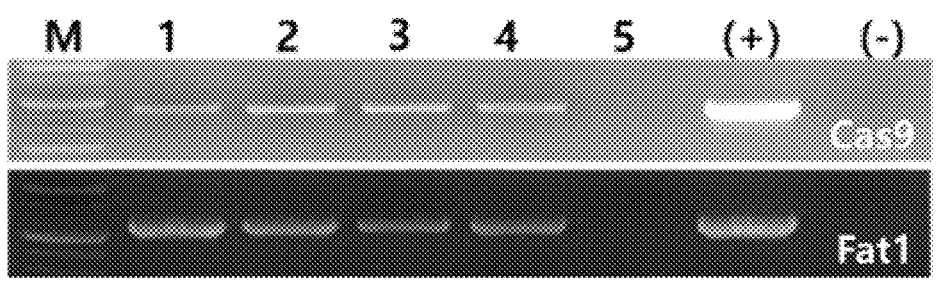
(b)
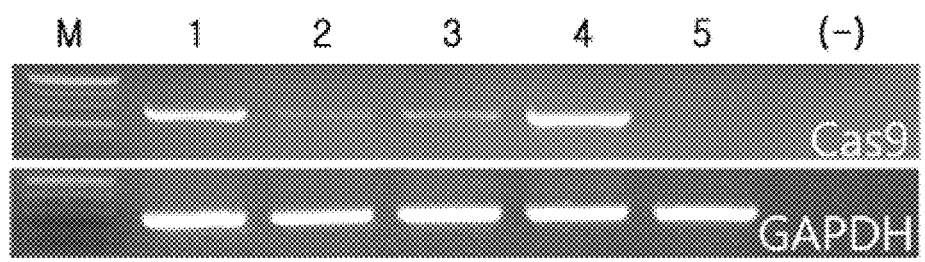
(c)

FIG. 51
(a) 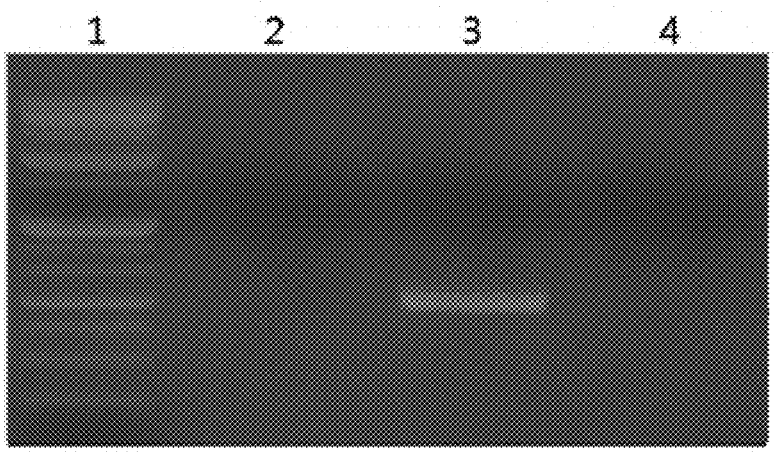
(b) 

FIG. 52
(a)
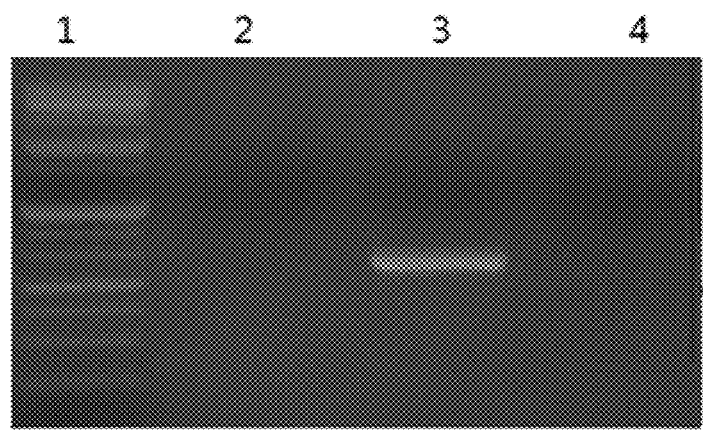
(b)
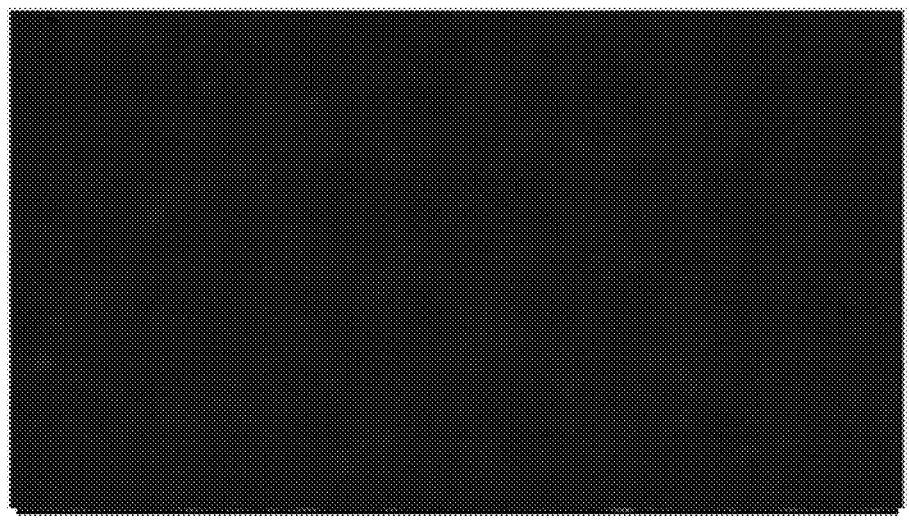

FIG. 55
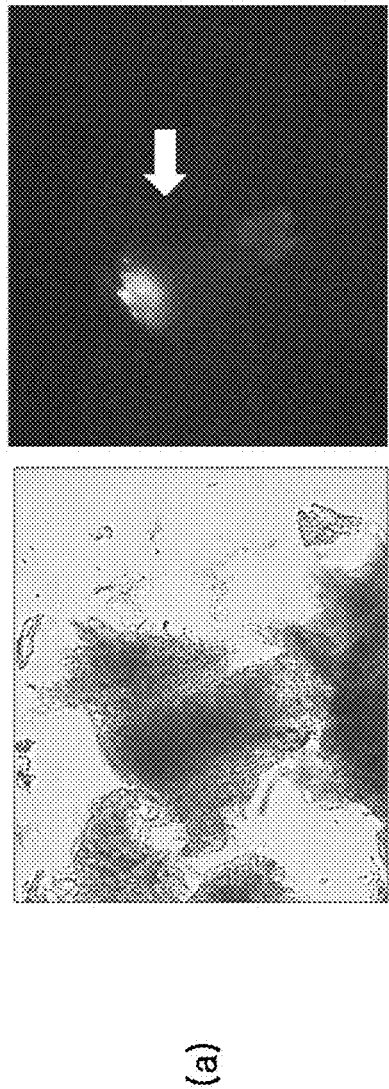
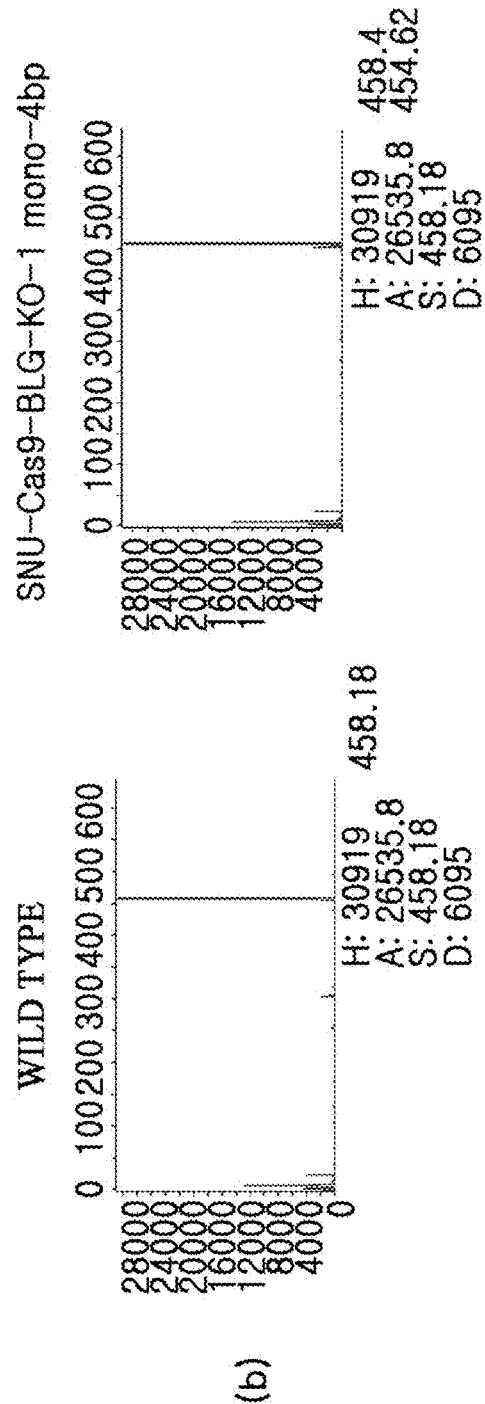
(a)
(b)

FIG. 56
(a)
(b)

FIG. 58

```
                        SEQUENCE LISTING

<160> NUMBER OF SEQ ID NOS: 55

<210> SEQ ID NO 1
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GFP_F_1 (primer)

<400> SEQUENCE: 1
ggggacaagt ttgtacaaaa aagcaggctt caccatggcc agcaaaggag aagaactt         58

<210> SEQ ID NO 2
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GFP_R_1 (primer)

<400> SEQUENCE: 2
ggggaccact ttgtacaaga aagctgggtc ttatttgtag agctcatcca tgcc             54

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_RFP_F_1 (primer)
```

<400> SEQUENCE: 3 gggggacaagt tgtacaaaa aagcaggctt caccatggat agcactgaga acgtcat        57

<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_RFP_R_1 (primer)

<400> SEQUENCE: 4
ggggaccact tgtacaaga aagctgggtc ctactggaac aggtggtggc                  50

<210> SEQ ID NO 5
<211> LENGTH: 313
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tp_PB_1 (transposon sequence)

<400> SEQUENCE: 5
ttaaccctag aaagatagtc tgcgtaaaat tgacgcatgc attcttgaaa tattgctctc      60
tctttctaaa tagcgcgaat ccgtcgctgt gcatttagga catctcagtc gccgcttgga    120
gctcccgtga ggcgtgcttg tcaatgcggt aagtgtcact gattttgaac tataacgacc    180
gcgtgagtca aaatgacgca tgattatctt ttacgtgact tttaagattt aactcatacg    240
ataattatat tgttatttca tgttctactt acgtgataac ttattatata tatattttct    300
tgttatagat atc                                                       313

<210> SEQ ID NO 6
<211> LENGTH: 235
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tp_PB_2 (transposon sequence)

<400> SEQUENCE: 6
tttgttactt tatagaagaa attttgagtt tttgtttttt tttaataaat aaataaacat      60
aaataaattg tttgttgaat ttattattag tatgtaagtg taaatataat aaaacttaat    120
atctattcaa attaataaat aaacctcgat atacagaccg ataaaacaca tgcgtcaatt    180
ttacgcatga ttatctttaa cgtacgtcac aatatgatta tctttctagg gttaa         235

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GFP_F_2 (primer)

<400> SEQUENCE: 7
cacatgaagc agcacgactt                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GFP_R_2 (primer)

<400> SEQUENCE: 8
agttcacctt gatgccgttc                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_RFP_F_2 (primer)

<400> SEQUENCE: 9
ccccgtaatg cagaagaaga                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_RFP_R_2 (primer)

<400> SEQUENCE: 10
ggtgatgtcc agcttggagt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GAPDH_F_1 (primer)

<400> SEQUENCE: 11
ggcgtgaacc acgagaagta                                               20

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GAPDH_R_1(primer)

<400> SEQUENCE: 12
ccctccacga tgccaaagt                                                19

<210> SEQ ID NO 13

```
<211> LENGTH: 292
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tp_SB_1

<400> SEQUENCE: 13
atacagttga agtcggaagt ttacatacac ttaagttgga gtcattaaaa ctcgttttc      60 aactactcca caaatttctt gttaacaaac aatagttttg gcaagtcagt taggacatct    120
actttgtgca tgacacaagt cattttccca acaattgttt acagacagat tatttcactt    180
ataattcact gtatcacaat tccagtgggt cagaagttta catacactaa gttgactgtg    240
cctttaaaca gcttggaaaa ttccagaaaa tgatgtcatg gctttagaag ct            292

<210> SEQ ID NO 14
<211> LENGTH: 315
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: tp_SB_2 (transposon sequence)

<400> SEQUENCE: 14
gtggaaggct actcgaaatg tttgacccaa gttaaacaat ttaaaggcaa tgctaccaaa     60
tactaattga gtgtatgtaa acttctgacc cactgggaat gtgatgaaag aaataaaagc    120
tgaaatgaat cattctctct actattattc tgatatttca cattcttaaa ataaagtggt    180
gatcctaact gacctaagac agggaatttt tactaggatt aaatgtcagg aattgtgaaa    240
aagtgagttt aaatgtattt ggctaaggtg tatgtaaact tccgacttca actgtatagg    300
gatcctctag ctaga                                                     315

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_GFP_F_1 (primer)

<400> SEQUENCE: 15
ggacttcctt tgtcccaaat ct                                              22

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_GFP_R_1 (primer)

<400> SEQUENCE: 16
tagcggctga agcactgc                                                   18

<210> SEQ ID NO 17
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_spCas9_F_1 (primer)

<400> SEQUENCE: 17
gacaagaagt acagcatcgg                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_spCas9_R_1 (primer)

<400> SEQUENCE: 18
caaccagctg ttcgaggaga                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_Fat1_F_1 (primer)

<400> SEQUENCE: 19
aaacacgaaa caggcgacca                                                20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_Fat1_R_1 (primer)

<400> SEQUENCE: 20
tttgtcgttg gccacgattg                                                20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GAPDH_F_2 (primer)

<400> SEQUENCE: 21
ggcgtgaacc acgagaagta                                                20

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
                                    oligonucleotide
<220> FEATURE:
<223> OTHER INFORMATION: pr_GAPDH_R_2 (primer)

<400> SEQUENCE: 22
ccctccacga tgccaaagt                                                19

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_PRNP_1 (sgRNA)

<400> SEQUENCE: 23
aaaaaccaac atgaagcatg tgg                                           23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_BLG_1 (sgRNA)

<400> SEQUENCE: 24 cccccctgaga gtgtatgtgg agg                                          23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_Rb1_1 (sgRNA)

<400> SEQUENCE: 25
tgacctcgcc ttggtgttcg agg                                           23

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_Nanog_1 (sgRNA)

<400> SEQUENCE: 26
accactgtcc ccgtctgtgg agg                                           23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_TP53_1 (sgRNA)
```

```
<400> SEQUENCE: 27
gcgcggacgc gggtgccggg cgg                                              23

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_IFNT_1 (sgRNA)

<400> SEQUENCE: 28
agtggagagt ctgttcattt ggg                                              23

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: gn_BCN_1 (sgRNA)

<400> SEQUENCE: 29
ttgcaagggc cagagccacc agg                                              23

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_PRNP_F_1 (primer)

<400> SEQUENCE: 30
gcaagaagcg accaaaacct                                                  20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_PRNP_R_1 (primer)

<400> SEQUENCE: 31
ggtgcatgtt ttcacgatag                                                  20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_BLG_F_1 (primer)

<400> SEQUENCE: 32
ttaaaggccg tgtctccagt                                                  20
```

```
<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_BLG_R_1 (primer)

<400> SEQUENCE: 33
gaaagccctg gataagcagc                                                 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_Rb1_F_1 (primer)

<400> SEQUENCE: 34
cccccaccaa ctgagtagaa                                                 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_Rb1_R_1 (primer)

<400> SEQUENCE: 35
gattccagaa tgagggagct                                                 20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_Nanog_F_1 (primer)

<400> SEQUENCE: 36
acctaccatc tcgctctgag                                                 20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_Nanog_R_1 (primer)

<400> SEQUENCE: 37
accaagaatc gaacccaggc                                                 20

<210> SEQ ID NO 38
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_TP53_F_1 (primer)

<400> SEQUENCE: 38
cttcagcctt tgcctttttg                                                    20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_TP53_R_1 (primer)

<400> SEQUENCE: 39
ttccggtcgt ccaaatactc                                                    20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_IFNT_F_1 (primer)

<400> SEQUENCE: 40
tcttccccat ggcttttgtg                                                    20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_IFNT_R_1 (primer)

<400> SEQUENCE: 41
tggagatgat aagagccctc                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_BCN_F_1 (primer)

<400> SEQUENCE: 42
tggctggcag tgaaacatta                                                    20

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: in_pr_BCN_R_1 (primer)

<400> SEQUENCE: 43

```
agggattgat ggtacagatg g                                              21
```

<210> SEQ ID NO 44
<211> LENGTH: 1996
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: HITI_RFP donor_1

<400> SEQUENCE: 44

```
cgtcgccgtc cagctcgacc aggcatatgt ggcgaattcg gaagcgggca gtgcaccaac      60
tacgccctgc tgaagctggc cggcgacgtg gagagcaacc ccggcccgg  atccatggtg     120 tctaagggcg aagagctgat taaggagaac atgcacatga agctgtacat ggagggcacc     180
gtgaacaacc accacttcaa gtgcacatcc gagggcgaag gcaagcccta cgagggcacc     240
cagaccatga gaatcaaggt ggtcgagggc ggccctctcc ccttcgcctt cgacatcctg     300
gctaccagct tcatgtacgg cagcagaacc ttcatcaacc acacccaggg catccccgac     360
ttctttaagc agtccttccc tgagggcttc acatgggaga gagtcaccac atacgaggac     420
gggggcgtgc tgaccgctac ccaggacacc agcctccagg acggctgcct catctacaac     480
gtcaagatca gaggggtgaa cttcccatcc aacggccctg tgatgcagaa gaaaacactc     540
ggctgggagg ccaacaccga gatgctgtac cccgctgacg gcggcctgga aggcagaagc     600
gacatggccc tgaagctcgt gggcggggc  cacctgatct gcaacttcaa gaccacatac     660
agatccaaga aacccgctaa gaacctcaag atgcccggcg tctactatgt ggaccacaga     720
ctggaaagaa tcaaggaggc cgacaaagag acctacgtcg agcagcacga ggtggctgtg     780
gccagatact gcgacctccc tagcaaactg ggcacaaaac ttaatggctc cgagggcaga     840
ggaagccttc taacatgcgg tgacgtggag gagaatcccg gcccttccgg gatgaccgag     900
tacaagccca cggtgcgcct cgccacccgc gacgacgtcc ccagggccgt acgcaccctc     960
gccgccgcgt cgccgactac ccccgccacg cgccacaccg tcgatccaga ccgccacatc    1020
gagcgggtca ccgagctgca agaactcttc ctcacgcgcg tcgggctcga catcggcaag    1080
gtgtgggtcg cggacgacgg cgccgcggtg gcggtctgga ccacgccgga gagcgtcgaa    1140 gcggggcgg  tgttcgccga gatcggcccg cgcatggccg agttgagcgg ttcccggctg    1200
gccgcgcagc aacagatgga aggtctcctg gcgccgcacc ggcccaagga gcccgcgtgg    1260
ttcctggcca ccgtcggcgt ctcgcccgac caccagggca agggtctggg cagcgccgtc    1320
gtgctccccg gagtggaggc ggccgagcgc gccggggtgc ccgccttcct ggagacctcc    1380
gcgccccgca acctcccctt ctacgagcgg ctcggcttca ccgtcaccgc cgacgtcgag    1440
gtgcccgaag accgcgcac  ctggtgcatg acccgcaagc ccggtgcctg aagatctttt    1500
tccctctgcc aaaaattatg gggacatcat gaagccccct gagcatctga cttctggcta    1560
ataaaggaaa tttattttca ttgcaatagt gtgttggaat ttttttgtgtc tctcactcgg    1620 aaggacatat gggagggcaa atcatttaaa acatcagaat gagtatttgg tttagagttt    1680
ggcaacatat gccatatgct ggctgccatg aacaaaggtg gctataaaga ggtcatcagt    1740
atatgaaaca gccccctgct gtccattcct tattccatag aaaagccttg acttgaggtt    1800
```

```
agattttttt tatattttgt tttgtgttat tttttttcttt aacatccccta aaattttcct    1860 tacatgtttt actagccaga ttttttcctcc tctcctgact actcccagtc atagctgtcc    1920
ctcttctctt atgaagatcc ctcgacctgc agcccaagct tggatccctc gagcgtcgcc    1980
gtccagctcg accagg                                                    1996

<210> SEQ ID NO 45
<211> LENGTH: 3984
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: HDR_RFP donor_1

<400> SEQUENCE: 45
cagccattgc cttttatggt aatcgtgcga gagggcgcag ggacttcctt tgtcccaaat      60
ctggcggagc cgaaatctgg gaggcgccgc cgcaccccct ctagcgggcg cgggcgaagc    120
ggtgcggcgc cggcaggaag gaaatgggcg gggagggcct tcgtgcgtcg ccgcgccgcc    180
gtccccttct ccatctccag cctcggggct gccgcagggg gacggctgcc ttcgggggg     240 acggggcagg gcggggttcg gcttctggcg tgtgaccggc ggctctagag cctctgctaa    300
ccatgttcat gccttcttct ttttcctaca gctcctgggc aacgtgctgg ttgttgtgct    360
gtctcatcat tttggcaaag aattcgccac catggtgagc aagggcgagg agctgttcac    420
cggggtggtg cccatcctgg tcgagctgga cggcgacgtg aacggccaca gttcagcgt    480 gtccggcgag ggcgagggcg atgccaccta cggcaagctg accctgaagt tcactatagg    540
gcgaattggg cccgacgtcg catgcgtgaa acagactttg aattttgacc ttctcaagtt    600
ggcgggagac gtggagtcca acccagggcc cataacttcg tataatgtat gctatacgaa    660
gttattaccc gggatggtga gcaagggcga ggaggataac atggccatca tcaaggagtt    720
catgcgcttc aaggtgcaca tggagggctc cgtgaacggc cacgagttcg agatcgaggg    780
cgagggcgag ggccgcccct acgagggcac ccagaccgcc aagctgaagg tgaccaaggg    840
tggccccctg cccttcgcct gggacatcct gtcccctcag ttcatgtacg gctccaaggc    900
ctacgtgaag caccccgccg acatccccga ctacttgaag ctgtccttcc ccgagggctt    960
caagtgggag cgcgtgatga acttcgagga cggcggcgtg gtgaccgtga cccaggactc   1020
ctccctgcag gacggcgagt tcatctacaa ggtgaagctg cgcggcacca acttcccctc   1080
cgacggcccc gtaatgcaga gaagaccat gggctgggag gcctcctccg agcggatgta   1140
ccccgaggac ggcgccctga agggcgagat caagcagagg ctgaagctga aggacggcgg   1200
ccactacgac gctgaggtca agaccaccta caaggccaag aagcccgtgc agctgcccgg   1260
cgcctacaac gtcaacatca gttggacat cacctcccac aacgaggact acaccatcgt   1320
ggaacagtac gaacgcgccg agggccgcca ctccaccggc ggcatggacg agctgtacaa   1380
ggctagcgag ggcagaggaa gccttctaac atgcggtgac gtggaggaga atcccggccc   1440
ttccgggatg accgagtaca agcccacggt gcgcctcgcc acccgcgacg acgtccccag   1500
ggccgtacgc accctcgccg ccgcgttcgc cgactacccc gccacgcgcc acaccgtcga   1560
tccagaccgc cacatcgagc gggtcaccga gctgcaagaa ctcttcctca cgcgcgtcgg   1620
gctcgacatc ggcaaggtgt gggtcgcgga cgacggcgcc gcggtggcgg tctggaccac   1680
gccggagagc gtcgaagcgg gggcggtgtt cgccgagatc ggcccgcgca tggccgagtt   1740
```

```
gagcggttcc cggctggccg cgcagcaaca gatggaaggt ctcctggcgc cgcaccggcc    1800
caaggagccc gcgtggttcc tggccaccgt cggcgtctcg cccgaccacc agggcaaggg    1860
tctgggcagc gccgtcgtgc tccccggagt ggaggcggcc gagcgcgccg gggtgcccgc    1920
cttcctggag acctccgcgc cccgcaacct ccccttctac gagcggctcg gcttcaccgt    1980
caccgccgac gtcgaggtgc ccgaaggacc gcgcacctgg tgcatgaccc gcaagcccgg    2040
tgcctgagat cttttccct ctgccaaaaa ttatggggac atcatgaagc cccttgagca    2100
tctgacttct ggctaataaa ggaaatttat tttcattgca atagtgtgtt ggaattttt    2160 gtgtctctca ctcggaagga catatgggag ggcaaatcat ttaaaacatc agaatgagta    2220
tttggtttag agtttggcaa catatgccat atgctggctg ccatgaacaa aggtggctat    2280
aaagaggtca tcagtatatg aaacagcccc ctgctgtcca ttccttattc catagaaaag    2340
ccttgacttg aggttagatt ttttttatat tttgttttgt gttattttt tctttaacat    2400 ccctaaaatt ttccttacat gttttactag ccagattttt cctcctctcc tgactactcc    2460
cagtcatagc tgtccctctt ctcttatgaa gatccctcga cctgcagccc aagcttggat    2520
ccctcgagtt ataacttcgt ataggatact ttatacgaag ttatcatatg ggagagctcc    2580
caaccacatg aagcagcacg acttcttcaa gtccgccatg cccgaaggct acgtccagga    2640
gcgcaccatt ttcttcaagg acgacggcaa ctacaagacc cgcgccgagg tgaagttcga    2700
gggcgacacc ctggtgaacc gcatcgagct gaagggcatc gacttcaagg aggacggcaa    2760
catcctgggg cacaagctgg agtacaacta caacagccac aacgtctata tcatggccga    2820
caagcagaag aacggcatca aggtgaactt caagatccgc cacaacatcg aggacggcag    2880
cgtgcagctc gccgaccact accagcagaa caccccatc ggcgacggcc ccgtgctgct    2940
gcccgacaac cactacctga gcacccagtc cgccctgagc aaagaccca acgagaagcg    3000 cgatcacatg gtcctgctgg agttcgtgac cgccgcgggg atcactcacg gcatggacga    3060
gctgtacaag taagaattca ctcctcaggt gcaggctgcc tatcagaagg tggtggctgg    3120
tgtggccaat gccctggctc acaaatacca ctgagatctt tttccctctg ccaaaaatta    3180
tggggacatc atgaagcccc ttgagcatct gacttctggc taataaagga aatttatttt    3240
cattgcaata gtgtgttgga attttttgtg tctctcactc ggaaggacat atgggagggc    3300
aaatcattta aacatcaga atgagtattt ggtttagagt ttggcaacat atgccatatg    3360
ctggctgcca tgaacaaagg tggctataaa gaggtcatca gtatatgaaa cagccccctg    3420
ctgtccattc cttattccat agaaaagcct tgacttgagg ttagattttt tttatatttt    3480
gttttgtgtt attttttct taacatccc taaaattttc cttacatgtt ttactagcca    3540 gattttcct cctcctga ctactcccag tcatagctgt ccctcttctc ttatgaagat    3600
ccctcgacct gcagcccaag cttggatccc tcgagttaat taacgagagc ataatattga    3660
tatgtgccaa agttgtttct gactgactaa taagtataat ttgtttctat tatgtatagg    3720
ttaagctaat tacttatttt ataatacaac atgactgttt ttaaagtaca aataagtttt    3780
atttttgtaa aagagagaat gtttaaaagt tttgttactt tatagaagaa attttgagtt    3840
tttgtttttt tttaataaat aaataaacat aaataaattg tttgttgaat ttattattag    3900
tatgtaagtg taaatataat aaaacttaat atctattcaa attaataaat aaacctcgat    3960
atacagaccg ataaaacaca tgcg                                          3984
```

<210> SEQ ID NO 46

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HITI_pr_RFP_F_1(primer)

<400> SEQUENCE: 46
tctgctaacc atgttcatgc                                                   20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HITI_pr_RFP_R_1(primer)

<400> SEQUENCE: 47
cagggaagga ctgcttaaag                                                   20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HDR_pr_RFP_F_1(primer)

<400> SEQUENCE: 48
tctgctaacc atgttcatgc                                                   20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HDR_pr_RFP_R_1(primer)

<400> SEQUENCE: 49
ttcacgtagg ccttggagc                                                    19

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_spCas9_F_2 (primer)

<400> SEQUENCE: 50
gacaagaagt acagcatcgg                                                   20

<210> SEQ ID NO 51
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: pr_spCas9_R_2 (primer)

<400> SEQUENCE: 51
caaccagctg ttcgaggaga                                              20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GAPDH_F_3 (primer)

<400> SEQUENCE: 52
ggcgtgaacc acgagaagta                                              20

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: pr_GAPDH_R_3 (primer)

<400> SEQUENCE: 53
ccctccacga tgccaaagt                                               19

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_BLG_F_1 (primer)

<400> SEQUENCE: 54
ttaaaggccg tgtctccagt                                              20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: in_pr_BLG_R_1 (primer)

<400> SEQUENCE: 55
gaaagccctg gataagcagc                                              20
```

TRANSGENIC ANIMALS AND TRANSGENIC EMBRYOS PRODUCING AN ENGINEERED NUCLEASE

RELATED APPLICATIONS

This application is a U.S. National Stage Application of International Application No. PCT/KR2019/010388 filed Aug. 14, 2019, which claims the benefit of priority to Republic of Korea Application No. 10-2019-0065613 filed Jun. 3, 2019 and to U.S. Application No. 62/764,905 filed Aug. 16, 2018. The entire contents of PCT/KR2019/010388 are incorporated herein by reference in their entirety.

SEQUENCE LISTING

The instant application contains a Sequence Listing which has been submitted electronically in ASCII format and is hereby incorporated by reference in its entirety. Said ASCII copy, created on Jul. 6, 2021, is named IPH-00101_SL.txt and is 24,437 bytes in size.

TECHNICAL FIELD

The details disclosed in the present specification relate to a transgenic animal and a transgenic embryo that produce components of an engineered nuclease.

Specifically, the details disclosed in the present specification relate to a chimeric transgenic animal and a chimeric transgenic embryo, which have a genome including a polynucleotide that encodes the component of an engineered nuclease.

More specifically, the details disclosed in the present specification relate to a transgenic animal and a transgenic embryo, which include a first cell that has a genome in which a polynucleotide encoding the component of an engineered nuclease is located in a first locus; and a second cell that has a genome in which a polynucleotide encoding the component of an engineered nuclease is located in a second locus which is different from the first locus.

Additionally, the details disclosed in the present specification relate to a transgenic animal and a transgenic embryo, which include a first cell that has a genome in which a first polynucleotide encoding the component of an engineered nuclease is located in a first locus; and a second cell that has a genome in which a second polynucleotide encoding the component of an engineered nuclease is located in a first locus. In this case, the sequence of the first polynucleotide is different from that of the second polynucleotide.

BACKGROUND ART

The current trend is that genetic manipulation using a gene editing tool including CRISPR/Cas9 is being applied to various species of animals and plants.

Conventional genetic manipulation has been relying on a method for providing a gene editing tool to a cell or individual from outside. However, this method has a problem in that efficiency of genetic manipulation is low when a gene editing tool is injected into a cell or individual from outside.

When a transgenic animal having a genome into which a gene encoding a gene editing tool is inserted is used, a gene editing tool may be expressed in an animal or cell, thus resulting in a higher efficiency of genetic manipulation.

Additionally, when a transgenic animal having a genome into which a gene encoding a gene editing tool is inserted is used, a plurality of animals in which various genes are knocked in or knocked out can be prepared. Through the above, a transgenic animal having a genome into which a gene encoding a gene editing tool is inserted can be used as a platform technology.

Furthermore, when the transgenic animal is a large animal, the utility may be better than that of a small animal.

Therefore, there is a need for the development of a large animal having a genome into which a gene encoding a gene editing tool is inserted, however, genetic manipulation in large animals is in a slow progress due to technical limitations compared to small animals.

DETAILED DESCRIPTION OF THE INVENTION

Technical Problem

In an embodiment, the present disclosure relates to a transgenic animal which includes a polynucleotide that encodes components of an engineered nuclease.

In another embodiment, the present disclosure relates to a transgenic embryo which includes a polynucleotide that encodes components of an engineered nuclease.

An object of the present disclosure is to enable more effective genetic manipulation using the transgenic animal or transgenic embryo, in which components of an engineered nuclease can be expressed.

Another object of the present disclosure is to prepare a plurality of cells, embryos, and/or animals, in which various genes are knocked in or knocked out using the transgenic animal or transgenic embryo, in which components of an engineered nuclease can be expressed.

Technical Solution

According to an aspect of the present disclosure, the present invention provides a transgenic animal comprising a first cell, which has a genome including a first toolbox, and a second cell, which has a genome including a second toolbox,
  in which the first toolbox and the second toolbox include at least one of a polynucleotide encoding an RNA-guided endonuclease and a polynucleotide encoding a guide nucleic acid that can specifically bind to a target site, respectively,
  in which the target site is an endo-polynucleotide of the animal or an exo-polynucleotide located between a first ITR sequence and a second ITR sequence included in the genome of the animal,
  in which the first toolbox is present in a first locus of the genome of the first cell, the second toolbox is present in a second locus of the genome of the second cell, and the first locus is different from the second locus.

According to another aspect of the present disclosure, the present invention provides a transgenic animal comprising a first cell, which has a genome including a first toolbox, and a second cell, which has a genome including a second toolbox,
  in which the first toolbox and the second toolbox comprise at least one of a polynucleotide encoding an RNA-guided endonuclease and a polynucleotide encoding a guide nucleic acid that can specifically bind to a target site, respectively,
  in which the target site is an endo-polynucleotide of the animal or an exo-polynucleotide located between a first ITR sequence and a second ITR sequence included in the genome of the animal, in which the sequence of the first toolbox is different from that of the second toolbox, the first toolbox is present in a first locus of the genome of the first cell, the second toolbox is present in a second locus of the genome of the second cell, and the first locus is the same as the second locus.

According to an aspect of the present disclosure, the present invention provides a transgenic embryo comprising a first cell, which has a genome including a first toolbox, and a second cell, which has a genome including a second toolbox, in which the first toolbox and the second toolbox include at least one of a polynucleotide encoding an RNA-guided endonuclease and a polynucleotide encoding a guide nucleic acid that can specifically bind to a target site, respectively, in which the target site is an endo-polynucleotide of the embryo or an exo-polynucleotide located between a first ITR sequence and a second ITR sequence included in the genome of the embryo, in which the first toolbox is present in a first locus of the genome of the first cell, the second toolbox is present in a second locus of the genome of the second cell, and the first locus is different from the second locus.

According to another aspect of the present disclosure, the present invention provides a transgenic embryo comprising a first cell, which has a genome including a first toolbox, and a second cell, which has a genome including a second toolbox, in which the first toolbox and the second toolbox include at least one of a polynucleotide encoding an RNA-guided endonuclease and a polynucleotide encoding a guide nucleic acid that can specifically bind to a target site, respectively, in which the target site is an endo-polynucleotide of the embryo or an exo-polynucleotide located between a first ITR sequence and a second ITR sequence included in the genome of the embryo, in which the exo-polynucleotide is positioned between a first ITR sequence and a second ITR sequence in the genome of the transgenic embryo, in which the sequence of the first toolbox is different from that of the second toolbox, the first toolbox is present in a first locus of the genome of the first cell, the second toolbox is present in a second locus of the genome of the second cell, and the first locus is the same as the second locus.

According to an aspect of the present disclosure, the present invention provides a transgenic animal comprising a first cell, which has a genome including a first toolbox and a target site, and a second cell, which has a genome including a second toolbox and a modified site, in which the first toolbox and the second toolbox comprise at least one of a polynucleotide encoding an RNA-guided endonuclease and a polynucleotide encoding a guide nucleic acid that can specifically bind to a target site, respectively, in which the target site includes a first region, a second region and a third region, in which the first region is positioned at the 5' end of the second region, and the third region is positioned at the 3' end of the second region, in which the modified site includes a fourth region, a fifth region and a sixth region, in which the fourth region is positioned at the 5' end of the fifth region, and the sixth region is positioned at the 3' end of the fifth region, in which the sequence of the first region is the same as the sequence of the fourth region, in which the sequence of the third region is the same as the sequence of the sixth region, in which the sequence of the second region is different from the sequence of the fifth region.

According to another aspect of the present disclosure, the present invention provides a transgenic embryo comprising a first cell, which has a genome including a first toolbox and a target site, and a second cell, which has a genome including a second toolbox and a modified site, in which the first toolbox and the second toolbox comprise at least one of a polynucleotide encoding an RNA-guided endonuclease and a polynucleotide encoding a guide nucleic acid that can specifically bind to a target site, respectively, in which the target site includes a first region, a second region and a third region, in which the first region is positioned at the 5' end of the second region, and the third region is positioned at the 3' end of the second region, in which the modified site includes a fourth region, a fifth region and a sixth region, in which the fourth region is positioned at the 5' end of the fifth region, and the sixth region is positioned at the 3' end of the fifth region, in which the sequence of the first region is the same as the sequence of the fourth region, in which the sequence of the third region is the same as the sequence of the sixth region, in which the sequence of the second region is different from the sequence of the fifth region.

According to an aspect of the present disclosure, the present invention provides a method for preparing a transgenic embryo in which a component of an engineered nuclease is expressed, the method comprises a microinjection of a vector into a fertilized egg or an embryo, in which the vector includes a transposon gene and a polynucleotide encoding the components of the engineered nuclease, in which the vector is a plasmid vector or a viral vector.

According to another aspect of the present disclosure, the present invention provides a method for preparing a transgenic embryo in which a component of an engineered nuclease is expressed, the method comprises:

i) preparing a transgenic donor cell in which the component of the engineered nuclease is expressed; and ii) transplanting the nucleus of the transgenic donor cell into an enucleated ovum.

According to a further aspect of the present disclosure, the present invention provides a method for preparing a transgenic animal in which a component of an engineered nuclease is expressed, the method comprises:

i) preparing a transgenic embryo in which the component of the engineered nuclease is expressed; and ii) transplanting the transgenic embryo into the uterus of a surrogate mother.

According to an aspect of the present disclosure, the present invention provides a method for preparing an embryo having a genome which includes a gene editing occurred in a target site present in the genome, the method comprises providing a guide nucleic acid capable of binding to the target site into a fertilized egg or an embryo, in which the fertilized egg or the embryo has a genome including a polynucleotide encoding an RNA-guided endonuclease, in which the guide nucleic acid is an RNA form, or a form incorporated into a plasmid vector or viral vector.

According to another aspect of the present disclosure, the present invention provides a method for preparing an embryo having a genome which includes a gene editing occurred in a target site present in the genome, the method comprises:
i) preparing a transgenic donor cell having a genome including a polynucleotide encoding an RNA-guided endonuclease and a gene editing which has occurred in a target site present in the genome; and
ii) transplanting the nucleus of the transgenic donor cell into an enucleated ovum.

According to a further aspect of the present disclosure, the present invention provides a method for preparing an animal having a genome which includes a gene editing occurred in a target site present in the genome, the method comprises:
i) preparing a embryo having a genome including a polynucleotide encoding an RNA-guided endonuclease and a gene editing which has occurred in a target site present in the genome; and
ii) transplanting the embryo into the uterus of a surrogate mother.

According to a still further aspect of the present disclosure, the present invention provides a method for preparing an embryo having a genome which includes a gene editing occurred in a target site present in the genome, the method comprises providing at least one of materials and conditions capable of affecting an expression control element into a fertilized egg or an embryo,
in which the fertilized egg or the embryo has a genome including:
i) a polynucleotide encoding an RNA-guided endonuclease;
ii) a polynucleotide encoding a guide nucleic acid capable of binding to the target site; and
iii) an expression control element, which is positioned in at least one among the 5' end of the polynucleotide encoding an RNA-guided endonuclease and the 5' end of the polynucleotide encoding the guide nucleic acid.

According to a further aspect of the present disclosure, the present invention provides a method for preparing an embryo having a genome which includes a gene editing occurred in a target site present in the genome, the method comprises:
i) preparing a transgenic donor cell having a genome,
in which the genome includes a polynucleotide encoding an RNA-guided endonuclease, a polynucleotide encoding a guide nucleic acid capable of binding to the target site, an expression control element which is positioned in at least one among the 5' end of the polynucleotide encoding an RNA-guided endonuclease and the 5' end of the polynucleotide encoding the guide nucleic acid,
in which the genome includes a gene editing, which has occurred in a target site present in the genome; and
ii) transplanting the nucleus of the transgenic donor cell into an enucleated ovum.

According to a still further aspect of the present disclosure, the present invention provides a method for preparing an animal having a genome which includes a gene editing occurred in a target site present in the genome, the method comprises:
i) preparing an embryo having a genome,
in which the genome includes a polynucleotide encoding an RNA-guided endonuclease, a polynucleotide encoding a guide nucleic acid capable of binding to the target site, an expression control element which is positioned in at least one among the 5' end of the polynucleotide encoding an RNA-guided endonuclease and the 5' end of the polynucleotide encoding the guide nucleic acid,
in which the genome includes a gene editing, which has occurred in a target site present in the genome; and
ii) transplanting the embryo into the uterus of a surrogate mother.

Effects of the Invention

According to the technology disclosed by the present specification, the following effects occur.

According to an embodiment disclosed by the present specification, there may be provided a transgenic animal which includes a polynucleotide that encodes the component of an engineered nuclease. Additionally, a transgenic animal in which genetic manipulation can be performed more effectively may be provided. Furthermore, a platform transgenic animal for the preparation of cells, embryos and/or animals, in which various genes are knocked in or knocked out may be provided.

According to another embodiment disclosed by the present specification, there may be provided a transgenic embryo which includes a polynucleotide that encodes the component of an engineered nuclease. Additionally, a transgenic embryo in which genetic manipulation can be performed more effectively may be provided. Furthermore, a platform transgenic embryo for the preparation of cells, embryos and/or animals, in which various genes are knocked in or knocked out may be provided.

BRIEF DESCRIPTION OF THE DRAWINGS

FIG. 11 illustrates some embodiments of a toolbox which includes a polynucleotide having a PAM sequence.

FIG. 12 illustrates a process of gene editing within a toolbox which includes a polynucleotide having a PAM sequence.

FIG. 30 shows images illustrating the results confirming the expression of a green fluorescent protein in the transgenic cow having a genome into which a toolbox including a gene encoding green fluorescent protein is inserted.

FIG. 33 shows images illustrating an offspring cow having a genome into which a toolbox including a fluorescent protein gene is inserted, and the expression of a fluorescent protein in primary cells of the offspring cow.

FIG. 41 shows a schematic diagram illustrating the process in which a donor polynucleotide, which targets a green fluorescent protein gene present in the genome of bovine primary cells, is knocked in.

FIG. 43 shows a schematic diagram illustrating a vector in which a toolbox including spCas9 gene is included, and images illustrating a transgenic embryo and a transgenic cow, each of which has a genome into which a toolbox including spCas9 gene is inserted.

FIG. 44 shows visual results illustrating the expression of a red fluorescent protein in primary cells of a transgenic cow having a genome into which a toolbox including spCas9 gene is inserted; results of DNA PCR illustrating the insertion of spCas9 gene into the genome of transgenic cow; and results of RT-PCR illustrating the expression of spCas9 gene which is inserted into the genome of transgenic cow.

FIG. 51 shows images illustrating the results confirming the knockin of mcherry gene by HITI.

FIG. 52 shows images illustrating the results confirming the knockin of mcherry gene by HDR.

FIG. 53 shows images illustrating an embryo in which mcherry gene, which is prepared via somatic cell nuclear transfer, is knocked in; and the mcherry expression in the embryo in which mcherry gene is knocked in.

FIG. 55 shows images illustrating the expression of a red fluorescent protein in primary cells of a transgenic cow having a genome into which a toolbox including polynucleotides that encode spCas9 gene and sgRNA is inserted; and the results of fPCR confirming the indels of beta-lactoglobulin gene in the fibroblasts of the transgenic cow.

FIG. 56 shows schematic diagrams illustrating part of the vectors in which the expression of RNA-guided endonuclease can be controlled.

FIG. 58 shows an image illustrating the sequence of a donor vector for HDR, in which the shaded parts among the entire sequences represent the first homology arm and the second homology arm, respectively.

BEST MODE FOR CARRYING OUT THE INVENTION

Figure 1:
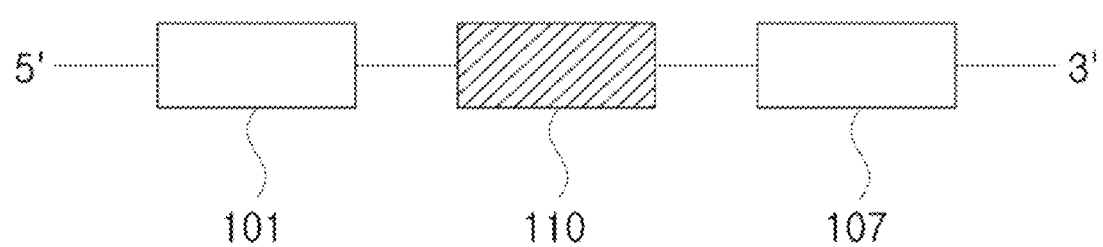
FIG. 1 illustrates a toolbox which includes a polynucleotide that encodes the component of an engineered nuclease.

According to an embodiment provided by the present specification, there may be provided a transgenic embryo which has a genome into which a polynucleotide encoding a component of an engineered nuclease is inserted.

For example, a transgenic fertilized egg or transgenic embryo, which has a genome including a polynucleotide encoding an RNA-guided endonuclease that is included between a first ITR sequence and a second ITR sequence, may be provided. Specifically, the embryo may be an embryo of an artiodactyl. Furthermore, a transgenic fertilized egg or transgenic embryo, which further includes a polynucleotide encoding a guide nucleic acid, which is capable of specifically binding to a target site present in the genome of the fertilized egg or embryo, between the first ITR sequence and the second ITR sequence, may be provided. At this time, an expression control element may be included in at least one among the 5' end of the polynucleotide encoding the RNA-guided endonuclease and the 5' end of the polynucleotide encoding the guide nucleic acid.

In another example, a transgenic embryo, which includes a first cell that has a genome including a first toolbox and a second cell that has a genome including a second toolbox, in which the first toolbox is present at a first locus, the second toolbox is present at a second locus, and the first locus and the second locus are different, may be provided. The first toolbox and the second toolbox may include at least one among a polynucleotide encoding an RNA-guided endonuclease and a polynucleotide encoding a guide nucleic acid that can specifically bind to a target site. The target site may be an endo-polynucleotide of the embryo or an exo-polynucleotide included in the genome of the embryo and may be included between a first ITR sequence and a second ITR sequence. At this time, the sequence of the first toolbox may be the same as or different from that of the second toolbox.

In another example, a transgenic embryo, which includes a first cell having a genome that includes a first toolbox and a second cell having a genome that includes a second toolbox, in which the first toolbox is present at a first locus, the second toolbox is present at a second locus and the first locus and the second locus are the same with each other, may be provided. The first toolbox and the second toolbox may include at least one among a polynucleotide encoding an RNA-guided endonuclease and a polynucleotide encoding a guide nucleic acid that can specifically bind to a target site. The target site may be an endo-polynucleotide of the embryo or an exo-polynucleotide included in the genome of the embryo and may be included between a first ITR sequence and a second ITR sequence. At this time, the sequence of the first toolbox is different from that of the second toolbox. The genome of the first cell may further include a third toolbox which has the same sequence as the first toolbox. The genome of the second cell may further include a fourth toolbox which has the same sequence as the second toolbox. The transgenic embryo may further include a third cell having a genome which does not include the polynucleotide encoding the RNA-guided endonuclease and the polynucleotide encoding the guide nucleic acid.

In another example, a transgenic embryo, which includes a first cell having a genome that includes a first toolbox and a target site, and a second cell having a genome that includes the target site, may be provided. The first toolbox may include at least one among a polynucleotide encoding a first RNA-guided endonuclease and a polynucleotide encoding a first guide nucleic acid that can bind to the target site, and the genome of the second cell may not include a polynucleotide encoding a second RNA-guided endonuclease and a polynucleotide encoding a second guide nucleic acid that can specifically bind to the target site. Additionally, an ITR sequence may be further included in 5' end and 3' end of the first toolbox. At this time, the sequence of the polynucleotide encoding the first RNA-guided endonuclease and the sequence of the polynucleotide encoding the second RNA-guided endonuclease may be the same as or different from each other, and the sequence of the polynucleotide encoding the first guide nucleic acid and the sequence of the polynucleotide encoding the second guide nucleic acid may be the same as or different from each other. The target site may be an endo-polynucleotide. Specifically, the target site may be a base sequence of 18 bp to 25 bp present on the genome of the transgenic embryo. The target site may be an exo-polynucleotide. The target site may be a sequence adjacent to the 5 'end or 3' end of a PAM sequence, and the target site and the PAM sequence may be included between a first ITR sequence and a second ITR sequence.

According to another embodiment provided by the present specification, there may be provided a method for preparing a transgenic embryo which has a genome into which a polynucleotide encoding a component of an engineered nuclease is inserted.

One method for preparing the transgenic embryo may include microinjecting a vector, which includes a transposon gene and a polynucleotide encoding a component of an engineered nuclease, into a fertilized egg or embryo. Additionally, the method may include microinjecting a transposase, which can interact with the transposon gene, into a fertilized egg or embryo. The transposase may be in the form of a protein, a polypeptide, or a polynucleotide encoding the transposase. The polynucleotide may be one which is included in a plasmid vector or viral vector. Furthermore, the polynucleotide encoding the transposase may be incorporated into a single vector together with the polynucleotide encoding the transposon gene and the component of the engineered nuclease and then microinjected into the fertilized egg or embryo. One type of a transgenic embryo that can be prepared by the above method, may include a first cell, in which a polynucleotide encoding a component of a first engineered nuclease has a genome included in a first locus, and a second cell, in which a polynucleotide encoding a component of a second engineered nuclease has a genome included in a second locus that is different from the first locus. At this time, the sequence of the polynucleotide encoding the component of the first engineered nuclease and the sequence of the polynucleotide encoding the component of the second engineered nuclease may be the same or different from each other. Another type of a transgenic embryo that can be prepared by the above method, may include a first cell, in which a polynucleotide encoding a component of a first engineered nuclease has a genome included in a first locus, and a second cell, in which a polynucleotide encoding a component of a second engineered nuclease has a genome included in the first locus. At this time, the sequence of the polynucleotide encoding the component of the first engineered nuclease and the sequence of the polynucleotide encoding the component of the second engineered nuclease may be the same or different from each other.

Another method for preparing a transgenic embryo may include preparing a transgenic donor cell, in which a component of an engineered nuclease is expressed, and transplanting the nucleus of the transgenic donor cell into an enucleated ovum. The preparing of the transgenic donor cell may include transforming a cell with a vector which includes a polynucleotide encoding a transposon gene and the component of the engineered nuclease. Additionally, the preparing of the transgenic donor cell may further include transforming the cell with a transposase that can interact with the transposon gene. The transposase may be in the form of a protein, a polypeptide, or a polynucleotide encoding the transposase. The polynucleotide may be one which is included in a plasmid vector or viral vector. Furthermore, the polynucleotides encoding the transposase may be incorporated into a single vector together with the polynucleotide encoding the transposon gene and the component of the engineered nuclease and then microinjected into a fertilized egg or embryo.

According to yet another embodiment provided by the present specification, there may be provided a transgenic animal having a genome into which a polynucleotide encoding a component of an engineered nuclease is inserted.

For example, a transgenic animal having a genome, which includes a polynucleotide encoding an RNA-guided endonuclease that is included between a first ITR sequence and a second ITR sequence, may be provided. Specifically, the animal may be an artiodactyl. Additionally, a transgenic animal, in which a polynucleotide encoding a guide nucleic acid that can specifically bind to a target site present in the animal is further included between the first ITR sequence and the second ITR sequence, may be provided. At this time, an expression control element may be included in one or more among the 5' end of a polynucleotide encoding an RNA-guided endonuclease and the 5' end of a polynucleotide encoding the guide nucleic acid.

In another example, a chimeric transgenic animal, which includes a first cell having a genome including a toolbox and a second cell having a genome not including a toolbox, may be provided. Specifically, a transgenic animal, which includes a first cell having a genome that includes a first toolbox and a target site, and a second cell having a genome that includes the target site, may be provided. The first toolbox may include at least one polynucleotide among a polynucleotide encoding a first RNA-guided endonuclease and a polynucleotide encoding a first guide nucleic acid that can bind to the target site, and the genome of the second cell may not include a polynucleotide encoding a second RNA-guided endonuclease and a polynucleotide encoding a second guide nucleic acid that can specifically bind to the target site. Additionally, an ITR sequence may be further included in the 5' end and 3' end of the first toolbox. At this time, the sequence of the polynucleotide encoding the first RNA-guided endonuclease and the sequence of the polynucleotide encoding the second RNA-guided endonuclease may be the same as or different from each other, and the sequence of the polynucleotide encoding the first guide nucleic acid and the sequence of the polynucleotide encoding the second guide nucleic acid may be the same as or different from each other. The target site may be an endo-polynucleotide. Specifically, the target site may be a base sequence of 18 bp to 25 bp present on the genome of the transgenic animal. The target site may be an exo-polynucleotide. The target site may be a sequence adjacent to the 5 'end or 3' end of a PAM sequence, and the target site and the PAM sequence may be included between a first ITR sequence and a second ITR sequence.

In another example, a transgenic animal, which includes a first cell that has a genome including a first toolbox and a second cell that has a genome including a second toolbox, in which the first toolbox is present at a first locus, the second toolbox is present at a second locus, and the first locus and the second locus are different, may be provided. The first toolbox and the second toolbox may include at least one among a polynucleotide encoding an RNA-guided endonuclease and a polynucleotide encoding a guide nucleic acid that can specifically bind to a target site. The target site may be an endo-polynucleotide of the animal or an exo-polynucleotide, which is included on a genome of the animal and may be included between a first ITR sequence and a second ITR sequence. At this time, the sequence of the first toolbox and the sequence of the second toolbox may be the same as or different from each other.

In another example, a transgenic animal, which includes a first cell that has a genome including a first toolbox and a second cell that has a genome including a second toolbox, in which the first toolbox is present at a first locus, the second toolbox is present at a second locus, and the first locus and the second locus are the same as each other, may be provided. The first toolbox and the second toolbox may include at least one among a polynucleotide encoding an RNA-guided endonuclease and a polynucleotide encoding a guide nucleic acid that can specifically bind to a target site. The target site may be an endo-polynucleotide of the animal or an exo-polynucleotide, which is included in a genome of the animal and may be included between a first ITR sequence and a second ITR sequence. At this time, the sequence of the first toolbox and the sequence of the second toolbox are different from each other. The genome of the first cell may further include a third toolbox, which has the same sequence as the first toolbox. The genome of the second cell may further include a fourth toolbox, which has the same sequence as the second toolbox. The transgenic animal may further include a third cell, which has a genome that does not include the polynucleotide encoding the RNA-guided endonuclease and the polynucleotide encoding the guide nucleic acid.

According to another exemplary embodiment provided by the present specification, there may be provided a method for preparing a transgenic animal which has a genome into which a polynucleotide encoding a component of an engineered nuclease is inserted.

One method for preparing the transgenic animal may include microinjecting a vector, which includes a transposon gene and a polynucleotide encoding a component of the engineered nuclease, into a fertilized egg or embryo. Additionally, the preparing of the transgenic embryo may further include microinjecting a transposase, which can interact with the transposon gene, into the fertilized egg or embryo.

Another method for preparing the transgenic animal may include preparing of a transgenic donor cell in which a component of an engineered nuclease is expressed, and transplanting the nucleus of the transgenic donor cell into an enucleated ovum of the animal. The preparing of the transgenic donor cell may include transforming a cell with a vector which includes a transposon gene and a polynucleotide encoding the component of the engineered nuclease. Additionally, the preparing of the transgenic donor cell may further include transforming the cell with a transposase that can interact with the transposon gene. The transposase may be in the form of a protein, a polypeptide, or a polynucleotide encoding the transposase. The polynucleotide may be one which is included in a plasmid vector or viral vector. Furthermore, the polynucleotide encoding the transposase may be in the form in which the polynucleotide is included in a single vector together with the transposon gene and the polynucleotide encoding the component of the engineered nuclease.

According to an embodiment provided by the present specification, a transgenic embryo, which has a gene-edited genome, may be provided.

For example, a transgenic embryo having a genome that includes a polynucleotide encoding an RNA-guided endonuclease and a polynucleotide encoding a guide nucleic acid between a first ITR sequence and a second ITR sequence, and in which an endo-polynucleotide is knocked out, may be provided. At this time, the guide nucleic acid can specifically bind to the endo-polynucleotide. The form in which the endo-polynucleotide is knocked out may be in i) a form in which at least one nucleotide is not included in the sequence of the endo-polynucleotide, ii) a form in which at least one nucleotide is further included in the sequence of the endo-polynucleotide, and iii) a form in which at least one nucleotide is deleted from the sequence of the endo-polynucleotide and at least one nucleotide is further included therein.

In another example, a transgenic embryo, which includes a first cell having a genome that includes a first toolbox and a target site and a second cell having a genome that includes a second toolbox and a modified site, may be provided. The sequence of the first toolbox may be the same as or different from that of the second toolbox. The target site may be an endo-polynucleotide. The target site may be an exo-polynucleotide. The modified site may be one in which the sequence of the target site has been changed by gene editing. Specifically, the target site may include a first region, a second region, and a third region, and the modified sequence may include a fourth region, a fifth region, and a sixth region. At this time, the sequence of the first region is the same as that of the fourth region, the sequence of the third region is the same as that of the sixth region, and the sequence of the second region is different from that of the fifth region. The second region and the fifth region may each include a PAM sequence. The third region and the sixth region may each include a PAM sequence. The sequence of the fifth region may be in i) a form in which at least one nucleotide is not included in the sequence of the second region, ii) a form in which at least one nucleotide is further included in the sequence of the second region, or iii) a form in which at least one nucleotide is deleted from the sequence of the second region and at least one nucleotide is further included therein. In the cases of ii) and iii), the at least one nucleotide which is additionally included may include one or more among an editing enabling component, a polynucleotide encoding a protein or RNA, a polynucleotide encoding a non-functional polypeptide, a polynucleotide encoding an untranslated RNA, an untranscribed polynucleotide, an artificial intron, and an expression control element.

In yet another example, a transgenic embryo, which includes a first cell having a genome that includes a first toolbox and a target site, and a second cell, which does not include a toolbox but has a genome including a modified gene, may be provided. At this time, the first toolbox may include one or more among a polynucleotide encoding an RNA-guided endonuclease and a polynucleotide encoding a guide nucleic acid. The modified site may be one in which the sequence of the target site has been changed by gene editing. Specifically, the target sequence may include a first region, a second region, and a third region, and the modified sequence may include a fourth region, a fifth region, and a sixth region. At this time, the sequence of the first region is the same as that of the fourth region, the sequence of the third region is the same as that of the sixth region, and the sequence of the second region is different from that of the fifth region. The sequence of the fifth region may be in i) a form in which at least one nucleotide is not included in the sequence of the second region, ii) a form in which at least one nucleotide is further included in the sequence of the second region, and iii) a form in which at least one nucleotide is deleted from the sequence of the second region and at least one nucleotide is further included therein.

According to another embodiment provided by the present specification, a transgenic animal which has a gene-edited genome may be provided.

For example, a transgenic animal having a genome that includes a polynucleotide encoding an RNA-guided endonuclease and a polynucleotide encoding a guide nucleic acid between a first ITR sequence and a second ITR sequence, and in which an endo-polynucleotide is knocked out, may be provided. At this time, the guide nucleic acid can specifically bind to the endo-polynucleotide. The form in which the endo-polynucleotide is knocked out may be any one among i) a form in which at least one nucleotide is not included in the sequence of the endo-polynucleotide, ii) a form in which at least one nucleotide is further included in the sequence of the endo-polynucleotide, and iii) a form in which at least one nucleotide is deleted from the sequence of the endo-polynucleotide and at least one nucleotide is further included therein.

In another example, a transgenic animal, which includes a first cell having a genome that includes a first toolbox and a target site and a second cell having a genome that includes a second toolbox and a modified site, may be provided. The sequence of the first toolbox may be the same as or different from that of the second toolbox. At this time, the first toolbox and/or the second toolbox may include one or more among a polynucleotide encoding an RNA-guided endonuclease and a polynucleotide encoding a guide nucleic acid. The target site may be an endo-polynucleotide. The target site may be an exo-polynucleotide. The modified site may be one in which the sequence of the target site has been changed by gene editing. Specifically, the target sequence may include a first region, a second region, and a third region, and the modified sequence may include a fourth region, a fifth region, and a sixth region. At this time, the sequence of the first region is the same as that of the fourth region, the sequence of the third region is the same as that of the sixth region, and the sequence of the second region is different from that of the fifth region. The second region and the fifth region may include a PAM sequence. The third region and the sixth region may include a PAM sequence. The sequence of the fifth region may be in i) a form in which at least one nucleotide is not included in the sequence of the second region, ii) a form in which at least one nucleotide is further included in the sequence of the second region, and iii) a form in which at least one nucleotide is deleted from the sequence of the second region and at least one nucleotide is further included therein. In the cases of ii) and iii), the at least one nucleotide which is further included thereto may include one or more among an editing enabling component, a polynucleotide encoding a protein or RNA, a polynucleotide encoding a non-functional polypeptide, a polynucleotide encoding an untranslated RNA, an untranscribed polynucleotide, an artificial intron, and an expression control element. The target site and the modified site may be sequences adjacent to the PAM sequence. The target site and the modified site may each include a first ITR sequence in the 5' direction and may each include a second ITR sequence in the 3' direction.

DETAILED DESCRIPTION OF THE INVENTION

Definition of Terms

Transformation (Genetic Modification)

As used herein, the term "transformation (genetic modification)" refers to artificially transforming a polynucleotide included in an animal genome in a cell. The transformation includes deleting and substituting part of the polynucleotide included in an animal genome of a cell, and inserting a nucleotide or polynucleotide into an animal genome.

As used herein, the term "transformation (genetic modification)" includes addition, modification, and deletion of a protein or RNA that can be expressed in a cell.

Site-Specific Transformation

As used herein, the term "site-specific transformation" refers to the transformation which occurs at a specific location on an animal genome in a cell. The specific location may be determined by a nucleotide sequence on an animal genome. For example, an RNA-guided endonuclease can recognize a nucleotide sequence, which is capable of a complementary binding to part of the guide nucleic acid, on the animal genome thereby causing site-specific transformation.

Transformed Cell (Transgenic Cell)

As used herein, the term "transformed cell (transgenic cell)" refers to a cell which includes a transformed part of an animal genome in a cell.

In an animal genome of a cell, a first cell including a transformed part may undergo a cell division. The animal genome of a second cell obtained through the cell division of the first cell may include part which has the same nucleotide sequence as that of the transformed part of the first cell. As used herein, the term "transformed cell" includes the first cell and the second cell.

Transgenic Animal (Transformed Animal)

As used herein, the term "transgenic animal (transformed animal)" refers to an animal that includes at least one transformed cell. An animal F0 may include a first transformed cell. The animal F0 may produce offspring F1. The at least one transformed cell which is included in the F1 and an offspring of the F1 may include an animal genome which includes part having the same nucleotide sequence as that of the transformed part in the animal genome of the first transformed cell. As used herein, the term "transgenic animal" includes the F0, the F1, and an offspring of the F1.

Even in the case where direct artificial manipulation for transformation is not applied during the production of an animal F1 or after the production of the animal F1, if the animal F1 includes a transformed cell, the animal F1 can be considered as a transgenic animal.

In the case where the F1 is obtained from the animal F0 after direct artificial manipulation is applied for transformation, the animal F1 can be considered as a transgenic animal.

Endo-Polynucleotide

As used herein, the term "endo-polynucleotide" refers to a polynucleotide which is included in an animal genome in a cell in which transformation has not occurred.

A first cell in which transformation has not occurred can undergo a cell division. A second cell which is obtained through the cell division of the first cell may be a transformed cell. The second cell may include a polynucleotide which has the same sequence as that of the endo-polynucleotide included in the first cell. As used herein, the term "endo-polynucleotide" includes a polynucleotide having the same sequence as that of the endo-polynucleotide of the first cell among the polynucleotides included in the second cell.

Exo-Polynucleotide

As used herein, the term "exo-polynucleotide" refers to a polynucleotide which is introduced into a cell. The cell may or may not be a transformed cell. The exo-polynucleotide may be inserted into an animal genome in a cell or may be present independently of an animal genome in a cell.

A first cell in which an exo-polynucleotide is introduced can undergo a cell division. A second cell which is obtained through the cell division of the first cell may include a polynucleotide that has the same sequence as that of the exo-polynucleotide. As used herein, the term "exo-polynucleotide" includes a polynucleotide that has the same sequence as that of the exo-polynucleotide of the first cell among the polynucleotides included in the second cell.

The animal (F0) including a cell in which an exo-polynucleotide is introduced can produce offspring (F1). The F1 and an offspring of the F1 may include a cell which includes a polynucleotide that has the same sequence as that of the exo-polynucleotide of the F0. As used herein, the term "exo-polynucleotide" includes a polynucleotide which has the same sequence as that of the exo-polynucleotide of the F0 among the polynucleotides included in a cell of the F1 and an offspring of the F1.

Insertion

As used herein, the term "insertion" includes "nucleotide insertion" and "polynucleotide insertion". As used herein, the term "nucleotide insertion" refers to addition of a nucleotide to the middle, 5' end, or 3' end of a nucleic acid. As used herein, the term "polynucleotide insertion" refers to addition of a polynucleotide to the middle, 5' end, or 3' end of a nucleic acid.

Deletion

As used herein, the term "deletion" includes "nucleotide deletion" and "polynucleotide deletion". As used herein, the term "nucleotide deletion" refers to deletion of a nucleotide included in a nucleic acid. As used herein, the term "polynucleotide deletion" refers to deletion of a polynucleotide included in a nucleic acid.

Substitution

As used herein, the term "substitution" includes "nucleotide substitution" and "polynucleotide substitution". As used herein, the term "nucleotide substitution" refers to substitution of a nucleotide included in a nucleic acid with another nucleotide. As used herein, the term "polynucleotide substitution" refers to substitution of a polynucleotide included in a nucleic acid with another polynucleotide.

Knockin (Knock-in)

As used herein, the term "knockin" refers to insertion or substitution of an exo-polynucleotide including a gene into an animal genome in a cell.

For example, an exo-polynucleotide including a human albumin gene can be inserted into a non-human animal genome in a cell. In this case, a cell including the non-human animal genome can be able to express human albumin, and this process may be called a knockin of human albumin gene.

Knockout (Knock-Out)

As used herein, the term "knockout" refers to render a gene present on an animal genome in a cell unable to function. A gene may be knocked out by transformation of the polynucleotide in the corresponding gene is located on an animal genome in a cell.

For example, an exo-polynucleotide including the human albumin gene can be inserted into a nucleotide sequence which corresponds to an exon of a non-human albumin gene present on a non-human animal genome in a cell. In this case, the cell cannot express the non-human albumin and this process may be called a knockout of the non-human albumin gene.

In another example, part of an exon of a non-human albumin gene present on the non-human animal genome in a cell may be deleted using an engineered nuclease, which targets the part of an exon of a non-human albumin gene as a target site. In this case, the cell cannot express the non-human albumin and this process may be called a knockout of a non-human albumin gene.

Engineered Nuclease

As used herein, the term "engineered nuclease" refers to a protein capable of site-specific transformation into the animal genome, or a complex including the protein. The protein may be a non-modified protein discovered in nature or modified/engineered protein.

The engineered nuclease of the present disclosure may include zinc finger nuclease (ZFN), transcription activator-like effector nuclease (TALEN), and CRISPR/enzyme system, but is not limited thereto.

Target Site

A target site of an engineered nuclease may refer to a region of a nucleic acid which can be recognized by a component of the engineered nuclease.

For example, the target site of CRISPR/enzyme system may be at least one nucleotide sequence that is identical or is able to have a complementary binding to partial region of the guide nucleic acid on a nucleic acid.

As used herein, as an example of the term "the same nucleotide sequence", the relationship between uracil (U) and thymine (T) may be included. As used herein, as an example of the term "nucleotide sequence capable of complementary binding", the relationship between uracil (U) and adenine (A) may be included.

A target site may be an endo-polynucleotide present on a genome.

A target site may be an exo-polynucleotide which is inserted into a genome.

CRISPR/Enzyme System

CRISPR/enzyme system refers to a complex which includes a protein capable of cleaving part of a target site by interaction with the target site on an animal genome in a cell or the target site of an exo-polynucleotide.

The CRISPR/enzyme system may include a guide nucleic acid and an RNA-guided endonuclease.

Guide Nucleic Acid

As used herein, the term "guide nucleic acid" refers to a nucleic acid which can bind to a target site of an animal genome in a cell or a target site of an exo-polynucleotide. As used herein, the term "guide nucleic acid" includes a single chain guide nucleic acid (single strand guide nucleic acid) and a guide nucleic acid consisting of a nucleic acid of at least two strands.

The single chain guide nucleic acid (single strand guide nucleic acid) may include a gRNA. The gRNA may include at least one among a protospacer domain, a first complementary domain, a second complementary domain, a proximal domain, and a tail domain.

The protospacer domain is a domain which includes a nucleotide sequence that can have a complementary binding to part of a target site of an animal genome, or part of a target site of an exo-polynucleotide The first complementary domain and the second complementary domain are domains which can have a complementary binding with each other thereby capable of an interaction with an RNA-guided endonuclease. The second complementary domain may be located downstream of the first complementary domain.

The proximal domain may be located downstream of the second complementary domain.

The tail domain may be located at 3' end of a gRNA.

The guide nucleic acid consisting of a nucleic acid of at least two strands may include a dual gRNA. The dual gRNA may include a crRNA and a tracrRNA. The crRNA may include a protospacer domain and a first complementary domain. The tracrRNA may include a second complementary domain, a proximal domain, and a tail domain.

RNA-Guided Endonuclease

As used herein, the term "RNA-guided endonuclease" refers to a polypeptide or protein which includes a domain capable of interacting with a polynucleotide and a domain capable of cleaving a middle of the polynucleotide.

An RNA-guided endonuclease may include SpCas9, CjCas9, StCas9, SaCas9, NmCas9, Cpf1 protein, and a mutant thereof, but is not limited thereto.

According to the modified/engineered purpose, an RNA-guided endonuclease may include dead Cas9, Cas9 nickase, eSpCas9, and SpCas9-HF1, but is not limited thereto.

The RNA-guided endonuclease can cleave a double strand by interacting with a nucleic acid or can cleave one strand of the double strand by interacting with a nucleic acid. Alternatively, the RNA-guided endonuclease can interact with a nucleic acid but may not cleave the nucleic acid.

In the case where the RNA-guided endonuclease interacts with a nucleic acid and thereby cleaves a double strand or a strand of the double strand, nucleotide insertion or polynucleotide insertion may occur in the cleaved region. Alternatively, in the case where the RNA-guided endonuclease interacts with a nucleic acid and thereby cleaves a double strand or a strand of the double strand, nucleotide deletion or polynucleotide deletion may occur in the cleaved region.

Target Site of CRISPR/Enzyme System

A target site of an animal genome in a cell or a target site of an exo-polynucleotide may be a nucleotide sequence adjacent to 5' end or 3' end of a protospacer-adjacent motif (PAM) sequence.

The PAM sequence may include NGG, NNGRRT, NNAGAAW, NNNNGATT, NNNVRYAC, and TTN, but is not limited thereto. The N may be any one among A, T, U, G, and C. The V may be any one among A, C, and G. The W may be any one among A and T. The Y may be any one of C and T.

The PAM sequence may vary depending on the RNA-guided endonuclease. For example, the PAM sequence for SpCas9 or a mutant thereof may be NGG. For example, the PAM sequence for SaCas9 or a mutant thereof may be NNGRRT. For example, the PAM sequence for StCas9 or a mutant thereof may be NNAGAAW. For example, the PAM sequence for NmCas9 or a mutant thereof may be NNNGATT. For example, the PAM sequence for CjCas9 or a mutant thereof may be NNNVRYAC. For example, the PAM sequence for Cpf1 and a mutant thereof may be TTN.

Transposon System

Transposon

As used herein, the term "transposon" refers to a polynucleotide which can be translocated within an animal genome in a cell. Additionally, the term "transposon" refers to a polynucleotide which can be translocated between a nucleic acid and an animal genome in a cell.

The transposon may be divided into Class I transposon (retrotransposon) and Class II transposon (DNA transposon).

Class I transposon is operated in such a manner that the RNA is transcribed from the transposon DNA of a nucleic acid or in an animal genome in a cell, and then the DNA which is reversely transcribed from the RNA is inserted into a different location in the animal genome.

Class II transposon is operated in such a manner that the transposon DNA in a nucleic acid or animal genome is cleaved in a cell, and the cleaved transposon DNA is inserted into a different location in the animal genome.

The Class II transposon may include a first polynucleotide at 5' end, a second polynucleotide at 3' end, and a third polynucleotide. The first polynucleotide and the second polynucleotide may include an inverted terminal repeat (hereinafter, ITR) sequence. The third polynucleotide may be located between a first polynucleotide and a second polynucleotide. The third polynucleotide may include an exo-polynucleotide. The third polynucleotide may include a polynucleotide encoding a transposase.

Unless otherwise specified, the term "transposon" refers to the case where the transposon is Class II transposon, however, in the case where there is no problem from the technical aspect even when "transposon" is interpreted as Class I transposon, it will not be necessary to interpret transposon as Class II transposon.

Transposase

As used herein, the term "transposase" refers to a protein, which can cleave the Class II transposon or insert the Class II transposon into an animal genome, by interaction with ITR sequences located at both ends of the Class II transposon located in a nucleic acid or animal genome in a cell.

The transposase may include hobo/Ac/Tam, P element, Sleeping Beauty (SB), Frog Prince, Hsmar1, Hsmar2, piggyBac (PB), Tol2, and a mutant thereof, but is not limited thereto.

The transposase can cleave transposons present in a nucleic acid or animal genome in a cell.

The transposase can insert a Class II transposon into an animal genome.

The location on which the transposase inserts the Class II transposon into an animal genome may not be related to the nucleotide sequence on the animal genome.

The location on which the transposase inserts the Class II transposon into an animal genome may be determined by a specific nucleotide sequence on the animal genome that can be recognized by the transposase. For example, in the case of Sleeping Beauty, the Sleeping Beauty transposase can insert a transposon by recognizing a TA sequence on the animal genome. Additionally, piggyBac transposase can insert a transposon by recognizing a TTAA sequence on the animal genome.

The transposase and the Class II transposon may be used for insertion of an exo-polynucleotide into an animal genome in a cell. For example, the exo-polynucleotide can be inserted into an animal genome in a cell by delivery, to a cell, of an exo-polynucleotide including an ITR sequence, which is capable of interacting with piggyBac transposase and piggyBac, at 5' end and 3' end, respectively.

In this case, there is no need to determine in advance the location on which the exo-polynucleotide is to be inserted, or change the nucleotide sequence of the exo-polynucleotide depending on the location where the exo-polynucleotide is to be inserted.

Additionally, there is no limit on the number of exo-polynucleotides that can be inserted into an animal genome in a cell. Accordingly, the expression level of the target protein of a cell can be increased by inserting a plurality of exo-polynucleotides encoding the target protein into an animal genome in a cell.

Additionally, the location at which the exo-polynucleotide is inserted by a transposase may be a location where a gene expression of a cell is not inhibited. For example, in the case of piggyBac transposase, a transposon can be inserted into an intron, 5' UTR, or 3' UTR in an animal genome.

Site-Specific Recombination

As used herein, the term "site-specific recombination" refers to a phenomenon in which two nucleotide sequences of the same or identical property on a nucleic acid or animal genome form a pair and thereby a reciprocal exchange occurs between the pair of nucleotide sequences. In this case, the nucleotide sequence where the reciprocal exchange occurs is called the recombinase recognition site (RRS). Additionally, the protein that interacts with a pair of RRSs and promotes site-specific recombination is called site-specific recombinase (SSR).

Recombinase Recognition Site

The recombinase recognition site (RRS) of the present disclosure may include loxp, rox, FRT, attP, attB, and a mutant thereof, but is not limited thereto. The loxp mutant may include loxp66, loxp71, loxp72, loxp2722, loxp5171, and loxpm2, but is not limited thereto. The rox mutant may include rox4R, rox6R, and rox2N, but is not limited thereto. The FRT mutant may include F3, F5, F10, F11, F12, F13, F14, F15, and F16, but is not limited thereto.

In the RRS, two may form a pair and thereby interact with SSR. In the loxp or a loxp mutant, two of the same RRSs may form a pair. In the rox or a rox mutant, two of the same RRSs may form a pair. In the FRT or an FRT mutant, two of the same RRSs may form a pair. The attP may form a pair with attB.

Site-Specific Recombinase

The site-specific recombinase (SSR) or recombinase of the present disclosure may include Cre, Dre, Flp, KD, B2, B3, lambda, HK022, HP1, gamma delta, ParA, Tn3, Hin, Gin, Pin, phiC31, Bxb1, R4, or a mutant thereof, but is not limited thereto.

The SSR can interact with a pair of RRSs. The Cre or a Cre mutant may specifically interact with loxp or a loxp mutant. The Dre or a Dre mutant may specifically interact with rox or a rox mutant. The Flp or Flp mutant may specifically interact with FRT or an FRT mutant. The PhiC31 or a phiC31 mutant may specifically interact with attP and attB.

Types of Site-Specific Recombination

The site-specific recombination of the present disclosure may include insertion, deletion, inversion, and exchange.

The site-specific recombination may be reversible or irreversible.

Insertion

When one of a pair of RRSs is located on a first nucleic acid and the other is located on a second nucleic acid, an insertion of the second nucleic acid may occur in the first nucleic acid through an interaction with an SSR, which is specific to the pair of RRSs.

When the insertion is reversible, the second nucleic acid may be deleted through an interaction with an SSR.

Deletion

When a pair of RRSs is located in the same direction with respect to a nucleic acid, a deletion of a polynucleotide located between the pair of RRSs may occur through an interaction with an SSR, which is specific to the pair of RRSs.

When the deletion is reversible, an insertion of a polynucleotide located between the pair of RRSs may occur.

Inversion

When a pair of RRSs is located in an opposite direction with respect to a nucleic acid, an inversion of a polynucleotide located between the pair of RRSs may occur through an interaction with an SSR, which is specific to the pair of RRSs.

When the inversion is reversible, an inversion of a polynucleotide located between the pair of RRSs may occur again.

Exchange

When RRS A and RRS B form a pair and RRS C and RRS D form a pair, the RRS A and RRS C may be located on a first nucleic acid, and the RRS B and RRS D may be located on a second nucleic acid. In the first nucleic acid, the RRS C may be located further downstream of the RRS A, and in the second nucleic acid, the RRS D may be located further downstream of the RRS B. In this case, an interaction with the SSR, which is specific to the first pair of RRSs, and an interaction with the SSR, which forms a pair with the second pair of RRSs, may occur. An exchange may occur between a polynucleotide, which is located between RRS A and RRS C, and a polynucleotide, which is located between RRS B and RRS D.

When the exchange is reversible, an exchange may occur again between a polynucleotide, which is located between RRS A and RRS C, and a polynucleotide, which is located between RRS B and RRS D.

Marker Gene

As used herein, the term "marker gene" refers to a gene which is inserted into an animal genome in a cell so as to select the cells for which the intended transformation is achieved. When an exo-polynucleotide containing a polynucleotide encoding a marker gene is introduced into a cell and then the exo-polynucleotide is inserted into an animal genome, the marker gene may be expressed in the cell thus being helpful in the selection of cells.

The marker gene may include an antibiotic resistance gene, antigen gene, luciferase gene, beta-galactosidase gene, a gene encoding fluorescent protein, surface marker gene, and suicide gene, but is not limited thereto.

Antibiotic Resistance Gene

When the marker gene is an antibiotic resistance gene, cell selection may be performed by culturing along with an antibiotic compound. The antibiotic compound may include ampicillin, chloramphenicol, tetracycline, and kanamycin, but is not limited thereto.

Antigen Gene

When the marker gene is a gene encoding an antigen or a gene including nucleotide which can act as an antigen, cell selection may be performed by culturing along with an antibody which can specifically act on the antigen. The antigen may include a surface antigen. The surface antigen may include a CD molecule. The antibody can interact with a magnetic particle or a fluorophore.

Luciferase Gene

When the marker gene is a luciferase gene, cell selection may be performed by culturing along with luciferin.

Beta-Galactosidase Gene

When the marker gene is a beta-galactosidase gene, cell selection may be performed by culturing along with 5-bromo-4-chloro-3-indolyl-beta-d-galactopyranoside (X-gal).

Gene Encoding Fluorescent Protein (Fluorescent Protein Gene)

When the marker gene is a gene encoding fluorescent protein, cell selection may be performed by measuring the fluorescence signal. The fluorescent protein may include a green fluorescent protein (hereinafter, GFP), yellow fluorescent protein (hereinafter, YFP), and red fluorescent protein (hereinafter, RFP), but is not limited thereto.

Suicide Gene

When the marker gene is a suicide gene, cell selection may be performed by culturing along with a prodrug which forms a pair with the suicide gene. The suicide gene may include a thymidine kinase gene, cytosine deaminase gene, cytochrome P450 gene, nitroreductase gene, purine nucleoside phosphorylase gene, and carboxypeptidase G2 gene, but is not limited thereto. The prodrug may include acyclovir, ganciclovir, 5-fluorocytosine, cyclophosphamide, ifosfamide, 5-[aziridin-1-yl]-2,4-dinitrobenzamide (CB1954), 6-methylpurine-2-deoxyriboside (MeP-dR), arabinofuranosyl-2-fluoroadenine monophosphate (F-araA), and N,N-[(2-chloroethyl)(2-mesyloxyethyl)amino]benzoic acid) (CM-DA), but is not limited thereto.

Expression Control Element

As used herein, the term "expression control element" includes a transcription control element, post-transcriptional processing control element, translation control element, and posttranslational modification control element.

Transcription Control Element

As used herein, the term "transcription control element" refers to a material or nucleotide sequence which is capable of initiating, promoting, inhibiting, or terminating the synthesis of mRNA from RNA or a polynucleotide encoding a polypeptide.

The transcription control element may include an enhancer, silencer, repressor, activator, inhibitor, promoter, transcription stop codon, and loxp-transcription stop codon-loxp (hereinafter, LTL), but is not limited thereto. The transcription stop codon may include a poly T sequence (The term "poly T sequence" is be used interchangeably with the term "poly A sequence") and an AATAAA sequence, but is not limited thereto.

Post-Transcriptional Processing Control Element

As used herein, the term "post-transcriptional processing control element" refers to a chemical compound, polynucleotide, or enzyme which is capable of causing a modification on the structure of an mRNA synthesized from a polynucleotide.

The post-transcriptional processing control element may include a chemical compound, polynucleotide, or enzyme that can cause 5' capping, 3' cleavage, 3' polyadenylation, or splicing, but is not limited thereto.

Translation Control Element

As used herein, the term "translation control element" refers to a material or nucleotide sequence which is capable of initiating, promoting, inhibiting, or terminating the synthesis of a polypeptide from an mRNA.

The translation control element may include a 3' untranslated region (hereinafter, 3' UTR), a 5' untranslated region (hereinafter, 5'UTR), an exon, an intron, a start codon, a stop codon, Kozak sequence, IRES, a polynucleotide encoding 2A peptide, loxp-stop codon-loxp (hereinafter, LSL), but is not limited thereto.

Posttranslational Modification Control Element

As used herein, the term "posttranslational modification control element" refers to a chemical compound, polynucleotide, or enzyme that can cause modification on the structure of a polypeptide synthesized from mRNA.

The posttranslational modification control element may include a chemical compound or enzyme that can cause glycosylation, folding, ubiquitination, sumoylation, acetylation, and phosphorylation of the polypeptide which is transcribed and translated from the polynucleotide, but is not limited thereto.

Promoter

The "promoter" of the present disclosure is a nucleic acid sequence which interacts with an RNA polymerase in a nucleic acid and thereby initiates transcription. The "promoter" of the present disclosure includes a constitutive promoter, a tissue-specific promoter, and an inducible promoter.

Constitutive Promoter

The "constitutive promoter" of the present disclosure refers to a promoter which allows transcription to be initiated regardless of environmental changes in a cell. The constitutive promoter may include CMV promoter, CAG promoter, and U6 promoter, but is not limited thereto.

Tissue-Specific Promoter

The "tissue-specific promoter" of the present disclosure refers to a promoter which is capable of initiating transcription only in a specific tissue of an animal. The tissue-specific promoter may include a mammary gland tissue-specific promoter or reproductive organ-specific promoter, but is not limited to.

The mammary gland tissue-specific promoter may include alpha-casein promoter, beta-casein promoter, kappa-casein promoter, mu-casein promoter, and beta-lactoglobulin promoter, but is not limited to.

The reproductive organ-specific promoter may include an ovarian-specific promoter and testis-specific promoter, but is not limited to.

Inducible Promoter

The "inducible promoter" of the present disclosure refers to a promoter which initiates transcription in response to changes in intracellular environment or extracellular environment. The inducible promoter may include a chemically inducible promoter, temperature inducible promoter, and light inducible promoter, but is not limited to.

The chemically inducible promoter may include an antibiotic-inducible promoter, alcohol-inducible promoter, steroid-inducible promoter, and metal-inducible promoter, but is not limited to. The antibiotic-inducible promoter may include Tet-on promoter, and Tet-off promoter, but is not limited to. The steroid-inducible promoter may include estrogen-inducible promoter, but is not limited to. The metal-inducible promoter may include a copper-inducible promoter, but is not limited to.

The temperature inducible promoter may include heat shock-inducible promoter and a cold shock-inducible promoter, but is not limited to. The heat shock-inducible promoter may include Hsp promoter, but is not limited to.

Delivery

As used herein, the term "delivery" may refer to the introduction of an exo-polynucleotide into the organ, tissue, cell, or subcellular organelle of a living organism.

As used herein, the term "delivery" may also refer to the introduction of a polypeptide or protein into the organ, tissue, cell, or subcellular organelle of a living organism.

In the present disclosure, the term "delivery" may be used interchangeably with the term "provision".

Non-Viral Delivery

The delivery may include non-viral delivery.

The non-viral delivery may use a naked nucleic acid vector. The naked nucleic acid vector may include a circular nucleic acid vector and a linear nucleic acid vector. The circular nucleic acid vector may include a plasmid vector, but is not limited thereto.

The non-viral delivery may use a non-viral vector. The non-viral vector may include artificial chromosome, liposome, a polymer, a lipid-polymer hybrid, an inorganic nanoparticle, and an organic nanoparticle, but is not limited thereto.

The non-viral delivery may include microinjection, gene gun, electroporation, sonoporation, photoporation, magnetofection, and hydroporation, but is not limited thereto.

Viral Delivery

The gene delivery may include viral delivery.

The viral delivery may use an RNA-based viral vector. The RNA-based viral vector may include an oncoretroviral vector, a lentiviral vector, and a human foamy viral vector, but is not limited thereto.

The viral delivery may use a DNA-based viral vector. The DNA-based viral vector may include adenoviral vector, adeno-associated viral vector, Epstein-Barr viral vector, herpes simplex viral vector, and poxviral vector, but is not limited thereto.

In the case of viral delivery, it has an advantage in that the delivery efficiency of a large size gene is excellent.

Microinjection

As used herein, the term "microinjection" refers to injecting a material into an organ, tissue, cell, or subcellular organelle of a living organism. The material may include a chemical compound, polynucleotide, or polypeptide.

As used herein, the term "microinjection" may include gamete microinjection, zygote microinjection, embryo microinjection, and somatic cell microinjection.

As used herein, the term "gamete microinjection" refers to microinjecting a material containing a polynucleotide into a gamete. As used herein, the term "gamete microinjection" includes a technique of microinjecting a material containing a polynucleotide into a gamete and obtaining a transgenic animal through a fertilization step, a differentiation step, etc.

As used herein, the term "zygote microinjection" refers to microinjecting a material containing a polynucleotide into a zygote. As used herein, the term "zygote microinjection" includes a technique of microinjecting a material containing a polynucleotide into a zygote and obtaining a transgenic animal through a differentiation step, etc.

As used herein, the term "embryo microinjection" refers to microinjecting a material containing a polynucleotide into an embryo. As used herein, the term "embryo microinjection" includes a technique of microinjecting a material containing a polynucleotide into an embryo and obtaining a transgenic animal through a differentiation step, etc.

The "somatic cell microinjection" of the present disclosure refers to microinjecting a material containing a polynucleotide into a somatic cell.

Nuclear Transfer

As used herein, the term "nuclear transfer" refers to removing the nucleus from an oocyte and introducing a donor nucleus obtained from another cell into the oocyte. As used herein, the term "somatic cell nuclear transfer (SCNT)" refers to a nuclear transfer in which the cell containing the donor nucleus is a somatic cell.

As used herein, the term "nuclear transfer" includes a technique of removing the nucleus from an oocyte of an animal and obtaining an animal that includes the same genetic information as the animal cell containing a donor nucleus through a step of introducing the donor nucleus obtained from an animal cell, a reprogramming step, a differentiation step, and a transplantation step through a surrogate mother. As used herein, when the animal including the donor nucleus is a somatic cell, the term "somatic cell nuclear transfer (SCNT)" includes a technique of obtaining an animal that includes the same genetic information as the somatic cell through the steps described above.

A transgenic animal may be prepared through a delivery into a cell including the donor nucleus. For example, a transgenic animal may be prepared through somatic cell nuclear transfer (SCNT) after the somatic cell microinjection.

Animal

The animal of the present disclosure may include a non-human animal.

The animal may include a mammal.

The mammal may include an ungulate.

The ungulate may include a perissodactyl. The perissodactyl may include horses, but is not limited thereto.

The ungulate may include an artiodactyl. The artiodactyl may include pigs, deer, cows, sheep, and goats, but is not limited thereto.

The mammal may include a rodent. The rodent may include rats and mice, but is not limited thereto.

The mammal may include a lagomorph. The lagomorph may include rabbits and hares, but is not limited thereto.

Bioreactor

The "bioreactor" of the present disclosure refers to an organism which can cause a biological or chemical reaction that occurs in a living organism.

The organism may include a cell, a cell line, and an animal. The organism may include a transgenic cell, a transgenic cell line, and a transgenic animal. For example, the bioreactor may be a transgenic mouse. Alternatively, the bioreactor may be a transgenic rat. Alternatively, the bioreactor may be a transgenic cow.

The bioreactor may be used to produce a target material. The target material may include a target protein. For example, when the bioreactor is a transgenic cow in which the human albumin gene is knocked in, the transgenic cow may be used to produce human albumin.

[Part I] Toolbox

1. Definition of Toolbox

As used herein, the term "toolbox" refers to an exo-polynucleotide which is inserted or can be inserted into an animal genome in a cell. The cell into which the toolbox can be inserted may or may not be a transformed cell.

As used herein, the term "toolbox" may refer to an exo-polynucleotide for transformation of an animal genome in a cell. For example, the toolbox may include a polynucleotide encoding a target protein in an animal genome in a cell. In another example, the toolbox may include components of an engineered nuclease or a polynucleotide encoding components of an engineered nuclease capable of performing site-specific transformation in an animal genome in a cell. In another example, the toolbox may include a transposon.

2. Toolbox Components

A toolbox may include a first end region at 5' end, a second end region at 3' end, and the core domain located between the first end region and the second end region.

The first end region and the second end region may include at least one editing enabling component. The first end region and the second end region may include the same polynucleotide. The first end region and the second end region may include a polynucleotide different from each other.

An ITR sequence may be included in the first end region and the second end region, and a polynucleotide present between the ITR sequences may be included in the core domain.

The core domain may include an editing enabling component.

The core domain may include a polynucleotide encoding a protein or RNA.

The core domain may include a polynucleotide encoding a non-functional peptide.

The core domain may include a polynucleotide encoding an artificial intron.

The core domain may include a polynucleotide encoding a non-functional RNA.

The core domain may include an untranscribed polynucleotide.

The core domain may include an untranslated polynucleotide.

The core domain may include an expression control element.

The core domain may include a promoter.

2-1. Editing Enabling Component 2-1-1. Recombinase Recognition Site

A toolbox may include at least one polynucleotide encoding an RRS. The RRS may include loxp, rox, FRT, attP, attB, and a mutant thereof, but is not limited thereto. The loxp mutant may include loxp66, loxp71, loxp72, loxp2722, loxp5171, and loxpm2, but is not limited thereto. The rox mutant may include rox4R, rox6R, and rox2N, but is not limited thereto. The FRT mutant may include F3, F5, F10, F11, F12, F13, F14, F15, and F16, but is not limited thereto.

2-1-2. Inverted Terminal Repeat (ITR) Sequence

A toolbox may include at least one ITR sequence. The ITR sequence can interact with hobo/Ac/Tam, P element, Sleeping Beauty (SB), Frog Prince, Hsmar1, Hsmar2, piggyBac (PB), Tol2, or a mutant thereof.

2-1-3. Engineered Nuclease Target Site

A toolbox may include at least one engineered nuclease target site. The engineered nuclease target site may include a target site of the CRISPR/enzyme system. The target site may be a nucleotide sequence adjacent to the 5' end or 3' end of a PAM sequence A toolbox may include part of the target site of an engineered nuclease at one end thereof. A toolbox may include another part of the target site of an engineered nuclease and a PAM sequence, at the other end thereof.

2-2. Polynucleotide Encoding Protein or RNA 2-2-1. Target Protein

A toolbox may include at least one polynucleotide encoding a protein. The type of the target protein is not limited as long as the target protein can be produced in a cell or animal which becomes the subject of the transformation technology.

The target protein may include components of an engineered nuclease. For example, the target protein may include ZFN, TALEN, RNA-guided endonuclease, or a modified/engineered form thereof, but is not limited thereto.

The target protein may include a protein derived from a non-human animal. For example, the target protein may include non-human albumin, a non-human interleukin, a non-human insulin, a non-human erythropoietin, a non-human antibody, non-human omega-3, or a modified/engineered form thereof, but is not limited thereto.

The target protein may include a protein derived from humans. For example, target protein may include human albumin, a human interleukin, a human insulin, a human erythropoietin, a human gamma chain, a human delta chain, a human alpha chain, a human mu chain, a human epsilon chain, a human kappa chain, a human lambda chain, or a modified/engineered forms thereof, but is not limited thereto.

2-2-2. Marker Gene

A toolbox may include at least one polynucleotide encoding a marker gene. The marker gene may include an antibiotic resistance gene, antigen gene, luciferase gene, beta-galactosidase gene, a fluorescent protein gene, and suicide gene, but is not limited thereto.

2-2-3. Site-Specific Recombinase

A toolbox may include at least one polynucleotide encoding an SSR. The SSR may include Cre, Dre, Flp, KD, B2, B3, lambda, HK022, HP1, gamma delta, ParA, Tn3, Hin, Gin, Pin, phiC31, Bxb1, R4, or a mutant thereof, but is not limited thereto.

2-2-4. Transposase

A toolbox may include at least one polynucleotide encoding a transposase. The transposase may include hobo/Ac/Tam, P element, Sleeping Beauty (SB), Frog Prince, Hsmar1, Hsmar2, piggyBac (PB), Tol2, and a mutant thereof, but is not limited thereto.

2-2-5. Endonuclease

A toolbox may include at least one polynucleotide encoding an endonuclease. The endonuclease may include ZFN, TALEN, and RNA-guided endonuclease, but is not limited thereto.

The toolbox may include at least one polynucleotide encoding an RNA-guided endonuclease. The RNA-guided endonuclease may include Cas9 or a mutant of Cas9. The RNA-guided endonuclease may include Cpf1 or a mutant of Cpf1, but is not limited thereto.

2-2-6. Guide Nucleic Acid

A toolbox may include at least one polynucleotide which encodes at least one among crRNA, tracrRNA, and gRNA.

2-3. Polynucleotide Encoding Non-Functional Polypeptide

A toolbox may include at least one polynucleotide encoding a non-functional polypeptide.

The polynucleotide encoding a non-functional polypeptide may include part of a polynucleotide encoding a target protein, part of a marker gene, part of a polynucleotide encoding a site-specific recombinase, part of a polynucleotide encoding a transposase, and part of a polynucleotide encoding an endonuclease, but is not limited thereto.

The polynucleotide encoding a non-functional polypeptide may include a stop codon.

The polynucleotide encoding a non-functional polypeptide may include an LSL.

The polynucleotide encoding a non-functional polypeptide may include a polynucleotide encoding a 2A peptide.

The polynucleotide encoding a non-functional polypeptide may include an IRES.

2-4. Polynucleotide Encoding Untranslated RNA

A toolbox may include at least one polynucleotide encoding untranslated RNA.

The polynucleotide encoding untranslated RNA may include a guide nucleic acid.

The polynucleotide encoding untranslated RNA may include an AATAAA sequence.

The polynucleotide encoding untranslated RNA may include a poly T.

The polynucleotide encoding untranslated RNA may not include a start codon.

The polynucleotide encoding untranslated RNA may not include a Kozak sequence.

2-5. Untranscribed Polynucleotide

A toolbox may include at least one untranscribed polynucleotide.

The untranscribed polynucleotide may be a promoter.

The nucleotide sequence of the untranscribed polynucleotide may be a nucleotide sequence which is not present in an animal genome in a cell. In this case, when an engineered nuclease which targets the untranscribed polynucleotide as a target site is used, a site-specific transformation can be performed while not interacting with the animal genome in a cell.

The nucleotide sequence of the untranscribed polynucleotide may be the same as that of part of a polynucleotide encoding a protein or RNA, which can be normally expressed in cells. In this case, a promoter may not be located upstream of the untranscribed polynucleotide.

The untranscribed polynucleotide may be used as an engineered nuclease target site. For example, in the case where a toolbox including an untranscribed polynucleotide is inserted in an animal genome in a cell, a site-specific transformation may occur in the untranscribed polynucleotide by introducing Cas9, and gRNA, which is the same as part of the untranscribed polynucleotide or capable of complementary binding thereto, into a cell.

2-6. Artificial Intron

A toolbox may include at least one artificial intron.

The artificial intron may be included within a toolbox individually or in combination with a polynucleotide encoding a target protein.

The artificial intron may be located within a transcription unit of a polynucleotide encoding a target protein.

The artificial intron may include a splice donor site at 5' end and a splice acceptor site at 3' end.

At least one polynucleotide encoding an RRS may be included between the splice donor site and the splice acceptor site of the artificial intron.

The artificial intron may include a stop codon.

The artificial intron may include an enhancer.

The artificial intron may be deleted by splicing.

The artificial intron may be selected from any group consisting of a) an intron which is derived from a natural intron of a target gene itself, b) an intron which is modified by substitution, deletion and/or insertion of a nucleotide derived from the natural intron, c) a natural intron from a different target gene, d) an intron which is derived from a different intron, e) a chimeric intron which consists of different intron sequences induced from at least one natural intron sequence of a target gene and/or different gene, f) a novel synthesized synthase intron, and g) a combination thereof.

The artificial intron may increase or decrease the expression of a polynucleotide encoding a target protein.

The artificial intron may increase or decrease the expression of a polynucleotide within a genome.

2-7. Expression Control Element

A toolbox may include at least one expression control element.

The expression control element may include a transcription control element. The transcription control element is the same as suggested above.

The expression control element may include a post-transcriptional processing control element. The post-transcriptional processing control element is the same as suggested above.

The expression control element may include a translation control element. The translation control element is the same as suggested above.

The expression control element may include a posttranslational modification control element. The posttranslational modification control element is the same as suggested above.

2-8. Promoter

A toolbox may include a promoter.

The promoter may include a constitutive promoter. The constitutive promoter is the same as suggested above.

The promoter may include a tissue-specific promoter. The tissue-specific promoter is the same as suggested above.

The promoter may include an inducible promoter. The inducible promoter is the same as suggested above.

2-9. Construction of Toolbox 2-9-1. ITR Sequence-Recombinase Recognition Site or Engineered Nuclease Target Site-ITR Sequence A first end region and a second end region of a toolbox may include an ITR sequence. The core domain of the toolbox may include at least one recombinase recognition site.

The toolbox can provide a location at which an insertion or exchange of an exo-polynucleotide can be achieved without giving a fatal effect on gene expression of an animal genome in a cell.

2-9-2. ITR Sequence-Engineered Nuclease Target Site-ITR Sequence

A first end region and a second end region of a toolbox may include an ITR sequence. The core domain of the toolbox may include at least one engineered nuclease target site.

The toolbox can provide a location at which an insertion or exchange of an exo-polynucleotide can be achieved without giving a fatal effect on gene expression of an animal genome in a cell.

2-9-3. ITR Sequence-Polynucleotide Encoding Engineered Nuclease-Recombinase Recognition Site-ITR Sequence A first end region and a second end region of a toolbox may include an ITR sequence. The core domain of the toolbox may include a polynucleotide encoding an RNA-guided endonuclease. The core domain of the toolbox may include at least one recombinase recognition site.

A polynucleotide encoding a guide nucleic acid can be inserted into the toolbox using the at least one recombinase recognition site. The target site at which a site-specific transformation may occur may be changed using the recombinase recognition site.

The at least one recombinase recognition site may include recombinase recognition site 1 (RRS1) and recombinase recognition site 2 (RRS2). The recombinase recognition site 1 (RRS1) may be located upstream of a polynucleotide encoding an RNA-guided endonuclease, and the recombinase recognition site 2 (RRS2) may be located downstream of a polynucleotide encoding an RNA-guided endonuclease. A polynucleotide encoding an RNA-guided endonuclease within the toolbox may be exchanged with a different exo-polynucleotide using the recombinase recognition site 1 (RRS1) and recombinase recognition site 2 (RRS2).

2-9-4. ITR Sequence-Polynucleotide Encoding RNA-Guided Endonuclease-Polynucleotide Encoding a Guide Nucleic Acid-Recombinase Recognition Site-Expression Control Element-ITR Sequence A first end region and a second end region of a toolbox may include an ITR sequence. The core domain of the toolbox may include a polynucleotide encoding an RNA-guided endonuclease. The core domain of the toolbox may include a polynucleotide encoding a guide nucleic acid. The core domain of the toolbox may include at least one recombinase recognition site. The core domain of the toolbox may include at least one from an element controlling the expression of an RNA-guided endonuclease and an element controlling the expression of a guide nucleic acid.

The at least one recombinase recognition site may be located upstream or downstream of a polynucleotide encoding an RNA-guided endonuclease. An element controlling the expression of a polynucleotide encoding an RNA-guided endonuclease may be inserted or deleted using the at least one recombinase recognition site.

The at least one recombinase recognition site may be located upstream or downstream of a polynucleotide encoding a guide nucleic acid. An element controlling the expression of a polynucleotide encoding a guide nucleic acid may be inserted or deleted using the at least one recombinase recognition site.

The at least one recombinase recognition site may include recombinase recognition site 1 (RRS1) and recombinase recognition site 2 (RRS2). The recombinase recognition site 1 (RRS1) may be located upstream of a polynucleotide encoding a guide nucleic acid, and the recombinase recognition site 2 (RRS2) may be located downstream of a polynucleotide encoding a guide nucleic acid. A polynucleotide encoding a guide nucleic acid within the toolbox may be deleted using the recombinase recognition site 1 (RRS1) and recombinase recognition site 2 (RRS2).

2-9-5. ITR Sequence-Marker Gene-ITR Sequence

A first end region and a second end region of a toolbox may include an ITR sequence. The core domain of the toolbox may include a polynucleotide encoding at least one marker gene. The at least one marker gene may include a suicide gene.

A marker gene may be knocked out by site-specific transformation of a polynucleotide encoding the marker gene.

2-9-6. Recombinase Recognition Site-Polynucleotide Encoding Transposase-Recombinase Recognition Site A first end region of a toolbox may include a recombinase recognition site 1 (RRS1). A second end region of the toolbox may include a recombinase recognition site 2 (RRS2) which forms a pair with the recombinase recognition site 1 (RRS1). The core domain of the toolbox may include a polynucleotide encoding a transposase. The transposase may include an excision-only transposase.

A transposon included in an animal genome in a cell may be deleted using the toolbox.

2-9-7. Engineered Nuclease Target Site-ITR Sequence-Exo-Polynucleotide-ITR Sequence-Engineered Nuclease Target Site A first end region and a second end region of a toolbox may include an engineered nuclease target site. The core domain of the toolbox may include a first ITR sequence, a second ITR sequence, and an exo-polynucleotide. The polynucleotide encoding a target protein may be located between the first ITR sequence and the second ITR sequence.

An exo-polynucleotide may be inserted in an animal genome in a cell using the toolbox while performing site-specific transformation. Additionally, only an exo-polynucleotide may be deleted by a transposase while maintaining site-specific transformation in an animal genome in a cell.

3. Toolbox Functions

A toolbox may be used for expression of a protein or nucleic acid necessary for transformation of an animal genome in a cell. For example, a toolbox may include a polynucleotide encoding Cas9. When a gRNA, which has part of a nucleotide sequence in an animal genome including the toolbox as a target site, is introduced into a cell, the gRNA may form a complex with the Cas9 which is expressed in a cell and thereby induce site-specific transformation in the target site in the animal genome.

A toolbox may be used for knockin of a gene in an animal genome in a cell. For example, a toolbox may include a polynucleotide encoding human interleukin. The toolbox can be inserted into a bovine genome in a cell so that the cell expresses a human interleukin.

A toolbox may be used for knockout of a gene present in an animal genome in a cell. For example, a toolbox may be inserted in the middle of a polynucleotide encoding an exon of a bovine albumin in a bovine genome in a cell and thereby prevent the cell from expressing bovine albumin.

A toolbox may provide a site capable of transformation in an animal genome in a cell. For example, a toolbox may include a nucleotide sequence which can be an engineered nuclease target site. For example, a toolbox may include a polynucleotide encoding a green fluorescent protein (GFP). When the bovine genome in a cell includes the toolbox, a gRNA, which targets part of the nucleotide sequence of a polynucleotide encoding the green fluorescent protein (GFP), and a Cas9 may be introduced into a cell and thereby site-specific transformation may be induced into part of the nucleotide sequence of a polynucleotide encoding the green fluorescent protein (GFP) within the toolbox, not in a nucleotide sequence outside of the toolbox.

[Part II] Toolbox Insertion

1. Toolbox Delivery Vector

A toolbox may be delivered for insertion of a toolbox into an animal genome in a cell. A nucleic acid delivery vector including the toolbox may be a naked nucleic acid vector, a non-viral vector, or a viral vector.

2. Toolbox Insertion Method 2-1. Use of Homologous Recombination

A first homology arm may be located at 5' end of a first end region of a toolbox. A second homology arm may be located at 3' end of a second end region. The first homology arm may have the same nucleotide sequence as part of an animal genome in a cell. The second homology arm may have the same nucleotide sequence as part of an animal genome in a cell.

The first homology arm and the second homology arm can interact with part of the genome in a cell. A toolbox can be inserted into a genome through the interaction.

2-2. Use of Site-Specific Recombination

A first end region of a toolbox may include an RRS1. A second end region of the toolbox may include an RRS2.

At least one recombinase may be provided for introduction of the toolbox into a cell. The recombinase may include a first recombinase which can interact with the RRS1. The recombinase may include a second recombinase which can interact with the RRS2. The first recombinase and the second recombinase may be the same with each other. For example, when the RRS1 is loxp and the RRS2 is a loxp mutant, the first recombinase and the second recombinase may be Cre.

For the introduction of the at least one recombinase into a cell, a naked nucleic acid vector, a non-viral vector, a viral vector, each of which includes a polynucleotide encoding a recombinase, or a recombinase polypeptide may be used.

For the introduction of the toolbox into a cell, the nucleic acid including the toolbox and the at least one recombinase may be provided in an individual form. For example, the nucleic acid including the toolbox may be delivered by a DNA plasmid vector and the recombinase may be delivered by a recombinase polypeptide.

For the introduction of the toolbox into a cell, the nucleic acid including the toolbox and the at least one recombinase may be provided by one delivery vector. For example, the nucleic acid including the toolbox and a polynucleotide encoding a recombinase may be provided by one DNA plasmid vector.

2-3. Use of Transposon System

A first end region and a second end region of a toolbox may include an ITR sequence.

For the introduction of the toolbox into a cell, a transposase may be provided. The transposase can interact with the ITR sequence.

For the introduction of the transposase into a cell, a naked nucleic acid vector, a non-viral vector, a viral vector, each of which includes a polynucleotide encoding a transposase, or a transposase polypeptide may be used.

The nucleic acid including the toolbox and the transposase may be provided in an individual form. For example, the nucleic acid including the toolbox may be delivered by a DNA plasmid vector and the transposase may be delivered by a polypeptide.

The nucleic acid including the toolbox and the transposase may be provided in an individual form. For example, the nucleic acid including a toolbox may be delivered by a DNA plasmid vector and the transposase may be delivered by a separate DNA plasmid vector which includes a polynucleotide encoding a transposase.

The nucleic acid including the toolbox and the transposase may be introduced into a cell by one delivery vector. For example, the nucleic acid including the toolbox and a polynucleotide encoding a transposase may be provided by one DNA plasmid vector.

2-4. Use of Engineered Nuclease 2-4-1. Use of Homology Directed Repair (HDR)

A first homology arm may be located at 5' end of a first end region of a toolbox. A second homology arm may be located at 3' end of a second end region of the toolbox. The first homology arm may have the same nucleotide sequence as part of an animal genome in a cell. The second homology arm may have the same nucleotide sequence as part of an animal genome in a cell.

For the introduction of the toolbox into a cell, any one of nucleic acid delivery vectors including the toolbox may be used.

For the introduction of the toolbox into a cell, an engineered nuclease may be provided. The engineered nuclease may specifically act on an engineered nuclease target site present in an animal genome. The engineered nuclease target site present in the animal genome may be located on a nucleotide sequence, which is the same as or complementary to the first homology arm; may be located on a nucleotide sequence, which is the same as or complementary to the second homology arm; or may be located between a nucleotide sequence, which is the same as or complementary to the first homology arm, and a nucleotide sequence, which is the same as or complementary to the second homology arm.

The at least one engineered nuclease may be provided in any one selected from a naked nucleic acid vector, a non-viral vector, a viral vector, each of which includes a polynucleotide encoding each component of an engineered nuclease, an engineered nuclease protein, a complex including an engineered nuclease protein, and a combination thereof.

For example, a complex including a Cas9 protein and a gRNA may be provided. In another example, a naked nucleic acid vector which includes a polynucleotide encoding Cas9 and a polynucleotide encoding a gRNA may be provided.

For the introduction of the toolbox into a cell, a nucleic acid including the toolbox and the at least one engineered nuclease may be provided in a separate form. For example, the nucleic acid including the toolbox may be provided by a DNA plasmid vector, and the engineered nuclease may be provided as a complex including the Cas9 protein and the gRNA. In another example, the nucleic acid including the toolbox may be provided by a DNA plasmid vector, and the engineered nuclease may be provided by a naked nucleic acid vector, which includes a polynucleotide encoding Cas9 and a polynucleotide encoding a gRNA.

For the introduction of the toolbox into a cell, the nucleic acid including the toolbox and the engineered nuclease may be provided by one vector. For example, the nucleic acid including the toolbox, a polynucleotide encoding Cas9, and a polynucleotide including a gRNA may be provided by one DNA plasmid vector.

2-4-2. Use of Homology-Independent Target Insertion (HITI)

A first end region of a toolbox may include a first engineered nuclease target site. A second end region of the toolbox may include a second engineered nuclease target site. The first engineered nuclease target site and the second engineered nuclease target site may include the same nucleotide sequence with each other.

For the introduction of the toolbox into a cell, at least one engineered nuclease may be provided. The engineered nuclease may include a first engineered nuclease which can specifically act on the first engineered nuclease target site. The engineered nuclease may include a second engineered nuclease which can specifically act on the second engineered nuclease target site. The first engineered nuclease and the second engineered nuclease may be the same with each other.

The at least one engineered nuclease may be provided in any one selected from a naked nucleic acid vector, a non-viral vector, a viral vector, each of which includes a polynucleotide encoding each component of an engineered nuclease, an engineered nuclease protein, a complex including an engineered nuclease protein, and a combination thereof.

For the introduction of the toolbox into a cell, a nucleic acid including the toolbox and the at least one engineered nuclease may be provided in a separate form. For example, the nucleic acid including the toolbox may be provided by a DNA plasmid vector, and the engineered nuclease may be provided as a complex including the Cas9 protein and the gRNA. In another example, the nucleic acid including the toolbox may be provided by a DNA plasmid vector, and the engineered nuclease may be provided by a naked nucleic acid vector, which includes a polynucleotide encoding Cas9 and a polynucleotide encoding a gRNA.

For the introduction of the toolbox into a cell, the nucleic acid including the toolbox and the at least one engineered nuclease may be provided by one vector. For example, the nucleic acid including the toolbox, a polynucleotide encoding Cas9, and a polynucleotide including a gRNA may be provided by one DNA plasmid vector.

3. Toolbox Insertion Locus 3-1. Single Toolbox Insertion

An animal genome in a cell may include one toolbox.

The one toolbox may be included in any one of autosomes in an animal genome.

The toolbox may be included in any one of sex chromosomes in an animal genome. The toolbox may be included in the X chromosome of an animal genome. The toolbox may be included in the Y chromosome of an animal genome.

3-2. Multiple Toolboxes Insertion

An animal genome in a cell may include two or more toolboxes.

All of the two or more toolboxes may be identical to each other.

One of the two or more toolboxes may be different from one of the rest.

The difference between toolboxes may refer to a difference of the sequence between these toolboxes.

For example, a first toolbox, which includes a polynucleotide encoding an RNA-guided endonuclease, and a second toolbox, which includes a polynucleotide encoding a guide nucleic acid capable of binding to a target site, may be regarded as two different toolboxes.

All of the two or more polynucleotides may be included in one chromosome. The chromosome may be an autosome or sex chromosome.

The two or more toolboxes may include at least a first toolbox and a second toolbox. In this case, the first toolbox may be located on a first chromosome, and the second toolbox may be located on a second chromosome, which is different from the first chromosome.

The first chromosome may be an autosome.
The first chromosome may be a sex chromosome.
The second chromosome may be an autosome.
The second chromosome may be a sex chromosome.

3-3. Characteristics of Insertion Locus

A toolbox may be located between nucleotide sequences which can interact with a transposase. The nucleotide sequences which can interact with the transposase may include TA and TTAA, but are not limited thereto.

A toolbox may be located on a polynucleotide which can be involved in the expression of any protein or RNA in an animal genome in a cell.

For example, a toolbox may be located on any one selected from a polynucleotide encoding a protein or RNA, a promoter of a polynucleotide encoding a protein or RNA, 5' UTR, intron, exon, and 3' UTR. The toolbox may knock out the protein or RNA in an animal genome in a cell. For example, when the toolbox is located at an exon of beta-lactoglobulin gene in a bovine genome, it is possible to prevent the expression of beta-lactoglobulin in the cell including the bovine genome.

A toolbox may be located on a polynucleotide in an animal genome in a cell, which is not involved in the expression of any protein or RNA.

Additionally, a toolbox may be located within a safe harbor in an animal genome in a cell.

When the animal genome is a mouse genome, the safe harbor of the mouse genome may include a rosa26 locus, which is already well known.

When the animal genome is a bovine genome, the safe harbor of the bovine genome may include the location which is already well known in the bovine genome. The safe harbor of the bovine genome may include the loci shown in Table 1 below, but is not limited thereto. Each of the loci described in Table 1 below may be located between a gene located closest to 5' end (5' gene) and a gene located closest to 3' end (3' gene).

TABLE 1

| Bovine Genome Chromosome | Locus No. | 5' Gene | 3' Gene |
|---|---|---|---|
| 1 | 1-1 | MIS184 | HUNK |
|  | 1-2 | ENSBTAG00000025847.3 | ENSBTAG00000011051.5 |
| 2 | 2-1 | SLC38A11 | COBLL1 |
| 3 | 3-1 | GBP5 | GBP4 |
|  | 3-2 | PEX19 | PEA15 |
|  | 3-3 | PDE4B | OB-R |
|  | 3-4 | PDE4B | LEPR |
| 4 | 4-1 | GNAT3 | PHTF2 |
|  | 4-2 | TSGA13 | MKLN1 |
|  | 4-3 | NPVF | C7orf31 |
|  | 4-4 | ENSBTAG00000001198.5 | ENSBTAG00000046257.1 |
| 5 | 5-1 | ATXN7L3B | CAPS2 |
|  | 5-2 | TMEM5 | AVPR1A |
|  | 5-3 | XRCC6BP1 | CTDSP2 |
|  | 5-4 | MPST | KCTD17 |
| 6 | 6-1 | DKK2 | GIMD1 |
|  | 6-2 | PLAC8 | COQ2 |
|  | 6-3 | LCORL | SLIT2 |
| 7 | 7-1 | ERAP2 | LNPEP |
|  | 7-2 | C7H5orf30 | NUDT12 |
| 9 | 9-1 | STXBP5 | SAMD5 |
| 10 | 10-1 | ALDH6A1 | VSX2 |
| 11 | 11-1 | PTP | LRRTM4 |
|  | 11-2 | PSMD13 | — |
| 12 | 12-1 | ENSBTAG00000010680.5 | U2 |
| 14 | 14-1 | CSMD3 | CSMD3 |
| 15 | 15-1 | SMAP | INSC |
| 17 | 17-1 | ORAI1 | RNF34 |
| 18 | 18-1 | HSD17B2 | CDH13 |
| 21 | 21-1 | TRPM1 | APBA2 |
| 22 | 22-1 | bta-mir-2370 | DENND6A |
| 25 | 25-1 | AUTS2 | ENSBTAG00000047342 |
| 26 | 26-1 | MKI67 | EBF3 |
|  | 26-2 | EMX2 | RAB11FIP2 |
| X | X-1 | WWC3 | DDX3Y |
|  | X-2 | ARAF | SYN1 |
|  | X-3 | PBDC1 | MAGEE2 |

When a toolbox is located on a polynucleotide, which is not involved in the expression of proteins or RNAs in an animal genome in a cell, or is located within the safe harbor in an animal genome in a cell, the toolbox may be utilized as an artificial safe harbor for additionally transformation. For example, when the toolbox located in the safe harbor in a bovine genome includes a loxp, an exo-polynucleotide can be inserted into the toolbox by delivering the exo-polynucleotide including the loxp and Cre recombinase without affecting on the expression of any protein or RNA in an animal genome in a cell.

4. Transformed Cell into which Toolbox is Inserted 4-1. Single Cell 4-1-1. Ploidy A transformed cell including at least one toolbox may be a diploid cell. The diploid cell may include a stem cell, a somatic cell, an oogonial stem cell, an oogonium, a primary oocyte, a spermatogonial stem cell, a spermatogonium, a primary spermatocyte, and a zygote. The transformed cell including at least one toolbox may be a haploid cell. The haploid cell may include a secondary oocyte, an ovum, a secondary spermatocyte, and a sperm.

4-1-2. Zygosity

A transformed cell may include at least one pair of homologous chromosomes. The at least one pair of homologous chromosomes may include a first chromosome and a second chromosome which are in the relationship of homologous chromosomes.

A transformed cell including two or more toolboxes may be a homozygote.

In the transformed cell which is a homozygote, all of the type, number, and location of the toolboxes included in the first chromosome and the second chromosome may be the same.

In the transformed cell which is a homozygote, both the type and the number of the toolboxes included in the first chromosome and the second chromosome may be the same.

In the transformed cell which is a homozygote, the type of the toolboxes included in the first chromosome and the second chromosome may be the same.

In the transformed cell which is a homozygote, both the first chromosome and the second chromosome may not include any toolbox.

A transformed cell including two or more toolboxes may be a heterozygote.

In the transformed cell which is a heterozygote, a first chromosome may not include a toolbox and a second chromosome may include at least one toolbox.

Alternatively, in the transformed cell which is a heterozygote, a second chromosome may not include a toolbox which is the same as that included in the first chromosome.

4-2. Cell Colony

A transformed cell including at least one toolbox may form a cell colony. The cell colony may be a cell population which is cultured from a single cell.

4-2-1. Homologous Cell Colony

Each cell included in a homologous cell colony may include a single toolbox. The single toolbox possessed by each cell may be the same. In each cell, the single toolbox may be located at the same position.

Each cell included in the homologous cell colony may include two or more toolboxes. The two or more toolboxes may include an $n^{th}$ toolbox ($n>=1$, n is an integer). In each cell, both of the type and the location of the $n^{th}$ toolbox may be the same.

The two or more toolboxes may be the same with each other. Alternatively, one of the two or more toolboxes may be different from the other of the remaining toolboxes, Hereinafter, unless otherwise specified, the expression of "the toolbox included in a first cell is the same as that included in a second cell" means that the type, number, and location of the toolboxes included in the first cell are perfectly the same as the type, number, and location of the toolboxes included in the second cell.

4-2-2. Chimeric Cell Colony

A chimeric cell colony refers to a cell colony other than a homologous cell colony.

A chimeric cell colony may include both a cell, which has a genome where a toolbox is not included, and a cell, which has a genome where at least one toolbox is included.

A chimeric cell colony may include a first cell and a second cell, each of which has a genome where at least one toolbox is included. In this case, at least one among the type, number, and locus of the toolboxes included in the genome of the first cell may not be the same as the type, number, and locus of the toolboxes included in the genome of the second cell.

For example, in the case of a cell colony where a first toolbox is included in the genome of a first cell and a first toolbox of the same type is included in the genome of a second cell, the cell colony may be a chimeric cell colony when i) the number of the first toolboxes included in the genome of the first cell is different from that of the first toolboxes included in the genome of the second cell, or ii) the locus of the first toolbox included in the genome of the first cell is different from that of the first toolbox included in the genome of the second cell.

In another example, in the case of a cell colony where a first toolbox is included in the genome of a first cell and a second toolbox of a different type is included in the genome of a second cell, the cell colony may also be a chimeric cell colony when i) the number of the first toolboxes included in the genome of the first cell is the same as that of the second toolboxes included in the genome of the second cell, and ii) all loci of the first toolbox included in the genome of the first cell are the same as those of the second toolbox included in the genome of the second cell.

Additionally, in the case of a cell colony where a first toolbox is included in the genome of a first cell and a second toolbox of a different type is included in the genome of a second cell, the cell colony may also be a chimeric cell colony when i) the number of the first toolboxes included in the genome of the first cell is different from that of the second toolboxes included in the genome of the second cell, or ii) the locus of the first toolbox included in the genome of the first cell is different from that of the second toolbox included in the genome of the second cell.

As used herein, the term "locus" may be specified by one or more of the endogenous gene located closest to 5' end and the endogenous gene located closest to 3' end with reference to the toolbox.

As used herein, the term "locus of a toolbox" may be specified by one or more of the endogenous genes located closest to the 5' end and the endogenous genes located closest to the 3' end with reference to the toolbox.

That is, when the endogenous gene located closest to the 5' end of the first toolbox is different from that located closest to the 5' end of the second toolbox, the locus of the first toolbox is different from that of the second toolbox. Additionally, when the endogenous gene located closest to the 3' end of the first toolbox is different from that located closest to the 3' end of the second toolbox, the locus of the first toolbox is different from that of the second toolbox.

5. Selection of Transformed Cell into which Toolbox is Inserted 5-1. Selection of Transformed Cell Using Antibiotic Resistance Gene The core domain of a toolbox may include an antibiotic resistance gene. Animal cells including the toolbox can survive when the cell is treated with the antibiotic. Accordingly, animal cells including the toolbox can be separated from those not including the toolbox.

5-2. Selection of Transformed Cell Using Antigen-Antibody Response

The core domain of a toolbox may include a polynucleotide which encodes an antigen, or a nucleotide which can act as an antigen. Animal cells including the toolbox can interact with antibodies specific to the antigen. Accordingly, animal cells including the toolbox can be distinguished from those not including the toolbox.

5-3. Selection of Transformed Cell Using Fluorescent Protein

The core domain of a toolbox may include a polynucleotide encoding a fluorescent protein. Animal cells including the toolbox may be measured of the fluorescence signal. Accordingly, animal cells including the toolbox can be distinguished from those not including the toolbox.

5-4. Selection of Transformed Cell Using Surface Marker Gene

The core domain of a toolbox may include a polynucleotide encoding a surface marker. Animal cells including the toolbox can interact with antibodies specific to the surface marker. The antibodies can interact with magnetic particles or fluorophores. Accordingly, animal cells including the toolbox can be distinguished from those not including the toolbox via a magnetic property or fluorescence signal.

6. Transgenic Animal into which Toolbox is Inserted 6-1. Individual Transgenic Animal into which Toolbox is Inserted A transgenic animal may include one or more transformed cells where each transformed cell includes at least one toolbox.

6-1-1. Homologous

Each of the cells included in a homologous transgenic animal may include individually a single toolbox. The single toolbox possessed by each cell may be the same. In each cell, a single toolbox may be located on the same chromosome.

Each of the cells included in a homologous transgenic animal may include two or more toolboxes. The two or more toolboxes may include an $n^{th}$ toolbox (n>=1, n is an integer). In each cell, all of the chromosomes on which the $n^{th}$ toolbox is located may be the same.

The two or more toolboxes may be the same with each other. Alternatively, one of the two or more toolboxes may be different from the other of the remaining toolboxes.

The homologous transgenic animal may include a transformed cell which is a homozygote.

The homologous transgenic animal may include a transformed cell which is a heterozygote.

6-1-2. Chimeric

A chimeric transgenic animal refers to a transgenic animal other than a homologous transgenic animal.

The chimeric transgenic animal may include a homozygote transformed cell.

The chimeric transgenic animal may include a heterozygote transformed cell.

The chimeric transgenic animal may include both a cell, which has a genome where a toolbox is not included, and a cell, which has a genome where at least one toolbox is included.

The chimeric transgenic animal may include a first cell and a second cell, each of which has a genome that includes at least one toolbox. In this case, in a chimeric transgenic animal, at least one among the type, number, and locus of the toolboxes included in the genome of the first cell may not be the same as the type, number, and locus of the toolboxes included in the genome of the second cell.

For example, in the case of a transgenic animal, which includes a first cell having a genome that includes a first toolbox and a second cell having a genome that includes the first toolbox, the transgenic animal may be a chimeric transgenic animal when i) the number of the first toolboxes included in the genome of the first cell is different from that of the first toolboxes included in the genome of the second cell, or ii) at least one of the loci of the first toolbox included in the genome of the first cell is different from that of the first toolbox included in the genome of the second cell.

In another example, in the case of a transgenic animal, which includes a first cell having a genome that includes a first toolbox and a second cell having a genome that includes a second toolbox which is a type different from the first toolbox, the transgenic animal may be a chimeric transgenic animal when i) the number of the first toolboxes included in the genome of the first cell is the same as that of the second toolboxes included in the genome of the second cell, and ii) all loci of the first toolbox included in the genome of the first cell are the same as those of the second toolbox included in the genome of the second cell.

Additionally, in a case of a transgenic animal, which includes a first cell having a genome that includes a first toolbox and a second cell having a genome that includes a second toolbox which is a type different from the first toolbox, the transgenic animal may be a chimeric transgenic animal when i) the number of the first toolboxes included in the genome of the first cell is different from that of the second toolboxes included in the genome of the second cell, or ii) at least one of the loci of the first toolbox included in the genome of the first cell is different from that of the second toolbox included in the genome of the second cell.

6-2. Method of Preparing Individual Transgenic Animal into which Toolbox is Inserted A method for preparing a transgenic animal into which a toolbox is inserted includes a method for preparing a transgenic animal from an animal cell, a method for preparing a transgenic animal via delivery of a toolbox to a tissue or organ of an animal, and a method for preparing a transgenic animal by breeding between transgenic animals. The method for preparing a transgenic animal from an animal cell includes a method for preparing a transgenic animal from a wild-type animal cell and a method for preparing a transgenic animal from a cell of a transgenic animal.

The transgenic animal produced by any one of the above methods may be any one of a chimeric transgenic animal or a homologous transgenic animal.

6-2-1. Method for Preparing a Transgenic Animal from an Animal Cell

A transgenic animal may be prepared including a process of delivery of a toolbox to a wild-type animal cell.

For example, a transgenic animal may be prepared by injecting a polynucleotide into a wild-type somatic cell by somatic cell microinjection followed by somatic cell nuclear transfer (hereinafter, SCNT). The transgenic animal may be a homologous transgenic animal.

For example, a transgenic animal may be prepared by gamete microinjection into a wild-type gamete. The transgenic animal may be a chimeric transgenic animal.

For example, a transgenic animal may be prepared by zygote microinjection into a wild-type zygote. The transgenic animal may be a chimeric transgenic animal.

For example, a transgenic animal may be prepared by embryo microinjection into a wild-type embryo. The transgenic animal may be a chimeric transgenic animal.

A transgenic animal may be prepared using a transgenic animal cell.

For example, a transgenic animal may be prepared via SCNT using a transgenic somatic cell. The transgenic animal may be a homologous transgenic animal.

For example, a transgenic animal may be prepared via SCNT after somatic cell microinjection into a transgenic somatic cell. The transgenic animal may be a homologous transgenic animal.

For example, a transgenic animal may be prepared by gamete microinjection into a transgenic gamete. The transgenic animal may be a chimeric transgenic animal.

For example, a transgenic animal may be prepared by zygote microinjection into a transgenic zygote. The transgenic animal may be a chimeric transgenic animal.

For example, a transgenic animal may be prepared by embryo microinjection into a transgenic embryo. The transgenic animal may be a chimeric transgenic animal.

6-2-2. Method for Preparing a Transgenic Animal Via Delivery of a Toolbox to a Tissue or Organ of an Animal A transgenic animal may be prepared by toolbox delivery to a tissue or organ of an animal.

For example, a transgenic animal may be prepared by microinjection to a mammary gland tissue of an animal. The transgenic animal may be a chimeric transgenic animal.

For example, a transgenic animal may be prepared by microinjection to a reproductive organ of an animal. The offspring obtained from a gamete of the transgenic animal may also be a transgenic animal. The transgenic animal may be a chimeric transgenic animal.

6-2-3. Breeding of Transgenic Animals

A transgenic animal may be prepared by breeding between a transgenic animal and a wild-type animal.

Alternatively, a transgenic animal may be prepared by breeding between a first transgenic animal and a second transgenic animal.

The second transgenic animal may be an offspring of the first transgenic animal or may be blood-related to the first transgenic animal. Alternatively, the second transgenic animal may not be blood-related to the first transgenic animal.

The transgenic animal obtained from the breeding may include a toolbox, which is the same as part of the toolboxes included in an animal genome of the first transgenic animal, at the same location.

The transgenic animal obtained from the breeding may include a toolbox, which is the same as part of the toolboxes included in an animal genome of the second transgenic animal, at the same location.

The transgenic animal obtained from the breeding may be a homologous transgenic animal.

The transgenic animal obtained from the breeding may include a transformed cell, which is a homozygote. The transgenic animal obtained from the breeding may include a transformed cell, which is a heterozygote.

7. Use of Transgenic Animal into which Toolbox is Inserted
7-1. Animals with Improved Varieties A transgenic animal into which a toolbox is inserted may be used as an animal with improved varieties. The animal with improved varieties may include a cow, in which a polynucleotide encoding beta-lactoglobulin is knocked out, and a cow, in which a polynucleotide encoding omega-3 is knocked in, but is not limited thereto.

7-2. Disease Animal Model

A transgenic animal into which a toolbox is inserted may be used as a disease animal model. The disease animal model may include a cow in which a polynucleotide encoding a tumor suppressor protein is knocked out, but is not limited thereto.

7-3. Disease-Resistant Animal

A transgenic animal into which a toolbox is inserted may be used as a disease-resistant animal. The disease-resistant animal may include a cow in which a polynucleotide encoding a prion protein is knocked out, but is not limited thereto.

7-4. Use of by-Products

The organs, meat, skin, hairs, and body fluids of a transgenic animal, into which a toolbox is inserted, may be used, but parts of the transgenic animal to be used are not limited thereto.

7-5. Bioreactor

A transgenic animal into which a toolbox is inserted may be used as a bioreactor. The body fluids of the transgenic animal may be obtained. The body fluids may include milk, blood, or urine. Biomolecules may be obtained from the body fluid of the transgenic animal. The biomolecule may include a protein. The protein may include a target protein.

[Part III] Transformation Using RRS within Toolbox
1. Structure for Insertion of RRS into Toolbox A transformed cell may include at least one toolbox in an animal genome. Any one of the toolboxes may include at least one RRS.

1-1. The Case where One RRS is Included

A toolbox may include one RRS.

For example, a first end region of a toolbox may include one RRS. In another example, a second end region of a toolbox may include one RRS. In still another example, the core domain of a toolbox may include one RRS.

1-2. The Case where Two or More RRSs are Included

A toolbox may include two or more RRSs. The two or more RRSs may include RRS1 and RRS2. The RRS1 may be located in any one among a first end region, a second end region, and the core domain of a toolbox. The RRS2 may be located in any one among a first end region, a second end region, and the core domain of a toolbox.

For example, both the RRS1 and the RRS2 may be located in the core domain. In a different example, the RRS1 may be located in a first end region and the RRS2 may be located in a second end region.

The RRS1 and the RRS2 may be the same with each other. The RRS1 and the RRS2 may be located in the same direction with each other. Alternatively, the RRS1 and the RRS2 may be located in the opposite direction with each other.

The RRS1 and the RRS2 may be different from each other. The RRS1 and the RRS2 may be located in the same direction with each other. Alternatively, the RRS1 and the RRS2 may be located in the opposite direction with each other.

The RRS1 and the RRS2 may be different from each other. An SSR 1, which can specifically interact with the RRS1, and an SSR 2, which can specifically interact with the RRS2, may be the same with each other or different from each other.

The RRS1 and the RRS2 may be different from each other. The RRS1 and the RRS2 may form a pair and thereby a mutual exchange may occur. Alternatively, the RRS1 and the RRS2 may not form a pair and thereby a mutual exchange may not occur.

2. SSR for Use of RRS within Toolbox 2-1. SSR Provided from Animal Genome

An animal genome in a cell may include a polynucleotide encoding an SSR which is specific to any one of RRSs included in the toolbox. The polynucleotide encoding the SSR may be included in the toolbox including the RRS. The polynucleotide encoding the SSR may be included in a different toolbox.

2-2. SSR Provided from One Other than Animal Genome

When a polynucleotide encoding an SSR, which can interact with any one of RRSs included in the toolbox, is not present in an animal genome in a cell, the SSR may be provided. The form of providing the SSR may be a naked nucleic acid vector, a non-viral vector, a viral vector, each of which includes a polynucleotide encoding an SSR, or a recombinase polypeptide.

3. Site-Specific Recombination Using RRS within Toolbox 3-1. Polynucleotide Insertion Using RRS A toolbox may include at least one RRS.

An exo-polynucleotide, which includes an RRS that forms a pair with any one of the RRSs included in the toolbox, may be provided to a cell including the toolbox.

In this case, an insertion of the exo-polynucleotide into the toolbox may occur via interaction with an SSR which is specific to the pair of RRSs.

3-2. Deletion of Polynucleotide Using RRS

A toolbox may include two or more RRSs. The two or more RRSs may include RRS1 and RRS2.

The RRS1 and the RRS2 may form a pair and may be located in the same direction. For example, in the core domain of the toolbox, two loxps may be located in the same direction.

In this case, a polynucleotide located between the pair of RRSs may be deleted via an interaction with an SSR which is specific to the pair of RRSs. For example, when the core domain of the toolbox includes a polynucleotide encoding a gRNA between the two loxps, the polynucleotide encoding a gRNA may be deleted from the toolbox by providing Cre recombinase.

3-3. Inversion of Polynucleotide Using RRS

A toolbox may include two or more RRSs. The two or more RRSs may include RRS1 and RRS2.

The RRS1 and the RRS2 may form a pair and may be located in the opposite direction.

In this case, a polynucleotide located between the pair of RRSs may be inverted via an interaction with an SSR which is specific to the pair of RRSs.

3-4. Exchange of Polynucleotides Using RRS

A toolbox may include two or more RRSs. The two or more RRSs may include RRS1 and RRS2.

The RRS1 and the RRS2 may not form a pair. For example, the core domain of the toolbox may include loxp (RRS1) and loxp2722 (RRS2). The loxp may be located upstream of loxp2722.

Exo-polynucleotides, each of which includes RRS3 that forms a pair with RRS1 and RRS4 that forms a pair with RRS2, may be provided to a cell including the toolbox. For example, the exo-polynucleotides may include loxp (RRS3) and loxp2722 (RRS4). The loxp may be located upstream of loxp2722.

In this case, an interaction with an SSR, which is specific to RRS1 and RRS3, and an interaction with an SSR, which is specific to and RRS2 and RRS4, may occur. Additionally, an exchange may occur between a polynucleotide located between RRS1 and RRS2 and a polynucleotide located between RRS3 and RRS4.

For example, when an untranscribed polynucleotide is located between loxp and loxp2722 of the toolbox and a polynucleotide encoding a gRNA is located between loxp and loxp2722 of the exo-polynucleotide, the untranscribed polynucleotide in the toolbox and the polynucleotide encoding a gRNA of the exo-polynucleotide may be exchanged by providing Cre recombinase.

3-5. Site-Specific Recombination Using Two or More RRS Present within One Toolbox A toolbox may include two or more RRSs. The two or more RRSs may include RRS1 and RRS2.

The RRS1 and the RRS2 may not form a pair. For example, the core domain of the toolbox may include loxp (RRS1) and loxp2722 (RRS2). The loxp may be located upstream of loxp2722.

A first exo-polynucleotide, which includes RRS3 that forms a pair with RRS1, and a second exo-polynucleotide, which includes RRS4 that forms a pair with RRS2, may be provided to a cell including the toolbox.

For example, the first exo-polynucleotide may include loxp (RRS3) and the second exo-polynucleotide may include loxp2722 (RRS4).

In this case, an interaction with an SSR, which is specific to RRS1 and RRS3, and an interaction with an SSR, which is specific to and RRS2 and RRS4, may occur. Additionally, the first exo-polynucleotide can be inserted into the location of RRS1, and the second exo-polynucleotide can be inserted into the location of RRS2. That is, all of two or more types of exo-polynucleotides can be inserted into a cell which has an animal genome including a toolbox that includes two or more RRSs.

As described above, not only the two or more types of exo-polynucleotides may be respectively inserted into the toolbox at a desired time, but also the two or more types of exo-polynucleotides already present in the toolbox may be deleted or exchanged.

In an embodiment, the toolbox may include loxp, loxp mutant, rox, and attP.

For example, a first exo-polynucleotide which consists of a rox variant (that forms a pair with the rox included in the toolbox) and Cas9 may be provided to a cell including the toolbox. In this case, an insertion of the first exo-polynucleotide into the toolbox may occur via an interaction with Dre which is specific to the rox and a rox variant thereof.

In another example, a first exo-polynucleotide which consists of a rox variant (that forms a pair with the rox included in the toolbox) and Cas9; and a second exo-polynucleotide which consists of attB (that forms a pair with the attP included in the toolbox) and a gRNA may be provided to a cell including the toolbox. In this case, an insertion of the first exo-polynucleotide and the second exo-polynucleotide into the toolbox may occur via an interaction with Dre (which is specific to the rox and a rox variant thereof) and an interaction with PhiC31 (which is specific to the attP and attB). In this case, since Cas9 and gRNA can be simultaneously expressed in a cell including the toolbox, the CRISPR/enzyme system can be operated even when Cas9 or gRNA is not separately delivered.

Additionally, in another example, a first exo-polynucleotide which consists of a rox variant (that forms a pair with the rox included in the toolbox) and Cas9; and a second exo-polynucleotide which is present between loxp or a loxp mutant that form a pair with the loxp and a loxp variant included in the toolbox may be provided to a cell including the toolbox. In this case, an insertion of the first exo-polynucleotide into the toolbox may occur via an interaction with a Dre, which is specific to the rox and a rox variant thereof; and an exchange of the second exo-polynucleotide may occur via an interaction with a Cre, which is specific to the loxp and a loxp variant thereof.

3-6. Site-Specific Recombination in Desired Toolbox Among a Plurality of Toolboxes As described above, when an RRS included in any one toolbox present in an animal genome has a sequence which is different from that of an RRS included in a different toolbox in the same animal genome, a site-specific recombination may occur in a toolbox located at a desired locus.

For example, an exo-polynucleotide, which includes an RRS1 that forms a pair with an RRS1 of a first toolbox or an RRS1 variant thereof, may be provided to a transformed cell including an animal genome, in which the first toolbox that includes the RRS1 and a second toolbox that includes an RRS2 are included. In this case, an insertion of the exo-polynucleotide into the first toolbox may occur through an interaction with an SSR1 which is specific to the RRS1 or an RRS1 variant thereof.

In another example, an exo-polynucleotide, which is located between an RRS1 that forms a pair with an RRS1 of a toolbox or an RRS1 variant thereof and an RRS2 that forms a pair with an RRS2 of a first toolbox or an RRS2 variant thereof, may be provided to a transformed cell having an animal genome, in which the first toolbox that includes the RRS1 and the RRS2 and a second toolbox that includes the RRS1 and an RRS3 are included. In this case, an exchange between a polynucleotide, which is located between the RRS1 and the RRS2 of the first toolbox, and an exo-polynucleotide, which is located between the RRS1 or the RRS1 variant thereof and the RRS2 or the RRS2 variant thereof, may occur through an interaction with an SSR1 that is specific to the RRS1 or the RRS1 variant thereof, and an interaction with an SSR2 that is specific to the RRS2 or the RRS2 variant thereof.

Additionally, in another example, an exo-polynucleotide, which includes an RRS1 that forms a pair with an RRS1 of a first toolbox or an RRS1 variant thereof, may be provided to a transformed cell having an animal genome, in which the first toolbox that includes two or more RRS1s and a second toolbox that includes an RRS2 are included.

In this case, the RRS1 or the RRS1 variant thereof can interact with an SSR1, which is specific to the RRS1 or the RRS1 variant thereof. Additionally, after the polynucleotide located between two RRS1s in the first toolbox is deleted, an insertion of an exo-polynucleotide, which includes the RRS1 or the RRS1 variant thereof in the first toolbox, may occur.

4. Transformed Cell with Edited Toolbox

A transformed cell may include at least one toolbox. Any one of the at least one toolbox may include at least one RRS. A transformation via site-specific recombination may be possible using the at least one RRS.

The transformed cell may include an edited toolbox. The edited toolbox refers to a toolbox in which the site-specific recombination has occurred.

4-1. Single Cell
4-1-1. Ploidy

A transformed cell including at least one edited toolbox may be a diploid cell. The diploid cell is as described above.

A transformed cell including at least one edited toolbox may be a haploid cell. The haploid cell is as described above.

4-1-2. Zygosity

A transformed cell including two or more edited toolboxes may be a homozygote.

A transformed cell including two or more edited toolboxes may be a heterozygote.

4-2. Cell Colony

A transformed cell including at least one edited toolbox may form a cell colony.

4-2-1. Homologous Cell Colony

A homologous cell colony is characterized in that the toolboxes included in each cell are the same with each other and the edited toolboxes included in each cell are also the same with each other.

4-2-2. Chimeric Cell Colony

A chimeric cell colony refers to a cell colony other than a homologous cell colony.

5. Selection of Transformed Cell in which Edited Toolbox is Inserted 5-1. Selection of Transformed Cell Using Fluorescent Protein An edited toolbox may include a polynucleotide which encodes a fluorescent protein.

For example, an exo-polynucleotide encoding a fluorescent protein can be inserted into a toolbox including at least one RRS using site-specific recombination.

Accordingly, animal cells which include the edited toolbox can be distinguished from animal cells which do not include the edited toolbox.

5-2. Selection of Transformed Cell Using Antibiotic Resistance Gene

An edited toolbox may include an antibiotic resistance gene. An animal genome may include the edited toolbox.

For example, an exo-polynucleotide encoding an antibiotic resistance gene can be inserted into a toolbox including at least one RRS using site-specific recombination.

Animal cells including the edited toolbox can survive when the animal cells are treated with an antibiotic. Accordingly, animal cells which include the edited toolbox can be separated from animal cells which do not include the edited toolbox.

5-3. Selection of Transformed Cell Using Antigen-Antibody Response

An edited toolbox may include a polynucleotide encoding an antigen or a nucleotide capable of acting as an antigen. An animal genome may include the edited toolbox.

For example, an exo-polynucleotide which includes a nucleotide capable of acting as an antigen can be inserted into a toolbox including at least one RRS using site-specific recombination.

The animal cell including the edited toolbox can interact with an antibody specific to the antigen. Accordingly, animal cells which include the edited toolbox can be distinguished from animal cells which do not include the edited toolbox.

5-4. Selection of Transformed Cell Using Surface Marker Gene

An edited toolbox may include a polynucleotide encoding a surface marker. An animal cell may include the edited toolbox.

For example, a polynucleotide encoding a surface marker can be inserted into a toolbox including at least one RRS using site-specific recombination.

The animal cell including the edited toolbox can interact with an antibody specific to the surface marker. The antibody can interact with a magnetic particle or fluorophore. Accordingly, animal cells which include the edited toolbox can be distinguished from animal cells which do not include the edited toolbox via a magnetic property or fluorescence signal.

5-5. Selection of Transformed Cell Using Suicide Gene

A toolbox may include a polynucleotide encoding a suicide gene. An edited toolbox may not include the polynucleotide encoding the suicide gene.

For example, the core domain of the toolbox may sequentially include a loxp, a suicide gene, and a loxp variant. In this case, an exo-polynucleotide which includes the loxp at 5' end and includes the loxp variant at 3' end may be exchanged with the suicide gene by site-specific recombination.

Since animal cells including the edited toolbox do not include a suicide gene, apoptosis does not occur in these animal cells even when a prodrug is provided thereto. Accordingly, animal cells which include the edited toolbox can be distinguished from animal cells which do not include the edited toolbox.

6. Transgenic Animal in which Edited Toolbox is Inserted

6-1. Individual Transgenic Animal in which Edited Toolbox is Inserted

6-1-1. Homologous

Each cell included in a homologous transgenic animal may include at least one toolbox. The at least one toolbox may include at least one edited toolbox.

6-1-2. Chimeric

A chimeric transgenic animal refers to a transgenic animal other than a homologous transgenic animal.

6-2. Method for Preparing Transgenic Animal in which Edited Toolbox is Inserted A method for preparing a transgenic animal into which an edited toolbox is inserted may include a method for preparing a transgenic animal from an animal cell, a method for preparing a transgenic animal by delivery of an exo-polynucleotide or introduction of an SSR into a tissue or organ of an animal, and a method for preparing a transgenic animal by breeding between transgenic animals. The method for preparing a transgenic animal from an animal cell may include a method for preparing a transgenic animal from a cell of a transgenic animal into which a toolbox including at least one RRS is inserted.

The transgenic animal produced by any one of the above methods may be any one of a chimeric transgenic animal or a homologous transgenic animal.

6-2-1. Method for Preparing a Transgenic Animal from an Animal Cell

A transgenic animal into which an edited toolbox is inserted may be prepared from a cell of a transgenic animal into which a toolbox including at least one RRS is inserted.

For example, a transgenic animal may be prepared by introducing an SSR into a somatic cell into which a toolbox including at least one RRS is inserted, followed by SCNT. In another example, a transgenic animal may be prepared by introducing an SSR and a polynucleotide which includes at least one RRS, into a somatic cell into which a toolbox including at least one RRS is inserted by somatic cell microinjection, followed by SCNT. The transgenic animal may be a homologous transgenic animal.

For example, a transgenic animal may be prepared by introducing, via gamete microinjection, a polynucleotide including an SSR into a gamete into which a toolbox including at least one RRS is inserted. In another example, a transgenic animal may be prepared by introducing, via gamete microinjection, a polynucleotide including an SSR and a polynucleotide including at least one RRS into a gamete into which a toolbox including at least one RRS is inserted. The transgenic animal may be a chimeric transgenic animal.

For example, a transgenic animal may be prepared by introducing an SSR into a zygote into which a toolbox including at least one RRS is inserted. In another example, a transgenic animal may be prepared by introducing a polynucleotide including at least one RRS, via zygote microinjection, into a zygote into which a toolbox including at least one RRS is inserted, while treating the zygote with an SSR. The transgenic animal may be a chimeric transgenic animal.

For example, a transgenic animal may be prepared by introducing an SSR into an embryo into which a toolbox including at least one RRS is inserted. In another example, a transgenic animal may be prepared by introducing, a polynucleotide encoding an SSR and a polynucleotide including at least one RRS, via embryo microinjection, into an embryo into which a toolbox including at least one RRS is inserted. The transgenic animal may be a chimeric transgenic animal.

6-2-2. Method for Preparing a Transgenic Animal by Delivery of an Exo-Polynucleotide or Introduction of an SSR into a Tissue or Organ of an Animal A tissue or organ of an animal may include cells into which a toolbox including at least one RRS is inserted. A transgenic animal including an edited toolbox may be prepared by introducing an SSR or by delivery of an exo-polynucleotide, into a tissue or organ of the animal.

For example, a transgenic animal including an edited toolbox may be prepared by microinjection of a polynucleotide encoding an SSR and a polynucleotide including at least one RRS into a mammary gland tissue of the animal. The transgenic animal may be a chimeric transgenic animal.

For example, a transgenic animal into which an edited toolbox is inserted may be prepared by microinjection of an SSR into a reproductive organ of the animal. The offspring obtained from a gamete of the transgenic animal may be a transgenic animal. The transgenic animal may be a chimeric transgenic animal.

6-2-3. Breeding of Transgenic Animals

A transgenic animal may be prepared via breeding between a first transgenic animal and a second transgenic animal.

For example, a transgenic animal including an edited toolbox may be prepared by breeding between a first transgenic animal, into which a toolbox including at least one RRS is inserted, and a second transgenic animal, into which a toolbox including a polynucleotide encoding an SSR is inserted.

The second transgenic animal may be an offspring of the first transgenic animal or may be blood-related to the first transgenic animal. Alternatively, the second transgenic animal may not be blood-related to the first transgenic animal.

The transgenic animal obtained by the breeding may include a toolbox, which is the same as part of the toolbox included in the animal genome of the first transgenic animal, at the same location.

The transgenic animal obtained by the breeding may include a toolbox, which is the same as part of the toolbox included in the animal genome of the second transgenic animal, at the same location.

The transgenic animal obtained by the breeding may be a homologous transgenic animal.

The transgenic animal obtained by the breeding may include a transformed cell which is a homozygote. The transgenic animal obtained by the breeding may include a transformed cell which is a heterozygote.

7. Use of Transgenic Animal into which Edited Toolbox is Inserted 7-1. Animals with Improved Varieties A transgenic animal into which an edited toolbox is inserted may be used as an animal with improved varieties.

7-2. Disease Animal Model

A transgenic animal into which an edited toolbox is inserted may be used as a disease animal model.

7-3. Disease-Resistant Animal

A transgenic animal into which an edited toolbox is inserted may be used as a disease-resistant animal.

7-4. Use of by-Products

The organs, meat, skin, hairs, and body fluids of a transgenic animal, into which an edited toolbox is inserted, may be used, but parts of the transgenic animal to be used are not limited thereto.

7-5. Bioreactor

A transgenic animal into which an edited toolbox is inserted may be used as a bioreactor.

[Part IV] Transformation Using CRISPR/Enzyme System Component

1. Introduction of RNA-Guided Endonuclease and Guide Nucleic Acid into Cells Including Toolbox An RNA-guided endonuclease and a guide nucleic acid may be introduced in an animal genome in a cell that includes a toolbox for site-specific transformation.

The RNA-guided endonuclease may include Cas9, but is not limited thereto. The guide nucleic acid may include a gRNA, but is not limited thereto.

1-1. Introduction in Separate Form

The Cas9 and the gRNA may be introduced into a cell including a toolbox in a separate form.

The form in which the Cas9 is provided may include a DNA plasmid, a DNA linear fragment, an RNA linear fragment, and a protein. The RNA linear fragment may include an mRNA of Cas9.

The form in which the gRNA is provided may include a DNA plasmid, a DNA linear fragment, and an RNA linear fragment.

The form in which the Cas9 and the gRNA are provided together may include a ribonucleoprotein (RNP).

1-2. Single Delivery Vector

The Cas9 and the gRNA may be provided as a single delivery vector into a cell which includes a toolbox.

The form in which the Cas9 and the gRNA are provided may include a DNA linear fragment and an RNA linear fragment.

2. CRISPR/Enzyme System Components in Toolbox

A toolbox which is included in an animal genome in a cell may include at least one between an RNA-guided endonuclease and a guide nucleic acid.

A cell in which site-specific transformation occurs can express all or part of the components of the CRISPR/enzyme system and thus site-specific transformation can easily be performed.

2-1. RNA-Guided Endonuclease in Toolbox

A toolbox may include at least one polynucleotide encoding an RNA-guided endonuclease. The RNA-guided endonuclease may include Cas9 or a Cas9 mutant, but is not limited thereto.

2-1-1. Combination of Cas9 and Promoter

A toolbox may include at least one polynucleotide encoding Cas9.

The toolbox may include a promoter which can initiate the transcription of the Cas9. The promoter may be any one selected from a constitutive promoter, a tissue-specific promoter, and an inducible promoter.

2-1-2. Combination of Cas9, Promoter, and RRS

A toolbox may include at least one polynucleotide encoding Cas9. The toolbox may include a promoter which can initiate the transcription of the Cas9. The toolbox may include at least one RRS.

The toolbox may include at least one RRS at 5' end of the promoter capable of initiating the transcription of the Cas9.

The toolbox may include at least one RRS between the promoter, which is capable of initiating the transcription of the Cas9, and the polynucleotide encoding the Cas9.

The toolbox may include an RRS at 3' end of the polynucleotide encoding the Cas9.

The toolbox may include at least one RRS at 5' end of the polynucleotide encoding the Cas9 and may include at least one RRS at 3' end of the polynucleotide encoding the Cas9. In this case, any one of the RRSs at 5' end and any one of the RRSs at 3' end can interact with the same SSR. In this case, any one of the RRSs at 5' end and any one of the RRSs at 3' end may be the same with each other.

2-2. Guide Nucleic Acid in Toolbox

A toolbox may include at least one polynucleotide encoding a guide nucleic acid. The guide nucleic acid may include a gRNA, but is not limited thereto.

2-2-1. Combination of gRNA and Promoter

A toolbox may include at least one polynucleotide encoding a gRNA.

The toolbox may include a promoter capable of initiating the transcription of the gRNA. The promoter may be any one selected from a constitutive promoter, a tissue-specific promoter, and an inducible promoter. The constitutive promoter capable of initiating the transcription of the gRNA may include U6 promoter, but is not limited thereto.

2-2-2. Combination of gRNA, Promoter, and RRS

A toolbox may include at least one polynucleotide encoding a gRNA.

The toolbox may include a promoter capable of initiating the transcription of the gRNA. The toolbox may include at least one RRS.

The toolbox may include at least one RRS at 5' end of the promoter capable of initiating the transcription of the gRNA.

The toolbox may include at least one RRS between the promoter, which is capable of initiating the transcription of the gRNA, and a polynucleotide encoding the gRNA.

The toolbox may include an RRS at 3' end of the polynucleotide encoding the gRNA.

The toolbox may include at least one RRS at 5' end of the polynucleotide encoding the gRNA and may include at least one RRS at 3' end of the polynucleotide encoding the gRNA. In this case, any one of the RRSs at 5' end and any one of the RRSs at 3' end can interact with the same SSR. In this case, any one of the RRSs at 5' end and as any one of the RRSs at 3' end may be the same with each other.

2-3. RNA-Guided Endonuclease and Guide Nucleic Acid in Toolbox

A toolbox may include at least one polynucleotide encoding an RNA-guided endonuclease and may include at least one polynucleotide encoding a guide nucleic acid. The RNA-guided endonuclease may include Cas9, but is not limited thereto. The guide nucleic acid may include a gRNA, but is not limited thereto.

2-3-1. Combination of Cas9, gRNA, and Promoter

A toolbox may include at least one polynucleotide encoding Cas9.

The toolbox may include a promoter capable of initiating the transcription of the Cas9. The promoter may be any one selected from a constitutive promoter, a tissue-specific promoter, and an inducible promoter.

The toolbox may include at least one polynucleotide encoding a gRNA.

The toolbox may include a promoter capable of initiating the transcription of the gRNA. The promoter may be any one selected from a constitutive promoter, a tissue-specific promoter, and an inducible promoter. The constitutive promoter capable of initiating the transcription of the gRNA may include U6 promoter, but is not limited thereto.

2-3-2. Combination of Cas9, gRNA, Promoter, and RRS

A toolbox may include at least one polynucleotide encoding Cas9. The toolbox may include a promoter capable of initiating the transcription of the Cas9. The toolbox may include at least one polynucleotide encoding a gRNA. The toolbox may include a promoter capable of initiating the transcription of the gRNA. The toolbox may include at least one RRS.

The toolbox may include at least one RRS at 5' end of the promoter capable of initiating the transcription of the Cas9.

The toolbox may include at least one RRS between the promoter capable of initiating the transcription of the Cas9 and the polynucleotide encoding the Cas9.

The toolbox may include an RRS at 3' end of the polynucleotide encoding the Cas9.

The toolbox may include at least one RRS at 5' end of the polynucleotide encoding the Cas9 and may include at least one RRS at 3' end of the polynucleotide encoding the Cas9. In this case, any one of the RRSs at 5' end and any one of the RRSs at 3' end can interact with the same SSR. In this case, any one of the RRSs at 5' end and any one of the RRSs at 3' end may be the same with each other.

The toolbox may include at least one RRS at 5' end of the promoter capable of initiating the transcription of the gRNA.

The toolbox may include at least one RRS between the promoter capable of initiating the transcription of the gRNA and the polynucleotide encoding the gRNA.

The toolbox may include an RRS at 3' end of the polynucleotide encoding the gRNA.

The toolbox may include at least one RRS at 5' end of the polynucleotide encoding the gRNA and may include at least one RRS at 3' end of the polynucleotide encoding the gRNA. In this case, any one of the RRSs at 5' end and any one of the RRSs at 3' end can interact with the same SSR. In this case, any one of the RRSs at 5' end and any one of the RRSs at 3' end may be the same with each other.

3. Control of Operation of CRISPR/Enzyme System 3-1. Control of Expression of RNA-Guided Endonuclease A toolbox may include at least one polynucleotide encoding an RNA-guided endonuclease. The RNA-guided endonuclease may include Cas9, but is not limited thereto.

3-1-1. Control of Cas9 Transcription Using Promoter

A toolbox may include a polynucleotide encoding Cas9.

The toolbox may include a promoter that initiates the transcription of the polynucleotide encoding the Cas9. The promoter may include a tissue-specific promoter or inducible promoter.

In the case where the promoter is a tissue-specific promoter, the transcription of the polynucleotide encoding the Cas9 included in the toolbox may be initiated when the toolbox is included in a cell of particular tissue.

In the case where the tissue-specific promoter is a mammary gland tissue-specific promoter, the transcription of the polynucleotide encoding the Cas9 included in the toolbox may be initiated when the toolbox is included in a cell of a mammary gland tissue. The mammary gland tissue-specific promoter may include an alpha-casein promoter, a beta-casein promoter, a kappa-casein promoter, a mu-casein promoter, and a beta-lactoglobulin promoter, but is not limited thereto.

In the case where the tissue-specific promoter is a reproductive organ-specific promoter, the transcription of the polynucleotide encoding the Cas9 included in the toolbox may be initiated when the toolbox is included in a gamete. The reproductive organ-specific promoter may include an ovarian-specific promoter and a testis-specific promoter, but is not limited thereto.

In the case where the promoter that initiates the transcription of the polynucleotide encoding the Cas9 is a tissue-specific promoter, the site where site-specific transformation occurs in a transgenic animal including the toolbox may be limited. Additionally, the occurrence of unnecessary site-specific transformation in other tissues of the transgenic animal may be prevented.

In the case where the promoter is an inducible promoter, transcription may be initiated when particular condition is satisfied. The inducible promoter may include a chemically inducible promoter, a temperature inducible promoter, and a light inducible promoter, but is not limited thereto.

The chemically inducible promoter can initiate transcription when particular chemical compound is present. The chemically inducible promoter may include an antibiotic-inducible promoter, an alcohol-inducible promoter, a steroid-inducible promoter, and a metal-inducible promoter, but is not limited thereto. The antibiotic-inducible promoter may include a Tet-on promoter and a Tet-off promoter, but is not limited thereto. The steroid-inducible promoter may include an estrogen-inducible promoter, but is not limited thereto. The metal-inducible promoter may include a copper-inducible promoter, but is not limited thereto.

A temperature inducible promoter can initiate transcription when the temperature condition is satisfied. The temperature inducible promoter may include a heat shock-inducible promoter and a cold shock-inducible promoter, but is not limited thereto. The heat shock-inducible promoter may include an Hsp promoter, but is not limited thereto.

A light inducible promoter can initiate transcription when the wavelength condition of light is satisfied.

In the case where the promoter that initiates the transcription of the polynucleotide encoding the Cas9 is an inducible promoter, it is possible to control the time when the site-specific transformation occurs in a transformed cell or animal that includes the toolbox.

3-1-2. Insertion of Promoter Using RRS

A toolbox may include a polynucleotide encoding Cas9.

The toolbox may include an RRS at 5' end of the polynucleotide encoding the Cas9.

A nucleic acid may include a polynucleotide encoding a promoter. The promoter may include a constitutive promoter, a tissue-specific promoter, or an inducible promoter. The nucleic acid may include an RRS at one end or both ends of the polynucleotide encoding the promoter. The RRS may form a pair with the RRS included in the toolbox.

An SSR that can interact with the nucleic acid and the RRS may be provided to the toolbox. The polynucleotide encoding the promoter may be inserted to the toolbox. In this case, the transcription of the polynucleotide encoding the Cas9 may not be initiated before the polynucleotide encoding the promoter is inserted and may be initiated after the polynucleotide encoding the promoter is inserted.

3-1-3. Control of Cas9 Transcription Using Transcription Stop Codon

A toolbox may include a polynucleotide encoding Cas9.

The toolbox may include a promoter that initiates the transcription of the polynucleotide encoding the Cas9. The promoter may be a constitutive promoter, a tissue-specific promoter, or an inducible promoter.

The toolbox may include an RRS1, a transcription stop codon, and an RRS2. The RRS1, the transcription stop codon, and the RRS2 may be sequentially located between the polynucleotide encoding Cas9 and the promoter that initiates the transcription of the polynucleotide encoding Cas9. The RRS1 and the RRS2 may be the same with each other. The RRS1 and the RRS2 may include a loxp, but are not limited thereto.

An SSR that can interact with the RRS1 and the RRS2 may be provided to the toolbox. The SSR may include a Cre, but is not limited thereto. In the toolbox, a polynucleotide including a transcription stop codon located between the RRS1 and the RRS2 may be deleted. In this case, the mRNA transcribed from the polynucleotide encoding the Cas9 may not be transcribed before the transcription stop codon is deleted and may be transcribed after the transcription stop codon is deleted.

3-1-4. Control of Cas9 Translation Using Stop Codon

A toolbox may include a polynucleotide encoding Cas9.

The toolbox may include a promoter that initiates the transcription of the polynucleotide encoding the Cas9. The promoter may be a constitutive promoter, a tissue-specific promoter, or an inducible promoter.

The toolbox may include an RRS1, a stop codon, and an RRS2. The RRS1, the transcription stop codon, and the RRS2 may be sequentially located between the promoter that initiates the transcription of the polynucleotide encoding the Cas9 and the polynucleotide encoding the Cas9. The RRS1 and the RRS2 may be the same with each other. The RRS1 and the RRS2 may include a loxp, but are not limited thereto.

An SSR that can interact with the RRS1 and the RRS2 may be provided to the toolbox. The SSR may include Cre recombinase, but is not limited thereto. In the toolbox, a polynucleotide including a stop codon located between the RRS1 and the RRS2 may be deleted. In this case, the mRNA transcribed from the polynucleotide encoding the Cas9 may not be transcribed before the stop codon is deleted and may be transcribed after the stop codon is deleted.

3-2. Control of Guide Nucleic Acid Expression

A toolbox may include at least one polynucleotide encoding a guide nucleic acid. The guide nucleic acid may include a gRNA, but is not limited thereto.

3-2-1. Promoter Insertion Using RRS

A toolbox may include a polynucleotide encoding a gRNA.

The toolbox may include an RRS at 5' end of the polynucleotide encoding the gRNA.

A nucleic acid may include a polynucleotide encoding a promoter. The promoter may include a constitutive promoter, a tissue-specific promoter, or an inducible promoter. The constitutive promoter may include a U6 promoter. The nucleic acid may include an RRS at one end or both ends of the polynucleotide encoding the promoter. The RRS may form a pair with the RRS included in the toolbox.

An SSR that can interact with the nucleic acid and the RRS may be provided to the toolbox. A polynucleotide encoding the promoter may be inserted to the toolbox. In this case, the transcription of the polynucleotide encoding a gRNA may not be initiated before the promoter is inserted and may be initiated after the e promoter is inserted.

3-2-2. Control of gRNA Transcription

A toolbox may include a polynucleotide encoding a gRNA.

The toolbox may include a promoter that initiates the transcription of the polynucleotide encoding the gRNA. The promoter may be a constitutive promoter, a tissue-specific promoter, or an inducible promoter. The constitutive promoter may include a U6 promoter.

The toolbox may include an RRS1, a transcription stop codon, and an RRS2. The transcription stop codon may include a poly T sequence. The transcription stop codon may include an AATAAA sequence. The RRS1, the transcription stop codon, and the RRS2 may be sequentially located between the promoter that initiates the transcription of the polynucleotide encoding the gRNA and the polynucleotide encoding gRNA. The RRS1 and the RRS2 may be the same with each other. The RRS1 and the RRS2 may include a loxp, but are not limited thereto.

An SSR that can interact with the RRS1 and the RRS2 may be provided to the toolbox. The SSR may include Cre recombinase, but is not limited thereto. In the toolbox, a polynucleotide including a transcription stop codon located between the RRS1 and the RRS2 may be deleted.

In this case, the polynucleotide encoding the gRNA may not be expressed before the transcription stop codon is deleted and may be expressed after the transcription stop codon is deleted.

4. Target Site of CRISPR/Enzyme System

An animal genome in a cell may include at least one toolbox.

The at least one toolbox may include a first toolbox. The first toolbox may include a polynucleotide encoding a guide nucleic acid.

Alternatively, the first toolbox may include a polynucleotide encoding an RNA-guided endonuclease but may not include a polynucleotide encoding a guide nucleic acid. In this case, a guide nucleic acid or a polynucleotide encoding a guide nucleic acid may be introduced into a cell by a separate delivery vector.

The guide nucleic acid may include a protospacer domain. The protospacer domain may include a nucleotide sequence which is the same as or can have a complementary binding with a target site located in an animal genome in a cell or exo-polynucleotide.

The RNA-guided endonuclease may include Cas9, but is not limited thereto. The guide nucleic acid may include a gRNA, but is not limited thereto.

4-1. Animal Genome

The animal genome in a cell may include a target site for a gRNA. The target site may be a nucleotide sequence adjacent to the 5' end or 3' end of a PAM sequence. The PAM sequence may include NGG, but is not limited thereto.

The target site may be located on a polynucleotide which can be involved in the expression of a polypeptide or RNA in the animal genome in a cell.

The target site may be located on any one among the promoter, 5' UTR, exon, intron, and 3' UTR of a polynucleotide, which encodes a polypeptide or RNA in the animal genome in a cell.

In this case, the expression level of a polypeptide or RNA within the cell may be affected through the CRISPR/enzyme system.

The target site may be located within the safe harbor of the animal genome in a cell.

In the case where the animal genome is a mouse genome, the safe harbor of the mouse genome may include the rosa26 locus which is already well-known.

In the case where the animal genome is a bovine genome, the safe harbor of the bovine genome may include the loci in Table 1, but is not limited thereto.

In this case, it is possible to perform site-specific transformation that does not give a fatal effect on the above cells and transgenic animals including these cells, through the CRISPR/enzyme system.

4-2. Exo-Polynucleotide

At least one toolbox which is included in the animal genome may include a target toolbox.

As used herein, the term "target toolbox" may refer to a toolbox including a target site, which can be recognized by a component of the engineered nuclease, as a component.

The target toolbox may include at least one target site for a gRNA. The target site may be a nucleotide sequence adjacent to 5' end or 3' end of a PAM sequence. The PAM sequence may include NGG, but is not limited thereto.

The target toolbox may be a toolbox which is the same as the first toolbox.

The target toolbox may be a toolbox which is different from the first toolbox.

The target site may be located on any one among the promoter, 5' UTR, exon, intron, and 3' UTR of a polynucleotide, which encodes a polypeptide or RNA within the target toolbox.

The polypeptide may include part of a target protein. In this case, the expression level of the target protein of cells including the target toolbox and a transgenic animal including these cells may be affected through the CRISPR/enzyme system.

The polypeptide may include a polypeptide which is expressed by a marker gene. In this case, the marker gene may be knocked out through the CRISPR/enzyme system and thereby may be used for selection of transformed cells. For example, when a target toolbox which is included in an animal genome in a cell includes a polynucleotide that encodes thymidine kinase, the thymidine kinase can be knocked out through site-specific transformation by the CRISPR/enzyme system, which targets part of the exons of the thymidine kinase as a target site. The cells in which site-specific transformation has occurred can be selected by treating the cells including the target toolbox with ganciclovir.

The polypeptide may include part of a recombinase. In this case, the site-specific recombination in a cell can be inhibited by knockout of a polynucleotide encoding the recombinase through the CRISPR/enzyme system.

The polypeptide may include a transposase. In this case, transposon insertion into a cell or transposon deletion out of a cell may be inhibited by knockout of a polynucleotide encoding a transposase through the CRISPR/enzyme system.

The polypeptide may include part of an RNA-guided endonuclease. In this case, site-specific transformation in a cell can be prevented by knockout of the RNA-guided endonuclease through the CRISPR/enzyme system. For example, when a target toolbox which is included in an animal genome in a cell includes a polynucleotide encoding Cas9, the Cas9 can be knocked out through site-specific transformation by the CRISPR/enzyme system, which targets part of the exons of the Cas9 as a target site. In the cell including the toolbox, it is possible to prevent the occurrence of site-specific transformation (off-target activity) in a place other than the target site, by reducing the Cas9 expression in a cell while simultaneously performing site-specific transformation within the target toolbox.

The RNA may include part of a guide nucleic acid. In this case, the site-specific transformation in a cell can be prevented by knockout of the guide nucleic acid through the CRISPR/enzyme system. For example, when a target toolbox which is included in an animal genome in a cell includes a polynucleotide encoding a gRNA, the gRNA can be knocked out through site-specific transformation by the CRISPR/enzyme system, which targets a protospacer domain of the gRNA as a target site. In the cell including the toolbox, it is possible to prevent the occurrence of site-specific transformation (off-target activity) in a place other than the target site, by reducing the gRNA expression in a cell while simultaneously performing site-specific transformation within the target toolbox. Additionally, when the cell including the target toolbox can express an RNA-guided endonuclease, it is possible to prevent off-target activity while not affecting the expression of the RNA-guided endonuclease.

The target site may be located on a polynucleotide which encodes a non-functional polypeptide within the target toolbox. Alternatively, the target site may be located on a polynucleotide which encodes an untranslated RNA within the target toolbox. Alternatively, the target site may be located on an untranscribed polynucleotide within the target toolbox.

When an animal genome in a cell includes two or more of target toolboxes which are the same with one another, it is possible to perform multiple identical site-specific transformations through a single CRISPR/enzyme system. For example, when a target toolbox which is included in a bovine genome in a cell includes an untranscribed polynucleotide, it is possible to perform a site-specific insertion of a polynucleotide encoding omega-3 through the CRISPR/enzyme system, which targets part of the untranscribed polynucleotide as a target site. When the bovine genome includes two or more of the target toolboxes, a polynucleotide encoding omega-3 can be inserted into each target toolbox, and thus, it is possible to prepare a cell or transgenic cow which has a high expression level of omega-3.

When an animal genome in a cell includes two or more of target toolboxes which are different from one another, it is possible to perform multiple different site-specific transformations through the CRISPR/enzyme system in which guide nucleic acids are varied. For example, the bovine genome in a cell may include a first target toolbox and a second target toolbox. The first target toolbox may include a first target site and the second target toolbox may include a second target site. The nucleotide sequence of the first target site may be different from that of the second target site. A polynucleotide encoding a human immunoglobulin heavy chain may be knocked-in in the first toolbox through the CRISPR/enzyme system which includes a first gRNA that is the same as or can have a complementary binding to the first target site. A polynucleotide encoding a human immunoglobulin light chain may be knocked-in in the second toolbox through the CRISPR/enzyme system which includes a second gRNA that is the same as or can have a complementary binding to the second target site. The cells or transgenic cow including these cells, which include both the first target toolbox and the second target toolbox can produce human antibodies by expressing both the human immunoglobulin heavy chain and the human immunoglobulin light chain.

5. Site-Specific Transformation Using CRISPR/Enzyme System

An animal genome in a cell may include at least one toolbox. The at least one toolbox may include at least any one among a first toolbox, second toolbox, and third toolbox.

The first toolbox may include at least one polynucleotide encoding an RNA-guided endonuclease. In this case, it is possible to perform site-specific transformation by the CRISPR/enzyme system via delivery of a guide nucleic acid or polynucleotide encoding the guide nucleic acid into a cell including the toolbox.

The second toolbox may include at least one polynucleotide encoding a guide nucleic acid. In this case, it is possible to perform site-specific transformation through the CRISPR/enzyme system by introducing an RNA-guided endonuclease or by delivery of a polynucleotide encoding an RNA-guided endonuclease, into a cell including the toolbox.

The third toolbox may include at least one polynucleotide encoding an RNA-guided endonuclease and at least one polynucleotide encoding a guide nucleic acid. In this case, it is possible to perform site-specific transformation through the CRISPR/enzyme system in the cell.

The animal genome in the cell which includes the at least one toolbox may include a target site for the guide nucleic acid. The target site may be a nucleotide sequence adjacent to the 5' end or 3' end of a PAM sequence.

The at least one toolbox may include a target toolbox. The target toolbox may include a target site for the guide nucleic acid. The target site may be a nucleotide sequence adjacent to the 5' end or 3' end of a PAM sequence. The target toolbox may be a toolbox which is the same as that of the first toolbox. Alternatively, the target toolbox may be a toolbox which is different from that of the first toolbox.

The RNA-guided endonuclease may include Cas9, but is not limited thereto. The guide nucleic acid may include a gRNA, but is not limited thereto.

5-1. Non-Homologous End Joining (NHEJ)

In the case where double strands of DNA are both cleaved, that is, an occurrence of a double strand break, the binding back of the cleaved DNA strands by the DNA ligase is called non-homologous end joining (NHEJ).

An animal genome in a cell may include at least any one among the first toolbox, second toolbox, and third toolbox. Cas9 may be expressed in the cell or may be delivered into the cell. A gRNA may be expressed in the cell or delivered into the cell.

The gRNA can have a complementary binding with a target site of the animal genome in a cell or target toolbox. The Cas9 can interact with the gRNA and thereby cause a double strand break in the target site.

In this case, a nucleotide or polynucleotide may be inserted during the non-homologous end joining (NHEJ) process. Alternatively, a nucleotide or polynucleotide may be deleted during the non-homologous end joining (NHEJ) process. Due to the insertion or deletion, a modification may occur in the nucleotide sequence at the target site.

5-2. Homologous Recombination

An animal genome in a cell may include at least any one among the first toolbox, second toolbox, and third toolbox. Cas9 may be expressed in the cell or delivered into the cell. A gRNA may be expressed in the cell or delivered into the cell.

A donor polynucleotide or donor may be delivered into the cell. A first homology arm may be located at the 5' end of the donor. A second homology arm may be located at the 3' end of the donor.

The first homology arm may have a nucleotide sequence the same as part of an animal genome in a cell and the second homology arm may have a nucleotide sequence the same as part of an animal genome in a cell. In this case, the donor polynucleotide may be inserted between the same nucleotide sequence as that of the first homology arm and the same nucleotide sequence as that of the second homology arm, in an animal genome in a cell.

Alternatively, the first homology arm may have the same nucleotide sequence as part of a target toolbox in a cell and the second homology arm may have the same nucleotide sequence as part of a target toolbox in a cell. In this case, a donor may be inserted between the same nucleotide sequence as that of the first homology arm and the same nucleotide sequence as that of the second homology arm, in a target toolbox in a cell.

The donor may include a toolbox.

5-3. Homology-Independent Targeted Integration (HITI)

An animal genome in a cell may include at least any one among the first toolbox, second toolbox, and third toolbox. Cas9 may be expressed in the cell or delivered into the cell. A gRNA may be expressed in the cell or delivered into the cell.

A donor may be delivered into the cell.

A target site having the same nucleotide sequence as that located at the target site in the animal genome in a cell may be located at the 5' end and 3' end of the donor. In this case, a double strand break may occur, by the CRISPR/enzyme system, at a target site located at the animal genome in the cell, a target site at 5' end of a donor, and a target site at 3' end of a donor. A donor can be inserted between double strand breaks of the animal genome through a non-homologous end joining (NHEJ).

Alternatively, a target site having the same nucleotide sequence as that located at the target site in the target toolbox in a cell may be located at the 5' end and 3' end of the donor. In this case, a double strand break may occur, by the CRISPR/enzyme system, at a target site located at the target toolbox in the cell, a target site at 5' end of a donor, and a target site at 3' end of a donor. A donor can be inserted between double strand breaks of the target toolbox through a non-homologous end joining (NHEJ).

The donor may include a toolbox.

5-4. Knockin (Knock-in)

An animal genome in a cell may include at least any one among the first toolbox, second toolbox, and third toolbox. Cas9 may be expressed in the cell or delivered into the cell. A gRNA may be expressed in the cell or delivered into the cell.

A donor polynucleotide may be delivered into the cell. In this case, the donor can be inserted into an animal genome in a cell or into the inside of a target toolbox through homologous recombination. Alternatively, the donor can be inserted into an animal genome in a cell or into the inside of a target toolbox through HITI.

For example, at least one nucleotide of the sequence present in the target site in an animal genome or the target site inside of the target toolbox in a cell may be deleted, and the donor polynucleotide may be added.

In another example, the donor polynucleotide may be added into the sequence present in the target site in an animal genome or the target site inside of the target toolbox in a cell.

In the case where the donor includes a polynucleotide encoding a protein or RNA, in the cell into which the donor is inserted, the polynucleotide encoding a protein or RNA may be knocked in and thereby the protein or RNA may be expressed.

5-5. Knockout (Knock-Out)

An animal genome in a cell may include at least any one among the first toolbox, second toolbox, and third toolbox. Cas9 may be expressed in the cell or delivered into the cell. A gRNA may be expressed in the cell or delivered into the cell.

A donor polynucleotide may be delivered into the cell. In this case, the donor can be inserted into a target site in an animal genome or into a target site inside of a target toolbox in a cell through homologous recombination. Alternatively, the donor can be inserted into a target site in an animal genome or into a target site inside of a target toolbox in a cell through HITI.

A donor polynucleotide may not be delivered into the cell. In this case, the nucleotide insertion, polynucleotide insertion, nucleotide deletion, or polynucleotide deletion may occur at the target site in an animal genome or at the target site inside of a target toolbox in a cell.

For example, at least one nucleotide present in a target site in an animal genome or in a target site inside of a target toolbox in a cell may be deleted.

In another example, at least one nucleotide present in a target site in an animal genome or in a target site inside of a target toolbox in a cell may be deleted, and at least one nucleotide may be additionally added thereto.

In the case where the target site in the animal genome or the target site inside of the target toolbox in the cell is located on a polynucleotide encoding a protein or RNA, the protein or RNA may be knocked out and thereby the expression level may be reduced.

6. Site-Specific Transformed Cell by CRISPR/Enzyme System

An animal genome of a transformed cell may include at least one toolbox. The at least one toolbox may include any one among the first toolbox, second toolbox, and third toolbox. The first toolbox may include at least one polynucleotide encoding an RNA-guided endonuclease. The second toolbox may include at least one polynucleotide encoding a guide nucleic acid. The third toolbox may include at least one polynucleotide encoding an RNA-guided endonuclease and may include at least one polynucleotide encoding a guide nucleic acid.

A site-specific transformed cell may include cells in which site-specific transformation has occurred at a target site in the animal genome in the cell.

A site-specific transformed cell may include cells in which site-specific transformation has occurred at a target site inside of a target toolbox in the cell.

6-1. Single Cell 6-1-1. Ploidy

A site-specific transformed cell may be a diploid cell. The diploid cell is as described above.

A site-specific transformed cell may be a haploid cell. The haploid cell is as described above.

6-1-2. Zygosity

A site-specific transformed cell may include at least one pair of homologous chromosomes. The at least one pair of homologous chromosomes may include a first chromosome and a second chromosome, which are in a relationship of homologous chromosomes.

The site-specific transformed cell may be a homozygote.

In the site-specific transformed cell which is a homozygote, all of the type, number, and location of the site-specific transformation included in the first chromosome and the second chromosome may be the same.

In the site-specific transformed cell which is a homozygote, both the type and the number of the site-specific transformation included in the first chromosome and the second chromosome may be the same.

In the site-specific transformed cell which is a homozygote, the type of the site-specific transformation included in the first chromosome and the second chromosome may be the same.

In the site-specific transformed cell which is a homozygote, all of the type, number, and location of the toolboxes and the site-specific transformation included in the first chromosome and the second chromosome may be the same.

In the site-specific transformed cell which is a homozygote, both the type and the number of the toolboxes and the site-specific transformation included in the first chromosome and the second chromosome may be the same.

In the site-specific transformed cell which is a homozygote, the type of the toolboxes and the site-specific transformation included in the first chromosome and the second chromosome may be the same.

Alternatively, in the site-specific transformed cell which is a homozygote, both of the first chromosome and the second chromosome may not include any toolbox and both of the first chromosome and the second chromosome may not include any site-specific transformation.

The site-specific transformed cell may be a heterozygote.

In the site-specific transformed cell which is a heterozygote, the first chromosome may not include any toolbox and the second chromosome may include at least one toolbox.

In the site-specific transformed cell which is a heterozygote, the first chromosome may not include site-specific transformation and the second chromosome may include at least one site-specific transformation.

In the site-specific transformed cell which is a heterozygote, the second chromosome may not include a toolbox which is the same as that included in the first chromosome.

In the site-specific transformed cell which is a heterozygote, the second chromosome may not include site-specific transformation which is the same as that included in the first chromosome.

6-2. Cell Colony

A site-specific transformed cell may form a cell colony.

6-2-1. Homologous Cell Colony

A homologous cell colony is characterized in that the toolboxes possessed by each cell are the same with each other and all of the type, number, and location of the site-specific transformation included in each cell are also the same with each other.

6-2-2. Chimeric Cell Colony

A chimeric cell colony refers to a cell colony other than a homologous cell colony.

For example, a chimeric cell colony may include both a first cell, which has a genome in which site-specific transformation has occurred in a first target site by the CRISPR/enzyme system, and a second cell, which does not have a genome in which site-specific transformation has occurred in a first target site by the CRISPR/enzyme system 7. Selection of Site-Specific Transformed Cell Using CRISPR/Enzyme System 7-1. Selection of Transformed Cell Using Fluorescent Protein A transformed cell may include at least one target toolbox. The transformed cell may include at least one toolbox. Any one of the at least one toolbox may be a target toolbox which includes a polynucleotide that encodes a fluorescent protein. For example, a polynucleotide encoding a target protein can be inserted into the transformed cell through site-specific transformation which uses the exons of a polynucleotide that encodes a fluorescent protein as a target site.

The site-specific transformed cells may be different from cells in which site-specific transformation has not occurred with regard to the fluorescence signal. Accordingly, the site-specific transformed cells can be distinguished.

The site-specific transformed cell may include a polynucleotide encoding a fluorescent protein. For example, a donor including a polynucleotide encoding a fluorescent protein can be inserted into a transformed cell including at least one target toolbox through site-specific transformation. The donor may include a polynucleotide encoding a target protein.

The site-specific transformed cells express fluorescent proteins and thus fluorescence signals can be measured. Accordingly, the site-specific transformed cells can be distinguished from the animal cells in which the site-specific transformation has not occurred.

7-2. Selection of Transformed Cell Using Antibiotic Resistance Gene

A site-specific transformed cell may include an antibiotic resistance gene.

For example, a donor which includes a polynucleotide encoding an antibiotic resistance gene can be inserted into a transformed cell including at least one target toolbox through site-specific transformation. The donor may include a polynucleotide encoding a target protein.

The site-specific transformed cell can express an antibiotic resistance gene and thus the cell can survive even when the cell is treated with an antibiotic compound. Accordingly, the site-specific transformed cells can be separated from the animal cells in which the site-specific transformation has not occurred.

7-3. Selection of Transformed Cell Using Antigen-Antibody Reaction

A site-specific transformed cell may include at least one target toolbox. The site-specific transformed cell may include at least one toolbox. Any one of the at least one toolbox may be a target toolbox which includes a polynucleotide encoding an antigen or a nucleotide capable of acting as an antigen. For example, a polynucleotide encoding a target protein can be inserted into a transformed cell, which includes a target toolbox that includes a polynucleotide encoding an antigen, through site-specific transformation in which exons of a polynucleotide encoding an antigen are used as a target site.

The site-specific transformed cells may be different from the cells in which site-specific transformation has not occurred, with respect to the expression level of an antigen. Accordingly, the site-specific transformed cells can be distinguished through antigen-antibody reaction.

A site-specific transformed cell may include a polynucleotide encoding an antigen or a nucleotide capable of acting as an antigen. For example, a donor which includes a nucleotide capable of acting as an antigen can be inserted into a transformed cell which includes a target site in an animal genome through site-specific transformation. The donor may include a polynucleotide encoding a target protein.

The nucleotide capable of acting as an antigen inserted into the site-specific transformed cell can interact with a specific antibody. Accordingly, the site-specific transformed cells can be distinguished from animal cells in which the site-specific transformation has not occurred.

7-4. Selection of Transformed Cell Using Surface Marker Gene

A site-specific transformed cell may include at least one target toolbox. The site-specific transformed cell may include at least one toolbox. Any one of the at least one toolbox may be a target toolbox which includes a polynucleotide encoding a surface marker gene. For example, a polynucleotide encoding a target protein can be inserted into the transformed cell through site-specific transformation, in which exons of a polynucleotide encoding a surface marker gene are used as a target site.

The site-specific transformed cells may be different from the cells in which site-specific transformation has not occurred, with regard to the level of the surface marker expressed on the surface. The surface marker can interact with a specific antibody. The antibody can interact with magnetic particles or fluorophores. Accordingly, the site-specific transformed cells can be distinguished from the cells in which site-specific transformation has not occurred, based on magnetic property or fluorescence signal.

The site-specific transformed cell may include a polynucleotide encoding a surface marker. For example, a donor which includes a polynucleotide encoding a surface marker can be inserted into a transformed cell, which includes at least one target toolbox, through site-specific transformation. The donor may include a polynucleotide encoding a target protein.

The site-specific transformed cell can express the surface marker on the cell surface. The surface marker can interact with a specific antibody. The antibody can interact with magnetic particles or fluorophores. Accordingly, the site-specific transformed cells can be distinguished from the cells in which site-specific transformation has not occurred, based on magnetic property or fluorescence signal.

7-5. Selection of Transformed Cell Using Suicide Gene

A site-specific transformed cell may include a polynucleotide encoding a suicide gene in an animal genome or within a toolbox. A site-specific transformed cell in which the suicide gene is knocked out through site-specific transformation can be prepared.

For example, when the transformed cell includes a toolbox that includes a polynucleotide encoding thymidine kinase, a donor can be inserted through site-specific transformation in which part of the nucleotide sequence of the exons of the polynucleotide encoding thymidine kinase is used as a target site.

The site-specific transformed cell is characterized in that a suicide gene is knocked out, and thus, even when a prodrug is treated thereon, no apoptosis occurs. Accordingly, the site-specific transformed cells can be distinguished from the animal cells in which site-specific transformation has not occurred.

8. Site-Specific Transgenic Animal Using CRISPR/Enzyme System 8-1. Individual Site-Specific Transgenic Animal Using CRISPR/Enzyme System 8-1-1. Homology Each cell included in a homologous site-specific transgenic animal may include at least one toolbox. The at least one toolbox may include at least one among a first toolbox, a second toolbox, and a third toolbox. The first toolbox may include at least one polynucleotide encoding an RNA-guided endonuclease. The second toolbox may include at least one polynucleotide encoding a guide nucleic acid. The third toolbox may include at least one polynucleotide encoding an RNA-guided endonuclease and may include at least one polynucleotide encoding a guide nucleic acid.

The RNA-guided endonuclease may include Cas9, but is not limited thereto. The guide nucleic acid may include a gRNA, but is not limited thereto.

Each cell, which is included in a homologous site-specific transgenic animal, may include at least one site-specific transformation in a target site of an animal genome.

Each cell, which is included in a homologous site-specific transgenic animal, may include at least one site-specific transformation in a target site of inside of a toolbox.

8-1-2. Chimeric

A chimeric site-specific transgenic animal refers to a transgenic animal other than a homologous transgenic animal.

For example, a chimeric site-specific transgenic animal may include both a first cell, which has a genome in which site-specific transformation has occurred in a first target site by the CRISPR/enzyme system; and a second cell, which does not have a genome in which site-specific transformation has occurred in the first target site by the CRISPR/enzyme system.

8-2. Preparation Method of Site-Specific Transgenic Animal Using CRISPR/Enzyme System The methods of preparing a site-specific transgenic animal include a method for preparing a site-specific transgenic animal from an animal cell, a method for preparing a site-specific transgenic animal by delivery of an exo-polynucleotide into a tissue or organ of an animal, and a method for preparing a site-specific transgenic animal by breeding between transgenic animals. The method for preparing a site-specific transgenic animal from an animal cell includes a method for preparing a site-specific transgenic animal from a cell of a transgenic animal into which at least one toolbox is inserted.

The site-specific transgenic animal prepared by any one of the above methods may be any one of a chimeric site-specific transgenic animal or a homologous site-specific transgenic animal.

8-2-1. Method for Preparing a Site-Specific Transgenic Animal from an Animal Cell A site-specific transgenic animal may be prepared from a transformed cell including at least one toolbox.

For example, a site-specific transgenic animal may be prepared by performing site-specific transformation in a target site present in an animal genome or inside of a target toolbox in a somatic cell via somatic cell microinjection of a gRNA into the somatic cell, into which a first toolbox is inserted, followed by SCNT. The site-specific transgenic animal may be a homologous site-specific transgenic animal.

For example, a site-specific transgenic animal, in which a donor polynucleotide is inserted into a target site present in an animal genome or inside of a target toolbox of a gamete including a third toolbox, may be prepared via gamete microinjection of the donor polynucleotide into the gamete. The site-specific transgenic animal may be a chimeric site-specific transgenic animal.

For example, a site-specific transgenic animal, in which NHEJ has occurred in a target site present in an animal genome or inside of a target toolbox of a zygote including a second toolbox, may be prepared via zygote microinjection of a polynucleotide encoding Cas9 into the zygote. The site-specific transgenic animal may be a chimeric site-specific transgenic animal.

For example, a site-specific transgenic animal may be prepared by inducing NHEJ in a target site present inside of a target toolbox via embryo microinjection of a polynucleotide encoding Cas9 and a polynucleotide encoding a gRNA into an embryo including a target toolbox. The site-specific transgenic animal may be a chimeric site-specific transgenic animal.

8-2-2. Method for Preparing a Site-Specific Transgenic Animal by Delivery of an Exo-Polynucleotide into a Tissue or Organ of an Animal A tissue or organ of an animal may include a cell including at least one toolbox. A site-specific transgenic animal may be prepared by introducing Cas9, a gRNA, or a donor polynucleotide into a tissue or organ of the animal.

For example, when the mammary gland tissue of the animal includes a cell into which a first toolbox is inserted, a site-specific transgenic animal may be prepared, in which a protein which is specifically expressed in the mammary gland is knocked out, via microinjection of a gRNA which targets, as a target site, part of the nucleotide sequence of a polynucleotide encoding the protein specifically expressed in the mammary gland in an animal genome, into the mammary gland tissue. The site-specific transgenic animal may be a chimeric site-specific transgenic animal.

For example, when the mammary gland tissue of the animal includes a cell into which a target toolbox is inserted, a site-specific transgenic animal in which a donor is inserted into the target toolbox may be prepared via microinjection of a polynucleotide encoding Cas9, a polynucleotide encoding a gRNA, and a donor polynucleotide into the mammary gland tissue. The site-specific transgenic animal may be a chimeric site-specific transgenic animal.

For example, when a reproductive organ of the animal includes a cell into which a second toolbox is inserted, a site-specific transformation may be induced in a target site present in an animal genome or inside of a target toolbox in a cell of a reproductive organ via microinjection of a polynucleotide encoding Cas9 into the reproductive organ of the animal. The offspring obtained from a gamete of the site-specific transgenic animal may also be a site-specific transgenic animal. The site-specific transgenic animal may be a chimeric site-specific transgenic animal.

8-2-3. Preparation Method of Transgenic Animal Via Breeding

A site-specific transgenic animal may be prepared via breeding between a first transgenic animal and a second transgenic animal.

For example, an offspring, in which site-specific transformation has occurred in a target site present in an animal genome or inside of a target toolbox, may be prepared via breeding between a first transgenic animal including a first toolbox and a second transgenic animal including a second toolbox.

The second transgenic animal may be an offspring of the first transgenic animal or may be blood-related to the first transgenic animal. Alternatively, the second transgenic animal may not be blood-related to the first transgenic animal.

The site-specific transgenic animal obtained via breeding may include a toolbox, which is the same as part of the toolboxes included in an animal genome of the first transgenic animal, at the same location.

The site-specific transgenic animal obtained via breeding may include a toolbox, which is the same as part of the toolboxes included in an animal genome of the second transgenic animal, at the same location.

The site-specific transgenic animal obtained via breeding may be a homologous site-specific transgenic animal.

The site-specific transgenic animal obtained from the breeding may include a homozygote site-specific transformed cell. The transgenic animal obtained via breeding may include a heterozygote site-specific transformed cell.

9. Use of Site-Specific Transgenic Animal Using CRISPR/Enzyme System 9-1. Animals with Improved Varieties The site-specific transgenic animal may be used as an animal with improved varieties.

9-2. Disease Animal Model

The site-specific transgenic animal may be used as a disease animal model.

9-3. Disease-Resistant Animal

The site-specific transgenic animal may be used as a disease-resistant animal.

9-4. Use of by-Products

The organs, meat, skin, hairs, and body fluids of the site-specific transgenic animal may be used, but parts of the site-specific transgenic animal to be used are not limited thereto.

9-5. Bioreactor

The site-specific transgenic animal may be used as a bioreactor.

[Part V] Toolbox Excision

1. Toolbox Excision by Transposase

An animal genome in a cell may include at least one toolbox. A transposon toolbox among the at least one toolbox may include an ITR polynucleotide in a first end region and a second end region.

1-1. Use of Transposase within Animal Genome 1-1-1. Construction for Toolbox Excision The animal genome may include at least one polynucleotide encoding a transposase which can interact with the ITR polynucleotide. The transposase may include an excision-only transposase.

The polynucleotide encoding the transposase may be located within a transposon toolbox.

As used herein, the term "transposon toolbox" may refer to a toolbox which includes a polynucleotide encoding a transposon as a component.

The polynucleotide encoding the transposase may be located within a toolbox other than the transposon toolbox.

The polynucleotide encoding the transposase may be located outside of the toolbox.

A promoter controlling the transcription of the polynucleotide encoding the transposase may be located upstream of the polynucleotide encoding the transposase. The promoter may be any one among a constitutive promoter, a tissue-specific promoter, and an inducible promote.

An LSL may be located between the promoter controlling the transcription of the transposase and the polynucleotide encoding the transposase.

1-1-2. Toolbox Excision Mechanism

The transposase expressed in a cell can delete the transposon toolbox present in the cell from the animal genome.

In the case where the promoter controlling the transcription of the polynucleotide encoding the transposase is a tissue-specific promoter, the transposase can be expressed in a cell of particular tissue of a transgenic animal including the animal genome. In this case, the transposon toolbox in the animal genome in a cell included in particular tissue can be deleted via interaction with the ITR polynucleotide of the transposon toolbox.

In the case where the promoter controlling the transcription of the polynucleotide encoding the transposase is an inducible promoter, the transposase can be expressed only when certain conditions are satisfied. In this case, the transposon toolbox in the animal genome in a cell which satisfies the certain conditions can be deleted through the interaction with the ITR polynucleotide of the transposon toolbox.

In the case where an LSL is located between the promoter controlling the transcription of the transposase and the polynucleotide encoding the transposase, the transposase can be expressed only when the stop codon present in the LSL is deleted via site-specific recombination by introducing Cre recombinase into the cell. In this case, the transposon toolbox in the animal genome in a cell including Cre recombinase can be deleted through the interaction with the ITR polynucleotide of the transposon toolbox.

1-2. Use of Transposase Outside of Animal Genome 1-2-1. Construction for Toolbox Excision The animal genome may not include the polynucleotide encoding a transposase which can interact with the ITR polynucleotide.

In this case, the polynucleotide encoding the transposase may be delivered into the cell. A promoter controlling the transcription of the polynucleotide encoding the transposase may be located upstream of the polynucleotide encoding the transposase. The promoter may be any one among a constitutive promoter, a tissue-specific promoter, and an inducible promoter. An LSL may be located between the promoter controlling the transcription of the transposase and the polynucleotide encoding the transposase.

The transposase itself may be introduced into the cell.

The transposase may include an excision-only transposase.

1-2-2. Toolbox Excision Mechanism

The transposase introduced into the cell can delete the transposon toolbox present in the cell from the animal genome.

In the case where the promoter controlling the transcription of the polynucleotide encoding a transposase is a tissue-specific promoter, the transposase introduced into a certain tissue of a transgenic animal including the animal genome can be expressed. In this case, the transposon toolbox in the animal genome in a cell where the transposase is introduced can be deleted through the interaction with the ITR polynucleotide of the transposon toolbox.

In the case where the promoter controlling the transcription of the polynucleotide encoding the transposase is an inducible promoter, the transposase introduced into the cell can be expressed only when certain conditions are satisfied. In this case, the transposon toolbox in the animal genome in a cell which satisfies the certain conditions can be deleted through the interaction with the ITR polynucleotide of the transposon toolbox.

In the case where an LSL is located between the promoter controlling the transcription of the transposase and the polynucleotide encoding the transposase, the transposase can be expressed only when the stop codon present in the LSL is deleted via site-specific recombination by introducing together with Cre recombinase. In this case, the transposon toolbox in the animal genome in a cell including Cre recombinase can be deleted through the interaction with the ITR polynucleotide of the transposon toolbox.

2. Toolbox Excision by Site-Specific Recombinase

An animal genome in a cell may include at least one toolbox. Among the at least one toolbox, a first end region of the RRS toolbox may include an RRS1 and a second end region may include an RRS2.

As used herein, the term "RRS toolbox" may refer to a toolbox which includes an RRS as a component.

The RRS1 and the RRS2 may be the same or different from each other.

The RRS1 and the RRS2 may be a pair with each other.

A SSR 1, which can interact with the RRS1, and A SSR 2, which can interact with the RRS2, may be the same SSR with each other.

2-1. Use of Site-Specific Recombinase within Animal Genome 2-1-1. Construction for Toolbox Excision The animal genome in a cell may include at least one polynucleotide encoding the SSR.

The polynucleotide encoding the SSR may be located within an SSR toolbox.

The polynucleotide encoding the SSR may be located in a toolbox other than the SSR toolbox.

The polynucleotide encoding the SSR may be located outside of the toolbox.

A promoter controlling the transcription of the polynucleotide encoding the SSR may be located upstream of the polynucleotide encoding the SSR. The promoter may be any one among a constitutive promoter, a tissue-specific promoter, and an inducible promoter. An LSL may be located between the promoter controlling the transcription of the polynucleotide encoding the SSR and the polynucleotide encoding the SSR.

2-1-2. Toolbox Excision Mechanism

The SSR expressed in a cell can delete the RRS toolbox from an animal genome through the interaction with the RRS1 and the RRS2.

In the case where the promoter controlling the transcription of the polynucleotide encoding the SSR is a tissue-specific promoter, the SSR can be expressed in a certain tissue of a transgenic animal including the animal genome. In this case, the RRS toolbox in the animal genome in a cell included in a certain tissue can be deleted through the interaction with the RRS1 and the RRS2 at both ends of the RRS toolbox.

In the case where the promoter controlling the transcription of the polynucleotide encoding the SSR is an inducible promoter, the SSR can be expressed only when certain conditions are satisfied. In this case, the RRS toolbox in the animal genome in a cell, which satisfies the certain conditions, can be deleted through the interaction with the RRS1 and the RRS2 at both ends of the RRS toolbox.

In the case where an LSL is located between the promoter controlling the transcription of the SSR and the polynucleotide encoding the SSR, the SSR can be expressed only when the stop codon present in the LSL is deleted via site-specific recombination by introducing Cre recombinase into the cell. In this case, the RRS toolbox in the animal genome in a cell including Cre recombinase can be deleted through the interaction with the RRS1 and the RRS2 at both ends of the RRS toolbox.

2-2. Use of Site-Specific Recombinase Outside of Animal Genome 2-2-1. Construction for Toolbox Excision The animal genome may not include the polynucleotide encoding the SSR.

In this case, the polynucleotide encoding the SSR may be delivered into the cell. A promoter controlling the transcription of the polynucleotide encoding the SSR may be located upstream of the polynucleotide encoding the SSR. The promoter may be any one among a constitutive promoter, a tissue-specific promoter, and an inducible promoter. An LSL may be located upstream of the polynucleotide encoding the SSR.

Alternatively, the SSR itself may be introduced into the cell.

2-2-2. Toolbox Excision Mechanism

The SSR introduced into the cell can delete the RRS toolbox from the animal genome through the interaction with the RRS1 and the RRS2.

In the case where the promoter controlling the transcription of the polynucleotide encoding the SSR is a tissue-specific promoter, the SSR introduced into a cell of certain tissue of a transgenic animal including the animal genome can be expressed. In this case, the RRS toolbox in the animal genome in the cell, into which the SSR is introduced, can be deleted through the interaction with the RRS1 and the RRS2 at both ends of the RRS toolbox.

In the case where the promoter controlling the transcription of the polynucleotide encoding the SSR is an inducible promoter, the SSR introduced into a cell can be expressed only when certain conditions are satisfied. In this case, the RRS toolbox in the animal genome in a cell which satisfies the certain conditions can be deleted through the interaction with the RRS1 and the RRS2 at both ends of the RRS toolbox.

In the case where an LSL is located between the promoter controlling the transcription of the SSR and the polynucleotide encoding the SSR, the SSR can be expressed only when the stop codon present in the LSL is deleted via site-specific recombination by introducing together with Cre recombinase. In this case, the RRS toolbox in the animal genome in a cell including Cre recombinase can be deleted through the interaction with the RRS1 and the RRS2 at both ends of the RRS toolbox.

Hereinafter, specific embodiments according to the details disclosed by the present disclosure will be described.

[Toolbox Including at Least One Between RNA-Guided Endonuclease and Guide Nucleic Acid]

1. Toolbox Construction

The toolboxes disclosed by some embodiments of the present disclosure may include a first ITR sequence, at least one between the polynucleotide encoding an RNA-guided endonuclease and the polynucleotide encoding a guide nucleic acid, and a second ITR sequence.

Since the first ITR sequence, a polynucleotide encoding an RNA-guided endonuclease, a polynucleotide encoding a guide nucleic acid and a second ITR sequence were described above, the detailed explanation is omitted.

The construction of the toolbox will be described in detail by referring to FIG. 1.

The toolbox (100) may include a polynucleotide encoding the component of an engineered nuclease (110) between a first ITR sequence (101) and a second ITR sequence (107).

Figure 2:
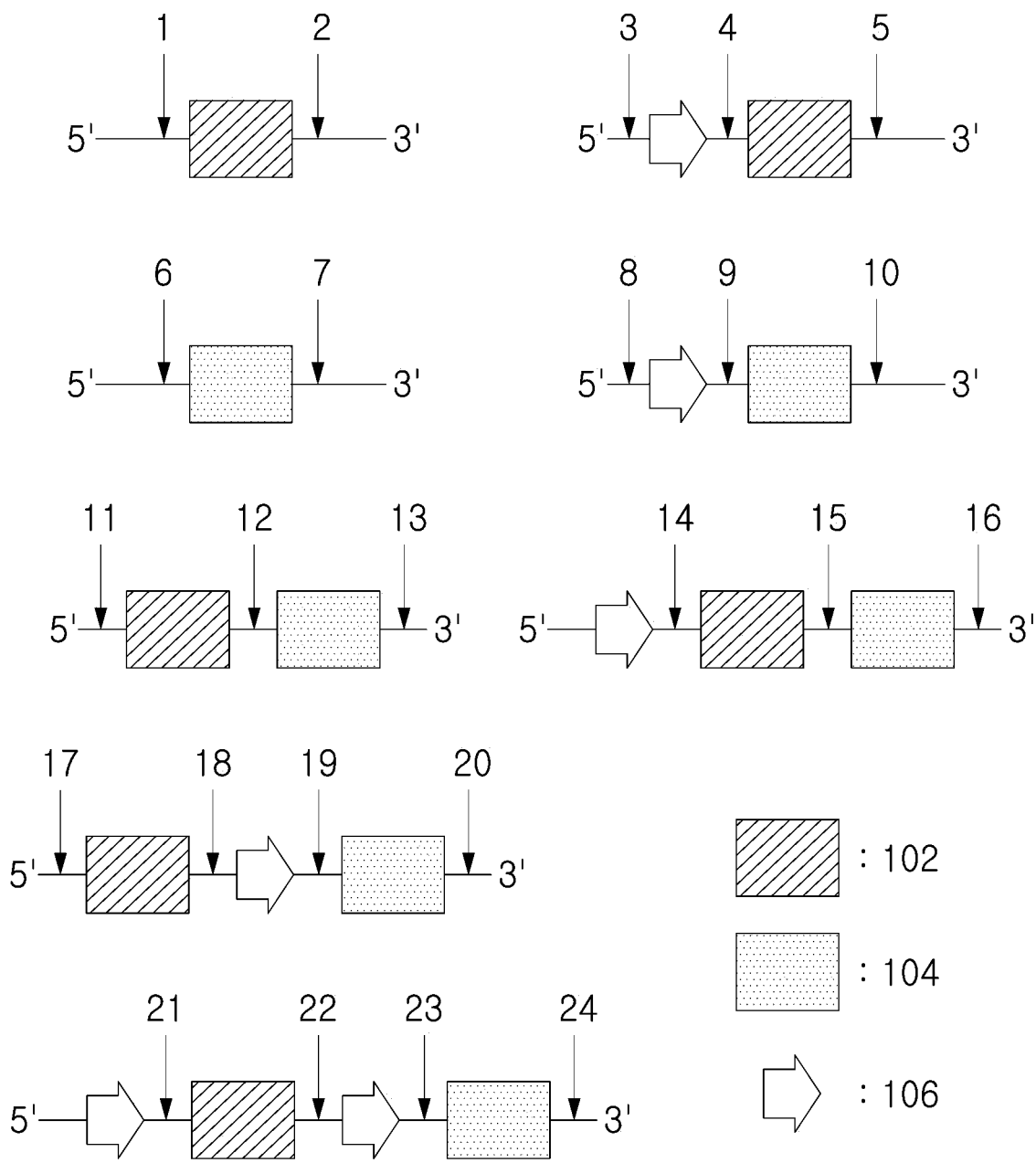
FIG. 2 illustrates some embodiments of a polynucleotide that encodes the component of an engineered nuclease.

FIG. 2 illustrates various embodiments of the polynucleotide encoding the component of the engineered nuclease (110).

The polynucleotide encoding the component of the engineered nuclease (110) may include at least one between a polynucleotide encoding an RNA-guided endonuclease (102) and a polynucleotide encoding a guide nucleic acid (104).

The RNA-guided endonuclease may be a Cas9 protein or Cpf1 protein which constitutes the engineered nuclease complex; and the guide nucleic acid may be a gRNA which constitutes the engineered nuclease complex.

Additionally, the polynucleotide encoding the component of the engineered nuclease (110) may further include a polynucleotide encoding a promoter (106) for the expression of the RNA-guided endonuclease and/or guide nucleic acid.

The toolbox (100) may further include a recombinase recognition site (RRS).

The type and the number of the recombinase recognition site (RRS) may be one or more.

The location in which the recombinase recognition site (RRS) may be present within the toolbox (100) may be various. For example, the recombinase recognition site (RRS) may be located in one or more locations among the 1 to 24 indicated in FIG. 2.

The type, number, and/or location of the recombinase recognition site (RRS) may be designed in consideration of the changes in the construction of a toolbox.

The changes in the construction may include the exchange or deletion of the polynucleotide included in the toolbox, and may include the insertion of the polynucleotide which is not included in the toolbox into the toolbox.

Using FIG. 2, some embodiments in which the construction of the toolbox are changed according to the construction of toolbox, which includes a recombinase recognition site (RRS), are described hereinbelow.

For example, in the case where a toolbox is designed to include a recombinase recognition site (RRS) in 5' direction and 3' direction with reference to the polynucleotide encoding the RNA-guided endonuclease (102), the polynucleotide encoding the RNA-guided endonuclease included in the toolbox can be exchanged with a different type of a polynucleotide through site-specific recombination. Specifically, when different types of recombinase recognition sites (RRSs) are included at locations 4 and 5 of FIG. 2, the polynucleotide encoding the RNA-guided endonuclease included in the toolbox can be exchanged with a different type of a polynucleotide through site-specific recombination.

In another example, in the case where a toolbox is designed to include a recombinase recognition site (RRS) which can form a pair in 5' direction and 3' direction with reference to the polynucleotide encoding the RNA-guided endonuclease (102), the polynucleotide encoding the RNA-guided endonuclease included in the toolbox can be deleted through site-specific recombination. Specifically, in the case where a polynucleotide encoding a loxp is included at locations 4 and 5 of FIG. 2, the polynucleotide encoding the RNA-guided endonuclease included in the toolbox can be deleted through site-specific recombination.

In still another example, in the case where a toolbox is designed to include a recombinase recognition site (RRS) in 5' direction and/or 3' direction with reference to a polynucleotide encoding an RNA-guided endonuclease (102), a polynucleotide which is not included in the toolbox can be inserted into the toolbox through site-specific recombination. Specifically, in the case where a recombinase recognition site (RRS) is included at location 5 of FIG. 2, a polynucleotide which is not included in the toolbox can be inserted into the toolbox through site-specific recombination.

Additionally, the type, number, and/or location of the recombinase recognition site (RRS) may be designed in consideration of the expression control of an RNA or protein, which is encoded by a polynucleotide that constitutes the toolbox.

Using FIG. 2, some embodiments in which the expression of an RNA or protein is controlled according to the construction of the toolbox, which includes a recombinase recognition site (RRS), are described hereinbelow.

The control of the expression of an RNA or protein encoded by a polynucleotide that constitutes the toolbox may include the insertion of the polynucleotide encoding a promoter at a later stage using the recombinase recognition site (RRS).

For example, in the case where a recombinase recognition site (RRS) is included in 5' direction of the polynucleotide encoding the RNA-guided endonuclease, it is possible to control the expression of the RNA-guided endonuclease by inserting a promoter for transcription and/or translation of the polynucleotide encoding the RNA-guided endonuclease through site-specific recombination.

Specifically, in the case where a recombinase recognition site (RRS) is included in 17 of FIG. 2, it is possible to control the expression of the RNA-guided endonuclease by inserting a promoter for transcription and/or translation of the polynucleotide encoding an RNA-guided endonuclease through site-specific recombination.

The control of the expression of an RNA or protein encoded by a polynucleotide that constitutes the toolbox may include temporary termination of the expression by the polynucleotide encoding the promoter already present in the toolbox using a recombinase recognition site (RRS).

For example, in the case where a polynucleotide encoding a first recombinase recognition site (RRS1)-stop codon-a polynucleotide encoding a first recombinase recognition site (RRS1) (hereinafter, RSR1); or a first recombinase recognition site (RRS1)-transcription stop codon-a polynucleotide encoding a first recombinase recognition site (RRS1) (hereinafter, RTR1) is included between the polynucleotide encoding the RNA-guided endonuclease (102) and the promoter (106) for transcription and/or translation of the polynucleotide encoding the RNA-guided endonuclease, the RNA-guided endonuclease cannot be expressed until a polynucleotide encoding the RSR1 and/or RTR1 is deleted through site-specific recombination, and ultimately, an engineered nuclease complex cannot be formed.

Specifically, in the case where a polynucleotide encoding the RSR1 or RTR1 is included in 21 of FIG. 2, the RNA-guided endonuclease cannot be expressed until a polynucleotide encoding the RSR1 and/or RTR1 is deleted through site-specific recombination, and ultimately, an engineered nuclease complex cannot be formed.

As described above, the toolbox may have various constitutions, and the effects which can be exhibited in cells or animals having a genome into which a toolbox is inserted can also vary according to the construction of the toolbox.

Hereinafter, cells and fertilized eggs having a genome into which the toolbox is inserted will be described.

2. Cell and Fertilized Egg Including Genome into which Toolbox is Inserted 2-1. Constitution of Cell and Fertilized Egg Including Genome into which Toolbox is Inserted 2-1-1. Genome or Chromosome into which Toolbox is Inserted The toolbox provided by the present disclosure can be inserted into the genome of a cell.

The location of a genome at which the toolbox can be inserted into may be random.

The number of the toolbox which can be inserted into a genome may be one.

The number of the toolbox which can be inserted into a genome may be two or more.

The type of the toolbox which can be inserted into a genome may be one or more.

For example, a first toolbox and a second toolbox may be inserted into the genome. In this case, the sequence of the first toolbox may be the same as or different from that of the second toolbox.

When the cell is a eukaryotic cell, the toolbox provided by the present disclosure may be inserted into the chromosome.

The location of chromosome at which the toolbox can be inserted into may be random.

The number of the toolbox which can be inserted into the chromosome may be one.

The number of the toolbox which can be inserted into the chromosome may be two or more.

The type of the toolbox which can be inserted into the chromosome may be one or more.

For example, a first toolbox and a second toolbox may be inserted into the chromosome. In this case, the sequence of the first toolbox may be the same as or different from that of the second toolbox.

Hereinafter, assuming the case where one type of toolbox is inserted into the chromosome, the locations of the chromosome at which the toolbox is inserted will be described in detail.

Figure 3:
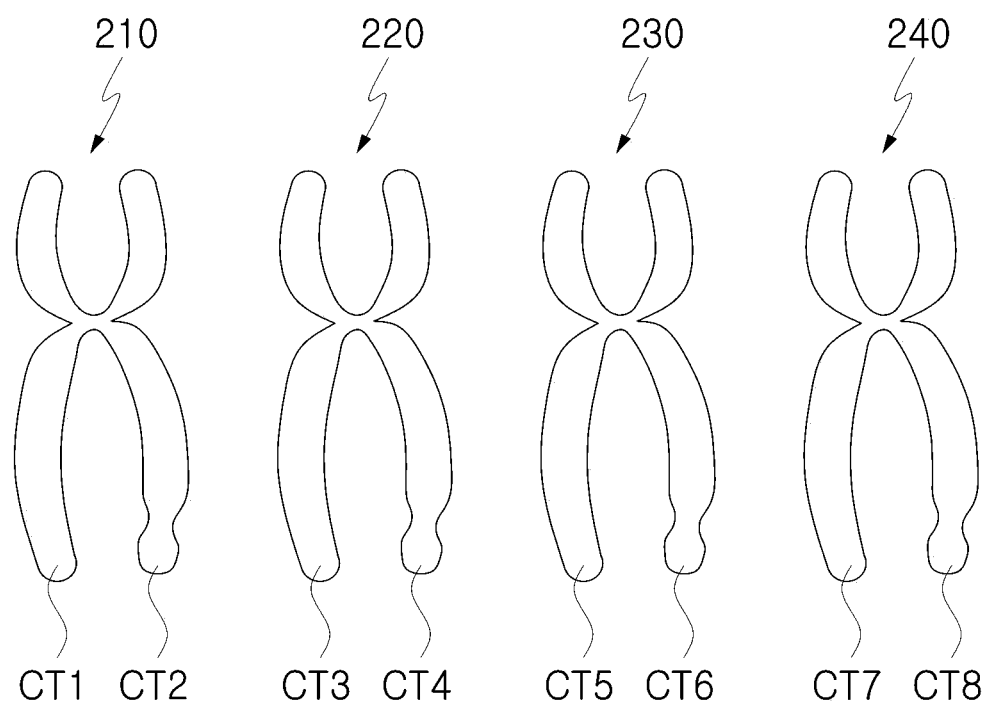
FIG. 3 illustrates chromosomes formed from the genome present in a cell.

For the convenience of explanation, the following description assumes that there are four chromosomes which are formed from a genome present in one cell. FIG. 3 illustrates 4 chromosomes formed from the genome present in one cell.

As illustrated in FIG. 3, the first chromosome (210) and the second chromosome (220) illustrated in FIG. 3 are in a relationship of homologous chromosomes, and the third chromosome (230) and the fourth chromosome (240) are also in a relationship of homologous chromosomes.

The first chromosome (210) consists of a first chromatid (CT1) and a second chromatid (CT2), and the second chromosome (220) consists of a third chromatid (CT3) and a fourth chromatid (CT4). Additionally, the third chromosome (230) consists of a fifth chromatid (CT5) and a sixth chromatid (CT6), and the fourth chromosome (240) consists of a seventh chromatid (CT7) and an eighth chromatid (CT8).

Figure 4:
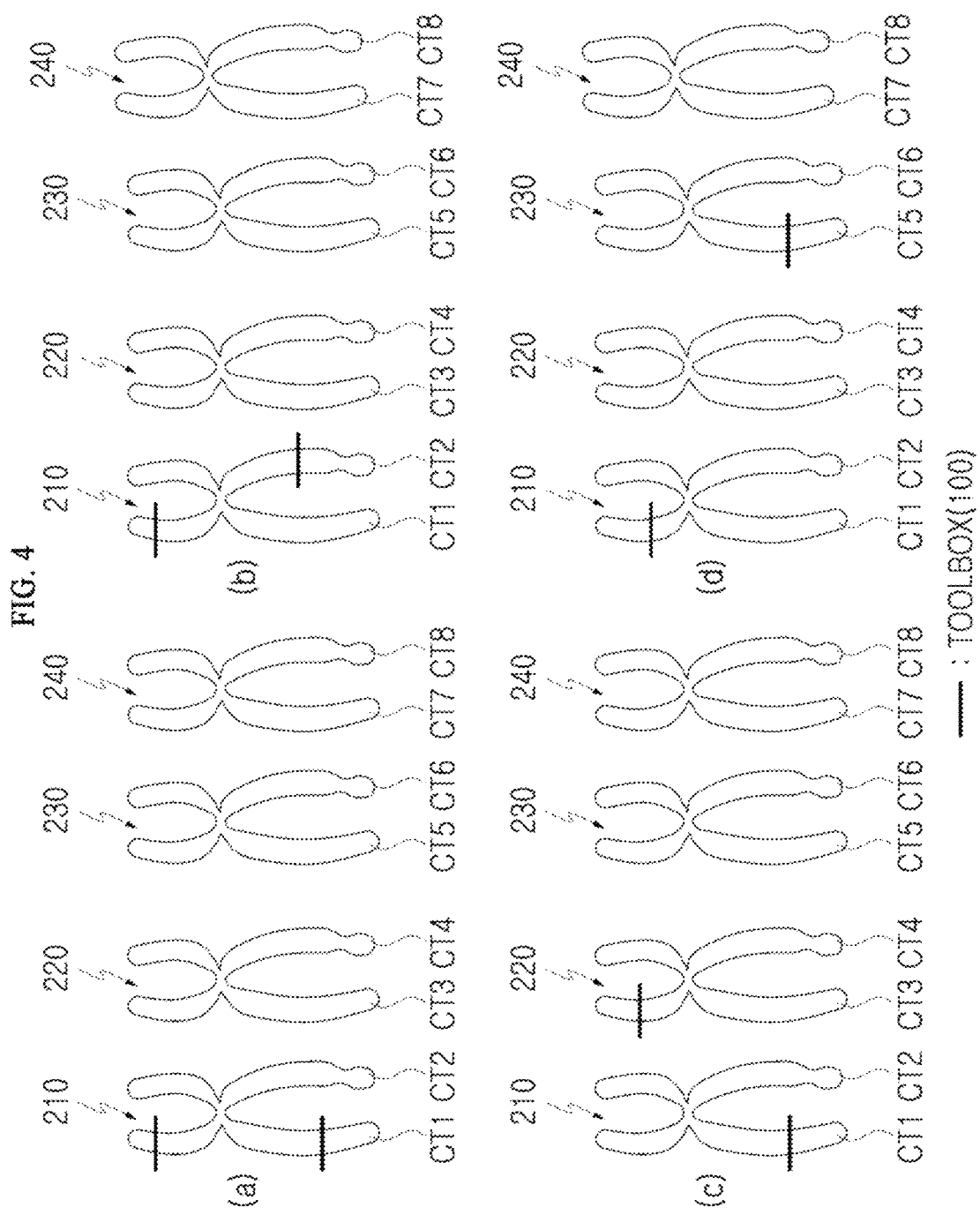
FIG. 4 illustrates several forms of a toolbox inserted into chromosome.

FIG. 4 illustrates some embodiments of a toolbox in which the toolbox (100) is inserted into any one of a first chromatid to an eighth chromatid (CT1 to CT8).

The toolbox (100) can be inserted into only one among the first chromatid to the eighth chromatid (CT1 to CT8).

The toolbox (100) can be inserted into two or more among the first chromatid to the eighth chromatid (CT1 to CT8).

For example, the toolbox (100) can only be inserted into the first chromatid (CT1) among the chromosomes of a cell (see FIG. 4(a)).

In another example, the toolbox (100) can be inserted into the first chromatid (CT1) and the second chromatid (CT2) of the first chromosome (210) among the chromosomes of a cell (see FIG. 4(b)).

In still another example, the toolbox (100) can be inserted into the first chromatid (CT1) of the first chromosome (210) and into the third chromatid (CT3) of the second chromosome (220) among the chromosomes of a cell (see FIG. 4(c)). In this case, the first chromosome (210) and the second chromosome (220) may be in a relationship of homologous chromosomes.

In still another example, the toolbox (100) can be inserted into the first chromatid (CT1) of the first chromosome (210) and into the fifth chromatid (CT5) of the third chromosome (230) among the chromosomes of a cell (see FIG. 4(d)). In this case, the first chromosome (210) and the third chromosome (230) may not be in a relationship of homologous chromosomes.

2-1-2. Type of Cells Having Genome or Chromosome into which Toolbox is Inserted

A toolbox may be inserted into the genome and/or chromosome of a somatic cell, a gamete, or a stem cell.

For the convenience of explanation, the following description assumes that the type of a toolbox inserted into the genome and/or chromosome of a somatic cell, a gamete, or a stem cell is one type, and the toolbox is the toolbox (100) described above.

Figure 5:
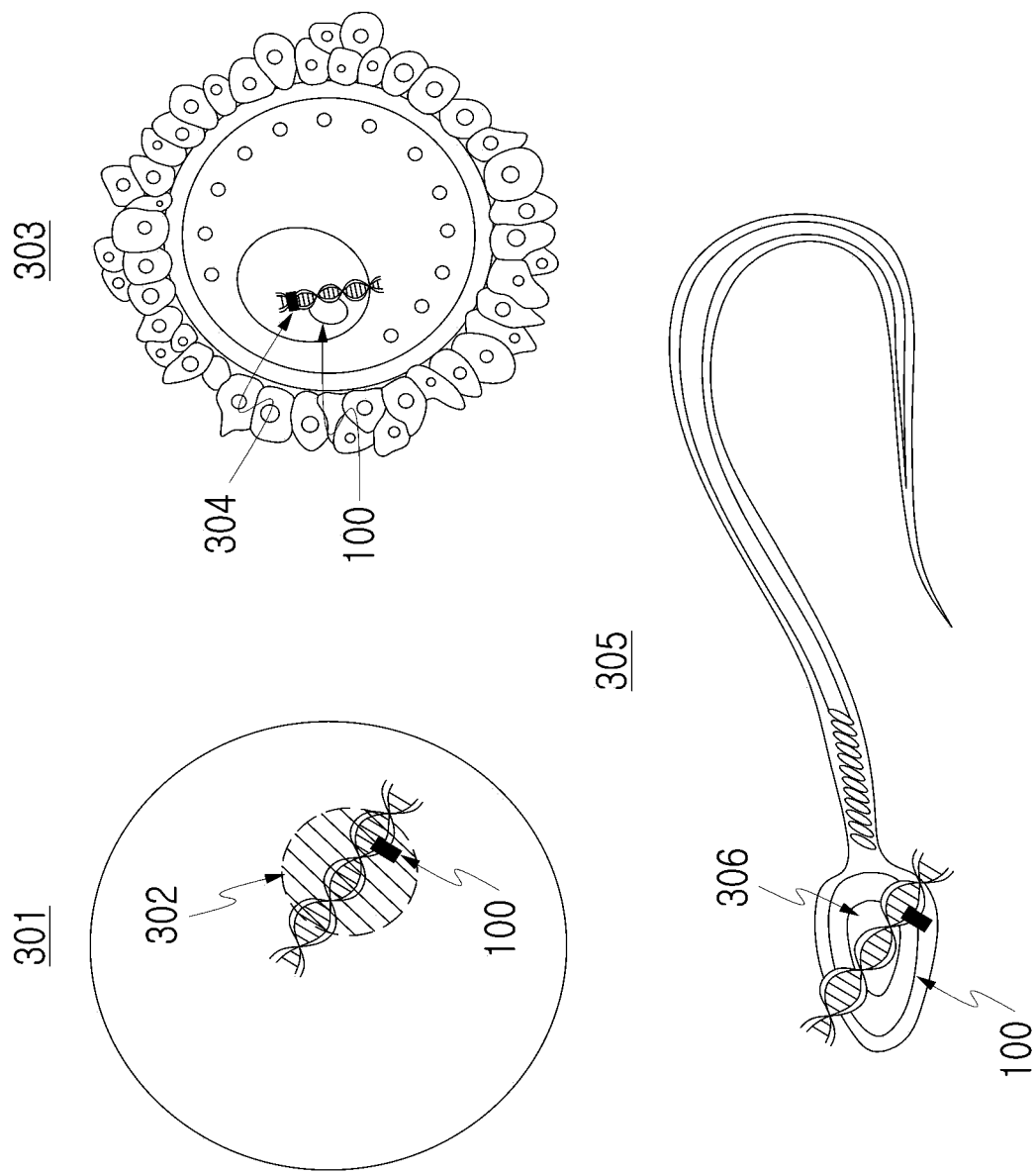
FIG. 5 illustrates a somatic cell and a germ cell, which respectively have a genome into which a toolbox is inserted.

FIG. 5 illustrates a somatic cell (301) and a gamete, which respectively have a genome into which the toolbox (100) is inserted. The gamete may be an ovum (303) and a sperm (305).

The genome and/or chromosome, into which the toolbox (100) is inserted, may be included in the nucleus (302) of the somatic cell, the nucleus (304) of the ovum, and the nucleus (306) of the sperm.

The toolbox (100), which is inserted into the genome of the cell, may be transcribed and/or translated according to the expression mechanism of each cell. In this case, the expression of the endo-polynucleotide, which has been already present in the genome of the cell, may not be affected.

2-1-3. Fertilized Egg Including Genome into which Toolbox is Inserted

A toolbox may be inserted into the genome or chromosome of a fertilized egg (fertilized ovum) or embryo.

According to an embodiment of the present specification, a transformed fertilized egg or transgenic embryo, which has a genome including a polynucleotide encoding an RNA-guided endonuclease that is included between a first ITR sequence and a second ITR sequence, can be provided. Specifically, the embryo may be an embryo of an artiodactyl.

Additionally, a transformed fertilized egg or transgenic embryo, which further includes polynucleotides encoding a guide nucleic acid, which be capable of specifically binding to a target site present in the genome of the fertilized egg or embryo, between the first ITR sequence and the second ITR sequence, can be provided. In particular, an expression control element may be included in at least one among the 5' end of the polynucleotide encoding an RNA-guided endonuclease and the 5' end of the polynucleotide encoding the guide nucleic acid.

Figure 6:
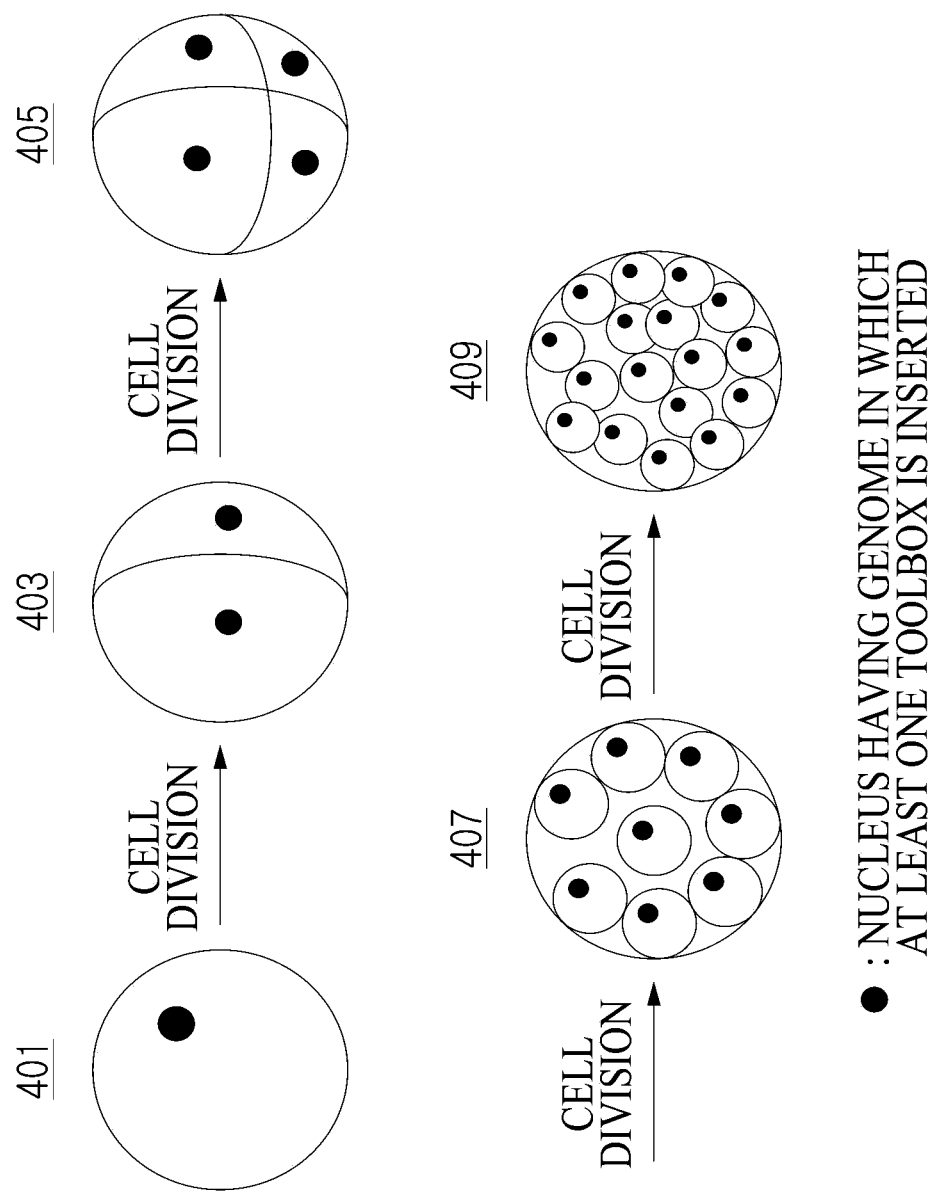
FIG. 6 illustrates a 1-cell stage fertilized egg which has a genome into which a toolbox is inserted; and a 2-cell stage embryo, a 4-cell stage embryo, an 8-cell stage embryo, and a 16-cell stage embryo which are divided from the 1-cell stage fertilized egg.

FIG. 6 illustrates a fertilized egg which has a genome into which the toolbox (100) is inserted; and a 2-cell stage embryo, a 4-cell stage embryo, an 8-cell stage embryo, and a 16-cell stage embryo by the cell division from the fertilized egg into which the toolbox (100) is inserted.

In the case where the stage in which the toolbox (100) has started to be inserted into the genome of the fertilized egg is a 1-cell stage fertilized egg, the 1-cell stage fertilized egg (401) into which the toolbox (100) is inserted may be homologous (see FIG. 6).

When the 1-cell stage fertilized egg (401) having a genome, into which the toolbox (100) is inserted, undergoes a cell division, the fertilized egg (401) may be developed into a 2-cell stage embryo (403), a 4-cell stage embryo (405), an 8-cell stage embryo (407), a 16-cell stage embryo (409), a morula, a blastula (blastocyst), or a gastrula, each of which consists of cells having a genome into which the toolbox (100) is inserted.

However, the number and the location of the toolbox (100), which is inserted into the genome of the 2' cell-stage embryo, may be different from the number and the location of the toolbox (100), which is inserted into the genome of the $2^{n+1}$ cell stage embryo (n is an integer of 0 or greater). Additionally, the location and the number of the toolbox (100), which is inserted into the genomes of the $2^{n+1}$ cells that constitute the $2^{n+1}$ cell stage embryo, may be different from one another.

This is because, although the location and the number of the toolbox, which is inserted into the nucleus of the 1-cell stage fertilized egg (401), can be maintained in the 2-cell stage embryo (403), more toolboxes may be additionally inserted due to the interaction between a first plasmid vector, a transposase and the genomes of the 2-cell stage embryo (403), as described above even in a state of the 2-cell stage embryo 403. Furthermore, this is because part of the toolbox (100) already inserted into the genome can be deleted due to the interaction between the genomes of the 2-cell stage embryo (403) and the transposase.

That is, according to an embodiment provided by the present specification, a transgenic embryo, which includes a first cell having a genome that includes a first toolbox and a second cell having a genome that includes a second toolbox, can be provided, in which in the transgenic embryo, the first toolbox may be present in a first locus and the second toolbox may be present in a second locus different from the first locus. The first toolbox and the second toolbox may each include at least one between a polynucleotide encoding an RNA-guided endonuclease and a polynucleotide encoding a guide nucleic acid that can specifically bind to a target site. The target site is an endo-polynucleotide of the embryo or an exo-polynucleotide included in the genome of the embryo, and may be included between a first ITR sequence and a second ITR sequence. In particular, the sequence of the first toolbox may be the same as or different from that of the second toolbox.

According to another embodiment provided by the present specification, a transgenic embryo, which includes a first cell having a genome that includes a first toolbox and a second cell having a genome that includes a second toolbox, can be provided, in which in the transgenic embryo, the first toolbox may be present in a first locus and the second toolbox may be present in a second locus where the first locus and the second locus are the same with each other. The first toolbox and the second toolbox may each include at least one between a polynucleotide encoding an RNA-guided endonuclease and a polynucleotide encoding a guide nucleic acid that can specifically bind to a target site. The target site is an endo-polynucleotide of the embryo or an exo-polynucleotide included in the genome of the embryo, and may be included between a first ITR sequence and a second ITR sequence. In particular, the sequence of the first toolbox is different from that of the second toolbox.

For example, the genome of the first cell may further include a third toolbox, in which the sequence of the third toolbox is the same as that of the first toolbox.

In another example, the genome of the second cell may further include a fourth toolbox, in which the sequence of the fourth toolbox is the same as that of the second toolbox.

The transgenic embryo may further include a third cell having a genome which does not include the polynucleotide encoding the RNA-guided endonuclease and the polynucleotide encoding the guide nucleic acid.

Figure 7:
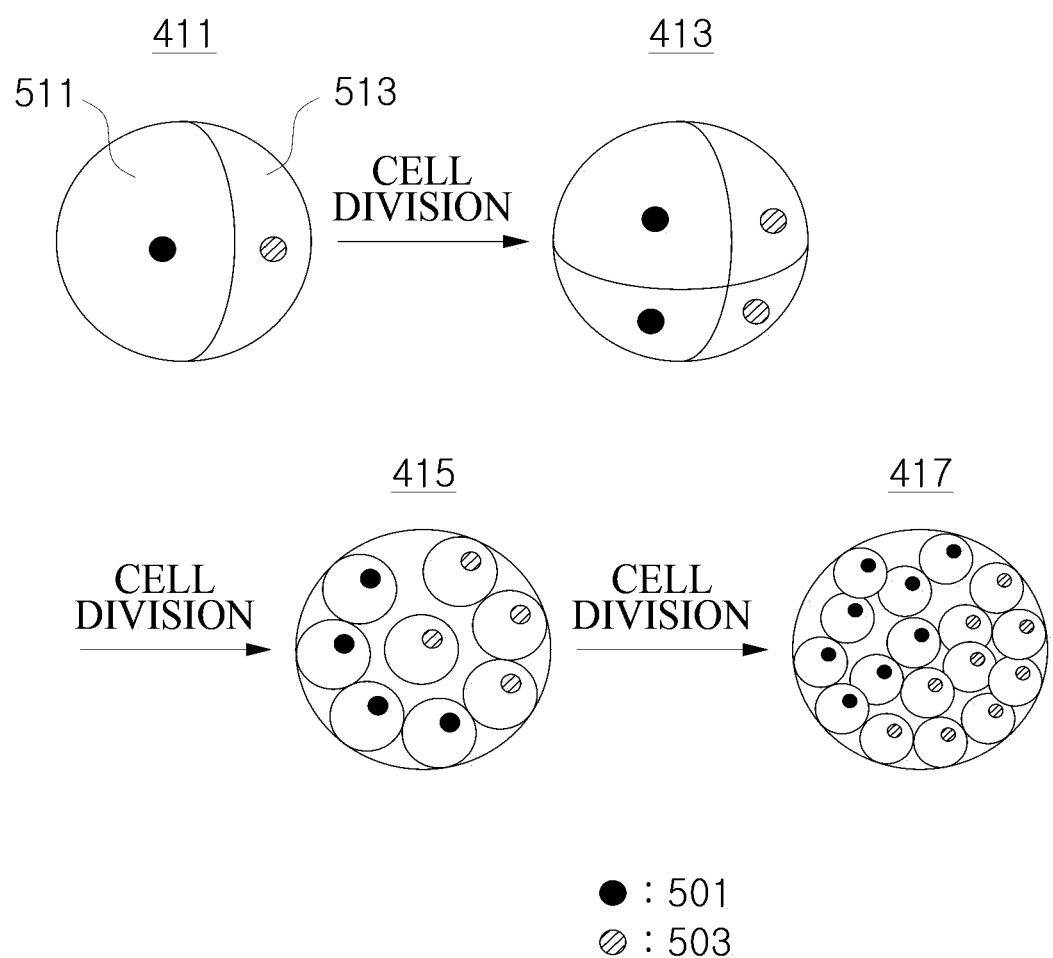
FIG. 7 illustrates a 2-cell stage embryo, a 4-cell stage embryo, an 8-cell stage embryo, and a 16-cell stage embryo, into which a toolbox is inserted into each genome of some cells.

FIG. 7 illustrates a 2-cell stage embryo, a 4-cell stage embryo, an 8-cell stage embryo, and a 16-cell stage embryo, into which a toolbox (100) is inserted into each genome of some cells. In FIG. 7, a first nucleus (501) represents a nucleus which has a genome where the toolbox (100) is inserted, and the second nucleus (503) represents a nucleus which has a genome where the toolbox (100) is not inserted.

In the case where the stage in which the toolbox (100) has started to be inserted into the genome is a $2^m$ cell stage embryo, the toolbox (100) can only be inserted into the genome of some cells among the cells that constitute the embryos after the $2^m$ cell stage (m is a natural number of 1 or greater). In this case as well, the toolbox can be inserted into the genomes of all cells that constitute the embryos. However, this can be explained from those described above, and thus, the explanations are provided being limited only to those cases where the toolbox is inserted into the genomes of some cells among the cells that constitute the embryos.

For example, in the case where the stage in which the toolbox (100) has started to be inserted into the genome of the fertilized egg is a 2-cell stage embryo, the toolbox (100) can only be inserted into the genome of a first cell (511) among the cells that constitute the 2-cell stage embryo (411).

When the 2-cell stage embryo (411), in which the toolbox (100) is inserted into the genome of one cell, undergoes a cell division, the 2-cell stage embryo (411) may be developed into a 4-cell stage embryo (413), an 8-cell stage embryo (415), a 16-cell stage embryo (417), a morula, a blastula, or a gastrula, in which the toolbox is inserted into only the genomes of some cells.

That is, according to some embodiments provided by the present specification, a chimeric transgenic embryo may be provided, in which the chimeric transgenic embryo may include a first cell, which has a genome that includes a toolbox, and a second cell, which has a genome that does not include a toolbox Specifically, a transgenic embryo may be provided, in which the transgenic embryo includes a first cell having a genome that includes a first toolbox and a target site; and a second cell having a genome that includes the target site.

The first toolbox may include at least one between a polynucleotide encoding a first RNA-guided endonuclease and a polynucleotide encoding a first guide nucleic acid that can bind to the target site; and the genome of the second cell may not include a polynucleotide encoding a second RNA-guided endonuclease and a polynucleotide encoding a second guide nucleic acid that can specifically bind to the target site. Additionally, an ITR sequence may be further included at 5' end and 3' end of the first toolbox.

In particular, the sequence of the polynucleotide encoding the first RNA-guided endonuclease and the sequence of the polynucleotide encoding the second RNA-guided endonuclease may be the same or different from each other; and the sequence of the polynucleotide encoding the first guide nucleic acid and the sequence of the polynucleotide encoding the second guide nucleic acid may be the same or different from each other.

The target site may be an endo-polynucleotide.

Specifically, the target site may be a nucleotide sequence of 18 bp to 25 bp present in the genome of the transgenic embryo.

The target site may be an exo-polynucleotide.

For example, the target site may be a sequence adjacent to the 5' end or 3' end of a PAM sequence; and the target site and the PAM sequence may be included between a first ITR sequence and a second ITR sequence.

However, in this case as well for the same reason as described above, the number and the location of the toolbox (100) inserted into the genome of the $2^m$ cell stage embryo may be different from the number and the location of the toolbox (100) inserted into the genome of the $2^{m+1}$ cell stage embryo. Additionally, the location and the number of the toolbox 100, which is inserted into the genomes of the $2^{m+1}$ cells that constitute the $2^{m+1}$ cell stage embryo, may be different from one another.

In the case where the stage in which the toolbox (100) has started to be inserted into the genome is a $2^m$ cell stage embryo, the toolbox (100) may be inserted into a different locus per each genome of cells that constitute the embryo after the $2^m$ cell stage (m is a natural number of 1 or greater).

2-2. Method for Producing Cells and/or Fertilized Eggs Including Genome into which Toolbox is Inserted Hereinafter, several methods for producing cells having a genome into which the toolbox (100) is inserted are described. For the convenience of explanation, it is assumed that there is one type of toolbox that can be inserted into the genome.

One method for preparing a cell into which the toolbox (100) is inserted may include delivering the toolbox (100) into a cell. In particular, the toolbox (100) may include a transposon gene and a polynucleotide that encodes the component of the engineered nuclease.

There may be various methods for delivering the toolbox (100) into a cell.

For example, the toolbox may be delivered into the cell by the introduction of the polynucleotide encoding the toolbox into the cell. The introduction of the polynucleotide encoding the toolbox into the cell may include a method in which the polynucleotide encoding the toolbox is incorporated into a plasmid vector and then introduced into the cell. Additionally, the introduction of the polynucleotide encoding the toolbox into the cell may include a method in which the polynucleotide encoding the toolbox is incorporated into a viral vector and then transduced into the cell.

One method for preparing a cell into which the toolbox (100) is inserted may include delivering a transposase into the cell.

There may be various methods for delivering the transposase into the cell.

For example, the transposase may be delivered into the cell by the introduction of the transposase in the form of a protein or polypeptide.

In another example, the transposase may be delivered into the cell by the introduction of the polynucleotide encoding the transposase into the cell.

The introduction of the polynucleotide encoding the transposase into the cell may include the incorporation of the polynucleotide encoding the transposase into a plasmid vector followed by the introduction of the resultant into the cell. Additionally, the introduction of the polynucleotide encoding the transposase into the cell may include the incorporation of the polynucleotide encoding a transposase into a viral vector followed by the transduction of the resultant into the cell.

The polynucleotide encoding the transposase may be incorporated together into a vector comprising a polynucleotide encoding the toolbox, and then delivered into a cell. Additionally, the polynucleotide encoding the transposase may be incorporated into a vector, which is different from the vector where the polynucleotide encoding the toolbox is included, and then delivered into a cell. In particular, the vector may be a non-viral vector or viral vector.

In the case where the polynucleotide encoding the transposase is incorporated into a plasmid vector and then introduced into the cell, the plasmid may be transported into the inside of the nucleus and then an mRNA encoding the transposase may be produced in the nucleus through transcription. The produced mRNA may be transported into the cytoplasm and interact with a ribosome and a tRNA in the cytoplasm, and the transposase may be expressed in the cytoplasm through the interaction. The transposase expressed by the above mechanism may be introduced into the inside of the nucleus.

Hereinafter, the mechanism by which the toolbox is inserted into the genome of a cell by the toolbox and a transposase delivered into the cell will be described. The toolbox (100) and the transposase delivered into the cell by the above-described method may be introduced into the cytoplasm of the cell. The toolbox (100) and the transposase introduced into the cytoplasm may be transported into the inside of the nucleus through nuclear pores.

In the inside of the nucleus, the transposase can interact with a first ITR sequence (101) and a second ITR sequence (107), which are components of the toolbox (100), the toolbox (100) can be inserted into the genome by the interaction. The constitution of the toolbox (100) can be referred to FIG. 1.

In the case where the toolbox (100) is incorporated into a plasmid vector and then delivered into the cell, the toolbox (100) can be deleted from the plasmid vector and the deleted toolbox (100) can be inserted into the genome of the cell.

The cell may be an isolated cell, or a non-isolated cell included in the organ or tissue of an animal.

One method for preparing a non-isolated cell having a genome, into which the toolbox (100) is inserted, may include delivering the toolbox (100) and the transposase by a method of direct injection into a tissue or organ of an individual.

Even in this case, the toolbox (100) can be inserted into the genome of the non-isolated cell in a manner similar to the mechanism in which the toolbox (100) is inserted into the genome of the isolated cell.

In the case where the tissue or organ is a reproductive tissue or reproductive organ, there is an advantage in that transformed gametes can be obtained continuously.

Hereinafter, several methods for producing a fertilized egg and/or embryo having a genome into which the toolbox (100) is inserted will be described. As described above, for the convenience of explanation, it is assumed that there is one type of a toolbox that can be inserted into the genome of a fertilized egg.

One method for producing a fertilized egg and/or embryo having a genome into which the toolbox (100) is inserted may include the microinjection of the toolbox (100) into the fertilized egg and/or embryo.

One method for producing a fertilized egg and/or embryo having a genome into which the toolbox (100) is inserted may include the microinjection of a transposase into the fertilized egg and/or embryo.

The method for the delivery of the toolbox and the transposase into the cell is described above and thus the specific details are omitted herein.

One exemplary method for preparing a transgenic embryo provided by the present specification may include the microinjection of a vector, which includes a transposon gene and a polynucleotide encoding the component of an engineered nuclease, into a fertilized egg or embryo. Additionally, the method may include the microinjection of a transposase, which can interact with the transposon gene, into a fertilized egg or embryo.

The transposase may be in the form of a protein, a polypeptide, or a polynucleotide encoding the transposase. The polynucleotide may be one which is incorporated into a plasmid vector or viral vector. Furthermore, the polynucleotide encoding the transposase may be incorporated into a single vector together with the polynucleotide encoding the transposon gene and the component of the engineered nuclease and then microinjected into the fertilized egg or embryo.

In an exemplary embodiment of a transgenic embryo that can be prepared by the above method, the transgenic embryo may include a first cell, in which a polynucleotide encoding the components of a first engineered nuclease has a genome included in a first locus and a second cell, in which a polynucleotide encoding the components of a second engineered nuclease has a genome included in a second locus that is different from the first locus. In particular, the sequence of the polynucleotide encoding the components of the first engineered nuclease and the sequence of the polynucleotide encoding the components of the second engineered nuclease may be the same or different from each other.

In another exemplary embodiment of a transgenic embryo that can be prepared by the above method, the transgenic embryo may include a first cell, in which a polynucleotide encoding the components of a first engineered nuclease has a genome included in a first locus and a second cell, in which a polynucleotide encoding the components of a second engineered nuclease has a genome included in the first locus. In particular, the sequence of the polynucleotide encoding the components of the first engineered nuclease and the sequence of the polynucleotide encoding the components of the second engineered nuclease may be the same or different from each other.

One method for preparing a fertilized egg and/or embryo, which has a genome into which the toolbox (100) is inserted, may include performing a somatic cell nuclear transfer (SCNT) using a genome into which the toolbox (100) is inserted.

An exemplary method for preparing a transgenic embryo provided by the present specification may include a method for preparing a transgenic donor cell, in which component of an engineered nuclease are expressed, and a method for transplanting the nucleus of the transgenic donor cell into an enucleated ovum.

The preparation of the transgenic donor cell may include transforming a cell with a vector which includes a polynucleotide encoding a transposon gene and the component of the engineered nuclease. Additionally, the preparation of the transgenic donor cell may further include transforming a cell with a transposase that can interact with the transposon gene.

The transposase may be in the form of a protein, a polypeptide, or a polynucleotide encoding the transposase. The polynucleotide may be one which is incorporated into a plasmid vector or viral vector. Furthermore, the polynucleotide encoding the transposase may be incorporated into a single vector together with the polynucleotide encoding the transposon gene and the component of the engineered nuclease and then microinjected into a fertilized egg or embryo.

The mechanism by which the toolbox (100) is inserted into the genome of a cell that constitutes the fertilized egg is similar to the mechanism by which the toolbox (100) is inserted into the genome of an isolated cell.

3. Transgenic Animal which Includes Genome into which Toolbox is Inserted 3-1. Transgenic Animal which Includes Genome into which Toolbox is Inserted According to some embodiments provided by the present specification, a transgenic animal including a genome into which a toolbox is inserted can be provided.

According to an exemplary embodiment provided by the present specification, a transgenic animal having a genome, which includes a polynucleotide encoding an RNA-guided endonuclease that is included between a first ITR sequence and a second ITR sequence, may be provided. Specifically, the animal may be an artiodactyl.

Additionally, a transgenic animal, in which the polynucleotide encoding a guide nucleic acid that can specifically bind to a target site present in the animal is further included between the first ITR sequence and the second ITR sequence, may be provided. In particular, an expression control element may be included in one or more between the 5' end of a polynucleotide encoding an RNA-guided endonuclease and the 5' end of a polynucleotide encoding the guide nucleic acid.

In the present disclosure, a transgenic animal having a genome into which a toolbox is inserted refers to an animal having at least one cell having a genome into which the toolbox is inserted. The transformation may include both a temporary transformation and a permanent transformation.

Furthermore, hereinafter, among the cells possessed by the transgenic animal, the cell into which the toolbox is inserted is called "toolbox engineered cell" and the cell into which the toolbox is not inserted is called "non-toolbox engineered cell".

However, in the present disclosure, the term "non-toolbox engineered cell" only refers to a cell which has a genome in a state where the toolbox is not inserted thereinto, and the term should not be understood as a term for a cell where the genome is genetically engineered for other purposes. That is, a cell which has other genetically manipulated genome although into which the toolbox is not inserted may also be a so-called "non-toolbox engineered cell" of the present disclosure.

A transgenic animal into which the toolbox is inserted may be a chimeric or homologous animal.

For example, the chimeric animal may refer to an animal which has a "non-toolbox engineered cell" in addition to the "toolbox engineered cell".

That is, according to some exemplary embodiments provided by the present specification, a chimeric transgenic animal, which includes a first cell having a genome that includes a toolbox and a second cell having a genome that does not include a toolbox, may be provided.

Specifically, a transgenic animal, which includes a first cell having a genome that includes a first toolbox and a target site; and a second cell having a genome that includes the target site, may be provided.

The first toolbox may include at least one polynucleotide between a polynucleotide encoding a first RNA-guided endonuclease and a polynucleotide encoding a first guide nucleic acid that can bind to the target site; and the genome of the second cell may not include a polynucleotide encoding a second RNA-guided endonuclease and a polynucleotide encoding a second guide nucleic acid that can specifically bind to the target site. Additionally, an ITR sequence may be further included at the 5' end and 3' end of the first toolbox.

In particular, the sequence of the polynucleotide encoding the first RNA-guided endonuclease and the sequence of the polynucleotide encoding the second RNA-guided endonuclease may be the same or different from each other; and the sequence of the polynucleotide encoding the first guide nucleic acid and the sequence of the polynucleotide encoding the second guide nucleic acid may be the same or different from each other.

The target site may be an endo-polynucleotide.

Specifically, the target site may be a nucleotide sequence of 18 bp to 25 bp present in the genome of the transgenic animal.

The target site may be an exo-polynucleotide.

For example, the target site may be a sequence adjacent to the 5' end or 3' end of a PAM sequence, and the target site and the PAM sequence may be included between a first ITR sequence and a second ITR sequence.

In another example, the chimeric animal may refer to an animal which has only a "toolbox engineered cell" but in which the locus at which a toolbox is inserted into the genome of each "toolbox engineered cell" which constitutes the animal is different.

That is, according to an exemplary embodiment provided by the present specification, a transgenic animal, which includes a first cell that has a genome including a first toolbox and a second cell that has a genome including a second toolbox, in which the first toolbox is present at a first locus, the second toolbox is present at a second locus, and the first locus and the second locus are different, may be provided. The first toolbox and the second toolbox may include at least one between a polynucleotide encoding an RNA-guided endonuclease and a polynucleotide encoding a guide nucleic acid that can specifically bind to a target site. The target site may be an endo-polynucleotide of the animal or an exo-polynucleotide, which is located between a first ITR sequence and a second ITR sequence, included in a genome of the animal. In particular, the sequence of the first toolbox and the sequence of the second toolbox may be the same or different.

According to another exemplary embodiment provided by the present specification, a transgenic animal, which includes a first cell that has a genome including a first toolbox and a second cell that has a genome including a second toolbox, in which the first toolbox is present at a first locus, the second toolbox is present at a second locus, and the first locus and the second locus are the same, may be provided. The first toolbox and the second toolbox may include at least one between a polynucleotide encoding an RNA-guided endonuclease and a polynucleotide encoding a guide nucleic acid that can specifically bind to a target site. The target site may be an endo-polynucleotide of the animal or an exo-polynucleotide, which is located between a first ITR sequence and a second ITR sequence, included in a genome of the animal. In particular, the sequence of the first toolbox and the sequence of the second toolbox are different.

For example, the genome of the first cell may further include a third toolbox, the sequence of which is the same as that of the first toolbox.

In another example, the genome of the second cell may further include a fourth toolbox, the sequence of which is the same as that of the second toolbox.

The transgenic animal may further include a third cell, which has a genome that does not include the polynucleotide encoding the RNA-guided endonuclease and the polynucleotide encoding the guide nucleic acid.

The homologous animal may refer to animals in which the locus at which the toolbox is inserted into the genome of each "toolbox engineered cell" which constitutes the animal is the same.

According to some exemplary embodiments disclosed by the present specification, a gamete or fertilized egg (and/or embryo) which has a genome into which the toolbox is inserted may be obtained from an animal including a cell which has a genome into which the toolbox is inserted, and the gamete may be a sperm or an ovum.

According to some exemplary embodiments disclosed by the present specification, an offspring including a cell which has a genome into which the toolbox is inserted may be produced from an animal including a cell which has a genome into which the toolbox is inserted.

According to some exemplary embodiments disclosed by the present specification, an additional gene editing may occur in an animal genome including a cell which has a genome into which the toolbox is inserted.

3-2. Method for Preparing Transgenic Animal Including Genome into which Toolbox is Inserted One method for producing an animal including a "toolbox engineered cell" by some exemplary embodiments provided in the present disclosure may include the transplantation of a fertilized egg or embryo, which has a genome into which a toolbox is inserted, into the uterus of a surrogate mother. After the transplantation of the fertilized egg or embryo into the uterus of the surrogate mother followed by a gestation period, an animal having a genome into which the toolbox is inserted can be produced.

One method for producing a fertilized egg or embryo having a genome into which the toolbox is inserted may include a microinjection (MI) of the toolbox and/or transposase.

The fertilized egg and/or embryo produced by the microinjection (MI) may be chimeric or homologous. Additionally, the animal obtained by the transplantation of the fertilized egg and/or embryo into the uterus of a surrogate mother may be chimeric or homologous.

Another method for producing a fertilized egg or embryo having a genome into which the toolbox is inserted may include performing a somatic cell nuclear transfer (SCNT).

The somatic cell nuclear transfer may include the transplantation of the nucleus of the somatic cell (301) having a genome into which the toolbox (100) of FIG. 5 is inserted into an enucleated oocyte. An animal including a "toolbox engineered cell" can be produced by the transplantation of the fertilized egg or embryo produced by the somatic cell nuclear transfer (SCNT) into the uterus of a surrogate mother.

The fertilized egg and/or embryo obtained by the somatic cell nuclear transfer (SCNT) may be homologous. Additionally, the animal produced using the fertilized egg and/or embryo may also be homologous. In this case, the genome of the fertilized egg, embryo, and/or animal produced by the somatic cell nuclear transfer (SCNT), which is homologous, may have a sequence which is the same as the genome of the somatic cell (301).

Another method for producing the fertilized egg or embryo having a genome into which a toolbox is inserted may include a method for in vitro fertilization between an ovum (303) and a sperm (305) having a genome into which the toolbox (100) is inserted; or a method for in vitro fertilization between the ovum (303) or the sperm (305) with a wild-type (WT) sperm or ovum.

The fertilized egg and/or embryo produced by in vitro fertilization may be chimeric or homologous. Additionally, the animal obtained by implantation of the fertilized egg and/or embryo into the uterus of a surrogate mother may be chimeric or homologous.

More specifically, one exemplary method for preparing a transgenic animal provided by the present specification may include a preparation of a transgenic embryo in which components of an engineered nuclease are expressed, and a transplantation of the transgenic embryo into the uterus of a surrogate mother.

One exemplary method for preparing a transgenic embryo may include a microinjection of a vector, which includes a transposon gene and a polynucleotide encoding the components of the engineered nuclease, into a fertilized egg or embryo. Additionally, the preparation of the transgenic embryo may further include a microinjection of a transposase, which can interact with the transposon gene, into the fertilized egg or embryo.

Another exemplary method for preparing a transgenic embryo may include a preparation of a transgenic donor cell in which components of an engineered nuclease are expressed, and a transplantation of the nucleus of the transgenic donor cell into an enucleated ovum of the animal.

The preparation of the transgenic donor cell may include a transformation of a cell with a vector which includes a transposon gene and a polynucleotide encoding the components of the engineered nuclease. Additionally, the preparation of the transgenic donor cell may further include transforming the cell with a transposase that can interact with the transposon gene.

The transposase may be in the form of a protein, a polypeptide, or a polynucleotide encoding the transposase. The polynucleotide may be one which is included in a plasmid vector or viral vector. Furthermore, the polynucleotide encoding the transposase may be in the form where the polynucleotide is included in a vector together with the transposon gene and the polynucleotide encoding the components of an engineered nuclease.

One method for producing an animal including a "toolbox engineered cell" by some exemplary embodiments provided in the present disclosure may include an injection of the toolbox and the transposase into a tissue of an animal. In this case, only part of the injected tissue may become a "toolbox engineered cell". The animal produced through the aforementioned method for injecting to a tissue may be a chimeric animal.

One method for producing an animal including a "toolbox engineered cell" by some exemplary embodiments provided in the present disclosure may include a natural breeding between a male which has a testis including a "toolbox engineered cell" or a female which has an ovary including a "toolbox engineered cell".

For example, the method may include a natural breeding between a male which has a testis including a "toolbox engineered cell" and a female which has an ovary including a "toolbox engineered cell".

In another example, the method may include a natural breeding between a male which has a testis including a "toolbox engineered" and a wild-type (WT) female; or natural breeding between a female which has an ovary including a "toolbox engineered" and a wild-type (WT) male.

The animal produced through the natural breeding described above may be a chimeric or homologous animal.

[Second Gene Editing Using Toolbox]

In the present disclosure, when a toolbox is inserted into a genome and transformed as described above, it is called first gene editing.

An additional second gene editing may occur using a toolbox which is inserted into a genome by the first gene editing. Additionally, an $(n+1)^{th}$ gene editing may occur using a genome in which the $n^{th}$ gene editing has occurred (n is a natural number of 2 or greater). The $n^{th}$ gene editing and the $(n+1)^{th}$ gene editing may occur in the genome of one cell or in the genome of another cell.

The "$n^{th}$ gene editing" may be a gene editing using a recombinase recognition site (RRS) that is included as a component of a toolbox.

Additionally, the "$n^{th}$ gene editing" may be a gene editing using components of an engineered nuclease expressed from the toolbox.

Furthermore, the "$n^{th}$ gene editing" may be a gene editing using a polynucleotide that has a PAM sequence included as a component of the toolbox.

For the convenience of explanation, hereinafter, second gene editing using a recombinase recognition site (RRS), which is included as a component of a toolbox, and/or a polynucleotide that encodes the components of an engineered nuclease will be described.

1. Second Gene Editing Using Recombinase Recognition Site (RRS) which is Included in Toolbox Hereinafter, second gene editing using a recombinase recognition site (RRS) present within a toolbox is described.

The second gene editing using the recombinase recognition site (RRS) may occur within the toolbox.

1-1. Secondary Gene Exchange Editing Using Recombinase Recognition Site (RRS)

1-1-1. Toolbox for Secondary Gene Exchange Editing Using Recombinase Recognition Site (RRS)

According to some exemplary embodiments of the present disclosure, a toolbox for exchange editing may be provided.

The toolbox for exchange editing may include a first ITR sequence, a polynucleotide encoding a first recombinase recognition site (RRS1), a polynucleotide encoding a second recombinase recognition site (RRS2), and a second ITR sequence.

A first polynucleotide may be included between the polynucleotide encoding the first recombinase recognition site (RRS1) and the polynucleotide encoding the second recombinase recognition site (RRS2). The first polynucleotide may be one or more selected from a polynucleotide encoding a protein or RNA, an untranscribed polynucleotide, a polynucleotide encoding an untranslated RNA, and a non-functional polynucleotide, but is not limited thereto.

Hereinafter, some exemplary embodiments of the toolbox for exchange editing will be described.

For example, the toolbox for exchange editing may be a toolbox, which includes a first ITR sequence, a polynucleotide encoding a first recombinase recognition site (RRS1), a polynucleotide encoding a first RNA-guided endonuclease, a polynucleotide encoding a second recombinase recognition site (RRS2), and a second ITR sequence.

In another example, the toolbox for exchange editing may be a toolbox, which includes a first ITR sequence, a polynucleotide encoding an RNA-guided endonuclease, a polynucleotide encoding a first recombinase recognition site (RRS1), a polynucleotide encoding a first guide nucleic acid, a polynucleotide encoding a second recombinase recognition site (RRS2), and a second ITR sequence.

In still another example, the toolbox for exchange editing may be a toolbox, which includes a first ITR sequence, a polynucleotide encoding a first recombinase recognition site (RRS1), a fluorescent protein gene, a polynucleotide encoding a second recombinase recognition site (RRS2), and a second ITR sequence.

In still another example, the toolbox for exchange editing may be a toolbox, which includes a first ITR sequence, a polynucleotide encoding a first recombinase recognition site (RRS1), a polynucleotide encoding a first target protein, a polynucleotide encoding a second recombinase recognition site (RRS2), and a second ITR sequence.

Hereinafter, a secondary gene exchange editing method using the toolbox for exchange editing described above will be described. That is, a method for exchanging particular polynucleotide will be described.

1-1-2. Secondary Gene Exchange Editing Method Using Recombinase Recognition Site (RRS)

In a genome into which the toolbox for exchange editing is inserted, a first polynucleotide which is present between the polynucleotide encoding the first recombinase recognition site (RRS1) and the polynucleotide encoding the second recombinase recognition site (RRS2) may be exchanged with a second polynucleotide.

One method for exchanging the first polynucleotide with the second polynucleotide may include a delivery of the second polynucleotide into a cell into which the toolbox for exchange editing is inserted.

There may be various methods for delivering the second polynucleotide into the cell.

For example, the second polynucleotide may be delivered into the cell by introducing the second polynucleotide into the cell. The introduction of a polynucleotide encoding the second polynucleotide into the cell may include a method for incorporating the second polynucleotide into a plasmid vector and then introducing the resultant into the cell. Additionally, the introduction of the second polynucleotide into the cell may include incorporating the second polynucleotide into a viral vector and then transducing the resultant into the cell.

The second polynucleotide is located between the polynucleotide encoding the third recombinase recognition site (RRS3) and the polynucleotide encoding the fourth recombinase recognition site (RRS4). In this case, the third recombinase recognition site (RRS3) may be one which forms a pair with the first recombinase recognition site (RRS1); and the fourth recombinase recognition site (RRS4) may be one which forms a pair with the second recombinase recognition site (RRS2).

Additionally, one method for exchanging a first polynucleotide with a second polynucleotide may include delivering a first recombinase and a second recombinase into the cell.

In this case, the first recombinase can interact with the first recombinase recognition site (RRS1) and/or the third recombinase recognition site (RRS3); and the second recombinase can interact with the second recombinase recognition site (RRS2) and/or the fourth recombinase recognition site (RRS4).

There may be various methods for delivering the recombinase into the cell.

For example, the recombinase may be delivered into the cell by introducing the recombinase as a protein into the cell.

In another example, the recombinase may be delivered into the cell by the introduction of the polynucleotide encoding the recombinase into the cell. The introduction of the polynucleotide encoding the recombinase into the cell may include a method for incorporating the polynucleotide encoding the recombinase into a plasmid vector and then introducing the resultant into the cell. Additionally, the introduction of the polynucleotide encoding the recombinase into the cell may include incorporating the polynucleotide encoding the recombinase into a viral vector and then transducing the resultant into the cell.

The first recombinase delivered into the cell by the method described above can interact with the polynucleotide encoding the first recombinase recognition site (RRS1) and the polynucleotide encoding the third recombination site (RRS3).

Additionally, the second recombinase delivered into the cell can interact with the polynucleotide encoding the second recombinase recognition site (RRS2) and the polynucleotide encoding the fourth recombinase recognition site (RRS4).

By the interaction, the first polynucleotide can be deleted from the toolbox, and the second polynucleotide can be inserted into the toolbox.

Hereinafter, various exemplary embodiments for exchange editing by the above method and the effects of exchange editing are described. These may vary according to the types of the first polynucleotide and/or the second polynucleotide.

The polynucleotide encoding a first RNA-guided endonuclease, which is included in the toolboxes for exchange editing according to some exemplary embodiments provided in the present disclosure, may undergo exchange editing for a polynucleotide encoding a second RNA-guided endonuclease and a second guide nucleic acid.

In this case, even without additional further treatment on the cell having a genome into which an exchange edited toolbox is inserted, the second RNA-guided endonuclease and the second guide nucleic acid are expressed and thereby an engineered nuclease complex can be formed, and third gene editing can occur in the genome.

The polynucleotide encoding the first guide nucleic acid, which is included in the toolboxes for the exchange editing according to some exemplary embodiments provided in the present disclosure, may undergo exchange editing for a polynucleotide encoding a second guide nucleic acid. The sequence of the first guide nucleic acid and the sequence of the second guide nucleic acid may be different from each other.

In this case, the target site of gene editing using an engineered nuclease may be changed by exchange editing.

The fluorescent protein gene, which is included in the toolboxes for exchange editing according to some exemplary embodiments provided in the present disclosure, may undergo exchange editing for a gene encoding target protein (target protein gene).

In this case, the fluorescent protein is not expressed in the cell by exchange editing. Using such a characteristic, it is possible to select whether the target protein gene is inserted into the genome of the cell.

The first target protein gene, which is included in the toolboxes for exchange editing according to some exemplary embodiments provided in the present disclosure, may undergo exchange editing for a second target protein gene.

By such second gene editing, the target protein can be expressed in the cell at the desired time.

The first target protein gene, which is included in the toolboxes for exchange editing according to some exemplary embodiments provided in the present disclosure, may undergo exchange editing for a polynucleotide encoding an RNA-guided endonuclease and a polynucleotide encoding a guide nucleic acid.

By such second gene editing, the RNA-guided endonuclease and guide nucleic acid can be expressed in the cell. The RNA-guided endonuclease and guide nucleic acid can form an engineered nuclease complex, and an additional third gene editing may occur in the genome of the cell by the formed engineered nuclease complex.

1-2. Secondary Gene Insertion Editing Using Recombinase Recognition Site (RRS)

1-2-1. Toolbox for Insertion Editing Using Recombinase Recognition Site (RRS)

A toolbox for insertion editing can be provided according to some exemplary embodiments of the present disclosure.

The toolbox for insertion editing may include a first ITR sequence, a polynucleotide encoding a first recombinase recognition site (RRS1), and a second ITR sequence.

Hereinafter, some exemplary embodiments of the toolbox for insertion editing will be described.

For example, the toolbox for insertion editing may be a toolbox, which includes a first ITR sequence, a polynucleotide encoding a first recombinase recognition site (RRS1), a polynucleotide encoding a first RNA-guided endonuclease, and a second ITR sequence.

In another example, the toolbox for insertion editing may be a toolbox, which includes a first ITR sequence, a polynucleotide encoding a first RNA-guided endonuclease, a polynucleotide encoding a first recombinase recognition site (RRS1), a polynucleotide encoding a first guide nucleic acid, and a second ITR sequence.

In still another example, the toolbox for insertion editing may be a toolbox, which includes a first ITR sequence, a polynucleotide encoding a first recombinase recognition site (RRS1), a polynucleotide encoding a first RNA-guided endonuclease, a polynucleotide encoding a first guide nucleic acid, and a second ITR sequence.

In still another example, the toolbox for insertion editing may be a toolbox, which includes a first ITR sequence, a polynucleotide encoding a first RNA-guided endonuclease, a polynucleotide encoding a first recombinase recognition site (RRS1), and a second ITR sequence.

In still another example, the toolbox for insertion editing may be a toolbox, which includes a first ITR sequence, a polynucleotide encoding a first recombinase recognition site (RRS1), a polynucleotide encoding a first guide nucleic acid, and a second ITR sequence.

Hereinafter, a method for secondary gene insertion editing using a toolbox for insertion editing described above will be described. That is, a method for inserting a particular polynucleotide will be described.

1-2-2. Method for Secondary Gene Insertion Editing Using Recombinase Recognition Site (RRS)

In a genome into which a toolbox for insertion editing is inserted, a first polynucleotide may be inserted into the location where the polynucleotide encoding the first recombinase recognition site (RRS1) is located.

One method for inserting the first polynucleotide may include a delivery of the first polynucleotide into a cell into which the toolbox for insertion editing is inserted.

There may be various methods for delivering the first polynucleotide into the cell.

For example, the first polynucleotide may be delivered into the cell by introducing the first polynucleotide into the cell. The introduction of a polynucleotide encoding the first polynucleotide into the cell may include a method for incorporating the first polynucleotide into a plasmid vector and then introducing the resultant into the cell. Additionally, the introduction of the first polynucleotide into the cell may include incorporating the first polynucleotide into a viral vector and then transducing the resultant into the cell.

The polynucleotide encoding the second recombinase recognition site (RRS2) is further included in the vector which includes the first polynucleotide. In this case, the second recombinase recognition site (RRS2) can form a pair with the first recombinase recognition site (RRS1).

Additionally, one method for inserting the first polynucleotide may include delivering a first recombinase into the cell.

In this case, the first recombinase can interact with the first recombinase recognition site (RRS1) and/or the second recombinase recognition site (RRS2).

The method for delivering the recombinase into the cell has been described above, and thus the detailed description is omitted herein.

The recombinase, which is delivered into the cell by the method described above, can interact with the polynucleotide encoding the first recombinase recognition site (RRS1) and the polynucleotide encoding the second recombinase recognition site (RRS2).

By the interaction, the first polynucleotide can be inserted into the toolbox.

Hereinafter, various exemplary embodiments for insertion editing by the above method and the effects of insertion editing thereof are described. These may vary according to the types of the toolbox for insertion editing and/or a first polynucleotide.

In the case where a polynucleotide encoding a first recombinase recognition site (RRS1) and a polynucleotide encoding a first RNA-guided endonuclease are included in a toolbox for inserting editing according to some exemplary embodiments provided in the present disclosure, a polynucleotide encoding a guide nucleic acid may be inserted into the toolbox.

In this case, an engineered nuclease complex may be formed within the cell by the transcription and/or translation of the polynucleotide encoding the first RNA-guided endonuclease and the polynucleotide encoding an inserted guide nucleic acid. An additional third gene editing may occur after the second gene editing (insertion editing), even without additional treatment, by the engineered nuclease complex formed within the cell.

In the case where a polynucleotide encoding a first RNA-guided endonuclease, a polynucleotide encoding a first recombinase recognition site (RRS1), and a polynucleotide encoding a first guide nucleic acid are included in toolboxes for insertion editing according to some exemplary embodiments provided in the present disclosure, a polynucleotide encoding a promoter for the transcription of the polynucleotide encoding a first guide nucleic acid can be inserted into the toolbox.

In this case, the first guide nucleic acid can be expressed at the time-point when the polynucleotide encoding the promoter is inserted, and through the expression, an engineered nuclease complex can be formed within the cell. That is, a first guide nucleic acid can be expressed at a desired time-point by controlling the time-point of inserting the polynucleotide encoding a promoter. Eventually, the time-point for third gene editing can be controlled through the second gene editing (insertion editing).

In the case where a polynucleotide encoding a first recombinase recognition site (RRS1), a polynucleotide encoding a first RNA-guided endonuclease, and a polynucleotide encoding a first guide nucleic acid are included in toolboxes for insertion editing according to some exemplary embodiments provided in the present disclosure, a polynucleotide encoding a promoter for the transcription and/or translation of the polynucleotide encoding a first RNA-guided endonuclease can be inserted into the toolbox.

In this case, the RNA-guided endonuclease can be expressed at the time-point when the polynucleotide encoding the promoter is inserted, and through the expression, an engineered nuclease complex can be formed within the cell. That is, a first RNA-guided endonuclease can be expressed at a desired time-point by controlling the time-point of inserting the polynucleotide encoding the promoter. Eventually, the time-point for third gene editing can be controlled through the second gene editing (insertion editing).

In the case where a polynucleotide encoding a first RNA-guided endonuclease and a polynucleotide encoding a first recombinase recognition site (RRS1) are included in toolboxes for insertion editing according to some exemplary embodiments provided in the present disclosure, a fluorescent protein gene can be inserted into the toolbox.

In this case, it is possible to select whether a polynucleotide encoding a first RNA-guided endonuclease, which is a component of the toolbox, is inserted into the genome by the insertion of the fluorescent protein gene.

In the case where a polynucleotide encoding a first recombinase recognition site (RRS1) and a polynucleotide encoding a first guide nucleic acid are included in toolboxes for insertion editing according to some exemplary embodiments provided in the present disclosure, a polynucleotide encoding a second guide nucleic acid can be inserted into the toolbox. In particular, the sequence of the second guide nucleic acid may be the same or different from the sequence of the first guide nucleic acid.

When the sequence of the second guide nucleic acid is the same as that of the first guide nucleic acid, a greater amount of guide nucleic acids may be expressed in the cell and the gene editing efficiency using the toolbox can be increased.

When the sequence of the second guide nucleic acid is different from that of the first guide nucleic acid, target sites for gene editing using the toolbox can be versatile.

1-3. Secondary Gene Deletion Editing Using Recombinase Recognition Site (RRS)

1-3-1. Toolbox for Deletion Editing Using Recombinase Recognition Site (RRS)

According to some exemplary embodiments of the present disclosure, a toolbox for deletion editing may be provided.

The toolbox for deletion editing may include a first ITR sequence, a polynucleotide encoding a first recombinase recognition site (RRS1), a first polynucleotide, a polynucleotide encoding a second recombinase recognition site (RRS2), and a second ITR sequence.

The first polynucleotide may include one or more selected from a polynucleotide encoding a protein or RNA, an untranscribed polynucleotide, a polynucleotide encoding an untranslated RNA and a non-functional polynucleotide, but is not limited thereto.

The first recombinase recognition site (RRS1) and the second recombinase recognition site (RRS2) may form a pair. For the convenience of explanation, hereinafter, it is assumed that the sequence of the first recombinase recognition site (RRS1) is the same as that of the second recombinase recognition site (RRS2).

Hereinafter, some exemplary embodiments of the toolbox for deletion editing are described.

For example, the toolbox for deletion editing may be a toolbox, which includes a first ITR sequence, a polynucleotide encoding a constitutive promoter, a polynucleotide encoding a first recombinase recognition site (RRS1), a stop codon, a polynucleotide encoding a second recombinase recognition site (RRS2), a polynucleotide encoding a first RNA-guided endonuclease, and a second ITR sequence.

In another example, a toolbox for deletion editing may be a toolbox, which includes a first ITR sequence, a polynucleotide encoding a constitutive promoter, a polynucleotide encoding a first recombinase recognition site (RRS1), a transcription stop codon, a polynucleotide encoding a second recombinase recognition site (RRS2), a polynucleotide encoding a first guide nucleic acid, and a second ITR sequence.

Hereinafter, a method for secondary gene deletion editing using the toolbox for deletion editing described above will be described. That is, a method for deleting particular polynucleotide will be described.

1-3-2. Method for Editing of Secondary Gene Deletion Using Recombinase Recognition Site (RRS)

In the genome into which a toolbox for deletion editing is inserted, a first polynucleotide present between the polynucleotide encoding a first recombinase recognition site (RRS1) and the polynucleotide encoding a second recombinase recognition site (RRS2) may be deleted.

One method for deleting the first polynucleotide may include delivering a first recombinase into a cell into which the toolbox for deletion editing is inserted.

The first recombinase can interact with the first recombinase recognition site (RRS1) and the second recombinase recognition site (RRS2).

The method for delivering a recombinase into the cell is described above and thus the details of the method are omitted herein.

The first recombinase, which is delivered into the cell by the method described above, can interact with a polynucleotide encoding the first recombinase recognition site (RRS1) and a polynucleotide encoding the second recombinase recognition site (RRS2).

The first polynucleotide can be deleted from the toolbox by the interaction.

Hereinafter, various exemplary embodiments of deletion editing by the above method and the effects of deletion editing thereof are described. These may vary according to the type of the first polynucleotide and/or the toolbox for deletion editing.

In the case where a polynucleotide encoding a constitutive promoter, a polynucleotide encoding a first recombinase recognition site (RRS1), a stop codon, a polynucleotide encoding a second recombinase recognition site (RRS2), and a polynucleotide encoding a first RNA-guided endonuclease are included in toolboxes for deletion editing according to some exemplary embodiments provided in the present disclosure, it is possible to delete the stop codon from the toolboxes.

In this case, the first RNA-guided endonuclease may be expressed by the deletion of the stop codon. That is, the time-point of the transcription and/or translation of particular polynucleotide included in the toolbox can be controlled by the deletion of partial component of the toolbox.

In the case where a polynucleotide encoding a constitutive promoter, a polynucleotide encoding a first recombinase recognition site (RRS1), a transcription stop codon (poly T), a polynucleotide encoding a second recombinase recognition site (RRS2), and a polynucleotide encoding a first guide nucleic acid are included in toolboxes for deletion editing according to some exemplary embodiments provided in the present disclosure, it is possible to delete the transcription stop codon (poly T) from the toolboxes.

In this case, the first guide nucleic acid may be expressed by the deletion of the transcription stop codon (poly T). That is, the time-point of the transcription and/or translation of particular polynucleotide included in the toolbox can be controlled by the deletion of partial component of the toolbox.

2. Second Gene Editing Using Component of Engineered Nuclease which is Expressed from Toolbox Hereinafter, second gene editing using components of an engineered nuclease which is expressed from a polynucleotide that is included in a toolbox inserted into a genome will be described.

The second gene editing using the components of an engineered nuclease may occur the outside of the toolbox or the inside of the toolbox.

2-1. Second Gene Editing Using Components of Engineered Nuclease which is Expressed from a Toolbox which does not Include Expression Control Element 2-1-1. Toolbox which does not Include Expression Control Element According to some exemplary embodiments of the present disclosure, a toolbox which does not include an expression control element may be provided.

The toolbox which does not include the expression control element may include a first ITR sequence, a polynucleotide encoding the components of an engineered nuclease, and a second ITR sequence.

Hereinafter, some exemplary embodiments of the toolbox which does not include the expression control element are described.

For example, the toolbox may be a toolbox which includes one polynucleotide encoding an RNA-guided endonuclease.

In another example, the toolbox may be a toolbox which includes two or more polynucleotides encoding an RNA-guided endonuclease. In this case, the sequences of the two or more polynucleotides encoding an RNA-guided endonuclease may be the same or different from each other.

When the sequences of the two or more polynucleotides encoding an RNA-guided endonuclease included in the toolbox are the same, the expression level of the same RNA-guided endonuclease is increased in a cell and thereby second gene editing efficiency can be increased.

In still another example, the toolbox may be a toolbox which includes one polynucleotide encoding a guide nucleic acid.

In still another example, the toolbox may be a toolbox which includes two or more polynucleotides encoding a guide nucleic acid. In this case, the sequences of the two or more polynucleotides encoding a guide nucleic acid may be the same or different.

When at least one sequence among the two or more polynucleotides encoding a guide nucleic acid included in the toolbox is the same, the expression level of the guide nucleic acid which has the same sequence can be increased in a cell and thereby second gene editing efficiency can be increased.

When at least one sequence among the two or more polynucleotides encoding a guide nucleic acid included in the toolbox is different, various types of guide nucleic acids can be expressed in a cell. In this case, second gene editing can occur at a greater number of target sites.

In still another example, the toolbox may be a toolbox which includes one or more types of a polynucleotide encoding an RNA-guided endonuclease and one or more types of a polynucleotide encoding a guide nucleic acid.

In this case, second gene editing may occur in a target site present in the genome of the cell after the toolbox is inserted into the genome of the cell, without additional treatment, by first gene editing. One or more of the guide nucleic acids expressed from the toolbox can be complementarily bound to the target site.

That is, when the toolbox, which includes the polynucleotide encoding the RNA-guided endonuclease and the polynucleotide encoding guide nucleic acid, without including the expression control element, is inserted into the genome, an $n^{th}$ (n is a natural number of 2 or greater) gene editing can occur in the genome without additional treatment.

Above-described the toolbox which does not include the expression control element may be inserted into the genome and/or chromosome of a cell.

Each toolbox having various constitutions described above may be inserted into the genome and/or chromosome of a cell via various combinations.

According to some exemplary embodiments provided in the present disclosure, a first toolbox and a second toolbox may be inserted into the genome of a single cell.

For example, the first toolbox may include a first ITR sequence, one or more types of polynucleotides encoding an RNA-guided endonuclease, and a second ITR sequence. The second toolbox may include a third ITR sequence, one or more types of polynucleotides encoding a guide nucleic acid, and a fourth ITR sequence.

According to some exemplary embodiments provided in the present disclosure, each of the first toolbox and the second toolbox may independently be inserted into the genome (and/or chromosome) of a different cell.

For example, a first toolbox may be inserted into the genome of a first cell present in a single subject, and a second toolbox may be inserted into the genome of a second cell present in the subject. The first toolbox may include one or more types of polynucleotides encoding an RNA-guided endonuclease. The second toolbox may include one or more types of polynucleotides encoding a guide nucleic acid.

The each different cell may be a non-isolated cell which is included in a single subject.

The each different cell may be a non-isolated cell which is included in a fertilized egg and/or embryo.

Hereinafter, a method for second gene editing using above-described the toolbox encoding components of an engineered nuclease without including the expression control element will be described.

2-1-2. Method of Second Gene Editing

In the present disclosure, a method for second gene editing in a cell, into which a toolbox that includes a polynucleotide encoding components of an engineered nuclease is inserted without including an expression control element, is provided. According to the construction of the toolbox inserted in the genome of the cell, various methods for second gene editing can be provided.

For example, one method for second gene editing in a cell having a genome, into which a polynucleotide encoding an RNA-guided endonuclease is inserted, may include delivering a guide nucleic acid into a cell.

Additionally, one method for second gene editing in a cell having a genome, into which a toolbox including a polynucleotide encoding an RNA-guided endonuclease is inserted, may include delivering a donor polynucleotide into the cell.

The delivery of the guide nucleic acid into a cell includes the introduction of a polynucleotide encoding the guide nucleic acid into the cell. Specifically, a polynucleotide encoding the guide nucleic acid may be introduced into the cell in the form of an RNA, or a polynucleotide encoding the guide nucleic acid may be incorporated into a vector and then the resultant may be introduced into the cell.

Additionally, the delivery of the donor polynucleotide into the cell includes the introduction of a vector including the donor polynucleotide into the cell.

In the case where the guide nucleic acid is delivered into a cell, the guide nucleic acid can bind to a target site.

Additionally, the RNA-guided endonuclease can be expressed in the cell from the polynucleotide that had been inserted in the toolbox by the expression system of the cell, and the RNA-guided endonuclease can cleave the target site present in the genome, in a state where the RNA-guided endonuclease forms a complex with the guide nucleic acid.

Once the target site is cleaved, an indel may occur in the target site by the repeated interactions of the repairing system by the non-homologous end joining (NHEJ) and the RNA-guided endonuclease, and accordingly, particular sequence near the target site may be disrupted. As a result, a gene including the particular sequence may reach a state where the gene no more can perform a normal function, that is, a knockout state.

Additionally, when the donor polynucleotide is provided into a cell along with the guide nucleic acid, the donor polynucleotide may be knocked in into the target site which was cleaved by the RNA-guided endonuclease.

In another example, one method for second gene editing in a cell having a genome, into which a toolbox including a polynucleotide encoding a guide nucleic acid is inserted, may include delivering an RNA-guided endonuclease into the cell.

Additionally, one method for second gene editing in a cell having a genome, into which a toolbox that includes a polynucleotide encoding a guide nucleic acid is inserted, may include delivering a donor polynucleotide into the cell.

The delivery of the RNA-guided endonuclease into a cell includes the delivery of the RNA-guided endonuclease into a cell in the form of a protein and/or polypeptide. Additionally, the delivery of the RNA-guided endonuclease into a cell may include the introduction of the polynucleotide encoding an RNA-guided endonuclease into the cell. The polynucleotide encoding an RNA-guided endonuclease may be introduced into the cell in a state where the polynucleotide is incorporated into a vector.

Figure 8:
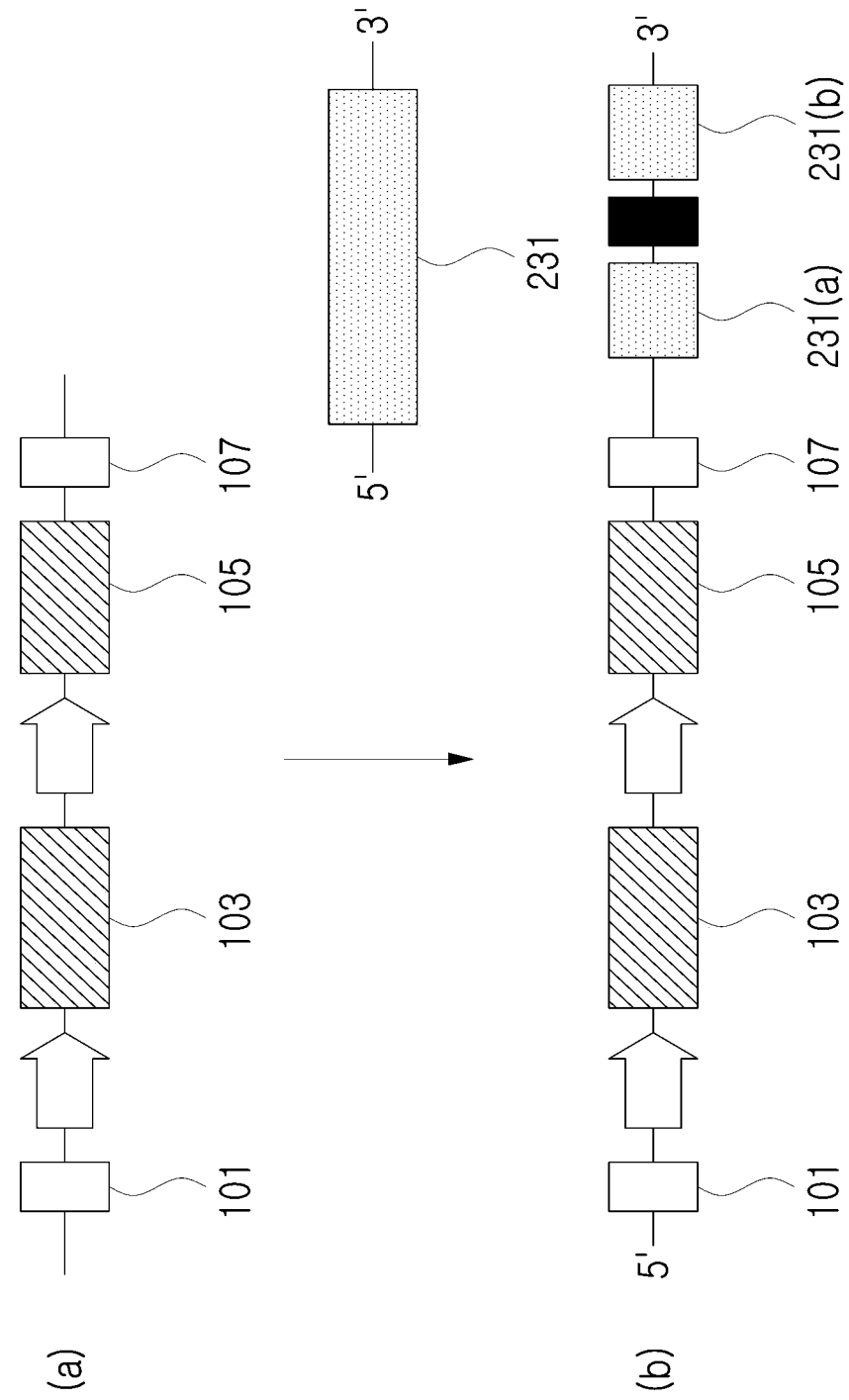
FIG. 8 illustrates: a toolbox, which includes a polynucleotide encoding an RNA-guided endonuclease without an expression control element and a polynucleotide encoding a guide nucleic acid; and a form that particular target site is cleaved within a genome into which the toolbox is inserted.

In another example, in a cell having a genome into which the toolbox (see FIG. 8(a)) that includes a polynucleotide encoding an RNA-guided endonuclease (103) and a polynucleotide encoding a guide nucleic acid (105) is inserted, even without additional treatment, a target gene to which the guide nucleic acid can bind may be knocked out.

FIG. 8(a) illustrates a toolbox, in which a polynucleotide encoding an RNA-guided endonuclease (103) and a polynucleotide encoding a guide nucleic acid (105) are included between a first ITR sequence (101) and a second ITR sequence (107).

Specifically, when the toolbox is inserted into the genome of a cell, the RNA-guided endonuclease and guide nucleic acid may be expressed by the expression mechanism in a cell. The guide nucleic acid can bind to the target site (231), which is present in the genome of the cell, and the RNA-guided endonuclease, in a state forming an engineered nuclease complex with the guide nucleic acid, can cleave the target site (231).

FIG. 8(b) illustrates a form, in which the target site (231) is cleaved, in the genome into which the toolbox (see FIG. 8(a)) that includes a polynucleotide encoding an RNA-guided endonuclease (103) and a polynucleotide encoding a guide nucleic acid (105) is inserted. The target site (231) may be divided into a first region (231(a)) and a second region (231(b)) by the complex of the polynucleotide encoding an RNA-guided endonuclease (103) and the polynucleotide encoding a guide nucleic acid (105).

That is, in the cell having a genome into which the toolbox is inserted, even without additional further treatment, a target gene including a target site having a sequence the same as or complementary to part of the sequence of the guide nucleic acid may be knocked out (see FIG. 8(b)).

However, when a donor polynucleotide is provided to the cell, it is also possible that the donor polynucleotide may be knocked in before the gene including the particular sequence is knocked out by the mechanism described above.

Additionally, in another example, in a cell having a genome into which a first toolbox including a polynucleotide encoding an RNA-guided endonuclease and a second toolbox including a polynucleotide encoding a guide nucleic acid are inserted, even without additional treatment, a target gene including a target site that has the same or a complementary sequence to part of the sequence of the guide nucleic acid may be knocked out.

Specifically, when the first toolbox and the second toolbox is inserted into a genome of a cell, the RNA-guided endonuclease and guide nucleic acid which is expressed by the expression mechanism in the cell can form an engineered nuclease complex, and the engineered nuclease complex can cleave the target site, to which a guide nucleic acid can have a complementary binding.

That is, in the cell having a genome into which both the first toolbox and the second toolbox are inserted, a target gene, which includes a target site to which the guide nucleic acid can have a complementary binding even without additional treatment, can be knocked out.

However, when the cell is provided with a donor polynucleotide, it is also possible that the donor polynucleotide may be knocked in before the target gene including the target site is knocked out by the above-described mechanism.

Contrary to the description above, the first toolbox may be inserted into the genome of a first cell of one individual, and the second toolbox may be inserted into the genome of a second cell of the individual.

In this case, an RNA-guided endonuclease may be expressed in the first cell by the expression mechanism in the cell, and a guide nucleic acid may be expressed in the second cell.

The RNA-guided endonuclease expressed in the first cell may be transported from the first cell by an intercellular delivery system. Additionally, the guide nucleic acid expressed in the second cell may be transported from the second cell by an intracellular delivery system. That is, the RNA-guided endonuclease expressed in the first cell and the guide nucleic acid expressed in the second cell of an individual may be present in the same cell, through the transport by the intercellular delivery system. In particular, the RNA-guided endonuclease and the guide nucleic acid may form a complex, and gene editing may occur in the genome of the cell.

For example, the RNA-guided endonuclease expressed in the first cell may migrate to the second cell, thereby forming a complex with the guide nucleic acid expressed in the second cell, and in this case, second gene editing may occur in the second cell.

In another example, the guide nucleic acid expressed in the second cell may migrate into the first cell, thereby forming a complex with the RNA-guided endonuclease expressed in the first cell, and in this case, second gene editing may occur in the first cell.

Additionally, in still another example, the RNA-guided endonuclease expressed in the first cell and the guide nucleic acid expressed in the second cell may migrate into a third cell, which is present in the individual. In this case, the RNA-guided endonuclease and the guide nucleic acid may form a complex in the third cell, and second gene editing may occur in the third cell.

The mechanism for second gene editing has been described above and thus the detailed description is omitted herein.

The above-described method for second gene editing may be a method for gene editing in an isolated cell.

One method for second gene editing in a non-isolated cell may include a method for injecting the above-described RNA, plasmid vector, polypeptide, and/or protein to the tissue or organ of an individual.

Furthermore, one method for second gene editing in a fertilized egg and/or embryo may include a method for microinjecting the above-described RNA, plasmid vector, polypeptide, and/or protein to a fertilized egg.

Hereinafter, a target site where second gene editing described above can occur will be described.

The target site where the gene editing can occur depends on the type of guide nucleic acids provided to a cell.

The provision of the guide nucleic acid may refer to a delivery of the guide nucleic acid from the outside of a cell into the cell.

Additionally, the provision of the guide nucleic acid may refer to a provision of the guide nucleic acid by the expression of the polynucleotide which is inserted into the genome of a cell. In this case, the polynucleotide inserted into the genome of a cell may be one which is included as a component of a toolbox.

For example, when one type of a guide nucleic acid is provided into a cell, gene editing may occur at a target site to which a guide nucleic acid can bind.

In another example, when two different types of a first guide nucleic acid and a second guide nucleic acid are provided into a cell, gene editing may occur at a first target site to which a first guide nucleic acid can bind and at a second target site to which a second guide nucleic acid can bind.

2-2. Second Gene Editing Using Component of Engineered Nuclease which is Expressed from Toolbox which Includes Expression Control Element 2-2-1. Toolbox which Includes Expression Control Element According to some exemplary embodiments of the present disclosure, a toolbox including an expression control element may be provided.

The expression control element may refer to an element for controlling the timing and/or location of expression of particular polynucleotide.

In the case of a toolbox in which the expression control element is included, the transcription and/or translation of part of the polynucleotide included in the inside of the toolbox may be inhibited unless the material and/or conditions that affect the expression control element are treated.

As used herein, the term "material and/or conditions that affect the expression control element" may refer to a material and/or conditions which can induce or cause to increase the transcription and/or translation of a polynucleotide, in which the transcription and/or translation of the polynucleotide is inhibited by the expression control element.

The toolbox including the expression control element may include a first ITR sequence, an expression control element, a polynucleotide that encodes the components of an engineered nuclease, and a second ITR sequence.

The expression control element may be an element that controls the transcription and/or translation of the polynucleotide that encodes the components of the engineered nuclease.

In particular, the transcription and/or translation of the polynucleotide that encodes the components of an engineered nuclease may be inhibited unless the material and/or conditions that affect the expression control element are treated.

In the case of a cell having a genome into which the toolbox including the expression control element is inserted, the components of an engineered nuclease cannot be expressed without the treatment of the material and/or conditions that affect the expression control element. In this case, second gene editing cannot occur unless the engineered nuclease is additionally delivered into the inside of the cell from the outside.

Figure 9:
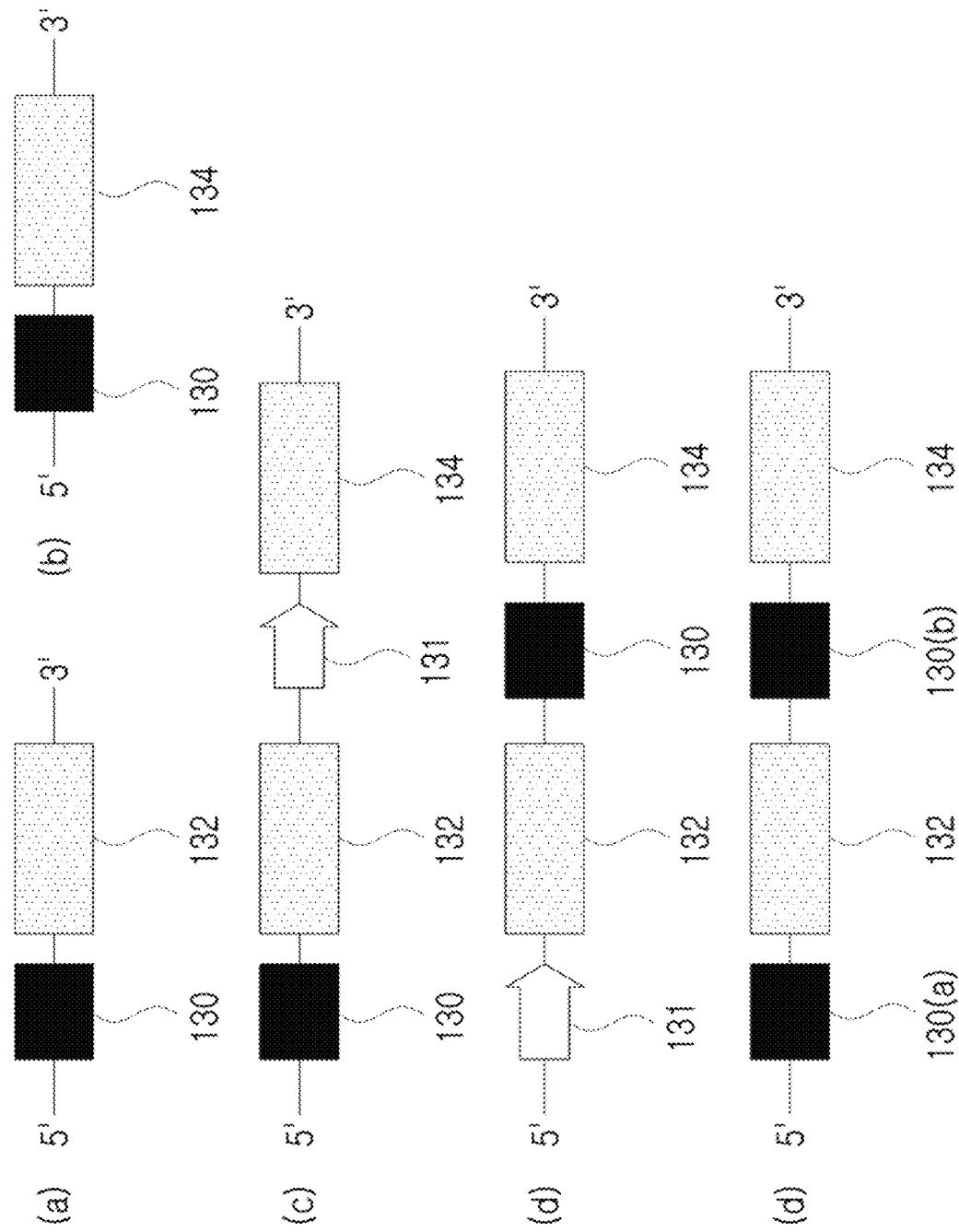
FIG. 9 illustrates some embodiments of a toolbox which includes an expression control element.

Hereinafter, some exemplary embodiments of the toolbox including the expression control element will be described. FIG. 9 illustrates some exemplary embodiments of the toolbox including the expression control element (130).

For example, the toolbox may include a polynucleotide encoding an RNA-guided endonuclease (132) and the expression control element (130) (see FIG. 9 (*a*)).

In another example, the toolbox may include a polynucleotide encoding a guide nucleic acid (134) and the expression control element (130) (see FIG. 9(*b*)).

In still another example, the toolbox may include a polynucleotide encoding an RNA-guided endonuclease and a polynucleotide encoding a guide nucleic acid, and may include an expression control element in one or more of the 5' end of the polynucleotide encoding an RNA-guided endonuclease and the 5' end of the polynucleotide encoding the guide nucleic acid.

Specifically, the toolbox may include a polynucleotide encoding an RNA-guided endonuclease (132) and a polynucleotide encoding a guide nucleic acid (134), and may include the expression control element (130) at the 5' end of the polynucleotide encoding the RNA-guided endonuclease. Additionally, a polynucleotide encoding a promoter (131) may be included at the 5' end of the polynucleotide encoding the guide nucleic acid (134) (see FIG. 9(*c*)).

Specifically, the toolbox may include a polynucleotide encoding an RNA-guided endonuclease (132) and a polynucleotide encoding a guide nucleic acid (134), and may include the expression control element (130) at the 5' end of the polynucleotide encoding the guide nucleic acid (134). Additionally, a polynucleotide encoding a promoter (131) may be included at the 5' end of the polynucleotide encoding the RNA-guided endonuclease (132) (see FIG. 9(*d*)).

Specifically, the toolbox may include a polynucleotide encoding an RNA-guided endonuclease (132) and a polynucleotide encoding a guide nucleic acid (134), and may include the expression control element (130(*a*)) at the 5' end of the polynucleotide encoding an RNA-guided endonuclease (132) and may include the expression control element (130(*b*)) at the 5' end of the polynucleotide encoding the guide nucleic acid (see FIG. 9(*e*)).

Even in the case where both a polynucleotide encoding an RNA-guided endonuclease and a polynucleotide encoding a guide nucleic acid are included in a genome, when the expression control element is additionally included in at least one of the 5' end of the polynucleotide encoding the RNA-guided endonuclease and the 5; end of the polynucleotide encoding the guide nucleic acid, it is not possible to conclude that second gene editing can occur without particular treatment.

Figure 10:
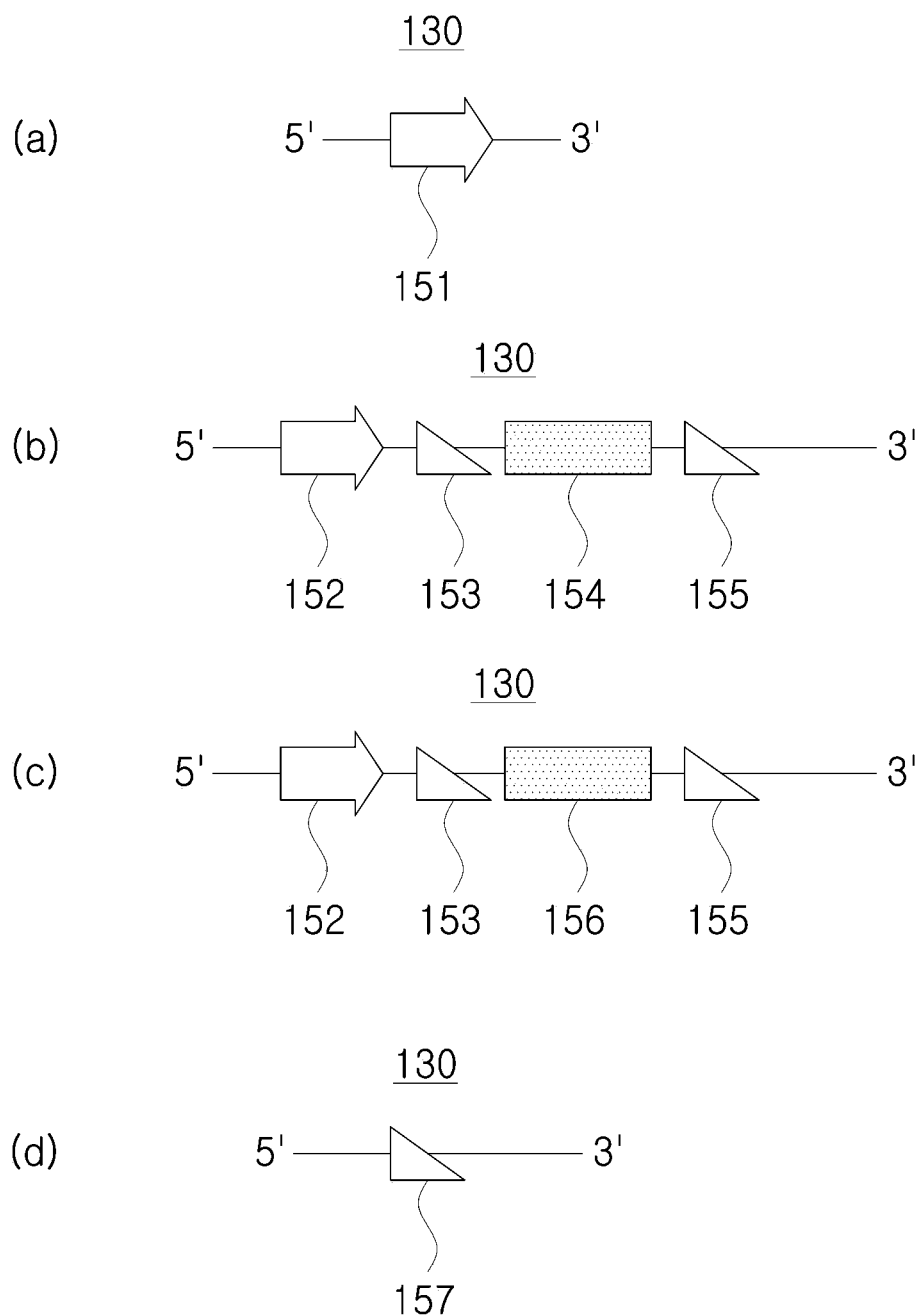
FIG. 10 illustrates some embodiments of an expression control element.

Hereinafter, some specific embodiments of the expression control element (130) are disclosed. FIG. 10 illustrates some embodiments of an expression control element.

For example, the expression control element (130) may include a polynucleotide encoding an inducible promoter (151) (see FIG. 10 (*a*)).

In the case where the polynucleotide encoding an inducible promoter (151) is inserted in a genome of a cell, the inducible promoter cannot be operated without the treatment of the material and/or conditions that affect the expression control element. In this case, the transcription and/or translation of the polynucleotide present at the 3' direction of the inducible promoter may not occur. Specifically, when the inducible promoter is a Tet-on promoter, if a material that affects the Tet-on promoter (e.g., tetracycline) is not treated, the transcription and/or translation of the polynucleotide present at the 3' direction of the Tet-on promoter may not occur.

In another example, the expression control element (130) may include a polynucleotide which encodes [recombinase recognition site (RRS) (153)-transcription stop codon (154)-recombinase recognition site (RRS) (155)] (hereinafter, RTR). An exo-polynucleotide may be additionally included between the recombinase recognition site (RRS) (153) and the transcription stop codon (154).

That is, in the present disclosure, the RTR may mean that an exo-polynucleotide is further included between the recombinase recognition site (RRS) (153) and the transcription stop codon (154).

The RTR may be included between a polynucleotide encoding a promoter (152) and a polynucleotide to be transcribed and/or translated (see FIG. 10(b)).

In the case where the RTR is inserted in the genome of a cell, the transcription stop codon cannot be deleted without the treatment of the material and/or conditions that affect the expression control element, and in this case, the transcription and/or translation of the polynucleotide present at the 3' direction of the RTR may not occur. Specifically, when the cell is not treated with a recombinase (e.g., Cre recombinase, Dre recombinase, etc.), which is a material that affects the RTR, the transcription of the polynucleotide present at the 3' direction of the RTR may not occur.

In still another example, the expression control element (130) may include a polynucleotide which encodes [recombinase recognition site (RRS) (153)-stop codon (156)-recombinase recognition site (RRS) (155)] (hereinafter, RSR). An exo-polynucleotide may additionally be included between the recombinase recognition site (RRS) (153) and the stop codon (156).

That is, in the present disclosure, the RSR may mean that an exo-polynucleotide may further be included between the recombinase recognition site (RRS) (153) and the stop codon (156).

The RSR may be included between a polynucleotide encoding a promoter (152) and a polynucleotide to be transcribed and/or translated (see FIG. 10(c)).

In the case where the RSR is inserted in the genome of a cell, the stop codon cannot be deleted without the treatment of the material and/or conditions that affect the expression control element, and in this case, the transcription and/or translation of the polynucleotide present at the 3' direction of the RSR may not occur. Specifically, when the cell is not treated with a recombinase (e.g., Cre recombinase, Dre recombinase, etc.), which is a material that affects the RSR, the transcription and/or translation of the polynucleotide present at the 3' direction of the RSR may not occur.

In still another example, it may be a case where the expression control element (130) does not include a polynucleotide encoding a promoter but includes a recombinase recognition site (RRS) (157) (see FIG. 10(d)).

In this case, the transcription and/or translation of the polynucleotide present at the 3' direction of the RRS may not occur, unless i) the recombinase recognition site (RRS) or a mutant thereof and a polynucleotide encoding a promoter, and ii) a recombinase which can interact with the recombinase recognition site (RRS) are treated on the cell.

Each toolbox including the expression control element (130) provided in the present disclosure may form a combination and thereby be inserted into the genome (and/or chromosome) of a cell.

That is, a first toolbox and a second toolbox may be inserted into the genome of a single cell, and in this case, any one or more of the first toolbox and the second toolbox may include the expression control element (130).

For example, the first toolbox may include the expression control element (130) and a polynucleotide encoding an RNA-guided endonuclease. The second toolbox may include a polynucleotide encoding a promoter and a polynucleotide encoding a guide nucleic acid.

In another example, the first toolbox may include the expression control element (130) and a polynucleotide encoding a guide nucleic acid. The second toolbox may include a polynucleotide encoding a promoter and a polynucleotide encoding an RNA-guided endonuclease.

In still another example, the first toolbox may include the expression control element (130) and a polynucleotide encoding a guide nucleic acid. The second toolbox may include the expression control element (130) and a polynucleotide encoding an RNA-guided endonuclease.

Even in this case, the expression of the components of the engineered nuclease can be inhibited by the expression control element (130), and thus it is not possible to conclude that second gene editing can occur without addition treatment of the material and/or conditions that affect the expression control element, even if the toolbox is inserted into a genome by the first gene editing.

2-2-2. Method for Second Gene Editing

The present disclosure provides a method for second gene editing by expressing the components of an engineered nuclease from a toolbox which includes the expression control element and a polynucleotide encoding the components of the engineered nuclease.

Various methods for second gene editing may be provided according to the construction of toolbox inserted into a genome.

For the convenience of explanation, hereinafter, a case where a polynucleotide encoding an RNA-guided endonuclease is included at the 3' end of the expression control element as the construction of the toolbox is assumed and will be described thereon.

For example, one method for second gene editing in a cell having a genome into which a toolbox including a polynucleotide encoding an inducible promoter and a polynucleotide encoding an RNA-guided endonuclease is inserted, may include the treatment of a material and/or conditions that can operate the inducible promoter; and the delivery of a guide nucleic acid. Furthermore, one method for second gene editing in the cell may include further providing a donor polynucleotide to the cell.

The treatment of the material and/or conditions that affect the expression control element, provision of a guide nucleic acid, and provision of the donor polynucleotide in the cell may be simultaneously treated and provided, and these may also be applicable to other exemplary embodiments below.

The material or conditions that can operate the inducible promoter have been described above and thus detailed explanation is omitted. Additionally, the method to provide the guide nucleic acid and/or donor polynucleotide to the cell has also been described above and thus detailed explanation is omitted.

When the material and/or conditions that can operate the inducible promoter is treated on the cell, the inducible promoter may be activated, and in this case, the polynucleotide present at the 3' end of the inducible promoter is transcribed and/or translated and thereby the RNA-guided endonuclease can be expressed.

The guide nucleic acid provided into the cell can bind to the target site present in the genome of the cell. Additionally, the RNA-guided endonuclease expressed by the above-described mechanism can cleave the target site while forming a complex with the guide nucleic acid, and in this case, the target gene including the target site may be knocked out.

Furthermore, when a donor polynucleotide is provided into the cell, the donor polynucleotide may be knocked in at a site where the target site is cleaved.

That is, by the treatment of the material and/or conditions that can operate the inducible promoter on the cell, the transcription and/or translation of the polynucleotide encoding an RNA-guided endonuclease located at the 3' end of the inducible promoter can be controlled in a timely fashion, and through the same, the gene editing can also be controlled in a timely fashion.

In another example, one method for second gene editing in a cell having a genome into which a toolbox including an RSR inserted between a polynucleotide encoding a promoter and a polynucleotide encoding an RNA-guided endonuclease is inserted may include providing a site-specific recombinase (SSR) and a guide nucleic acid to the cell. Furthermore, one method for second gene editing in the cell may include further providing a donor polynucleotide to the cell.

The provision of the site-specific recombinase (SSR) into a cell may include the provision of the site-specific recombinase (SSR) protein or the polynucleotide encoding the site-specific recombinase (SSR) into the cell. The polynucleotide encoding the site-specific recombinase (SSR) may be introduced into the cell by incorporating into a plasmid vector or viral vector.

The method for providing the guide nucleic acid and/or donor polynucleotide into a cell has been described above, and thus the detailed explanation is omitted.

When the site-specific recombinase (SSR) is delivered into the cell, the site-specific recombinase (SSR) and the recombinase recognition site (RRS) may interact with each other, and the stop codon may be deleted by the interaction. In this case, the RNA-guided endonuclease present at the 3' end of the RSR can be expressed.

The guide nucleic acid provided into the cell can bind to the target site present in the genome of the cell. Additionally, the expressed RNA-guided endonuclease can cleave the target site while forming a complex with the guide nucleic acid, and in this case, the target gene including the target site may be knocked out.

Furthermore, when a donor polynucleotide is provided into the cell, the donor polynucleotide may be knocked in at the site where the target site is cleaved.

That is, the transcription and/or translation of a polynucleotide encoding an RNA-guided endonuclease located at the 3' end of the polynucleotide encoding the RSR can be controlled in a timely fashion by the delivery of the recombinase (SSR), and through the same, the gene editing can also be controlled in a timely fashion.

In still another example, one method for second gene editing in a cell having a genome into which a toolbox including an RTR inserted between a polynucleotide encoding a promoter and a polynucleotide encoding a guide nucleic acid is inserted may include providing a site-specific recombinase (SSR) and an RNA-guided endonuclease to the cell. Furthermore, one method for second gene editing in the cell may include further providing a donor polynucleotide to the cell.

The method for providing the site-specific recombinase (SSR), RNA-guided endonuclease, and/or donor polynucleotide into the cell have been described above, and thus detailed explanation is omitted.

When the site-specific recombinase (SSR) is provided into the cell, the transcription stop codon can be deleted through the interaction between the site-specific recombinase (SSR) and the recombinase recognition site (RRS). In this case, the guide nucleic acid present at the 3' end of the RSR can be expressed. The guide nucleic acid can bind to the target site which is present in the genome of the cell.

The RNA-guided endonuclease provided into the cell can cleave the target site while forming a complex with the guide nucleic acid, and in this case, the target gene including the target site can be knocked out.

Furthermore, when a donor polynucleotide is provided into the cell, the donor polynucleotide may be knocked in at the site where the target site is cleaved.

That is, by the provision of the recombinase (SSR), the transcription and/or translation of the polynucleotide encoding the guide nucleic acid located at the 3' end of the polynucleotide encoding the RTR can be controlled in a timely fashion, and through the same, the gene editing can also be controlled in a timely fashion.

In still another example, one method for second gene editing in a cell having a genome into which a toolbox including a polynucleotide encoding a first recombinase recognition site (RRS1) and a polynucleotide encoding an RNA-guided endonuclease, without including a polynucleotide encoding a promoter is inserted, may include providing a first site-specific recombinase (SSR1) and a polynucleotide encoding a promoter into the cell. The first site-specific recombinase (SSR1) can interact with the first recombinase recognition site (RRS1). Furthermore, one method for second gene editing in the cell may include further providing a donor polynucleotide to the cell.

The method for providing the first site-specific recombinase (SSR1) and the donor polynucleotide into the cell has been described above and thus detailed description is omitted.

The polynucleotide encoding the promoter may be incorporated into a plasmid vector along with a recombinase recognition site (RRS), which forms a pair with the first recombinase recognition site (RRS1), and then provided into the cell.

When the first site-specific recombinase (SSR1) and the polynucleotide encoding a promoter are provided into the cell, the first site-specific recombinase (SSR1) and the first recombinase recognition site (RRS1) can interact with each other, and thereby the polynucleotide encoding a promoter can be inserted into a toolbox which is present in the genome of the cell. In this case, the RNA-guided endonuclease which is present at the 3' end of the first recombinase recognition site (RRS1) can be transcribed and/or translated.

The guide nucleic acid provided into the cell can bind to the target site present in the genome of the cell. Additionally, the expressed RNA-guided endonuclease can cleave the target site while forming a complex with the guide nucleic acid, and in this case, the target gene including the target site can be knocked out.

Furthermore, when a donor polynucleotide is provided into the cell, the donor polynucleotide can be knocked in at the site where the target site is cleaved.

That is, by the provision of the first site-specific recombinase (SSR1) and a polynucleotide encoding a promoter, the transcription and/or translation of the polynucleotide encoding an RNA-guided endonuclease located at the 3' end of the polynucleotide encoding the first recombinase recognition site (RRS1) can be controlled in a timely fashion, and through the same, the gene editing can also be controlled in a timely fashion.

Hereinafter, a method for second gene editing using a toolbox in which a polynucleotide encoding a guide nucleic acid is included at the 3' end of the expression control element will be described. However, the method for second gene editing using a toolbox in which a polynucleotide encoding an RNA-guided endonuclease is included at the 3' end of the expression control element and mechanism therein have been described in detail above, and thus the specific details of gene editing mechanism will be omitted.

For example, one method for second gene editing, in a cell having a genome into which a toolbox including an a polynucleotide encoding an inducible promoter and a polynucleotide encoding a guide nucleic acid is inserted, may include a treatment of a material and/or conditions that can operate an inducible promoter and a provision of an RNA-guided endonuclease to the cell. Furthermore, one method for second gene editing in the cell may include further providing a donor polynucleotide to the cell.

The treatment of the material and/or conditions that affect the expression control element in the cell, a provision of an RNA-guided endonuclease, and a provision of the donor polynucleotide may be simultaneously treated and provided, and these methods can also be applied to other exemplary embodiments below.

In another example, one method for second gene editing, in a cell having a genome into which a toolbox including an RTR between a polynucleotide encoding a promoter and a polynucleotide encoding a guide nucleic acid is inserted, may include the provision of a site-specific recombinase (SSR) and an RNA-guided endonuclease to the cell. Furthermore, one method for second gene editing in the cell may include further providing a donor polynucleotide to the cell.

In still another example, one method for second gene editing, in a cell having a genome into which a toolbox including a polynucleotide encoding a first recombinase recognition site (RRS1) and a polynucleotide encoding a guide nucleic acid without a polynucleotide encoding a promoter is inserted, may include providing a first site-specific recombinase (SSR1) and a polynucleotide encoding a promoter to the cell. Furthermore, one method for second gene editing in the cell may include further providing a donor polynucleotide to the cell.

As described above, one method for second gene editing in an isolated cell may include directly delivering, to the cell, various types of materials (e.g., materials that affect the expression control element), RNA, a plasmid vector, a viral vector, a polypeptide and/or a protein described above.

Additionally, one method for second gene editing in a non-isolated cell may include injecting, to the tissues or organs of an individual, various types of materials (e.g., materials that affect the expression control element), RNA, a plasmid vector, a viral vector, a polypeptide and/or a protein described above.

Furthermore, one method for second gene editing in a fertilized egg and/or embryo may include microinjecting (MI), to a fertilized egg in a state of a 1-cell stage pronucleus of an animal, various types of materials (e.g., materials that affect the expression control element), RNA, a plasmid vector, a viral vector, a polypeptide and/or a protein described above.

Additionally, one method for second gene editing in a fertilized egg and/or embryo may include microinjecting, to a fertilized egg in a state after a 2-cell stage of an animal, various types of materials (e.g., materials that affect the expression control element), RNA, a plasmid vector, a viral vector, a polypeptide and/or a protein described above.

As described above, in the case of a cell, a fertilized egg and/or embryo having a genome into which a toolbox including a polynucleotide encoding an RNA-guided endonuclease is inserted, it is not necessary to provide an RNA-guided endonuclease per gene editing. In this case, it is possible to solve the problems due to the large size of a polynucleotide encoding an RNA-guided endonuclease (e.g., low delivery efficiency).

2-3. Transgenic Embryo and Transgenic Animal in which Second Gene Editing has Occurred Using Component of Engineered Nuclease Expressed from Toolbox 2-3-1. Transgenic Embryo in which Second Gene Editing has Occurred Using Components of Engineered Nuclease 2-3-1-1. Construction of Transgenic Embryo in which Second Gene Editing has Occurred Using Components of Engineered Nuclease According to some exemplary embodiments of the present disclosure, a transgenic embryo is provided in which the embryo includes one or more cells (hereinafter, "a second gene editing cell") having a genome in which second gene editing has occurred using components of an engineered nuclease expressed from a toolbox.

According to an exemplary embodiment provided by the present specification, a transgenic embryo can be provided, in which the embryo has a genome that includes a polynucleotide encoding an RNA-guided endonuclease and a polynucleotide encoding a guide nucleic acid between a first ITR sequence and a second ITR sequence; and in which an endo-polynucleotide is knocked out. In particular, the guide nucleic acid can specifically bind to the endo-polynucleotide.

The form where the endo-polynucleotide is knocked out may be in any one form selected from i) a form in which at least one nucleotide in the sequence of the endo-polynucleotide is not included therein, ii) a form in which at least one nucleotide is additionally added to the sequence of the endo-polynucleotide, and iii) a form in which at least one nucleotide in the sequence of the endo-polynucleotide is deleted and at least one nucleotide is additionally added thereto.

As used herein, the term "second gene editing cell" refers to a cell having a genome in which second gene editing has occurred, and the term "second gene editing" may include gene editing using the above-described recombinase recognition site (RRS); gene editing using a toolbox which does not include an expression control element; and gene editing using a toolbox which includes an expression control element.

However, in the present disclosure, the term "second gene editing cell" simply refers to a cell having a genome in which second gene editing has occurred, but it does not matter whether or not a toolbox is included into the genome of the cell. That is, the cell in which second gene editing has occurred in the genome may be the "second gene editing cell" described in the present disclosure even when a toolbox is inserted into the genome; or may be the "second gene editing cell" described in the present disclosure even when a toolbox is not inserted into the genome.

Additionally, as used herein, the term "non-second gene editing cell" refers to a cell which has a genome in which second gene editing has not occurred. However, in the present disclosure, the term "non-second gene editing cell" simply refers to a cell having a genome in which second gene editing has not occurred, the cell which has a genome into which the toolbox (100) is inserted and where the above-described second gene editing has not occurred can also belong to the cell. That is, as long as second gene editing has not occurred, any cell which has a genome in which other genetic manipulation has occurred may be the "non-second gene editing cell" described in the present disclosure.

According to some exemplary embodiments of the present disclosure, the transgenic embryo in which second gene editing has occurred using components of an engineered nuclease that is expressed from a toolbox may be chimeric or homologous.

The homologous embryo may refer to a transgenic embryo which only has the "second gene editing cell".

The chimeric embryo may refer to a transgenic embryo which additionally has the "non-second gene editing cell", in addition to the "second gene editing cell".

One example of the chimeric transgenic embryo that can be provided in the present disclosure may be a transgenic embryo, which includes a first cell having a genome that includes a first toolbox and a target site and a second cell having a genome that includes a second toolbox and a modified site. The sequence of the first toolbox may be the same or different from that of the second toolbox.

In particular, the first toolbox and/or the second toolbox may include one or more selected from a polynucleotide encoding an RNA-guided endonuclease and a polynucleotide encoding a guide nucleic acid. Additionally, the first toolbox and/or the second toolbox may further include an expression control element to any one or more selected from the 5' end of the polynucleotide encoding the RNA-guided endonuclease and the 5' end of the polynucleotide encoding the guide nucleic acid. In this case, the guide nucleic acid can specifically bind to the target site.

The target site may be an endo-polynucleotide.

The target site may be an exo-polynucleotide. The modified site may be one in which the sequence of the target site has been changed by gene editing.

Specifically, the target site may include a first region, a second region, and a third region, and the modified site may include a fourth region, a fifth region, and a sixth region. In particular, the sequence of the first region is the same as that of the fourth region, the sequence of the third region is the same as that of the sixth region, and the sequence of the second region is different from that of the fifth region.

The second region and the fifth region may include a PAM sequence. The third region and the sixth region may include a PAM sequence.

The sequence of the fifth region may be in any one form selected from i) a form in which at least one nucleotide in the sequence of the second region is not included therein. ii) a form in which at least one nucleotide is additionally added to the sequence of the second region, and iii) a form in which at least one nucleotide in the sequence of the second region is deleted and at least one nucleotide is additionally added thereto. In the cases of ii) and iii), the at least one nucleotide which is additionally added thereto may include one or more selected from an editing enabling component, a polynucleotide encoding a protein or RNA, a polynucleotide encoding a non-functional polypeptide, a polynucleotide encoding an untranslated RNA, an untranscribed polynucleotide, an artificial intron, and an expression control element.

The target site may be an endo-polynucleotide of the fertilized egg and/or embryo.

The target site and the modified site may each be a sequence adjacent to a PAM sequence.

The target site and the modified site may each include a first ITR sequence at the 5' direction and may each include a second ITR sequence at the 3' direction.

Another example of the chimeric transgenic embryo that can be provided in the present disclosure may be a transgenic embryo, which includes a first cell that includes a first toolbox and a target site and a second cell that does not includes a toolbox but has a genome including a modified gene.

In particular, the first toolbox may include one or more selected from a polynucleotide encoding an RNA-guided endonuclease and a polynucleotide encoding a guide nucleic acid. Additionally, the first toolbox may additionally include an expression control element to any one selected from the 5' end of the polynucleotide encoding an RNA-guided endonuclease and the 5' end of the polynucleotide encoding a guide nucleic acid. In this case, the guide nucleic acid can specifically bind to the target site.

The modified site may be one in which the sequence of the target site has been changed by gene editing.

Specifically, the target site may include a first region, a second region, and a third region; and the modified site may include a fourth region, a fifth region, and a sixth region. In particular, the sequence of the first region is the same as that of the fourth region, the sequence of the third region is the same as that of the sixth region, and the sequence of the second region is different from that of the fifth region.

The sequence of the fifth region may be in any one form selected from i) a form in which at least one nucleotide in the sequence of the second region is not included therein. ii) a form in which at least one nucleotide is additionally added to the sequence of the second region, and iii) a form in which at least one nucleotide in the sequence of the second region is deleted and at least one nucleotide is additionally added thereto.

The target site may be an endo-polynucleotide of the fertilized egg and/or embryo.

The target site and the modified site may be a sequence adjacent to PAM sequence.

The target site and the modified site may each include a first ITR sequence at the 5' direction and may each include a second ITR sequence at the 3' direction.

Specifically, the target site and the PAM sequence may each be included between the first ITR sequence and the second ITR sequence, and the modified site and the PAM sequence may each be included between the first ITR sequence and the second ITR sequence.

Hereinafter, a method for preparing a transgenic embryo which includes one or more of the cells in which second gene editing occurred by an engineered nuclease which is expressed from a toolbox inserted into the genome will be described.

2-3-1-2. Method for Preparing Transgenic Embryo in which Second Gene Editing has Occurred Using Components of Engineered Nuclease One method for producing a fertilized egg and/or embryo, which has a genome in which second gene editing has occurred using components of an engineered nuclease that is expressed from a toolbox, may include a microinjection (MI) of the "element for second gene editing" to a fertilized egg.

In particular, the fertilized egg and/or embryo may be obtained by natural breeding or in vitro fertilization. The natural breeding and/or in vitro fertilization may be performed between a gamete, which is produced from an animal that has a genome into which a toolbox including a polynucleotide encoding the components of an engineered nuclease is inserted, and a gamete, which is produced from an animal with a different sex from the above animal.

As used herein, the term "element for second gene editing" refers to an element that is provided to a cell, embryo, or animal so as to enable second gene editing in the genome.

For example, the "element for second gene editing" may be any one or more selected from the material and/or conditions that affect the expression control element, a polynucleotide including a recombinase recognition site (RRS), a site-specific recombinase (SSR), an RNA-guided endonuclease, a guide nucleic acid, and a donor polynucleotide, but is not limited thereto.

More specifically, one exemplary method for preparing a transgenic embryo, in which gene editing has occurred provided by the present specification, may include a provision of a guide nucleic acid that can bind to the target site to a fertilized egg or embryo having a genome that includes a polynucleotide encoding an RNA-guided endonuclease. Additionally, one exemplary method for preparing a transgenic embryo, in which gene editing has occurred, may be to further provide a donor polynucleotide to the fertilized egg or embryo. In particular, the donor polynucleotide may be provided simultaneously with the guide nucleic acid. For example, the donor polynucleotide and the polynucleotide encoding the guide nucleic acid may be incorporated into a single vector and provided as such.

The fertilized egg or embryo may be one which is obtained by in vitro fertilization between a gamete, which is produced from an animal that has a genome including a polynucleotide encoding an RNA-guided endonuclease, and a gamete, which is produced from an animal with a different sex from the above animal.

More specifically, another exemplary method for preparing a transgenic embryo, in which gene editing has occurred provided by the present specification, may include a provision of any one among the materials and conditions that affect the expression control element, to a fertilized egg or embryo having a genome which includes a polynucleotide encoding an RNA-guided endonuclease and a polynucleotide encoding a guide nucleic acid that can specifically bind to a target site and which includes the expression control element in any one or more selected from the 5' end of the polynucleotide encoding the RNA-guided endonuclease and 5' end of the polynucleotide encoding the guide nucleic acid.

Additionally, one exemplary method for preparing a transgenic embryo, in which gene editing has occurred, may further provide a provision of a donor polynucleotide to the fertilized egg or embryo.

The donor polynucleotide may be simultaneously provided along with any one or more of the materials or conditions that affect the expression control element.

Another method for preparing a fertilized egg and/or embryo having a genome, in which second gene editing has occurred using components of an engineered nuclease expressed from a toolbox, may include performing a somatic cell nuclear transfer (SCNT).

In particular, the somatic cell used in the somatic cell nuclear transfer may have a genome into which a toolbox including a polynucleotide encoding the components of an engineered nuclease is inserted.

The somatic cell nuclear transfer (SCNT) may include transplanting the nucleus of the "second gene editing cell" produced by the method described above into an enucleated ovum. In particular, the "second gene editing cell" may be considered as a transgenic donor cell.

More specifically, one exemplary method for preparing a transgenic embryo, in which gene editing has occurred provided by the present specification, may include i) a method for preparing a transgenic donor cell having a genome which includes a polynucleotide encoding an RNA-guided endonuclease and in which gene editing has occurred at the target site, and ii) a method for transplanting the nucleus of the transgenic donor cell to an enucleated ovum.

The method for preparing the transgenic donor cell may include a provision of a guide nucleic acid that can bind to the target site to a cell having a genome that includes a polynucleotide encoding an RNA-guided endonuclease. The method for preparing the transgenic donor cell may further include a provision of a donor polynucleotide to a cell having a genome that includes the polynucleotide encoding the RNA-guided endonuclease.

In particular, the donor polynucleotide may be provided simultaneously with the guide nucleic acid. For example, the donor polynucleotide and the polynucleotide encoding a guide nucleic acid may be incorporated into a single vector, and provided as such.

More specifically, another exemplary method for preparing a transgenic embryo, in which gene editing has occurred, provided by the present specification, may include i) a method for preparing a transgenic donor cell having a genome which includes a polynucleotide encoding an RNA-guided endonuclease and the polynucleotide encoding a guide nucleic acid that can specifically bind to a target site, which includes an expression control element in one or more selected from the 5' end of the polynucleotide encoding an RNA-guided endonuclease and the 5' end of the polynucleotide encoding the guide nucleic acid, and in which gene editing has occurred at the target site, and ii) a method for transplanting the nucleus of the transgenic donor cell to an enucleated ovum.

The method for preparing a transgenic donor cell may include a provision of one or more selected from among materials and conditions that affect the expression control element, to a cell having a genome which includes a polynucleotide encoding an RNA-guided endonuclease and the polynucleotide encoding a guide nucleic acid that can specifically bind to the target site, and which includes the expression control element in one or more selected from the 5' end of the polynucleotide encoding an RNA-guided endonuclease and the 5' end of polynucleotide encoding the guide nucleic acid. Additionally, the method for preparing the transgenic donor cell may further include a provision of a donor polynucleotide to the cell.

The donor polynucleotide may be provided simultaneously along with at least one of the materials or conditions that affect the expression control element.

2-3-2. Transgenic Animal in which Second Gene Editing has Occurred Using Engineered Nuclease 2-3-2-1. Construction of Transgenic Animal in which Second Gene Editing has Occurred Using Engineered Nuclease According to some exemplary embodiments of the present disclosure, a transgenic animal may be provided, in which the transgenic animal includes one or more cells having a genome in which second gene editing has occurred using components of an engineered nuclease expressed from a toolbox (hereinafter, "second gene editing cell").

According to an exemplary embodiment provided by the present specification, a transgenic animal may be provided, in which the transgenic animal has a genome which includes a polynucleotide encoding an RNA-guided endonuclease and a polynucleotide encoding a guide nucleic acid between a first ITR sequence and a second ITR sequence, and in which an endo-polynucleotide is knocked out. In particular, the guide nucleic acid can specifically bind to the endo-polynucleotide.

The form in which the endo-polynucleotide is knocked out may be in any one form selected from i) a form in which at least one nucleotide in the sequence of the endo-polynucleotide is not included therein, ii) a form in which at least one nucleotide is additionally added to the sequence of the endo-polynucleotide, and iii) a form in which at least one nucleotide in the sequence of the endo-polynucleotide is deleted and at least one nucleotide is additionally added thereto.

The transgenic animal, in which second gene editing has occurred using components of an engineered nuclease that is expressed from a toolbox, may be a chimeric animal or homologous animal.

The homologous animal may refer to a transgenic animal which only has the "second gene editing cell".

The chimeric animal may refer to a transgenic animal which additionally has a "non-second gene editing cell", in addition to the "second gene editing cell".

An example of the chimeric transgenic animal that can be provided in the present disclosure may be a transgenic animal, which includes a first cell having a genome that includes a first toolbox and a target site, and a second cell having a genome that includes a second toolbox and a modified site. The sequence of the first toolbox may be the same or different from that of the second toolbox.

In particular, the first toolbox and/or the second toolbox may include one or more selected from a polynucleotide encoding an RNA-guided endonuclease and a polynucleotide encoding a guide nucleic acid. Additionally, the first toolbox and/or the second toolbox may further include an expression control element, in any one or more selected from the 5' end of the polynucleotide encoding the RNA-guided endonuclease and the 5' end of the polynucleotide encoding the guide nucleic acid. In this case, the guide nucleic acid can specifically bind to the target site.

The target site may be an endo-polynucleotide.

The target site may be an exo-polynucleotide.

The modified site may be one in which the sequence of the target site was changed by gene editing.

Specifically, the target sequence may include a first region, a second region, and a third region, and the modified sequence may include a fourth region, a fifth region, and a sixth region. In this case, the sequence of the first region is the same as that of the fourth region, the sequence of the third region is the same as that of the sixth region, and the sequence of the second region is different from that of the fifth region.

The second region and the fifth region may each include a PAM sequence. The third region and the sixth region may each include a PAM sequence.

The sequence of the fifth region may be in any one form selected from i) a form in which at least one nucleotide in the sequence of the second region is not included therein. ii) a form in which at least one nucleotide is additionally added to the sequence of the second region, and iii) a form in which at least one nucleotide in the sequence of the second region is deleted and at least one nucleotide is additionally added thereto. In the cases of ii) and iii), the at least one nucleotide which is additionally added thereto may include one or more selected from an editing enabling component, a polynucleotide encoding a protein or RNA, a polynucleotide encoding a non-functional polypeptide, a polynucleotide encoding an untranslated RNA, an untranscribed polynucleotide, an artificial intron, and an expression control element.

The target site and the modified site may be a sequence adjacent to a PAM sequence.

The target site and the modified site may each include a first ITR sequence at the 5' direction and may each include a second ITR sequence at the 3' direction.

Another example of the chimeric transgenic embryo that can be provided in the present disclosure may be a transgenic animal, which includes a first cell having a genome that includes a first toolbox and a target site, and a second cell, which does not include a toolbox but has a genome including a modified gene.

In particular, the first toolbox may include one or more selected from a polynucleotide encoding an RNA-guided endonuclease and a polynucleotide encoding a guide nucleic acid. Additionally, the first toolbox may further include an expression control element in any one or more selected from the 5' end of the polynucleotide encoding the RNA-guided endonuclease and the 5' end of the polynucleotide encoding the guide nucleic acid. In this case, the guide nucleic acid can specifically bind to the target site.

The modified site may be one in which the sequence of the target site has been changed by gene editing.

Specifically, the target sequence may include a first region, a second region, and a third region, and the modified sequence may include a fourth region, a fifth region, and a sixth region. In this case, the sequence of the first region is the same as that of the fourth region, the sequence of the third region is the same as that of the sixth region, and the sequence of the second region is different from that of the fifth region.

The sequence of the fifth region may be in any one form selected from i) a form in which at least one nucleotide in the sequence of the second region is not included therein. ii) a form in which at least one nucleotide is additionally added to the sequence of the second region, and iii) a form in which at least one nucleotide in the sequence of the second region is deleted and at least one nucleotide is additionally added thereto.

The target site may be an endo-polynucleotide of the animal.

The target site and the modified site may be a sequence adjacent to a PAM sequence.

The target site and the modified site may each include a first ITR sequence at the 5' direction and may each include a second ITR sequence at the 3' direction.

Specifically, the target site and the PAM sequence may each be included between the first ITR sequence and the second ITR sequence, the modified site and the PAM sequence may each be included between the first ITR sequence and the second ITR sequence.

Hereinafter, a method for preparing a transgenic animal will be described, in which the transgenic animal includes one or more cells having a genome in which second gene editing has occurred by an engineered nuclease that is expressed from a toolbox inserted into the genome.

2-3-2-2. Method for Preparing Transgenic Animal in which Second Gene Editing Occurred Using Engineered Nuclease One method for producing an animal which includes a "second gene editing cell" according to some exemplary embodiments provided in the present disclosure may include transplanting, to the uterus of a surrogate mother, a fertilized egg and/or embryo having a genome in which second gene editing has occurred by components of an engineered nuclease.

For example, as described above, an animal including the "second gene editing cell" can be produced by implanting the fertilized egg and/or embryo produced by microinjection (MI) of the "element for second gene editing" to the uterus of a surrogate mother. In this case, the produced animal may be chimeric or homologous.

In another example, an animal including the "second gene editing cell" can be produced by implanting, to the uterus of a surrogate mother, the fertilized egg and/or embryo produced by somatic cell nuclear transfer (SCNT) using a cell which has a genome in which second gene editing has occurred as described above. In this case, the produced animal may be homologous.

More specifically, one exemplary method for preparing a transgenic animal in which second gene editing has occurred provided by the present specification may include i) a method for preparing an embryo having a genome which includes a polynucleotide encoding an RNA-guided endonuclease and in which second gene editing has occurred at the target site, and ii) a method for implanting the embryo to a surrogate mother.

The method for preparing the embryo may include a provision of a guide nucleic acid that can bind to the target site to a fertilized egg or embryo, which has a genome including a polynucleotide encoding an RNA-guided endonuclease. Additionally, the method for preparing the embryo may further include a provision of a donor polynucleotide to the fertilized egg or embryo.

In particular, the donor polynucleotide may be provided simultaneously along with the guide nucleic acid. For example, the donor polynucleotide and the polynucleotide encoding the guide nucleic acid may be incorporated into a single vector, and provided as such.

The preparation of the embryo may include i) preparing a transgenic donor cell having a genome which includes a polynucleotide encoding an RNA-guided endonuclease and in which second gene editing has occurred at the target site, and ii) transplanting of the nucleus of the transgenic donor cell into an enucleated ovum.

The preparation of the transgenic donor cell may include a provision of a guide nucleic acid which can bind to the target site, to a cell having a genome that includes a polynucleotide encoding an RNA-guided endonuclease. Additionally, the preparation of the transgenic donor cell may further include a provision of a donor polynucleotide to a cell having a genome which includes the polynucleotide encoding the RNA-guided endonuclease.

In particular, the donor polynucleotide may be provided simultaneously along with the guide nucleic acid. For example, the donor polynucleotide and the polynucleotide encoding the guide nucleic acid may be incorporated into a single vector, and provided as such.

More specifically, another method for preparing a transgenic animal, in which gene editing has occurred, provided in the present disclosure may include i) preparation of an embryo having a genome which includes a polynucleotide encoding an RNA-guided endonuclease and the polynucleotide encoding a guide nucleic acid that can specifically bind to a target site, which includes an expression control element in one or more selected from the 5' end of the polynucleotide encoding the RNA-guided endonuclease and the 5' end of the polynucleotide encoding the guide nucleic acid, and in which gene editing has occurred at the target site, and ii) implantation of the embryo into a surrogate mother.

An exemplary method for preparing the embryo may include a provision of one or more selected from among materials and conditions that affect the expression control element, to a fertilized egg or embryo having a genome, which includes a target site, a polynucleotide encoding an RNA-guided endonuclease, and a polynucleotide encoding a guide nucleic acid that can specifically bind to the target site, and which includes an expression control element in one or more selected from the 5' end of the polynucleotide encoding the RNA-guided endonuclease and the 5' end of the polynucleotide encoding the guide nucleic acid. Additionally, the preparation of the embryo may further include a provision of a donor polynucleotide to the cell.

The donor polynucleotide may be provided simultaneously with one or more selected from among materials and conditions that affect the expression control element.

Another exemplary method for preparing the embryo may include i) preparation of a transgenic donor cell having a genome which includes a target site, a polynucleotide encoding an RNA-guided endonuclease and a polynucleotide encoding a guide nucleic acid that can specifically bind to the target site, and which includes an expression control element in one or more selected from the 5' end of the polynucleotide encoding the RNA-guided endonuclease and the 5' end of the polynucleotide encoding the guide nucleic acid; and ii) implantation of the nucleus of the transgenic donor cell into an enucleated oocyte.

The preparation of the transgenic donor cell may include a provision of one or more selected from among materials and conditions that affect the expression control element, to a cell having a genome, which includes a polynucleotide encoding an RNA-guided endonuclease and a polynucleotide encoding a guide nucleic acid that can specifically bind to the target site, and which includes the expression control element in one or more selected from the 5' end of the polynucleotide encoding the RNA-guided endonuclease and the 5' end of the polynucleotide encoding the guide nucleic acid. Additionally, the preparation of the transgenic donor cell may further include a provision of a donor polynucleotide to the cell.

The donor polynucleotide may be provided simultaneously with one or more selected from among materials and conditions that affect the expression control element.

One method for producing an animal that has a genome in which second gene editing has occurred according to some exemplary embodiments provided in the present disclosure may include an injection of the "element for second gene editing" described above to a tissue of an animal. The animal produced through the method of injection to the tissue described above may be a chimeric animal.

One method for producing an animal that has a genome in which second gene editing has occurred according to some exemplary embodiments provided in the present disclosure may include natural breeding of a male which has a testis including the "second gene editing cell" or a female which has an ovary including the "second gene editing cell".

For example, the natural breeding may be performed between the male which has a testis including the "second gene editing cell" and the female which has an ovary including the "second gene editing cell".

In another example, the natural breeding may be performed between a male which has a testis including the "second gene editing cell" and a wild-type (WT) female, or between a wild-type (WT) male and a female which has an ovary including the "second gene editing cell".

3. Second Gene Editing Using Toolbox which Includes Polynucleotide Having PAM Sequence Hereinafter, second gene editing in a polynucleotide having a PAM sequence included in a toolbox inserted into a genome will be described. The second gene editing may be a knockin of a donor polynucleotide.

That is, a toolbox including a polynucleotide having a PAM sequence artificially inserted into the genome may function as a target site that enables gene editing.

As described above, the toolbox can be located within the safe harbor, and thus, the occurrence of gene editing in the toolbox may not affect the expression of the protein or RNA in the genome in a cell.

3-1. Toolbox Including Polynucleotide Having PAM Sequence

According to some exemplary embodiments of the present disclosure, a toolbox including a first ITR sequence, a polynucleotide having a PAM sequence, and a second ITR sequence can be provided.

The toolbox may further include a polynucleotide encoding the components of an engineered nuclease. For example, the toolbox may further include one or more selected from a polynucleotide encoding an RNA-guided endonuclease and a polynucleotide encoding a guide nucleic acid.

Hereinafter, some exemplary embodiments of the polynucleotide having a PAM sequence will be described.

For example, a polynucleotide having a PAM sequence can include a marker gene, the details of the marker gene have been described above, and are thus omitted.

In another example, a polynucleotide having a PAM sequence may include a polynucleotide encoding an RNA-guided endonuclease and/or a polynucleotide encoding a guide nucleic acid.

In still another example, a polynucleotide having a PAM sequence may include a polynucleotide which does not include a start codon (AUG). When the polynucleotide having the PAM sequence does not include the start codon (AUG), the RNA or protein that is transcribed and/or translated by the polynucleotide artificially inserted into the genome may not occur.

That is, when the polynucleotide inserted from the outside does not include the start codon (AUG), the RNA or protein is not expressed, and thus there is an advantage in that the polynucleotide inserted from the outside can be utilized as a site to be cleaved by an engineered nuclease while maintaining the intracellular stability.

According to some exemplary embodiments of the present disclosure, a plurality of polynucleotides having a PAM sequence (hereinafter, artificial editing site) may be included within a single toolbox.

As used herein, the term "artificial editing site" refers to a polynucleotide having a PAM sequence present in a toolbox, and the artificial editing site can be included in a genome and function as a target site at which gene editing may occur.

For example, two artificial editing sites may be included in a single toolbox. That is, a first artificial editing site and a second artificial editing site may be included in a single toolbox.

The sequence of the first artificial editing site may be the same as that of the second artificial editing site.

The sequence of the first artificial editing site may be different from that of the second artificial editing site.

In another example, three or more artificial editing sites may be included in a single toolbox. However, for the convenience of explanation, the explanation will be provided for the case where two artificial editing sites can be included in a single toolbox.

The explanations herein below (explanations on the case where the number of artificial editing site is two) can be applicable to the relationship between two artificial editing sites randomly selected among n artificial editing sites even when the number of the artificial editing site is n (n is a natural number of 3 or greater).

FIG. 11 illustrates some embodiments of a toolbox which includes a polynucleotide having a PAM sequence.

FIG. 11(a) illustrates the toolbox (140(a)) in which a single polynucleotide having a PAM sequence (203) is included between a first ITR sequence (201) and a second ITR sequence (207).

FIG. 11(b) illustrates the toolbox (140(b)) in which a first artificial editing site (205) and a second artificial editing site (206) are included between a first ITR sequence (201) and a second ITR sequence (207). In particular, the sequence of the first artificial editing site (205) may be the same as that of the second artificial editing site (206).

FIG. 11(c) illustrates the toolbox (140(c)) in which a first artificial editing site (202) and a second artificial editing site (204) are included between a first ITR sequence (201) and a second ITR sequence (207). In particular, the sequence of the first artificial editing site (202) is different from that of the second artificial editing site (204).

The toolbox may be inserted into a genome or chromosome, and the form and the method as to how the toolbox is inserted into a genome or chromosome have been described above and thus detailed explanation is omitted.

Hereinafter, a method of second gene editing in a cell, fertilized egg, embryo, or animal having a genome into which a toolbox including a polynucleotide having a PAM sequence as described above is inserted, and a form of the genome in which second gene editing has occurred will be described.

3-2. Method of Second Gene Editing in Toolbox Including Polynucleotide Having PAM Sequence Hereinafter, the method of second gene editing in a cell into which a toolbox that includes a polynucleotide having a PAM sequence is inserted will be described. The method for inserting a toolbox that includes a polynucleotide having the PAM sequence into a cell can be sufficiently explained by the toolbox insertion method described previously, and thus the specific details thereon are omitted herein.

Various methods for second gene editing can be provided according to the construction of the toolbox inserted into the genome of a cell.

For the convenience of explanation, hereinafter, it is assumed that a polynucleotide encoding an RNA-guided endonuclease in a genome and described thereon.

For example, the polynucleotide encoding the RNA-guided endonuclease may be included in a toolbox which is the same as the toolbox that includes the polynucleotide having the PAM sequence or included in a toolbox which is different from the toolbox that includes the polynucleotide having the PAM sequence, and then inserted to a genome. In another example, the polynucleotide encoding the RNA-guided endonuclease may be inserted into the genome without being included into the component of the toolbox.

Hereinafter, the method for second gene editing will be explained using the toolbox illustrated in FIG. 11(a).

FIG. 12 illustrates a process of second gene editing using the toolbox illustrated in FIG. 11(a).

One method for second gene editing in a cell having a genome into which the toolbox (140(a)) including a single polynucleotide (203) having a PAM sequence is inserted may include a provision of a guide nucleic acid and donor polynucleotide (232) into a cell.

Part of the sequence of the guide nucleic acid may be the same as or complementary to part of the sequence of the polynucleotide having the PAM sequence (203).

There may be various methods for providing the guide nucleic acid to the cell.

For example, the guide nucleic acid may be provided into the cell by introducing a polynucleotide encoding the guide nucleic acid into the cell. The polynucleotide encoding the guide nucleic acid may be introduced in the form of an RNA, or may be incorporated into a plasmid vector or viral vector and then introduced into the cell.

In another example, the guide nucleic acid may be provided into the cell by the expression of the guide nucleic acid from a polynucleotide encoding the guide nucleic acid that is included in the toolbox (140(*a*)) or a toolbox different from the toolbox (140(*a*)). Additionally, the guide nucleic acid may be provided into the cell by the expression of the guide nucleic acid from a polynucleotide encoding the guide nucleic acid that is inserted into a genome.

In still another example, in the case where the guide nucleic acid is included in the toolbox (140(*a*)) or a toolbox different from the toolbox (140(*a*)) but is not normally expressed by the above-described expression control element, the guide nucleic acid may be provided into the cell by the treatment of the material and/or conditions that affect the expression control element. The material and/or conditions that affect the expression control element have been described above and thus the specific details are omitted herein.

There may be various methods for delivering the donor polynucleotide into the cell.

For example, the donor polynucleotide may be delivered into the cell by introducing a plasmid vector or viral vector that includes the donor polynucleotide, into the cell.

When the guide nucleic acid is provided into the cell by the method described above, the guide nucleic acid can interact with the RNA-guided endonuclease, and the guide nucleic acid and the RNA-guided endonuclease can form a complex in the cell.

Additionally, the guide nucleic acid delivered into the cell can specifically bind to the polynucleotide (203). The RNA-guided endonuclease can cleave the polynucleotide (203) in a state of forming a complex with the guide nucleic acid. In this case, the donor polynucleotide (232) delivered into the cell may be knocked in to the polynucleotide (203), and as a result, the polynucleotide (203) can be divided into two parts (203(*a*) and 203(*b*)) (see FIG. 12).

Then, a method for second gene editing will be explained using the toolbox illustrated in FIG. 11(*b*).

Figure 13:
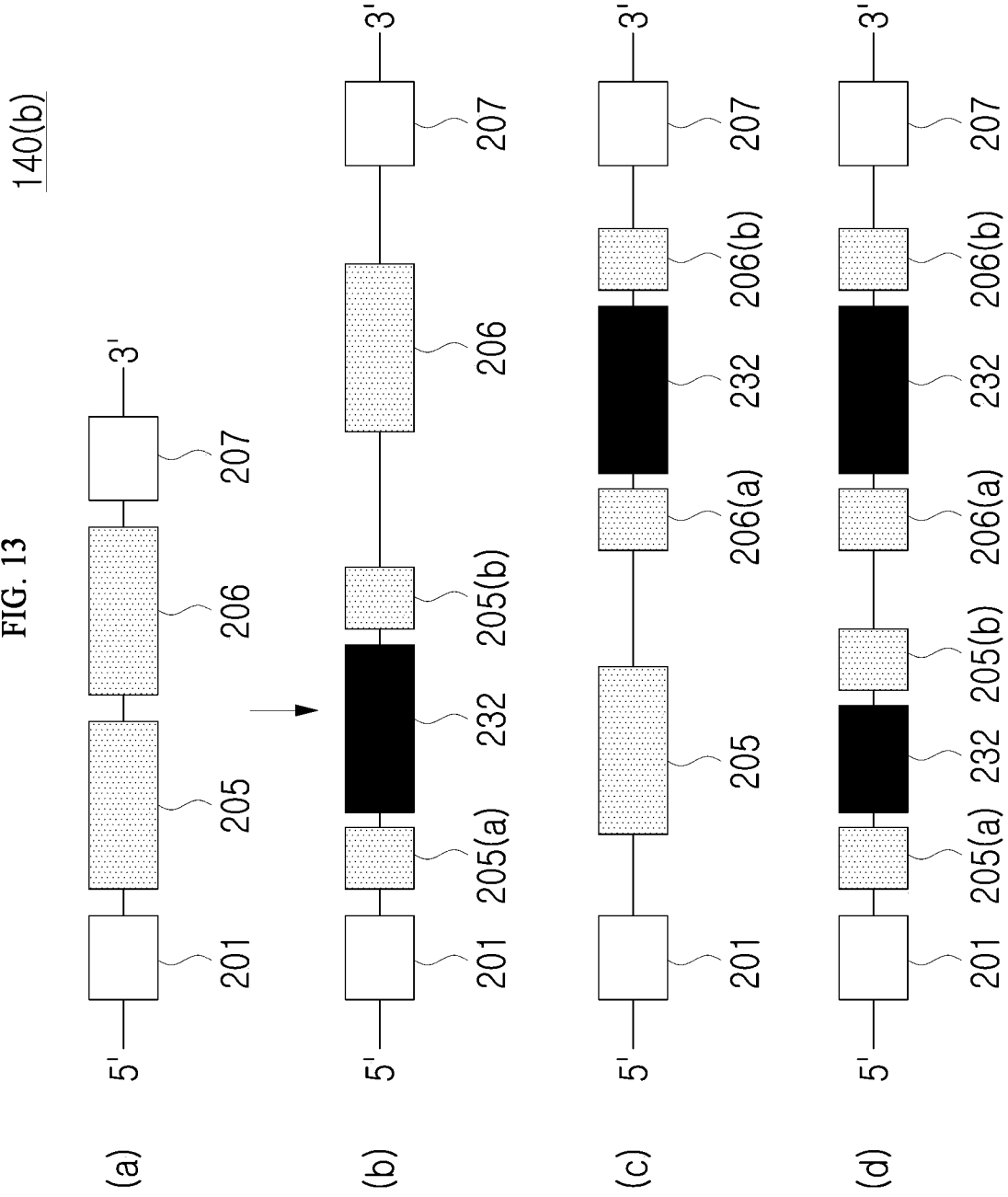
FIG. 13 illustrates another process of gene editing within a toolbox which includes a polynucleotide having a PAM sequence.

FIG. 13 illustrates a process of second gene editing using the toolbox illustrated in FIG. 11(*b*).

One method for second gene editing in a cell having a genome, into which the toolbox (140(*b*)) including a first artificial editing site (205) and a second artificial editing site (206) is inserted, may include a provision of a guide nucleic acid and donor polynucleotide into the cell.

As described above, the first artificial editing site (205) and the second artificial editing site (206) may include the same sequence.

The part of the sequence of the guide nucleic acid may be the same as or complementary to the sequence of the first artificial editing site (205) and/or the second artificial editing site (206).

There may be various methods for providing the guide nucleic acid into the cell.

For example, the guide nucleic acid may be provided into the cell by the introduction of a polynucleotide encoding the guide nucleic acid into the cell.

In another example, the guide nucleic acid may be provided into the cell by the expression of the guide nucleic acid from a polynucleotide encoding the guide nucleic acid which is included in the toolbox (140(*b*)) or a toolbox different from the toolbox (140(*b*)).

In still another example, in the case where the guide nucleic acid is included in the toolbox (140(*b*)) or a toolbox different from the toolbox (140(*b*)) but is not normally expressed by the above-described expression control element, the guide nucleic acid may be provided into the cell by the treatment of the material and/or conditions that affect the expression control element.

There may be various methods for delivering the donor polynucleotide into the cell, and these methods have been described above and thus the specific explanations thereon will be omitted herein.

When the guide nucleic acid is provided into the cell by the method described above, the guide nucleic acid can interact with the RNA-guided endonuclease and the guide nucleic acid and the RNA-guided endonuclease can form a complex within the cell.

Additionally, the guide nucleic acid provided into the cell can specifically bind to the first artificial editing site (205) and/or the second artificial editing site (206). The RNA-guided endonuclease can cleave the first artificial editing site (205) and/or the second artificial editing site (206) in a state forming a complex with the guide nucleic acid.

In this case, the donor polynucleotide (232) introduced into the cell can be knocked in to the first artificial editing site (205) and/or the second artificial editing site (206).

As a result, the first artificial editing site (205) can be divided into a first region (205(*a*)) and a second region (205(*b*)). Additionally, the second artificial editing site (206) can be divided into a first region (206(*a*)) and a second region (206(*b*)) (see FIG. 13(*b*) to see FIG. 13(*d*)).

In the case where the donor polynucleotide (232) is knocked in both to the first artificial editing site (205) and the second artificial editing site (206), a higher level of the polypeptide can be expressed in a cell where the donor polynucleotide (232) is knocked in. The polypeptide may be one which is encoded by the donor polynucleotide (232) (see FIG. 13).

Furthermore, a method for second gene editing will be explained using the toolbox illustrated in FIG. 11(*c*).

Figure 14:
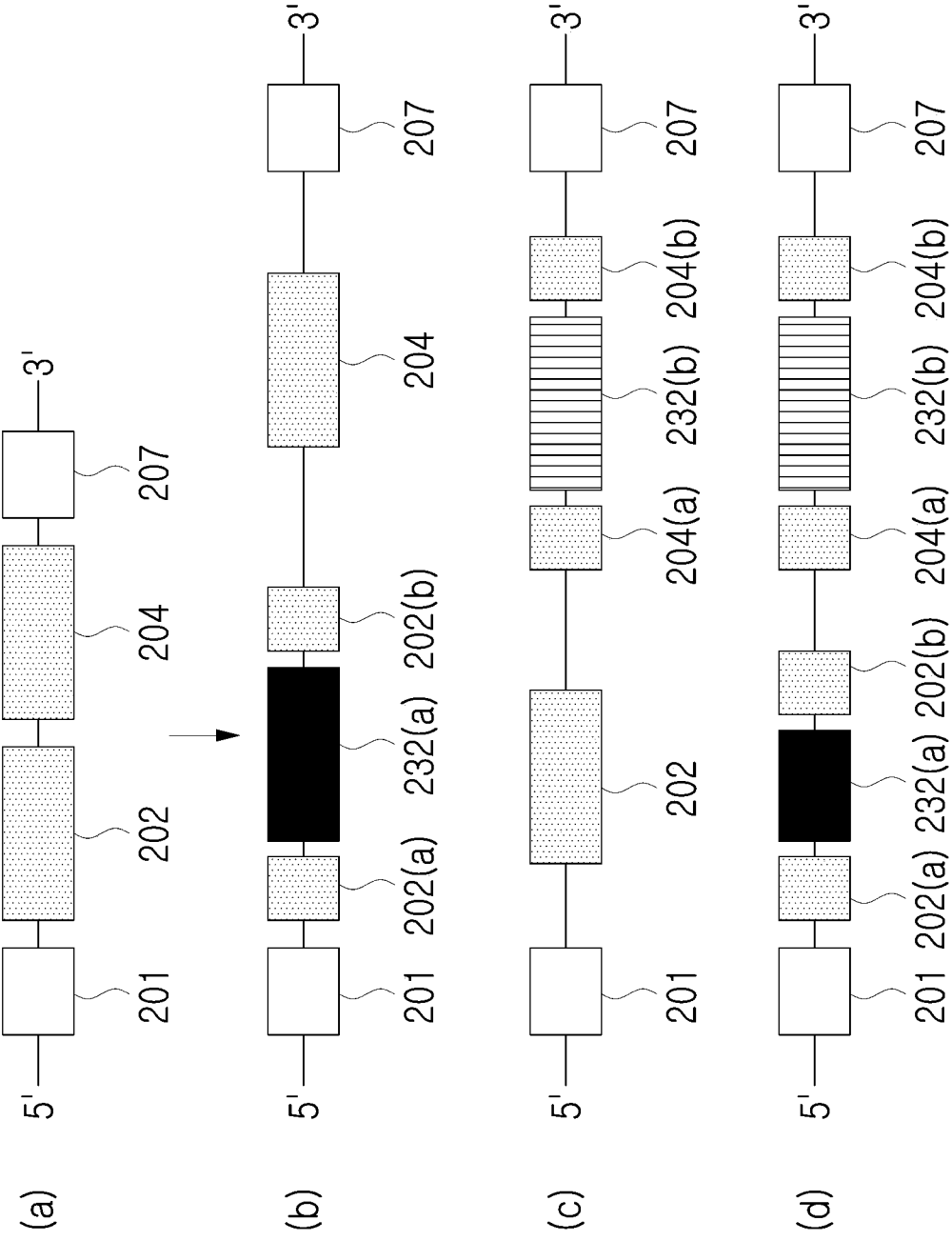
FIG. 14 illustrates a still another process of gene editing within a toolbox which includes a polynucleotide having a PAM sequence.

FIG. 14 illustrates a process of second gene editing using the toolbox illustrated in FIG. 11(*c*).

One method for second gene editing in a cell having a genome, into which the toolbox (140(*c*)) including a first artificial editing site (202) and a second artificial editing site (204) is inserted, may include a provision of a first guide nucleic acid, a second guide nucleic acid, a first donor polynucleotide (232(*a*)) and a second donor polynucleotide (232(*b*)) into the cell. As described above, the sequence of the first artificial editing site (202) is different from that of the second artificial editing site (204).

In this case, part of the sequence of the first guide nucleic acid may be the same as or complementary to part of the sequence of the first artificial editing site (202). Part of the sequence of the second guide nucleic acid may be the same as or complementary to part of the sequence of the second artificial editing site (204).

Additionally, the 5' end and 3' end of the first donor polynucleotide (232(a)) may include a sequence which is the same as part of the sequence of the first artificial editing site (202). Additionally, the 5' end and 3' end of the second donor polynucleotide (232(b)) may include a sequence which is the same as to part of the sequence of the second artificial editing site (204). That is, the 5' end and 3' end of the first donor polynucleotide (232(a)) and the second donor polynucleotide (232(b)) may include a sequence for homologous recombination.

There may be various methods for providing the first guide nucleic acid and the second guide nucleic acid into the cell.

For example, the first guide nucleic acid and the second guide nucleic acid may be provided into the cell by the introduction of the polynucleotide encoding the first guide nucleic acid and/or the second guide nucleic acid into the cell.

In another example, the first guide nucleic acid and/or the second guide nucleic acid may be provided into the cell by the expression of the first guide nucleic acid and the second guide nucleic acid from the polynucleotide encoding the first guide nucleic acid and/or the second guide nucleic acid, which is included in the toolbox 140(c) or a toolbox different from the toolbox 140(c). In this case, the polynucleotide encoding the first guide nucleic acid and the polynucleotide encoding the second guide nucleic acid may be included in the same or different toolbox and then provided into the cell.

In still another example, in the case where the first guide nucleic acid and/or the second guide nucleic acid is included in the toolbox 140(c) or a toolbox different from the toolbox 140(c) but is not normally expressed by the above-described expression control element, the first guide nucleic acid and/or the second guide nucleic acid may be provided into the cell by the treatment of the material and/or conditions that affect the expression control element. In this case as well, the polynucleotide encoding the first guide nucleic acid and the polynucleotide encoding the second guide nucleic acid may be included in the same or different toolbox and then provided into the cell.

There may be various methods for delivering the first donor polynucleotide and the second donor polynucleotide into the cell.

For example, the first donor polynucleotide and the second donor polynucleotide may be delivered into the cell by introducing a vector including the first donor polynucleotide and the second donor polynucleotide into the cell. In this case, the first and the second donor polynucleotide may be included in the same vector and then delivered into the cell. Alternatively, the first and the second donor polynucleotide may be included in a different vector and then delivered into the cell. The vector may be a plasmid vector or viral vector.

When the first guide nucleic acid and/or the second guide nucleic acid are provided into the cell by the method described above, the first guide nucleic acid and/or the second guide nucleic acid can interact with the RNA-guided endonuclease, and the first guide nucleic acid and/or the second guide nucleic acid can form a complex with the RNA-guided endonuclease in the cell.

The first guide nucleic acid provided into the cell can specifically bind to the first artificial editing site (202). The RNA-guided endonuclease can cleave the first artificial editing site (202) in a state forming a complex with the first guide nucleic acid. In this case, the first donor polynucleotide (232(a)) provided into the cell can be knocked in to the first artificial editing site (202).

Additionally, the second guide nucleic acid provided into the cell can specifically bind to the second artificial editing site (204). The RNA-guided endonuclease can cleave the second artificial editing site (204) in a state forming a complex with the second guide nucleic acid. In this case, the second donor polynucleotide (232(b)) provided into the cell can be knocked in to the second artificial editing site (204).

As a result, the first artificial editing site (202) can be divided into a first region (202(a)) and a second region (202(b)). Additionally, the second artificial editing site (204) can be divided into a first region (204(a)) and a second region (204(b)) (see FIG. 14 (b) to FIG. 14(d)).

The form of the toolbox (140(c)) in which second gene editing has occurred may be in a form where the first donor polynucleotide (232(a)) is knocked in to the first artificial editing site (202) (see FIG. 14(b)).

Additionally, another form of the toolbox (140(c)) in which second gene editing has occurred may be in a form where the second donor polynucleotide (232(b)) is knocked in to the second artificial editing site (204) (see FIG. 14(c)).

Furthermore, the form of the toolbox (140(c)) in which second gene editing has occurred may be in a form where the first donor polynucleotide (232(a)) is knocked in to the first artificial editing site (202), and the second donor polynucleotide (232(b)) is knocked in to the second artificial editing site (204) (see FIG. 14(d)).

That is, when second gene editing occurs in the toolbox (140(c)), the first donor polynucleotide (232(a)) and the second donor polynucleotide (232(b)), which have a sequence different from each other, may be knocked in to the first artificial editing site (202) and the second artificial editing site (204), respectively. In this case, a first polypeptide and a second polypeptide may be expressed in the cell where the first and the second donor polynucleotide (232) are knocked in. The first polypeptide may be one which is encoded by the first donor polynucleotide (232(a)), and the second polypeptide may be one which is encoded by the second donor polynucleotide (232(b)).

Unlike those examples described above, when a polynucleotide encoding an RNA-guided endonuclease is not inserted into the genome of the cell, second gene editing may be performed by additionally providing an RNA-guided endonuclease to the cell.

There may be various methods for delivering the RNA-guided endonuclease into the cell.

For example, the RNA-guided endonuclease may be delivered into the cell by introducing the RNA-guided endonuclease as a protein into the cell. Additionally, the RNA-guided endonuclease may be delivered into the cell by introducing the polynucleotide encoding the RNA-guided endonuclease into the cell. The introduction of the polynucleotide encoding the RNA-guided endonuclease into the cell may include incorporating the polynucleotide encoding the RNA-guided endonuclease into a plasmid vector or viral vector and then introduced into the cell.

As described above, one method for second gene editing in an isolated cell may include a method for directly delivering an RNA, a plasmid vector, a polypeptide and/or a protein described above to the isolated cell.

Furthermore, one method for second gene editing in a non-isolated cell may include a method for injecting an RNA, a plasmid vector, a polypeptide and/or a protein described above to the tissue or organ of an individual.

Furthermore, one method for second gene editing in a fertilized egg and/or embryo may include a method for microinjecting an RNA, a plasmid vector, a polypeptide and/or a protein to a fertilized egg of an animal in a state of 1-cell stage pronuclear.

Hereinafter, the effects of occurrence of second gene editing in a toolbox, which includes a polynucleotide having a PAM sequence will be described.

The effects due to second gene editing may vary according to the types of the polynucleotide including a PAM sequence included in a toolbox provided by some exemplary embodiments disclosed in the present disclosure.

For example, when the polynucleotide including the PAM sequence is a marker gene, if a donor polynucleotide is knocked in to the polynucleotide that includes the PAM sequence as a target site, the polynucleotide encoded by the marker gene cannot be expressed in the cell. Through such a characteristic, the cell in which the donor polynucleotide is knocked in to the genome can be selected. The details with regard to the selection of cells in which gene editing has occurred using a marker gene will be described later.

In another example, when the polynucleotide including the PAM sequence is a polynucleotide encoding an RNA-guided endonuclease, if a donor polynucleotide is knocked in to the polynucleotide that includes the PAM sequence as a target site, the polynucleotide encoding the RNA-guided endonuclease cannot be expressed in the cell.

In this case, the target site may be one which is cleaved using an RNA-guided endonuclease, which is expressed by the transcription and translation of the polynucleotide that includes the PAM sequence, and one in which the donor polynucleotide is knocked in. There is an advantage in that unwanted additional gene editing does not occur after the knockin of the donor polynucleotide because the RNA-guided endonuclease is no longer expressed in a cell.

Hereinafter, the construction of an embryo or animal in which second gene editing has occurred and which is produced using a cell, fertilized egg, embryo, or animal where the above-described toolbox including the polynucleotide having the PAM sequence is inserted into the genome, and a preparation method thereof will be described.

3-3. Transgenic Embryo and Animal in which Second Gene Editing has Occurred in Toolbox Including Polynucleotide Having PAM Sequence 3-3-1. Transgenic Embryo in which Second Gene Editing has Occurred in Toolbox Including Polynucleotide Having PAM Sequence 3-3-1-1. Construction of Transgenic Embryo in which Second Gene Editing has Occurred in Toolbox Including Polynucleotide Having PAM Sequence According to some exemplary embodiments of the present disclosure, a transgenic embryo can be provided, in which the transgenic embryo includes one or more of second gene editing cells (hereinafter, "PAM second gene editing cell") having a genome in which second gene editing has occurred in a polynucleotide having a PAM sequence included in a toolbox.

Additionally, as used herein, the term "PAM non-second gene editing cell" refers to a cell which includes a genome in which second gene editing has not occurred in a polynucleotide having a PAM sequence.

However, in the present disclosure, the term "PAM non-second gene editing cell" simply refers to a cell having a genome in which second gene editing has not occurred, and any cell having a genome in which the above-described second gene editing has not occurred and into which the toolbox (100) is inserted may also correspond thereto. That is, unless it is the case where second gene editing has not occurred in the polynucleotide having the PAM sequence, any cell having a genome with a different genetic manipulation may also become a "PAM non-second gene editing cell" according to the present disclosure.

A transgenic embryo including the "PAM second gene editing cell" may be chimeric or homologous.

The homologous embryo may refer to a transgenic embryo which has only the "PAM second gene editing cell".

The chimeric embryo may refer to a transgenic embryo which has the "PAM non-second gene editing cell", in addition to the "PAM second gene editing cell".

Hereinafter, a method for preparing a transgenic embryo which includes one or more cells that have a genome in which second gene editing has occurred in a polynucleotide having a PAM sequence that is inserted into the genome will be described.

3-3-1-2. Method for Preparing Transgenic Embryo in which Second Gene Editing has Occurred in Toolbox Including Polynucleotide Having PAM Sequence One method for producing a fertilized egg or embryo having a genome in which second gene editing has occurred in a polynucleotide having a PAM sequence included in a toolbox, may include microinjecting (MI) the "element for second gene editing" to a fertilized egg or embryo having a genome into which a polynucleotide having a PAM sequence is inserted.

As used herein, the term "element for second gene editing" refers to an element provided to a cell, embryo, or animal so as to enable second gene editing in the genome. For example, the "element for second gene editing" may be any one selected from the material and/or conditions that affect the expression control element, a polynucleotide including a recombinase recognition site (RRS), a site-specific recombinase (SSR), an RNA-guided endonuclease, a guide nucleic acid and donor polynucleotide, but is not limited thereto.

One method for producing a fertilized egg or embryo having a genome in which second gene editing has occurred in a polynucleotide having a PAM sequence included in a toolbox may include somatic cell nuclear transfer (SCNT). The somatic cell nuclear transfer (SCNT) may include transplantation of the nucleus of a cell in a polynucleotide having a PAM sequence produced by the above-described method, in which second gene editing has occurred, to an enucleated ovum.

3-3-2. Transgenic Embryo in which Second Gene Editing has Occurred in Toolbox Including Polynucleotide Having PAM Sequence 3-3-2-1. Construction of Transgenic Embryo in which Second Gene Editing has Occurred in Toolbox Including Polynucleotide Having PAM Sequence According to some exemplary embodiments of the present disclosure, a transgenic animal can be provided, in which the transgenic animal includes one or more of the PAM second gene editing cell that has a genome in which second gene editing occurred in a polynucleotide having a PAM sequence included in a toolbox.

A transgenic animal including the "PAM second gene editing cell" may be a chimeric animal or homologous animal.

The homologous animal may refer to a transgenic animal which has only the "PAM second gene editing cell".

The chimeric animal may refer to a transgenic animal which has the "PAM non-second gene editing cell" in addition to the "PAM second gene editing cell".

Hereinafter, a method for preparing a transgenic animal which includes one or more cells having a genome, in which second gene editing occurred in a polynucleotide having a PAM sequence included in a toolbox which is inserted into the genome will be described.

3-3-2-2. Method for Preparing Transgenic Animal in which Second Gene Editing has Occurred in Toolbox Including Polynucleotide Having PAM Sequence One method for producing an animal including the "PAM second gene editing cell" according to some exemplary embodiments provided in the present disclosure may include transplanting of a fertilized egg or embryo having a genome in which second gene editing occurred in a polynucleotide having a PAM sequence produced by the above-described method, into the uterus of a surrogate mother.

For example, as described above, an animal which includes the "PAM second gene editing cell" can be produced by implanting the fertilized egg and/or embryo produced by the microinjection (MI) of the "element for second gene editing" into the uterus of a surrogate mother. In this case, the produced animal may be chimeric or homologous.

In another example, as described above, an animal including the "PAM second gene editing cell" can be produced by implanting the fertilized egg and/or embryo produced by somatic cell nuclear transfer (SCNT) using the "PAM second gene editing cell" into the uterus of a surrogate mother. In this case, the produced animal may be homologous.

One method for producing an animal including the "PAM second gene editing cell" according to some exemplary embodiments provided in the present disclosure may include injecting the above-described "element for second gene editing" to a tissue of an animal having a genome into which a polynucleotide having a PAM sequence is inserted. The animal produced through the method of injection to the tissue may be a chimeric animal.

One method for producing an animal including the "PAM second gene editing cell" according to some exemplary embodiments provided in the present disclosure may include natural breeding between a male which has a testis including the "PAM second gene editing cell" and/or a female which has an ovary including the "PAM second gene editing cell".

For example, natural breeding can be performed between a male which has a testis including the "PAM second gene editing cell" and a female which has an ovary including the "PAM second gene editing cell".

In another example, natural breeding can be performed between a male which has a testis including the "PAM second gene editing cell" and a wild-type female; or between a wild-type male and a female which has an ovary including the "PAM second gene editing cell".

4. Use Aspects of Transgenic Animal Including Cell Having Genome in which Second Gene Editing Occurred Hereinafter, aspects for utilizing the transgenic animal including one or more of the above-described "second gene editing cell" and/or "PAM second gene editing cell" are described.

The "second gene editing" may be any one or more selected from gene editing using the recombinase recognition site (RRS), gene editing using an engineered nuclease which is expressed from a toolbox that does not include an expression control element, gene editing using an engineered nuclease which is expressed from a toolbox that includes an expression control element, and gene editing in a toolbox which includes a polynucleotide having a PAM sequence, which are described above, but is not limited thereto.

According to some exemplary embodiments provided in the present disclosure, one aspect of utilizing the transgenic animal may include bioreactors, animals with improved varieties, disease-resistant animals, and disease animal models.

For example, in the case where the "second gene editing cell" and/or "PAM second gene editing cell" is a cell where a donor polynucleotide is knocked in a genome, the transgenic animal may be utilized as a bioreactor.

In the case where the transgenic animal is a large animal, a polypeptide which can be expressed by the knocked-in donor polynucleotide can be obtained on a large scale.

The donor polynucleotide may be a polynucleotide encoding human albumin, a polynucleotide encoding human interleukin-2, a polynucleotide encoding human erythropoietin, a polynucleotide encoding human insulin, and a polynucleotide encoding omega-3, but is not limited thereto.

The donor polynucleotide may be in a form where a polynucleotide encoding a target protein and a polynucleotide encoding a linker are included. In this case, a fusion protein in which the target protein and the linker are included can be expressed in a cell having genome where the donor polynucleotide is knocked in. The linker in the expressed fusion protein can be cleaved and thereby the target protein can be obtained. The linker has been described above and thus the specific details thereon will be omitted herein.

Hereinafter, a process for producing a target protein from a transgenic animal including a cell that has a genome in which a polynucleotide encoding a target protein and a polynucleotide encoding a linker is knocked in to a donor polynucleotide is described.

Figure 15:
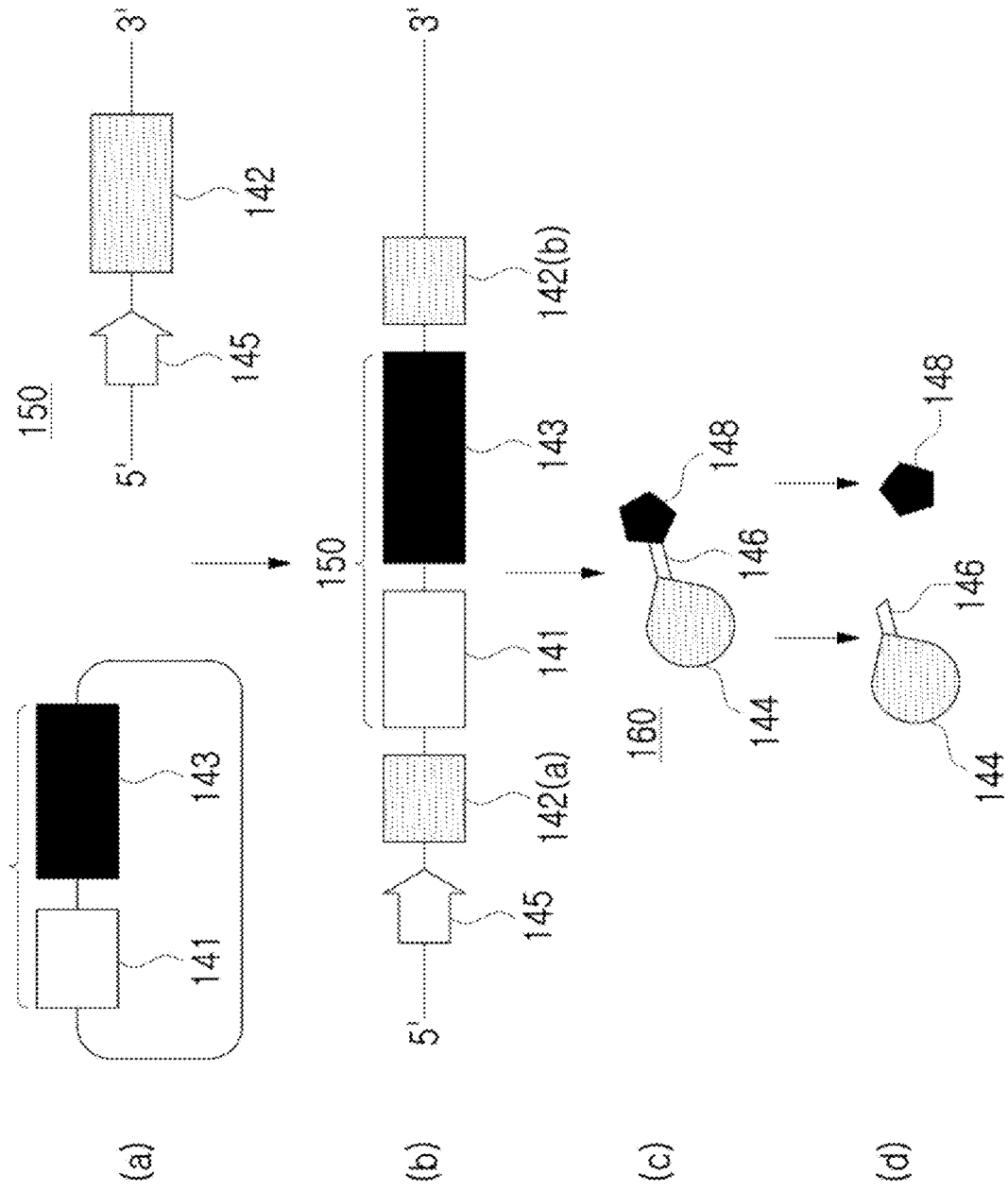
FIG. 15 illustrates a process of knocking in a polynucleotide encoding a target protein and a polynucleotide encoding a linker to a donor polynucleotide; and a producing process of a target protein from a cell, in which the donor polynucleotide is knocked in, or a transgenic animal which includes the cell.

FIG. 15 illustrates a process, in which a polynucleotide encoding a target protein and a polynucleotide encoding a linker are knocked in to a donor polynucleotide, and a target protein is produced from a transgenic animal including the cell, in which the donor polynucleotide is knocked in.

FIG. 15(a) illustrates the vector including a donor polynucleotide (150), and a promoter (145) and a target site (142) which are present in the genome of an animal.

FIG. 15(b) illustrates a form in which the donor polynucleotide (150) is knocked in to the target site (142).

FIG. 15(c) illustrates a fusion protein (160), which is expressed in a cell, embryo, or animal in which the donor polynucleotide (150) is knocked in.

FIG. 15(d) illustrates a form in which insulin (148) is obtained from the fusion protein (160).

Hereinafter, it is assumed that the donor polynucleotide (150) includes a polynucleotide (143) encoding human insulin and a polynucleotide encoding a linker (141).

When a guide nucleic acid and an RNA-guided endonuclease are provided into a cell, the guide nucleic acid and the RNA-guided endonuclease interact, thereby forming a complex within the cell, and the engineered nuclease complex can cleave the polynucleotide (142), which has a sequence the same as or complementary to that of part of the guide nucleic acid. When the donor polynucleotide (150) is provided into the cell, the donor polynucleotide (150) may be knocked in to the polynucleotide (142) (see FIG. 15(a)). The form where the donor polynucleotide (150) is knocked in is a form where the donor polynucleotide (150) is included between the first region (142(a)) and a second region (142(b)), which are produced by cleaving the polynucleotide (142).

The method for providing a guide nucleic acid and an RNA-guided endonuclease into a cell have been described above and thus the specific details thereon will be omitted herein.

Based on the description above, a fusion protein (160) may be expressed from an animal which includes one or more cells having a genome in which the donor polynucleotide (150) is knocked in. The fusion protein (160) may be in a form where the polypeptide (144) encoded by a first region (142(*a*)) of the polynucleotide, the linker (146), and the human insulin (148) are included. The fusion protein (160) can be obtained from the animal and purified (see FIG. 15(*c*)), and the human insulin (148) can be obtained by cleaving the linker (146) present in the obtained and/or purified fusion protein (160) (see FIG. 15 (*d*)).

As described above, a fusion protein including human insulin can be expressed in the animal's body using a donor polynucleotide having a construction in which the polynucleotide encoding human insulin and the polynucleotide encoding a linker are included, and thus the hypoglycemic shock may not occur in the animal's body due to the small size of human insulin.

In another example, when "second gene editing cell" and/or "PAM second gene editing cell" is a cell having a genome in which an exo-polynucleotide and/or an endo-polynucleotide is knocked out, the transgenic animal may be utilized as animals with improved varieties, disease-resistant animals, or disease animal models, but is not limited thereto.

The animals with improved varieties may refer to an animal where a polynucleotide encoding a whey protein is knocked out, or an animal where a polynucleotide encoding a target protein is inserted or knocked in.

Specifically, the animals with improved varieties may refer to an animal where a polynucleotide encoding a whey protein is knocked out. The whey protein may be beta-lactoglobulin, alpha-lactoglobulin, and bovine serum albumin, but is not limited thereto. When the whey protein is beta-lactoglobulin, the beta-lactoglobulin, which is known as a major allergy-inducing factor to those skilled in the art, may not be contained in the milk of the animal.

Specifically, the animals with improved varieties may refer to an animal where a polynucleotide encoding a target protein is inserted or knocked in. The target protein may be a polynucleotide encoding human albumin, a polynucleotide encoding human interleukin-2, a polynucleotide encoding human erythropoietin, a polynucleotide encoding human insulin, and a polynucleotide encoding omega-3, but is not limited thereto.

Specifically, the disease-resistant animal may refer to an infectious disease-resistant animal or mad cow disease (Bovine Spongiform Encephalopathy) preventing cow. The infectious disease may be trypanosomiasis, but is not limited thereto. The mad cow disease (Bovine Spongiform Encephalopathy) preventing cow may be a cow which includes a cell having a genome in which the polynucleotide encoding a prion protein is knocked out.

Specifically, the disease animal model may be a tumor animal model. The tumor animal model may be an animal which includes a cell having a genome in which the tumor suppressor gene is knocked out. For example, the tumor suppressor gene may be RB1 gene, p53 gene, pVHL gene, APC gene, ST5 gene, YPEL3 gene, ST7 gene, and ST14 gene, but is not limited thereto.

According to some exemplary embodiments provided in the present disclosure, one aspect of utilizing a transgenic animal which includes one or more of the "second gene editing cell" and/or "PAM second gene editing cell" may include obtaining a gamete or fertilized egg (and/or embryo) having a genome in which second gene editing has occurred from the transgenic animal. In this case, the gamete may be a sperm or ovum.

An offspring including the "second gene editing cell" and/or "PAM second gene editing cell" can be produced by fertilizing a gamete, which has a genome in which second gene editing has occurred, with another gamete, which is of wild-type (WT) or has a genome in which second gene editing has occurred.

In the case where the fertilized egg (and/or embryo), which has a genome in which second gene editing has occurred, is implanted into the uterus of a surrogate mother, an individual and/or offspring including the "second gene editing cell" can be produced.

[Selection of Transformed Cell Using Toolbox]

1. Selection of Transformed Cell Using Toolbox Including Fluorescent Protein Gene 1-1. Structure of Genome into which Toolbox Including Fluorescent Protein Gene is Inserted According to some exemplary embodiments provided in the present disclosure, a toolbox including a fluorescent protein gene (hereinafter, fluorescent toolbox) may be provided.

The fluorescent toolbox may have a structure in which the fluorescent protein gene is included between a polynucleotide encoding a first ITR sequence and a polynucleotide encoding a second ITR sequence.

According to some exemplary embodiments provided by the present disclosure, a cell including a genome into which the fluorescent toolbox is inserted may be provided. In particular, the location and the number of the fluorescent toolbox inserted into the cell may vary. The cell may be a somatic cell, gamete, or stem cell.

Additionally, according to some exemplary embodiments provided by the present disclosure, a fertilized egg and/or embryo including a genome into which the fluorescent toolbox is inserted may be provided. In particular, at least one of the cells that constitute the fertilized egg and/or embryo must include the fluorescent toolbox, and among the above cell, the number of cells which include the fluorescent toolbox is not limited.

The method for preparing a cell, fertilized egg, and/or embryo into which the fluorescent toolbox is inserted is similar to the above-described method for preparing the cell in which the toolbox is inserted, and thus specific explanations thereon will be omitted herein.

The fluorescent protein may be expressed in the cell, fertilized egg, and/or embryo having a genome into which the fluorescent toolbox is inserted, according to the expression mechanism. Fluorescence can be developed from the cell by the expression of the fluorescent protein, and a fluorescence signal can be provided from the outside of the cell according to the development of fluorescence.

Using the fluorescence signal provided to the outside of the cell, a cell, fertilized egg and/or embryo having a genome into which the fluorescent toolbox is inserted can be distinguished from an embryo and/or fertilized egg into which the fluorescent toolbox is not inserted.

If, a cell into which a toolbox provided by the present disclosure is inserted is prepared, and the above-described fluorescent toolbox is used when the cell, embryo, and/or fertilized egg into which the toolbox is inserted needs to be accurately selected, the cell, embryo, and/or fertilized egg into which the toolbox is inserted can easily be distinguished.

Additionally, in a cell having a genome into which 'n+1' (n is a natural number of 1 or greater) fluorescent toolboxes are inserted, a higher level of the fluorescent protein can be expressed compared to the cell having a genome into which 'n' fluorescent toolboxes are inserted. That is, the fluorescence signal provided in a cell having a genome, into which 'n+1' (n is a natural number of 1 or greater) fluorescent toolboxes are inserted, may be greater than the fluorescence signal provided in a cell having a genome, into which 'n' fluorescent toolboxes are inserted.

In this case, the cell into which the fluorescent toolbox is inserted can be more accurately selected by selecting the cell which provides a greater fluorescence signal.

Furthermore, in the case of a first embryo where the number of the fluorescent toolboxes included in the genome of the entire cell constituting the embryo is 'n+1', a greater amount of the fluorescent protein can be expressed compared to that expressed in a second embryo, where the number of the fluorescent toolboxes included in the genome of the entire cell constituting the embryo is 'n'. That is, the visual signal provided in the first embryo may be greater than the visual signal provided in the second embryo.

In this case, the embryo into which the fluorescent toolbox is inserted can be more accurately selected by selecting the first embryo which provides a greater fluorescence signal.

Hereinafter, a method for selecting a cell, embryo, and/or fertilized egg in which second gene editing has normally occurred, after second gene editing using such a fluorescent toolbox, will be described.

1-2. Selection of Transformed Cell Using Toolbox Including Fluorescent Protein Gene According to some exemplary embodiments provided by the present disclosure, a method for selecting a transformed cell, fertilized egg, and/or embryo in which second gene editing has occurred after second gene editing using a fluorescent toolbox can be provided. The second gene editing using the fluorescent toolbox may include knocking in a donor polynucleotide by having one region of the fluorescent protein gene included in the fluorescent toolbox as a target site.

For example, second gene editing, which has one region of the fluorescent protein gene as a target site, may occur in a cell having a genome into which a single fluorescent toolbox is inserted. In this case, the fluorescent protein cannot be expressed in the cell. That is, fluorescence cannot be developed in a cell where second gene editing has occurred, and as a result, no visual signal can be provided to the outside of the cell.

Therefore, according to the presence/absence of the visual signal to be provided to the outside of the cell, the cell in which second gene editing has occurred can be distinguished from the cell having a genome in which second gene editing has not occurred.

In another example, second gene editing may occur only in the first fluorescent toolbox in a cell having a genome into which a first fluorescent toolbox and a second fluorescent toolbox are inserted. In this case, the level of the fluorescent protein expressed in the cell in which second gene editing has occurred only in the first fluorescent toolbox (hereinafter, a first cell) may be smaller compared to that of the cell, in which second gene editing has not occurred and into which a first fluorescent toolbox and a second fluorescent toolbox are inserted. That is, a smaller amount of fluorescence may be developed in the first cell compared to the cell in which second gene editing has not occurred, and as a result, the visual signal provided to the outside of the first cell may be weaker.

Therefore, according to the intensity of the visual signal provided to the outside of the cell, the first cell in which second gene editing has occurred can be distinguished from the cell which has a genome in which second gene editing has not occurred.

The method and mechanism for second gene editing using the fluorescent toolbox may be explained by the above-described method and mechanism for second gene editing using a toolbox, and thus the specific details thereon will be omitted herein.

The above-described method for selecting the cell in which second gene editing has occurred may be utilized not only in an isolated cell but also in a non-isolated cell, fertilized egg, and/or embryo.

For example, in the case of an embryo where the number of the fluorescent toolboxes inserted into the genome of the entire cell that constitutes the embryo is 'n+2' (n is a natural number of 1 or greater), second gene editing may occur only in the 'n' fluorescent toolboxes (hereinafter, the embryo in which second gene editing has occurred only in the 'n' fluorescent toolboxes is expressed as "first embryo").

The level of the fluorescent protein expressed in the first embryo may be smaller compared to the embryo, which is in a state that second gene editing has not occurred and into which 'n+2' fluorescent toolboxes are inserted. That is, a smaller amount of fluorescence may be developed in the first embryo compared to the embryo in which second gene editing has not occurred, and as a result, the visual signal provided to the outside of the first embryo may be weak.

Therefore, according to the intensity of the visual signal provided to the outside of the embryo, the first embryo in which second gene editing has occurred can be distinguished from an embryo which has a genome in which second gene editing has not occurred.

In still another example, second gene editing may occur only in the 'n+1' fluorescent toolboxes in an embryo which has a genome into which 'n+2' fluorescent toolboxes are inserted. Hereinafter, the embryo in which second gene editing has occurred only in the 'n+1' fluorescent toolboxes is expressed as "second embryo".

Compared to the above-described first embryo, the amount of the fluorescent protein expressed in the second embryo may be smaller. That is, compared to the first embryo, a smaller amount of fluorescence may be developed in the second embryo where second gene editing has occurred in a greater number of target sites, and as a result, the visual signal provided to the outside of the second embryo may be weaker.

In this case, the embryo in which second gene editing has occurred can be more accurately selected by selecting the second embryo, which provides a weaker fluorescence signal.

2. Selection of Transformed Cell Using Toolbox Including Surface Protein Gene 2-1. Structure of Genome into which Toolbox Including Surface Protein Gene is Inserted According to some exemplary embodiments provided by the present disclosure, a toolbox including a surface protein gene (hereinafter, surface toolbox) can be provided.

The surface toolbox may have a structure in which a surface protein gene is included between a polynucleotide encoding a first ITR sequence and a polynucleotide encoding a second ITR sequence. For the convenience of explanation, hereinafter, a single surface toolbox is assumed to include a single surface protein gene.

According to some exemplary embodiments provided by the present disclosure, a cell including a genome into which the surface toolbox is inserted can be provided. In particular, the cell may be a somatic cell, gamete, or stem cell.

Additionally, according to some exemplary embodiments provided by the present disclosure, a fertilized egg and/or embryo including a genome into which the surface toolbox is inserted may be provided.

The surface protein may be expressed in a cell, fertilized egg and/or embryo having a genome into which the surface toolbox is inserted, according to the intracellular expression mechanism. In this case, the surface protein may appear on the surface of the cell, fertilized egg, and/or embryo.

Using the antibodies that can interact with the surface protein, a cell, fertilized egg, and/or embryo having a genome into which the surface toolbox is inserted can be distinguished from a cell, fertilized egg, and/or embryo having a genome into which the surface toolbox is not inserted. In this case, the antibodies can interact with magnetic particles or fluorophores.

Accordingly, using a magnetic property or fluorescence signal, a cell, embryo and/or fertilized egg having a genome into which the surface toolbox is inserted can be distinguished from a cell, embryo, and/or fertilized egg having a genome into which the surface toolbox is not inserted.

If, after the preparation of a cell into which a toolbox provided by the present disclosure is inserted, a surface toolbox described above is used when it is necessary to accurately select a cell, embryo and/or fertilized egg into which a toolbox is inserted, it will be possible to easily select the cell, embryo, and/or fertilized egg using antibodies that can interact with the surface protein.

Figure 16:
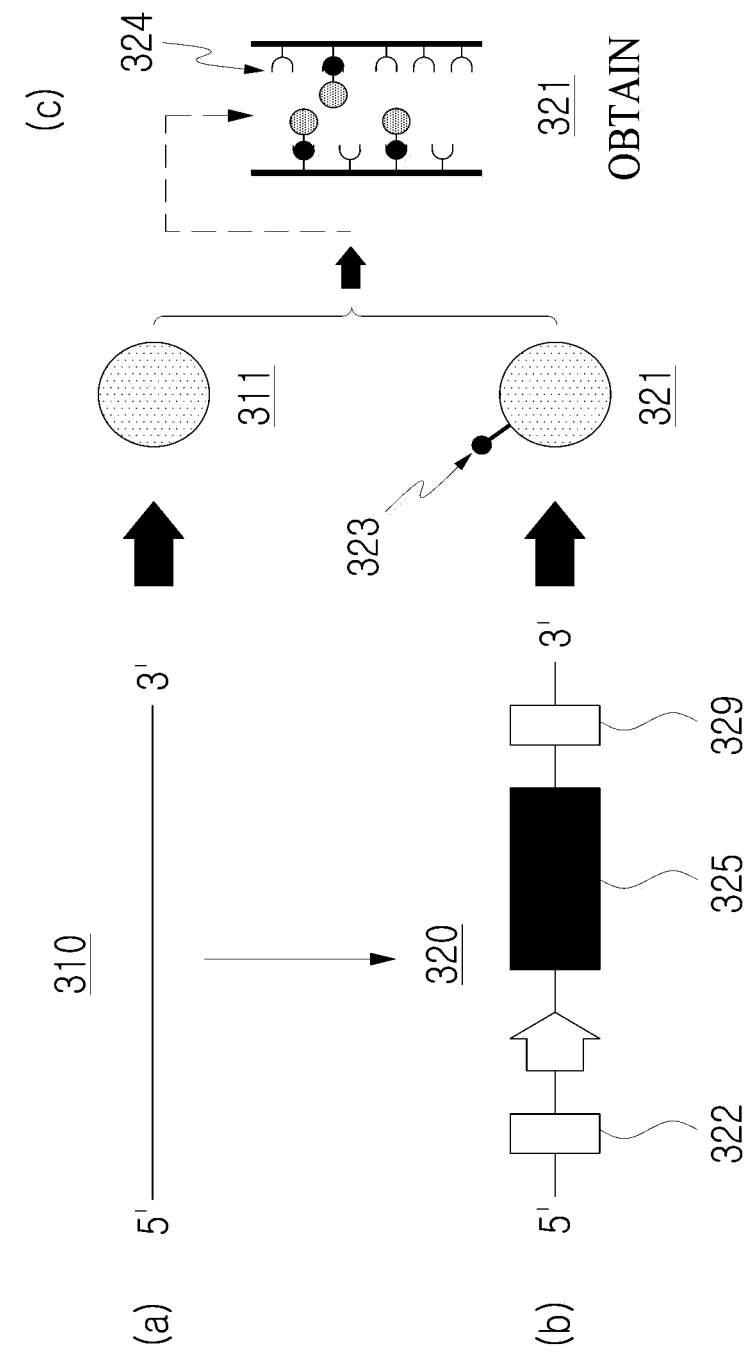
FIG. 16 illustrates a method to select cells having a genome into which a surface toolbox is inserted.

FIG. 16 illustrates an exemplary embodiment to select a cell having a genome into which the surface toolbox (320) is inserted. For the convenience of explanation, the cell is assumed to be an isolated cell.

FIG. 16(*a*) illustrates a genome (310) into which a surface toolbox is not inserted. A surface protein is not expressed on the surface of a cell (311) having such a genome (310).

FIG. 16(*b*) illustrates part of the genome into which the surface toolbox (320) is inserted. The surface toolbox (320) may have a structure in which the surface protein gene (325) is included between the first ITR sequence (322) and the second ITR sequence (329). The surface protein (323) can be expressed on the surface of the cell (321) having such a genome.

FIG. 16(*c*) illustrates a process of using chromatography for selecting a cell in which the surface protein is expressed among the cells in which a surface protein is expressed and the cells in which a surface protein is not expressed.

When cells (311 and 321) are flowed onto a chromatography including the antibody (324) so as to select a cell having a genome in which a surface toolbox is inserted, the cell (321) having a genome into which the surface toolbox (320) is inserted can be bound to the chromatography column by the interaction between an antibody (324) and a surface protein (323). That is, the cell (321) which is bound to the chromatography column by the interaction between the surface protein (323) and antibody (324) (see FIG. 16(*c*)).

Hereinafter, a method for selecting a cell, embryo, and/or fertilized egg in which second gene editing has normally occurred after the second gene editing using a surface toolbox will be described.

2-2. Selection of Transformed Cell Using Toolbox Including Surface Protein Gene

According to some exemplary embodiments provided by the present disclosure, a method for selecting a transformed cell, fertilized egg, and/or embryo in which second gene editing has occurred after the second gene editing using a surface toolbox can be provided. The second gene editing using the surface toolbox may include knocking in a donor polynucleotide to a surface protein gene which is included in the surface toolbox. As described above, the description will be given on the assumption that a single surface protein gene is included in a single surface toolbox.

For example, second gene editing which has a surface protein gene as a target may occur in a cell having a genome in which a single surface toolbox is inserted.

In this case, the surface protein cannot be expressed in the cell. That is, the surface protein cannot appear on the surface of the cell in which second gene editing has occurred, and as a result, the cell in which second gene editing has occurred cannot interact with an antibody that can interact with the surface protein.

Accordingly, according to the presence/absence of an interaction between the antibody and the cell, the cell having a genome in which second gene editing has occurred can be distinguished from the cell in which second gene editing has not occurred.

Even in the case of a cell having a genome into which two or more surface toolboxes are inserted, as described above, the cell in which second gene editing has occurred can be distinguished from the cell in which second gene editing has not occurred, according to the presence/absence of an interaction between the antibody and the cell.

In this case, the cell in which second gene editing has occurred can be selected in all of the surface toolboxes inserted into the genome.

The method and mechanism for second gene editing using the surface toolbox can be explained by the described above method and mechanism for second gene editing using a toolbox, and thus the specific explanation thereon will be omitted therein.

The above-described method for selecting the cell in which gene editing has occurred may be utilized not only in an isolated cell, but also in a non-isolated cell, fertilized egg, and/or embryo.

For example, in the case where the number of the surface toolbox inserted into the genome of the entire cell constituting the embryo is 'n' or more (n is a natural number of 2 or greater), second gene editing can occur in all of the 'n' surface toolboxes. In this case, the surface protein cannot be expressed in an embryo in which second gene editing has occurred. That is, the surface protein cannot appear on the surface of the embryo in which second gene editing has occurred, and as a result, the embryo in which second gene editing has occurred cannot interact with an antibody that can interact with the surface protein.

That is, the embryo in which second gene editing has occurred can be distinguished from the embryo in which second gene editing has not occurred, according to the presence/absence of an interaction between the antibody and the cell. In this case, the selected embryo may be a cell in which second gene editing has occurred in all of the surface toolboxes inserted into the genome of the entire cell that constitutes the embryo.

Figure 17:
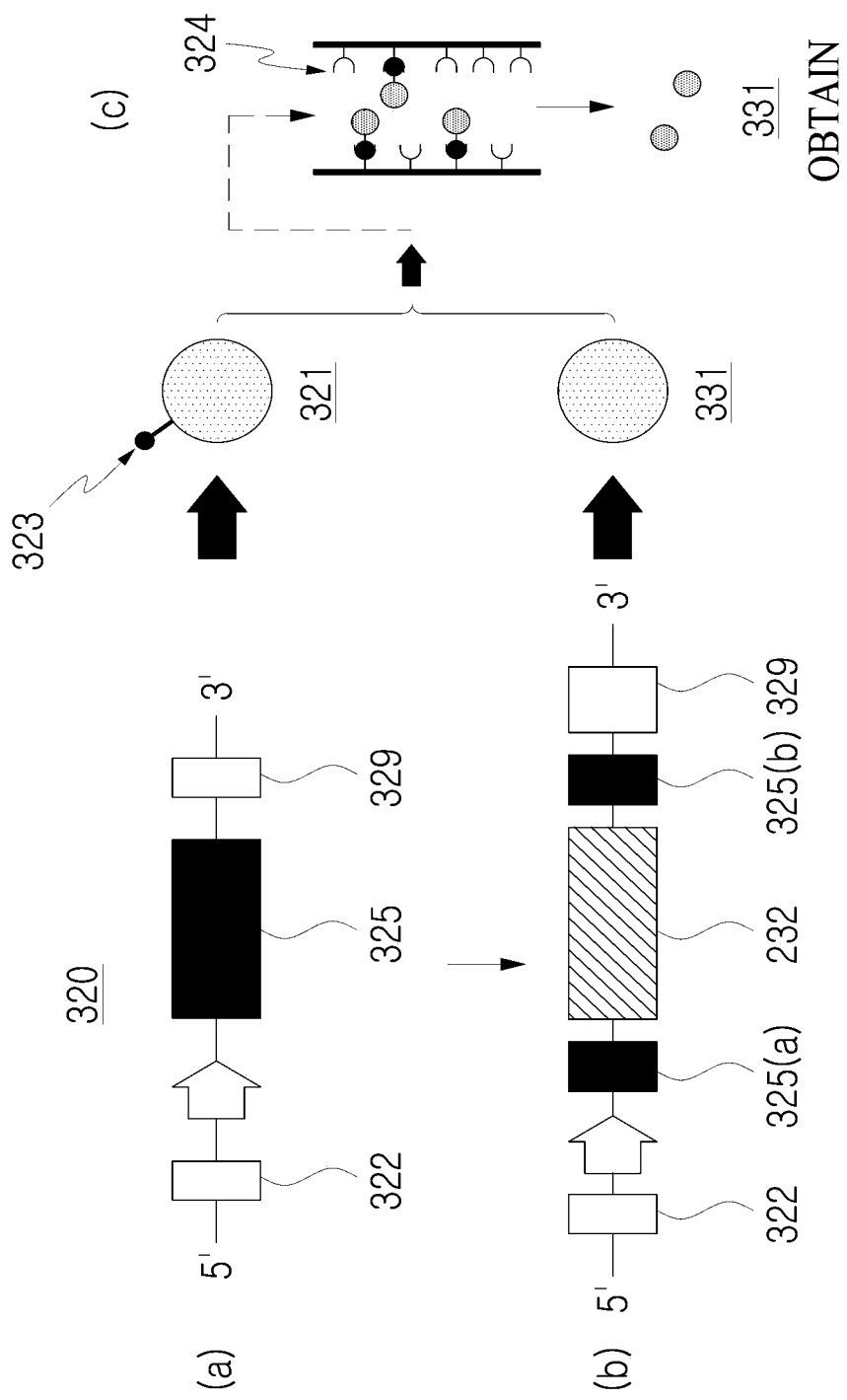
FIG. 17 illustrates a method to select cells in which gene editing has occurred in a surface toolbox.

FIG. 17 illustrates an exemplary embodiment for selecting the cell in which second gene editing has occurred in a cell having a genome into which a surface toolbox (320) is inserted. For the convenience of explanation, description is provided based on the assumption that the cell is an isolated cell.

FIG. 17(*a*) illustrates a genome and cell (321) in the case where second gene editing has not occurred in a cell having a genome into which the surface toolbox (320) is inserted.

FIG. 17(b) illustrates a genome and cell in the case where second gene editing has occurred in a cell having a genome into which the surface toolbox (320) is inserted.

In the case where a donor polynucleotide (232) is knocked in to a surface toolbox, which is inserted into a genome of a cell having a genome into which the surface toolbox (320) is inserted, and the surface protein gene (325) is divided into a first region (325(a)) and a second region (325(b)), the surface protein (323) is not expressed on the surface of the cell (331).

FIG. 17(c) illustrates a process using chromatography so as to select the cell in which a donor polynucleotide (232) is knocked in to a surface toolbox.

When the cell (331) where the donor polynucleotide (232) is knocked in, and the cell (321) where the donor polynucleotide (232) is not knocked in, are flowed onto the chromatography in which the antibody (324) is included, the cell (331) where the donor polynucleotide (232) is knocked in cannot be bound to the chromatography column. Using such a property, it is possible to select the cell in which second gene editing has occurred by obtaining the cell (331) which is not bound to the chromatography column (see FIG. 17(c)).

3. Selection of Transformed Cell Using Toolbox Including Suicide Gene 3-1. Structure of Genome into which Toolbox Including Suicide Gene is Inserted According to some exemplary embodiments provided by the present disclosure, a toolbox including a suicide gene (hereinafter, a suicide toolbox) can be provided.

FIG. 18(a) illustrates an exemplary embodiment of a suicide toolbox.

Referring to FIG. 18(a), the suicide toolbox (340) may have a structure in which a suicide gene (347) and an expression control element (345) capable of controlling the expression of the suicide gene are included between a first ITR sequence (343) and a second ITR sequence (349).

For the convenience of explanation, hereinafter, description is provided based on the assumption that a single suicide gene is included in a single suicide toolbox. Additionally, description is provided based on the assumption that the expression control element (345) is a Tet-on promoter and the suicide gene (347) is a thymidine kinase gene.

According to some exemplary embodiments provided by the present disclosure, a cell including a genome into which the suicide toolbox is inserted can be provided. In particular, the cell may be a somatic cell, gamete, or stem cell.

Additionally, according to some exemplary embodiments provided by the present disclosure, a fertilized egg and/or embryo including a genome into which the suicide toolbox is inserted can be provided.

When tetracycline is treated on the cell (341), fertilized egg, and/or embryo having a genome into which the suicide toolbox (340) is inserted, the thymidine kinase may be expressed in the cell, fertilized egg, and/or embryo, according to the intracellular expression mechanism.

When a prodrug (e.g., ganciclovir) is provided to the cell, fertilized egg and/or embryo in which thymidine kinase is expressed, part of the cell, fertilized egg and/or embryo may be apoptosized. The prodrug may interact with thymidine kinase, and as a result, the cell in which thymidine kinase is expressed can be apoptosized.

That is, the cell having a genome into which the suicide toolbox is inserted can be apoptosized by the treatment of a material and/or conditions that affect the expression control element, and a prodrug.

Hereinafter, a method for selecting a cell, embryo, and/or fertilized egg, in which second gene editing has normally occurred after second gene editing using a suicide toolbox, will be described.

3-2. Selection of Transformed Cell Using Toolbox Including Suicide Gene

According to some exemplary embodiments provided by the present disclosure, a method for selecting the transformed cell, fertilized egg, and/or embryo in which second gene editing has occurred after the second gene editing using a suicide toolbox can be provided. The second gene editing using the suicide toolbox may include knocking in a donor polynucleotide to a suicide gene which is included in the suicide toolbox. As described above, description will be provided based on the assumption that a single suicide gene is included in a single suicide toolbox.

The second gene editing may occur in a single cell having a genome into which a suicide toolbox is inserted, by having part of the suicide gene as a target site. In particular, even when a prodrug is provided to the cell in which gene editing has occurred by having part of the suicide gene as a target site, the cell is not apoptosized.

Therefore, according to the presence/absence of apoptosis after the treatment of the cell with tetracycline and a prodrug, the cell having a genome in which second gene editing has occurred can be distinguished from the cell having a genome in which second gene editing has not occurred.

That is, the cell which can survive even after the treatment with tetracycline and a prodrug may be the cell having a genome in which second gene editing has occurred.

Even in the case of a cell having a genome into which two or more suicide toolboxes are inserted, as described above, the cell having a genome in which second gene editing has occurred can be distinguished from the cell having a genome in which second gene editing has not occurred, according to the presence/absence of apoptosis. In this case, the selected cell may be a cell in which second gene editing has occurred in all of the suicide toolboxes inserted into a genome.

Hereinafter, referring to FIG. 18, description will be provided more specifically with regard to the presence/absence of apoptosis when a donor polynucleotide is knocked in or is not knocked in to a suicide gene that is included in a suicide toolbox.

Figure 18:
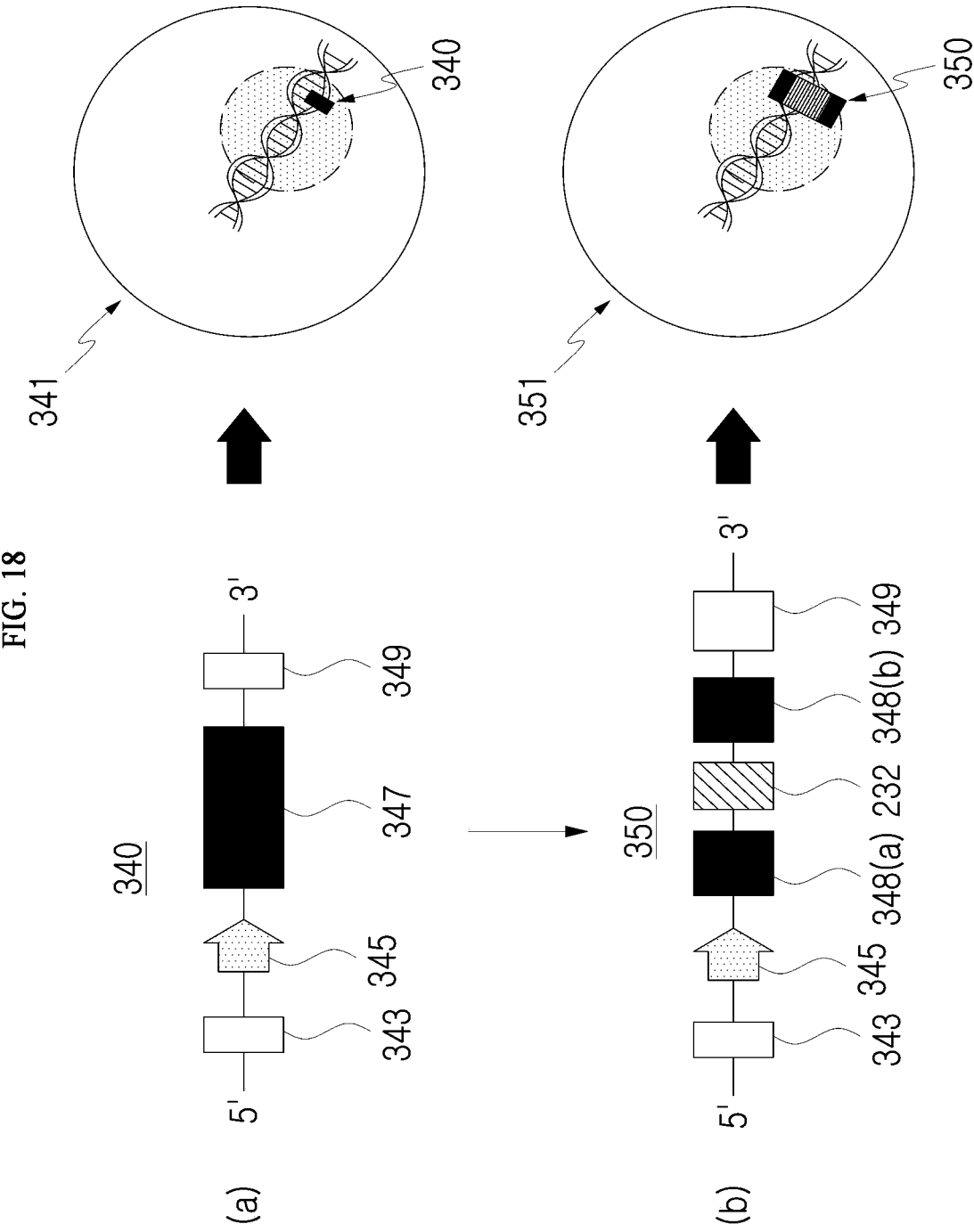
FIG. 18 illustrates a genome into which a suicide toolbox is inserted, a cell having a genome into which a suicide toolbox is inserted, a form in which gene editing has occurred in a suicide toolbox, and a cell in which gene editing has occurred in a suicide toolbox.

FIG. 18 illustrates an exemplary embodiment with regard to the selection of a cell in which second gene editing has occurred in a cell having a genome into which the suicide toolbox (340) is inserted. For the convenience of explanation, the cell is assumed to be an isolated cell.

In the case where the donor polynucleotide (232) is knocked in to a suicide toolbox (340) which is inserted into the genome of the cell, the suicide gene (347) may be divided into a first region (347(a)) and a second region (347(b)). In particular, even when the Tet-on promoter (345) operates by treating tetracycline on the cell (351), in which the donor polynucleotide (232) is knocked in, thymidine kinase cannot be expressed in the cell. In this case, even when the cell is provided with a prodrug, the cell (351) is not apoptosized (see FIG. 18(b)).

Meanwhile, in the case where the donor polynucleotide is not knocked in to a suicide toolbox (340) which is inserted into the genome of the cell, the Tet-on promoter (345) can be operated by treating the cell with tetracycline. The transcription and/or translation of the suicide gene (347) can be initiated by the operation of the Tet-on promoter (345), and thereby thymidine kinase can be expressed. Once the cell, in which thymidine kinase is expressed, is provided with a prodrug, the cell can be apoptosized.

In this case, a cell (351) which is not apoptosized can be obtained, and in this case, a cell in which second gene editing occurred can be selected (see FIG. 18(a)).

The above-described method for selecting the cell in which gene editing has occurred can be applied not only to an isolated cell but also to a non-isolated cell, fertilized egg, and/or embryo.

For example, when the number of suicide toolboxes inserted into the genome of the entire cell that constitutes the embryo is 'n' or greater (n is a natural number of 2 or greater), second gene editing may occur in all of the 'n' suicide toolboxes. In this case, even when the embryo is provided with tetracycline, thymidine kinase cannot be expressed in the above-described embryo in which second gene editing has occurred. In particular, even when the embryo is provided with a prodrug, the cell that constitutes the embryo is not apoptosized.

That is, according to the presence/absence of apoptosis of the cell that constitutes the embryo, an embryo in which second gene editing has occurred can be distinguished from an embryo in which second gene editing has not occurred. In this case, the embryos in which second gene editing has occurred in all of the surface toolboxes inserted into the genome can be selected.

[Selection of Sex Using Toolbox]

1. Selection of Sex by SRY Gene Insertion and/or SRY Gene Knockout

One method for selecting the sex according to some exemplary embodiments provided by the present disclosure may include insertion of SRY gene into the genome or knockout of SRY gene from the genome.

Hereinafter, a male individual in which SRY gene is inserted into the genome and a method for producing the male individual are described. Additionally, a female individual in which SRY gene is knocked out from a genome and a method for producing the female individual are described.

1-1. Production of Male Individual by SRY Gene Insertion

According to some exemplary embodiments provided in the present disclosure, a male animal having an XX chromosome into which an SRY gene is inserted can be provided.

For example, a male animal having a genome in which the SRY gene is inserted into an endo-polynucleotide can be provided.

In another example, a male animal having a genome in which the SRY gene is inserted into an exo-polynucleotide can be provided. The exo-polynucleotide may be present within a toolbox or may be present outside of a toolbox.

The SRY gene may be inserted into the genome via various mechanisms.

For example, the SRY gene can be inserted into the genome as a component of a toolbox. A method for the SRY gene, as a component of a toolbox, to be inserted into the genome of a cell, fertilized egg (and/or embryo) and/or tissue can be sufficiently explained by the above-described method for inserting a toolbox, and thus the specific explanation thereon will be omitted herein.

In another example, the SRY gene may be knocked in to a genome by an engineered nuclease complex which is expressed from a polynucleotide encoding an engineered nuclease inserted into the genome.

One method for the SRY gene to be inserted into the genome of a cell, fertilized egg (and/or embryo) and/or tissue by the engineered nuclease complex includes a provision of a donor polynucleotide including the SRY gene to the cell, fertilized egg (and/or embryo) and/or tissue.

In still another example, the SRY gene may be inserted into the genome using a recombinase recognition site (RRS).

One method for the SRY gene to be inserted into the genome of a cell, fertilized egg (and/or embryo) and/or tissue by the recombinase recognition site (RRS) includes a provision of the SRY gene, the recombinase recognition site (RRS), and a site-specific recombinase (SSR) to the cell, fertilized egg (and/or embryo) and/or tissue. In this case, the site-specific recombinase (SSR) can interact with the recombinase recognition site (RRS).

The method for providing the toolbox, transposase, donor polynucleotide, recombinase recognition site (RRS), site-specific recombinase (SSR), etc. to the cell, fertilized egg (and/or embryo) and/or tissue has been described above and thus specific explanations thereon will be omitted herein.

According to some exemplary embodiments provided in the present disclosure, a method for producing a male animal having an XX chromosome into which the SRY gene is inserted can be provided.

For example, one method for producing a male animal having an XX chromosome into which the SRY gene is inserted may include fertilizing a sperm having an X chromosome into which the SRY gene is inserted and a wild-type ovum.

The sperm having an X chromosome into which the SRY gene is inserted may be produced from an animal having a reproductive organ (or a reproductive tissue) having a genome into which the SRY gene is inserted.

In another example, one method for producing a male animal having an XX chromosome into which the SRY gene is inserted may include fertilizing an ovum having an X chromosome into which the SRY gene is inserted and a wild-type sperm.

The ovum having an X chromosome into which the SRY gene is inserted may be produced from an animal having a reproductive organ (or a reproductive tissue) having a genome into which the SRY gene is inserted.

Additionally, in another example, one method for producing a male animal having an XX chromosome into which the SRY gene is inserted may include implanting a fertilized egg and/or embryo having an XX chromosome into which the SRY gene is inserted, into the uterus of a surrogate mother.

The fertilized egg and/or embryo having an XX chromosome into which the SRY gene is inserted may be produced by the above-described somatic cell nuclear transfer (SCNT) or microinjection (MI).

Additionally, in another example, one method for producing a male animal having an XX chromosome into which the SRY gene is inserted may include injecting the above-described SRY toolbox, transposase, donor polynucleotide, recombinase recognition site (RRS), and/or site-specific recombinase (SSR), etc. to a reproductive organ or reproductive tissue of an animal.

Sperms can be obtained from a male animal having an XX chromosome produced by the above-described method.

1-2. Production of Individual Female by Knockout of SRY Gene 1-2-1. Production of Individual Female by Knockout of SRY Gene According to some exemplary embodiments provided in the present disclosure, a female animal having an XY chromosome in which an SRY gene is knocked out can be provided.

Hereinafter, a toolbox for SRY gene knockout and a method for producing an animal having a genome in which an SRY gene is knocked out will be described.

1-2-1-1. Toolbox for SRY Gene Knockout

According to some exemplary embodiments provided in the present disclosure, a toolbox for knockout of an SRY gene present on the Y chromosome (hereinafter, SRY knockout toolbox) can be provided.

The SRY knockout toolbox may have a constitution in which a polynucleotide encoding an engineered nuclease component is included between a first ITR sequence and a second ITR sequence. The SRY knockout toolbox may further include an expression control element.

For example, the SRY knockout toolbox may have a constitution in which a polynucleotide encoding a guide nucleic acid is included between a first ITR sequence and a second ITR sequence. In this case, part of the sequence of the guide nucleic acid is the same as or complementary to part of the sequence of the SRY gene.

In another example, the SRY knockout toolbox may have a constitution in which a polynucleotide encoding an RNA-guided endonuclease and a polynucleotide encoding a guide nucleic acid are included between a first ITR sequence and a second ITR sequence. Additionally, the SRY knockout toolbox may have a constitution in which an expression control element, which controls the transcription and/or translation of the polynucleotide encoding the RNA-guided endonuclease and/or the polynucleotide encoding the guide nucleic acid, is further included. In this case, part of the sequence of the guide nucleic acid is the same as or complementary to part of the sequence of SRY gene.

According to some exemplary embodiments provided by the present disclosure, a cell including a genome into which the SRY knockout toolbox is inserted can be provided. The cell may be a somatic cell, gamete, or stem cell.

According to some exemplary embodiments provided by the present disclosure, a fertilized egg and/or embryo including a genome into which the SRY knockout toolbox is inserted can be provided.

FIG. 19(a) illustrates an exemplary embodiment of a genome in which an SRY knockout toolbox (360) is inserted.

The SRY knockout toolbox (360) may have a constitution in which a polynucleotide encoding an RNA-guided endonuclease (363) and a polynucleotide encoding a guide nucleic acid (365) are included between a first ITR sequence (361) and a second ITR sequence (367). Part of the sequence of the guide nucleic acid may be the same as or complementary to part of the sequence of an SRY gene.

The SRY knockout toolbox (360) may include a polynucleotide encoding an inducible promoter (362) so as to control the transcription and/or translation of the polynucleotide encoding the RNA-guided endonuclease (363). For the convenience of explanation, the inducible promoter is assumed to be a Tet-on promoter.

Additionally, the SRY knockout toolbox (360) may include a polynucleotide encoding a promoter (364) for the transcription of the polynucleotide encoding the guide nucleic acid (365).

Hereinafter, a method for SRY gene knockout in a genome into which an SRY knockout toolbox is inserted, and a method for producing a female animal having a genome in which an SRY gene is knocked out are described.

1-2-1-2. SRY Gene Knockout Using Toolbox and Method for Producing Female Individual Having Genome in which SRY Gene is Knocked Out Hereinafter, several methods for knocking out an SRY gene in the genome of a cell are provided. For the convenience of explanation, the cell is assumed to be an isolated cell. Various methods for the knockout of the SRY gene can be provided according to the construction of an SRY toolbox inserted into the genome of the cell.

For example, one method for the knockout of an SRY gene in a cell having a genome, into which an SRY knockout toolbox including a polynucleotide encoding a guide nucleic acid that can specifically bind to the SRY gene is inserted, may include a provision of an RNA-guided endonuclease into a cell.

In another example, one method for the knockout of an SRY gene in a cell having a genome, into which an SRY knockout toolbox including a polynucleotide encoding expression control element, a polynucleotide encoding RNA-guided endonuclease, and a polynucleotide encoding a guide nucleic acid that can specifically bind to the SRY gene is inserted, may include a provision of conditions and/or a material that affect the expression control element into the cell.

The method for providing the RNA-guided endonuclease and/or the material that affects the expression control element into a cell has been described above, and thus specific explanation thereon will be omitted herein.

Figure 19:
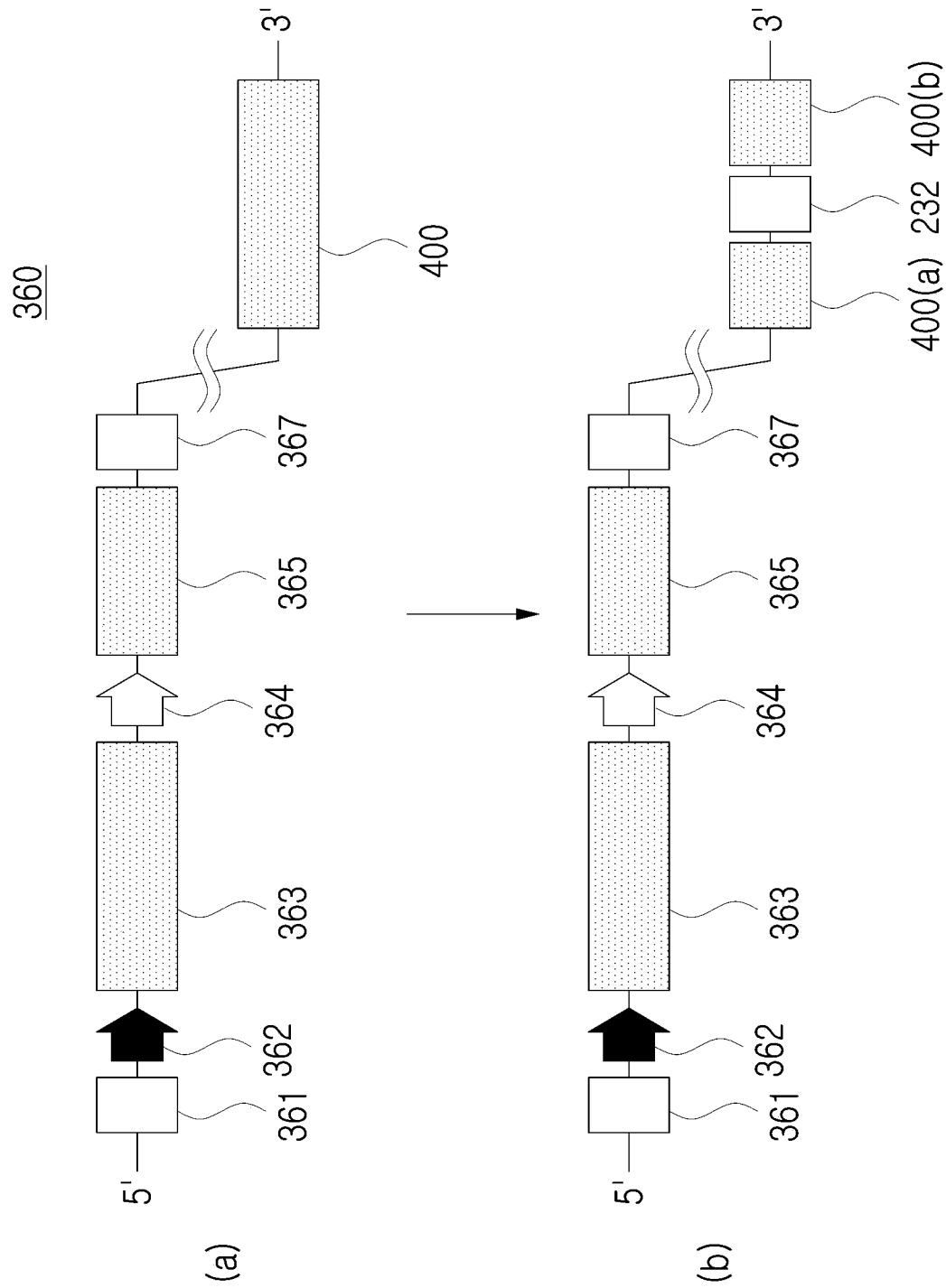
FIG. 19 illustrates a form of a genome into which an SRY knockout toolbox is inserted and a genome into which an SRY gene is knocked out in a genome into which an SRY knockout toolbox is inserted.

Referring to FIG. 19, the mechanism in which an SRY gene is knocked out will be specifically described.

FIG. 19(b) illustrates a form of a genome in which an SRY gene (400) is knocked out in a genome into which an SRY knockout toolbox (360) is inserted.

In a cell having a genome in which the SRY knockout toolbox (360) is included, the guide nucleic acid may be expressed within a cell by a polynucleotide encoding a promoter (364), and the expressed guide nucleic acid can complementary bind to an SRY gene (400), which is an endogenous gene present in the genome of the cell.

In the case where the cell having a genome into which the SRY knockout toolbox (360) is inserted is provided with tetracycline, the Tet-on promoter (362) can operate, and in this case, the RNA-guided endonuclease can be expressed in the cell. The RNA-guided endonuclease can cleave the SRY gene (400) while forming a complex with the guide nucleic acid.

That is, the SRY gene (400) can be knocked out in a male genome. In this case, the SRY gene (400) may be divided into a first region (400(a)) and a second region (400(b)).

In the present disclosure, a method for producing a female animal which has a genome in which an SRY gene is knocked out is provided.

For example, one method for producing a female animal having a genome in which an SRY gene is knocked out may include fertilizing a sperm having a Y chromosome in which the SRY gene is knocked out and an ovum.

The sperm having a Y chromosome in which the SRY gene is knocked out may be produced from an animal having a reproductive organ (or a reproductive tissue) having a genome into which the SRY gene is inserted. Additionally, the ovum may be a wild-type ovum.

In another example, one method for producing a female animal having a genome in which an SRY gene is knocked out may include implanting a fertilized egg and/or embryo having an XY chromosome in which the SRY gene is knocked out, into the uterus of a surrogate mother.

The fertilized egg and/or embryo having an XY chromosome in which the SRY gene is knocked out may be produced by the above-described somatic cell nuclear transfer (SCNT) or microinjection (MI).

In still another example, one method for producing a female animal having a genome in which an SRY gene is knocked out may include injecting the above-described expression control element and RNA-guided endonuclease to a reproductive organ or reproductive tissue of an animal Milk or ova can be obtained from a female animal having an XY chromosome produced by the above-described method.

1-2-2. Production of Female Individual by Motility-Damaging Gene Knockin

According to some exemplary embodiments provided in the present disclosure, the motility of sperm having a Y chromosome can be damaged via knockin of motility-damaging gene, and in this case, a female animal having an XX chromosome can be provided with a relatively high probability Hereinafter, the toolbox for knockin of motility-damaging gene and a method for producing sperms having a genome in which the motility-damaging gene is knocked in will be described.

1-2-2-1. Toolbox for Knockin of Motility-Damaging Gene

According to some exemplary embodiments provided in the present disclosure, a toolbox which can be used for the knockin of a motility-damaging gene (hereinafter, "Y chromosome target toolbox") can be provided to a polynucleotide that can be present only in Y chromosome.

For example, the toolbox may have a constitution in which a polynucleotide encoding a guide nucleic acid is included between a first ITR sequence and a second ITR sequence. In this case, the polynucleotide encoding the guide nucleic acid has a sequence which is the same as or complementary to part of the polynucleotide that can be present only in the Y chromosome.

In another example, the toolbox may have a constitution in which a polynucleotide encoding an RNA-guided endonuclease and a polynucleotide encoding a guide nucleic acid are included between a first ITR sequence and a second ITR sequence. Additionally, the toolbox may have a constitution in which an expression control element, which controls the transcription and/or translation of the polynucleotide encoding the RNA-guided endonuclease and/or the polynucleotide encoding the guide nucleic acid, is further included. In this case, part of the sequence of the guide nucleic acid may be the same as or complementary to part of the sequence of the polynucleotide that can be present only in the Y chromosome.

The polynucleotide which can be present only in the Y chromosome disclosed in the above-described exemplary embodiments may be an SRY gene.

The toolbox that can be used for the knockin of the motility-damaging gene may be the above-described SRY knockout toolbox.

According to some exemplary embodiments provided by the present disclosure, a cell including a genome into which the "Y chromosome target toolbox" is inserted can be provided. The cell may be a somatic cell, gamete, or stem cell.

Additionally, according to some exemplary embodiments provided by the present disclosure, a fertilized egg and/or embryo including a genome into which the "Y chromosome target toolbox" is inserted can be provided 1-2-2-2. Knockin of Motility-Damaging Gene Using Toolbox and Method of Producing Sperm in which Motility-Damaging Gene is Knocked in Hereinafter, several methods of knockin of a motility-damaging gene to the genome of a cell are provided. For the convenience of explanation, the cell is assumed to be an isolated cell. Various methods for the knockin of the motility-damaging gene can be provided according to the construction of the "Y chromosome target toolbox" inserted into the genome of the cell.

For example, one method for the knockin of the motility-damaging gene to the genome of a cell having a genome, into which the "Y chromosome target toolbox" including a polynucleotide encoding a guide nucleic acid is inserted, may include a provision of an RNA-guided endonuclease and motility-damaging gene into the cell.

In another example, one method for the knockin of the motility-damaging gene to the genome of a cell having a genome, into which the "Y chromosome target toolbox" including a polynucleotide encoding expression control element, a polynucleotide encoding RNA-guided endonuclease, and a polynucleotide encoding a guide nucleic acid is inserted, may include a provision of conditions and/or a material that affect the expression control element, and motility-damaging gene into the cell.

The provision of the motility-damaging gene into the cell may include the introducing a plasmid vector including the motility-damaging gene into the cell.

In the case where the material that affects the expression control element, the RNA-guided endonuclease and/or the motility-damaging gene are provided into the cell, the guide nucleic acid expressed in the cell can complementarily bind to the polynucleotide, which can be present only in the Y chromosome that is present in the genome of the cell. Additionally, the RNA-guided endonuclease which is injected or expressed by the expression system of the cell can cleave the polynucleotide that can be present only in the Y chromosome while forming a complex with the guide nucleic acid. In this case, the motility-damaging gene can be knocked in to the polynucleotide which can be present only in the Y chromosome.

In the present disclosure, provided is a method for producing sperms having a Y chromosome in which a motility-damaging gene is knocked in to an SRY gene.

For example, one method for producing sperms having a Y chromosome in which the motility-damaging gene is knocked in may include injecting the material that affects the expression control element, an RNA-guided endonuclease and/or motility-damaging gene to a reproductive organ or reproductive tissue of an animal.

In the reproductive organ or reproductive tissue of a male animal having a Y chromosome in which the motility-damaging gene is knocked in, sperms having a Y chromosome in which the motility-damaging gene is knocked in can be produced.

In another example, one method for producing sperms having a Y chromosome in which the motility-damaging gene is knocked in may include a direct provision, to a sperm, of the material that affects the expression control element, an RNA-guided endonuclease and/or motility-damaging gene described above.

The sperms having a Y chromosome in which the motility-damaging gene is knocked in, obtained by the above-described methods may have reduced motility, and as a result, these sperms may have a relative difficulty in fertilization with ova, compared to the sperm having an X chromosome.

In this case, the probability of producing a fertilized egg and/or embryo with an XX chromosome is higher than the probability of producing a fertilized egg and/or embryo with an XY chromosome, and as a result, the female individual having an XX chromosome can be produced.

2. Selection of Sex by Knockin of Fluorescent Protein Gene to X Chromosome and Y Chromosome One method for the selection of a sex according to some exemplary embodiments provided in the present disclosure may include performing knockin of each different type of a fluorescent protein gene, to a site adjacent to the gene which is present specifically in the X chromosome and the Y chromosome of an individual, respectively.

Hereinafter, the construction of toolbox, which is used for the knockin of a fluorescent protein gene to a site adjacent to a gene that is present specifically in the X chromosome and Y chromosome, respectively, and the operation mechanism of the toolbox in a cell having a genome into which the toolbox is inserted are described.

2-1. Toolbox for Knockin of Fluorescent Protein Gene to X Chromosome and Y Chromosome According to some exemplary embodiments provided in the present disclosure, provided is a toolbox (hereinafter, XY chromosome classification toolbox) for the knockin of each different fluorescent protein gene at a first target site, which is adjacent to a gene present specifically in the X chromosome of an animal, and at a second target site, which is adjacent to a gene present specifically in Y chromosome.

For the convenience of explanation, hereinafter, a gene present which is specifically in the X chromosome is assumed to be a DAX gene, and a gene which is present specifically in the Y chromosome is assumed to be an SRY gene.

For example, in the XY chromosome classification toolbox, a polynucleotide encoding a first guide nucleic acid and a polynucleotide encoding a second guide nucleic acid may be included between a first ITR sequence and a second ITR sequence. The first guide nucleic acid includes a sequence which is the same as or complementary to part of the sequence of the first target site, and the second guide nucleic acid includes a sequence which is the same as or complementary to part of the sequence of the second target site.

The first target site is a polynucleotide adjacent to a DAX gene and the second target site is a polynucleotide adjacent to an SRY gene.

In another example, in the XY chromosome classification toolbox, a polynucleotide encoding a first guide nucleic acid, a polynucleotide encoding a second guide nucleic acid, and a polynucleotide encoding an RNA-guided endonuclease may be included between a first ITR sequence and a second ITR sequence. In this case, the toolbox may include an expression control element which controls the expression of an RNA-guided endonuclease.

The first guide nucleic acid includes a sequence which is the same as or complementary to part of the sequence of the first target site, and the second guide nucleic acid includes a sequence which is the same as or complementary to part of the sequence of the second target site.

According to some exemplary embodiments provided by the present disclosure, a cell including a genome into which the XY chromosome classification toolbox is inserted can be provided. The cell may be a somatic cell, gamete, or stem cell.

Additionally, according to some exemplary embodiments provided by the present disclosure, a fertilized egg and/or embryo which includes a genome into which the XY chromosome classification toolbox is inserted can be provided.

FIG. 20(a) illustrates a form where the XY chromosome classification toolbox is inserted into the genome of an animal.

FIG. 20(b) illustrates a DAX gene (421) and an SRY gene (431), which are endogenous genes present in the genome into which the XY chromosome classification toolbox is inserted, and a target site (420) which is adjacent to the DAX gene the target site (430) which is adjacent to the SRY gene.

The XY chromosome classification toolbox (370) may include a polynucleotide encoding an RNA-guided endonuclease (373), a polynucleotide encoding a first guide nucleic acid (375), and a polynucleotide encoding a second guide nucleic acid (377) between a first ITR sequence (371) and a second ITR sequence (379).

The toolbox (370) includes a polynucleotide (372) encoding an inducible promoter which controls the expression of an RNA-guided endonuclease. For the convenience of explanation, the inducible promoter is assumed to be a Tet-on promoter. Additionally, the toolbox (370) may further include a promoter (374) which controls the expression of the first guide nucleic acid and a promoter (376) which controls the expression of the second guide nucleic acid.

The polynucleotide encoding the first guide nucleic acid (375) includes a sequence which is the same as or complementary to part of the sequence of the first target site (420), which is adjacent to a DAX gene (421), and the polynucleotide encoding the second guide nucleic acid (377) includes a sequence which is the same as or complementary to part of the sequence of the second target site (430), which is adjacent to an SRY gene (431).

Hereinafter, a method for the knockin of a first fluorescent protein gene to a first target site adjacent to a DAX gene and the knockin of a second fluorescent protein gene to a second target site adjacent to an SRY gene in the genome into which the XY chromosome classification toolbox is inserted, and a method for selecting the sex of each individual are described.

2-2. Method for Knockin of Fluorescent Protein Gene in X Chromosome and Y Chromosome and Method for Selecting Sex One method for the knockin of a fluorescent protein gene in a cell having a genome into which a toolbox, which includes a polynucleotide encoding a first guide nucleic acid and a polynucleotide encoding a second guide nucleic acid, is inserted may include a provision of an RNA-guided endonuclease, a first fluorescent protein gene, and a second fluorescent protein gene into the cell.

One method for the knockin of a fluorescent protein gene in a cell having a genome into which a toolbox, which includes a polynucleotide encoding an expression control element, a polynucleotide encoding an RNA-guided endonuclease, a polynucleotide encoding a first guide nucleic acid, and a polynucleotide encoding a second guide nucleic acid, is inserted may include a provision of a material and/or conditions that affect the expression control element, a first fluorescent protein gene, and a second fluorescent protein gene into the cell.

In this case, the 5' end and 3' end of the first fluorescent protein gene may include a sequence which is the same as part of the sequence of the first target site, and the 5' end and 3' end of the second fluorescent protein gene may include a sequence which is the same as part of the sequence of the second target site The introduction of the first fluorescent protein gene and a second fluorescent protein gene into the cell may include an introduction of a non-viral vector (e.g., plasmid vector) or viral vector, which includes the first fluorescent protein gene and a second fluorescent protein gene, into the cell.

Hereinafter, a mechanism for the knockin of the first fluorescent protein gene at a first target site present in the genome of a cell and a mechanism for the knockin of the second fluorescent protein gene at the second target site present in the genome of a cell will be more specifically described, referring to FIG. 20.

FIG. 20(c) illustrates the form of a genome in which the first fluorescent protein gene (423) is knocked in at the first target site (420) and the second fluorescent protein gene (433) is knocked in at the second target site (430), and a process of fluorescence expression by knockin.

The first guide nucleic acid can be expressed in a cell having a genome into which the XY chromosome classification toolbox (370) is inserted, by a polynucleotide (374) encoding a promoter that is included in the XY chromosome classification toolbox (370). In this case, the first guide nucleic acid can specifically bind to the first target site (420). Additionally, the RNA-guided endonuclease, which is expressed by the operation of the Tet-on promoter due to the treatment of tetracycline, can cleave the first target site (420), and the first fluorescent protein gene (423) can be knocked in to the first target site (420). In particular, the first target site (420) can be divided into a first region (420(a)) and a second region (420(b)).

Additionally, the second guide nucleic acid can be expressed in the cell by a polynucleotide encoding a promoter (376) included in the XY chromosome classification toolbox (370), and the second guide nucleic acid can complementarily bind to the second target site (430). Additionally, the RNA-guided endonuclease, which is expressed by the operation of the Tet-on promoter due to the treatment of tetracycline, can cleave the second target site (430), and the second fluorescent protein gene (433) can be knocked in to the second target site (430). In particular, the second target site (430) can be divided a first region (430(a)) and a second region (430(b)).

Hereinafter, as described above, a method for selecting the sex of an embryo and/or individual via knockin of a first fluorescent protein gene and a second fluorescent protein gene is described.

Figure 20:
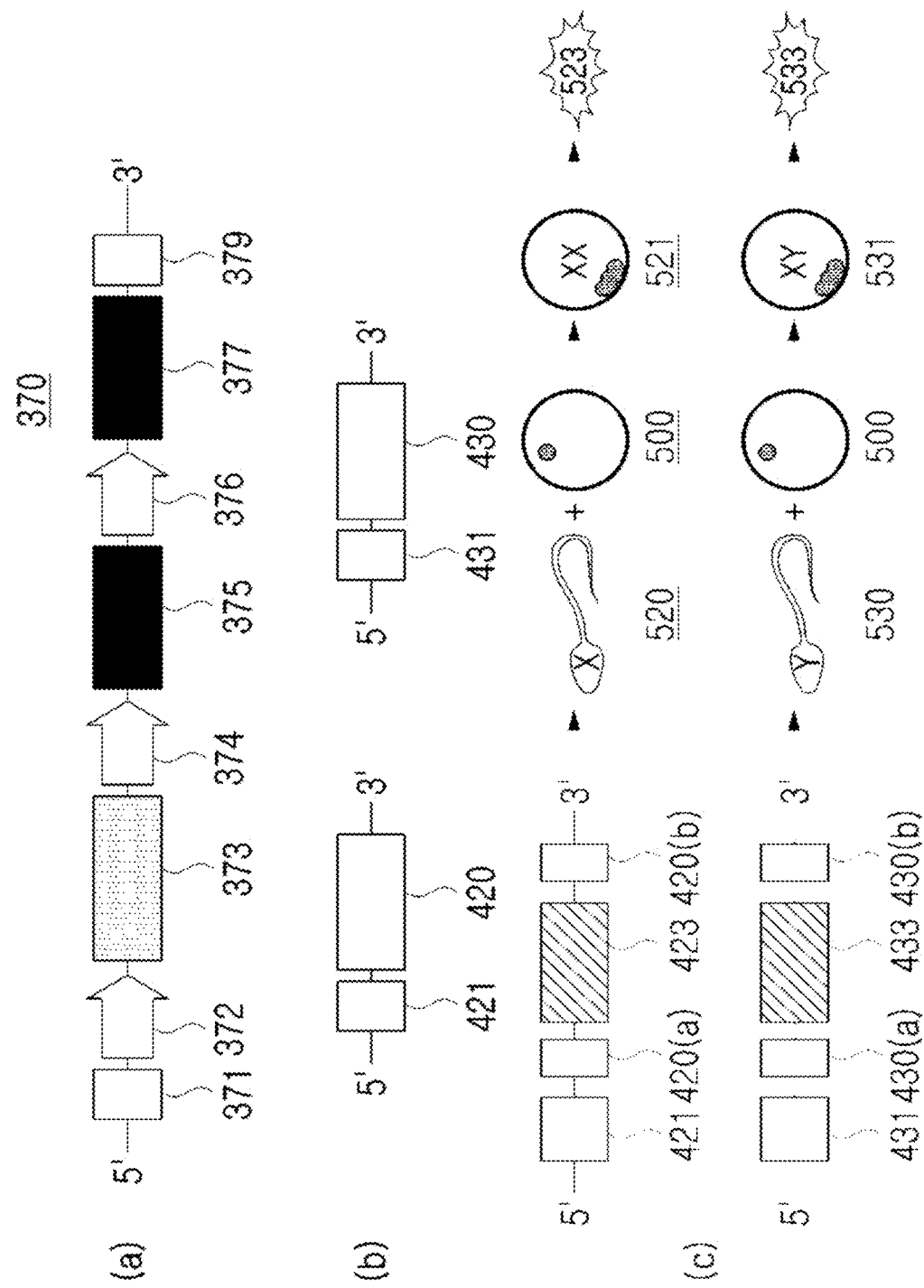
FIG. 20 illustrates genomes into which an XY chromosome classification toolbox is inserted, and a process in which embryos having XX chromosome and embryos having XY chromosome are classified by the XY chromosome classification toolbox.

For example, one method for selecting the sex by knockin of a first fluorescent protein gene and a second fluorescent protein gene may include injecting a material and/or conditions that affect the expression control element, an RNA-guided endonuclease, a first fluorescent protein gene, and/or a second fluorescent protein gene to a reproductive tissue and/or reproductive organ of a male having a genome in which the above-described toolbox is knocked in (see FIG. 20).

In the case where the first fluorescent protein gene (423) and/or the second fluorescent protein gene (433) are knocked in to the reproductive tissue and/or reproductive organ of the male, a first sperm (520) having an X chromosome in which the first fluorescent protein gene (423) is knocked in and a second sperm (530) having a Y chromosome in which the second fluorescent protein gene (433) is knocked in can be produced from the male.

In the case where the first sperm (520) and the wild-type ovum (500) are fertilized, a first embryo (521) having a genome in which a first fluorescent protein gene is knocked in can be produced. In the first embryo (521), a first fluorescent protein can be expressed. In this case, a first fluorescence (523) can be developed from the first embryo by the expression of the first fluorescent protein, and a fluorescence signal can be provided to the outside of the cell according to the development of fluorescence.

In the case where the second sperm (530) and the wild-type ovum (500) are fertilized, a second embryo (531) having a genome in which a second fluorescent protein gene is knocked in can be produced. In the second embryo (531), a second fluorescent protein can be expressed. In this case, a second fluorescence (533) can be developed from the second embryo by the expression of the second fluorescent protein, and a fluorescence signal can be provided to the outside of the cell according to the development of fluorescence.

That is, fluorescence signals different from each other can be provided from the first embryo having a genome in which the first fluorescent protein gene is knocked in, and from the second embryo having a genome in which the second fluorescent protein gene is knocked in, and as a result, the embryo (521) having XX chromosome and the embryo (531) having XY chromosome can be distinguished from each other.

In another example, one method for selecting the sex by knockin of a first fluorescent protein gene and a second fluorescent protein gene may include a microinjection (MI) of the material and/or conditions that affect the expression control element, an RNA-guided endonuclease, a first fluorescent protein gene and/or a second fluorescent protein gene into a fertilized egg at the time of fertilization of a gamete having a genome in which the above-described toolbox is knocked in.

In this case, an embryo in which the first fluorescent protein gene (423) or the second fluorescent protein gene (433) is knocked in can be produced.

As described above, mutually different fluorescent proteins can be expressed in an embryo having a genome in which the first fluorescent protein gene is knocked in and in an embryo having a genome in which the second fluorescent protein gene is knocked in. In this case, an embryo having an XX chromosome can be distinguished from an embryo having XY chromosome using a fluorescence signal.

When the embryos selected by the above methods are implanted into the uterus of a surrogate mother, individuals with a desired sex can be produced.

The use of the above-described method has advantages in that the fluorescent proteins can be expressed in an embryo at a relatively early stage thus enabling a more rapid selection and safer implantation of the rapidly selected embryo into the uterus of a surrogate mother.

[Toolbox Excision System]

1. Construction of Toolbox Excision System

An excision toolbox can be provided according to some exemplary embodiments of the present disclosure. The excision toolbox includes a "component for toolbox excision". The "component for toolbox excision" refers to a construction including a polynucleotide that enables to express an element, which is capable of excising the toolbox from a genome into which the toolbox is inserted.

The excision toolbox may include a polynucleotide that encodes the components of an engineered nuclease. For the convenience of explanation, it is assumed that a polynucleotide encoding an RNA-guided endonuclease is included in the excision toolbox.

Hereinafter, various types of construction of an excision toolbox, methods for preparing the excision toolboxes, and mechanisms by which various types of excision toolboxes are excised from a genome under particular conditions are more specifically disclosed.

1-1. Structure of Genome in which Toolbox, Having Construction Enabling Expression of Polynucleotide Encoding Transposase at Particular Conditions, is Inserted According to some exemplary embodiments of the present disclosure, an excision toolbox, in which the expression of a transposase is controlled by an inducible promoter and/or tissue-specific promoter, can be provided. The excision toolbox may be prepared by insertion or excision via site-specific recombination.

Hereinafter, when the excision toolbox is produced by the insertion via site-specific recombination, the construction and production method of excision toolbox will be described.

For example, the excision toolbox may have a constitution in which a polynucleotide encoding an inducible promoter and a polynucleotide encoding a transposase are included between a first ITR sequence and a second ITR sequence in a 5' to 3' direction.

In another example, the excision toolbox may have a constitution in which a polynucleotide encoding a tissue-specific promoter and a polynucleotide encoding a transposase are included between a first ITR sequence and a second ITR sequence in a 5' to 3' direction.

In still another example, the excision toolbox may have a constitution in which a polynucleotide encoding an inducible promoter, a polynucleotide encoding a first transposase, a polynucleotide encoding a tissue-specific promoter and a polynucleotide encoding a second transposase are included between a first ITR sequence and a second ITR sequence in a 5' to 3' direction.

Figure 21:
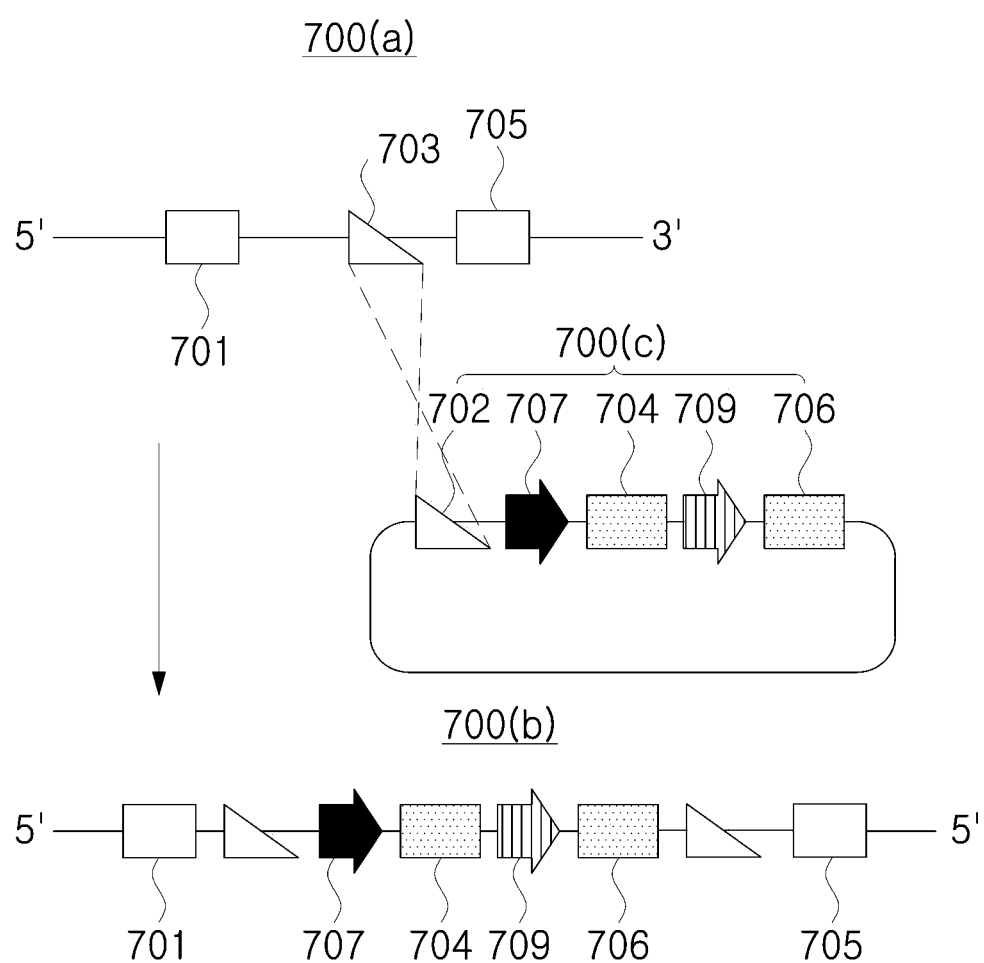
FIG. 21 illustrates an embodiment of an excision toolbox in which the expression of a transposase can be controlled by an inducible promoter and a tissue-specific promoter.

FIG. 21 illustrates an embodiment of an excision toolbox in which the expression of a transposase can be controlled by an inducible promoter and a tissue-specific promoter.

The excision toolbox (700(b)) may have a constitution in which a component (700(c)) for the toolbox excision is included between a first ITR sequence (701) and a second ITR sequence (705). Additionally, the excision toolbox (700(b)) may further include one or more recombinase recognition sites.

The component (700(c)) for the toolbox excision may include a polynucleotide encoding an inducible promoter (707), a polynucleotide encoding a first transposase (704), a polynucleotide encoding a tissue-specific promoter (709), and a polynucleotide encoding a second transposase (706). In this case, the polynucleotide encoding the first transposase (704) and the polynucleotide encoding the second transposase (706) may have the same sequence. The first transposase and the second transposase can interact with the first ITR sequence (701) and the second ITR sequence (705).

Hereinafter, a method for preparing the excision toolbox (700(b)) is described.

One method for preparing the excision toolbox (700(b)) may include a provision of a recombinase and the component (700(c)) for the toolbox excision to a cell having a genome into which the toolbox (700(a)) is inserted.

The recombinase can interact with the recombinase recognition site (RRS) (703), which is included in the toolbox (700(a)), and the recombinase recognition site (702), which is included in the component (700(c)) for the toolbox excision.

The method for providing the recombinase has been described above, and thus the specific details thereon will be omitted herein.

There may be various methods for providing the component (700(c)) for the toolbox excision into a cell. For example, the component for the toolbox excision can be provided into a cell by introducing a plasmid vector, which includes the component for the toolbox excision, into the cell.

As described above, the recombinase provided into the cell can interact with the recombinase recognition site (RRS) (703), which is included in the toolbox (700(a)), and the recombinase recognition site (702), which is included in the component for the toolbox excision; and the component for the toolbox excision may be inserted into a location of the recombinase recognition site (RRS) (703) of the toolbox (700(a)). Based on the above, the excision toolbox (700(b)) which enables the expression of a transposase under particular conditions can be prepared.

Hereinafter, a construction of an excision toolbox, which is produced by the excision of a stop codon via site-specific recombination, and a method for producing the same will be described.

For example, the excision toolbox may have a constitution in which a polynucleotide encoding an inducible promoter, a recombinase recognition site, and a polynucleotide encoding a transposase are included between a first ITR sequence and a second ITR sequence in a 5' to 3' direction.

In another example, the excision toolbox may have a constitution in which a polynucleotide encoding a tissue-specific promoter, a recombinase recognition site, and a polynucleotide encoding a transposase are included between a first ITR sequence and a second ITR sequence in a 5' to 3' direction.

In still another example, the excision toolbox may have a constitution in which a polynucleotide encoding an inducible promoter, a recombinase recognition site, a polynucleotide encoding a first transposase, a polynucleotide encoding a tissue-specific promoter, a recombinase recognition site, and a polynucleotide encoding a second transposase are included between a first ITR sequence and a second ITR sequence in a 5' to 3' direction.

Figure 22:
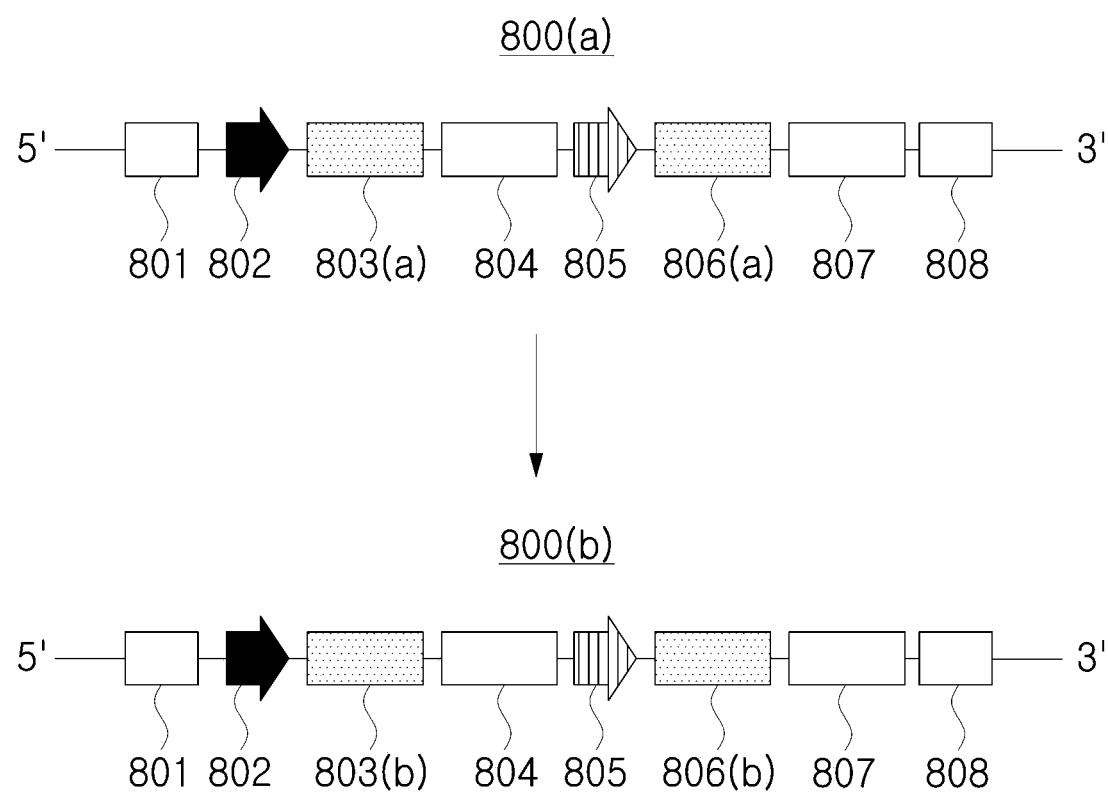
FIG. 22 illustrates another embodiment of an excision toolbox in which the expression of a transposase can be controlled by an inducible promoter and a tissue-specific promoter.

FIG. 22 illustrates another embodiment of an excision toolbox, in which the expression of a transposase can be controlled by an inducible promoter and a tissue-specific promoter.

The excision toolbox (800(b)) toolbox may have a constitution in which the component for the toolbox excision is included between a first ITR sequence (801) and a second ITR sequence (808).

The component for the toolbox excision may include a polynucleotide encoding an inducible promoter (802), a first recombinase recognition site (803(b)), a polynucleotide encoding a first transposase (804), a polynucleotide encoding a tissue-specific promoter (805), a second recombinase recognition site (806(b)), and a polynucleotide encoding a second transposase (807). The polynucleotide encoding the first transposase (804) and the polynucleotide encoding the second transposase (807) may be the same sequence. The first transposase and the second transposase can interact with the first ITR sequence (801) and the second ITR sequence (808).

Additionally, the first recombinase recognition site (803(b)) and the second recombinase recognition site (806(b)) may be the same sequence.

Hereinafter, a method for preparing the excision toolbox (800(b)) is described.

One method for preparing the excision toolbox (800(b)) may include a provision of a recombinase to a cell having a genome in which the toolbox (800(a)) is inserted.

The recombinase provided into the cell can interact with the recombinase recognition sites (RRSs) that constitutes a first RSR (803(a)) and second RSR (806(a)) which are included in the toolbox (800(a)). The first RSR (803(a)) and the second RSR (806(a)) may be the same sequence.

As described above, the stop codon can be deleted when the recombinase provided into the cell interacts with the recombinase recognition site (RRS) that constitutes the first RSR (803(a)) and the second RSR (806(a)).

Based on the above, the excision toolbox 800(b), in which a transposase can be expressed under particular conditions, can be produced.

1-2. Structure of Genome in which Toolbox, Having Construction Enabling Expression of Polynucleotide Encoding Recombinase at Particular Conditions, is Inserted According to some exemplary embodiments of the present disclosure, an excision toolbox, in which the expression of a recombinase is controlled by an inducible promoter and/or tissue-specific promoter, can be provided.

For example, the excision toolbox may have a constitution in which a polynucleotide encoding an inducible promoter, a polynucleotide encoding a recombinase, a polynucleotide encoding a constitutive promoter, and a polynucleotide encoding an RSR, and a polynucleotide encoding a transposase are included between a first ITR sequence and a second ITR sequence in a 5' to 3' direction.

In another example, the excision toolbox may have a constitution in which a polynucleotide encoding a tissue-specific promoter, a polynucleotide encoding a recombinase, a polynucleotide encoding a constitutive promoter, a polynucleotide encoding an RSR, and a polynucleotide encoding a transposase are included between a first ITR sequence and a second ITR sequence in a 5' to 3' direction.

In still another example, the excision toolbox may have a constitution in which a polynucleotide encoding an inducible promoter; a polynucleotide encoding a recombinase, a polynucleotide encoding a constitutive promoter, a polynucleotide encoding an RSR, and a polynucleotide encoding a first transposase, a polynucleotide encoding a tissue-specific promoter, a polynucleotide encoding a recombinase, a polynucleotide encoding a constitutive promoter, a polynucleotide encoding an RSR, and a polynucleotide encoding a second transposase are included between a first ITR sequence and a second ITR sequence in a 5' to 3' direction.

Figure 23:
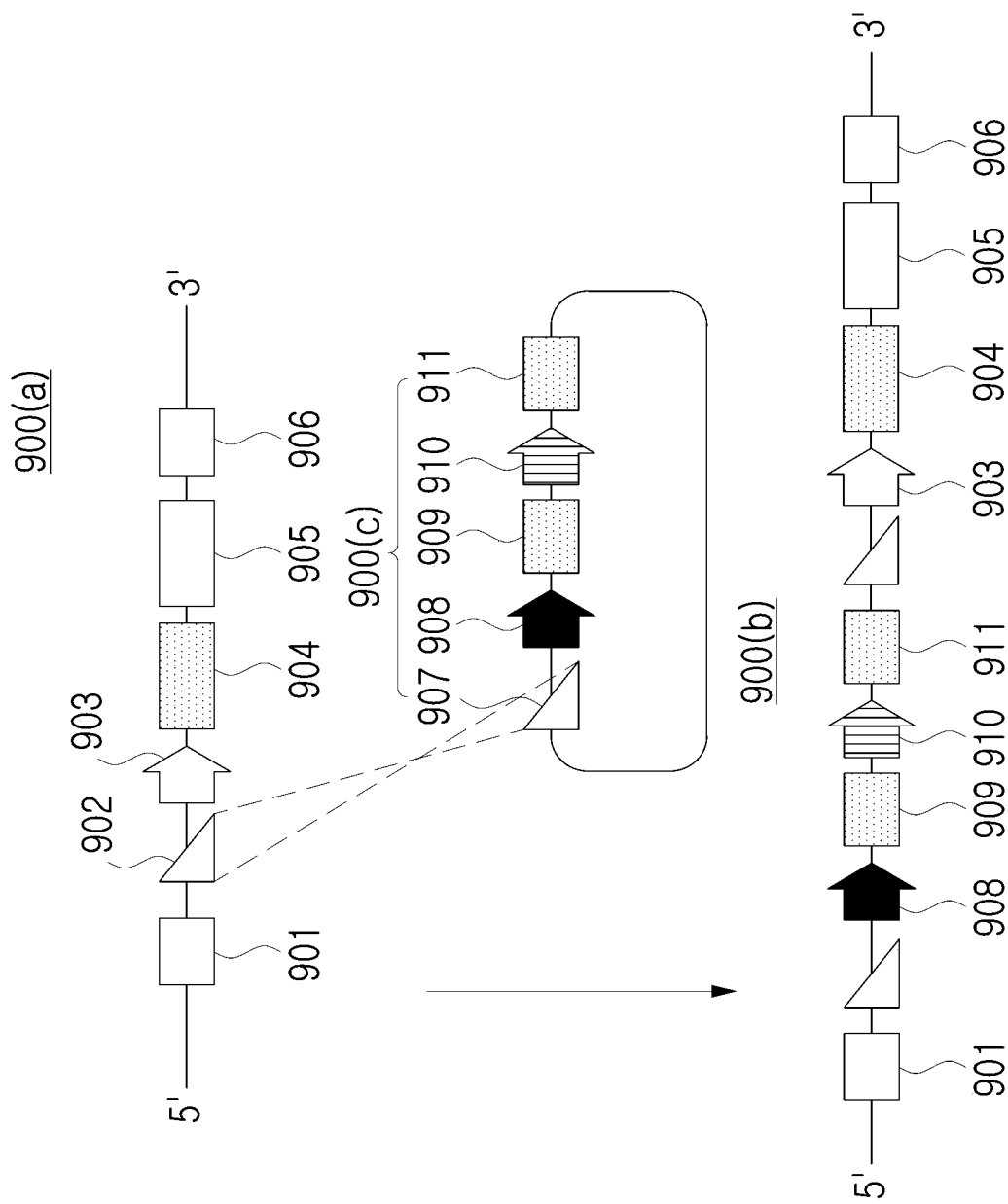
FIG. 23 illustrates an embodiment of an excision toolbox in which the expression of a recombinase can be controlled by an inducible promoter and a tissue-specific promoter.

FIG. 23 illustrates an embodiment of an excision toolbox in which the expression of a recombinase can be controlled by an inducible promoter and a tissue-specific promoter.

The excision toolbox (900(b)) may have a constitution in which a component for the toolbox excision is included between a first ITR sequence (901) and a second ITR sequence (906).

The component for the toolbox excision may include a polynucleotide encoding an inducible promoter (908), a polynucleotide encoding a first recombinase (909), a polynucleotide encoding a tissue-specific promoter (910), a polynucleotide encoding a second recombinase (911), a polynucleotide encoding a promoter (903), a polynucleotide encoding an RSR (904), and a polynucleotide encoding a transposase (905). Additionally, the component for the toolbox excision may further include one or more recombinase recognition sites (RRSs).

The polynucleotide encoding the first recombinase (909) and the polynucleotide encoding the second recombinase (911) have the same sequence. The first recombinase and the second recombinase can interact with the recombinase recognition site (RRS), which constitutes the polynucleotide encoding the RSR (904).

Hereinafter, a method for preparing the excision toolbox 900(b) is described.

One method for preparing the excision toolbox (900(b)) may include a provision of a third recombinase and the component (900(c)) for the toolbox excision to a cell having a genome into which the toolbox (900(a)) is inserted.

The method for providing the third recombinase and the component (900(c)) for the toolbox excision into a cell has been described above, and thus detailed explanation is omitted.

The third recombinase provided into the cell can interact with the recombinase recognition site (RRS) (902), which is included in the toolbox (900(a)), and the recombinase recognition site (RRS) (907), which is included in the component (900(c)) for the toolbox excision, which is provided into the cell.

By the above interactions, the component (900(c)) for the toolbox excision can be inserted into the location of the recombinase recognition site (RRS) (902) of the toolbox (900(a)). Based on the above, the excision toolbox (900(b)), in which a transposase can be expressed under particular conditions, can be prepared.

2. Excision Mechanism Using Excision Toolbox

Hereinafter, a mechanism by which the excision toolbox provided by the present disclosure is excised under particular conditions is described.

Additionally, the mechanism by which a donor polynucleotide which is knocked in a genome is excised from the genome by a material that is expressed from the excision toolbox provided by the present disclosure is described.

2-1. Excision Mechanism of Excision Toolbox 2-1-1. Excision Mechanism of Excision Toolbox Having Constitution in which Polynucleotide Encoding Transposase can be Expressed Under Particular Conditions The present disclosure provides an explanation on the excision mechanism of an excision toolbox, in which the expression of a transposase is controlled by the inducible promoter and tissue-specific promoter described above.

For the convenience of explanation, the inducible promoter is assumed to be a promoter which can be operated at a low temperature condition that may occur during the cell replication step, and the tissue-specific promoter is assumed to be a promoter that can be activated in a reproductive tissue. The reproductive tissue may be a testis or ovary.

Hereinafter, the mechanism by which the excision toolbox (700(b)) is excised from the genome of a cell during the cell replication step is described referring to FIG. 21. For the convenience of explanation, the cell is assumed to be an isolated cell.

During the cell replication step, a low temperature condition may be applied to the cell having a genome into which the above-described excision toolbox (700(b)) is inserted. At a low temperature condition, the inducible promoter (707) can be operated, and a first transposase can be expressed in the cell by the operation of the inducible promoter (707).

When the first transposase is expressed in the cell, the first transposase can interact with the first ITR sequence (701) and the second ITR sequence (705) present in the genome of the cell. In this case, the excision toolbox (700(b)) can be excised from the genome of the cell.

Accordingly, during the step where the cell having the genome into which the excision toolbox (700(b)) is inserted is replicated, the excision toolbox (700(b)) can be excised from the genome of the cell. In this case, a replicated cell having the genome into which the excision toolbox (700(b)) is inserted cannot be produced.

Next, a mechanism by which the excision toolbox (700(b)) is excised from a genome in a reproductive tissue is described.

In the above-described reproductive tissue having a genome into which the excision toolbox (700(b)) is inserted, the tissue-specific promoter (709) can operate, and a second transposase can be expressed in the reproductive tissue by the operation of the tissue-specific promoter (709).

When the second transposase is expressed in the reproductive tissue, the second transposase can interact with the first ITR sequence (701) and the second ITR sequence (705), which are present in the genome of the tissue. In this case, the excision toolbox (700(b)) can be excised from the genome of the reproductive tissue.

That is, the excision toolbox (700(b)) can be excised from the genome of a reproductive tissue. Accordingly, a gamete having a genome into which the excision toolbox (700(b)) is inserted cannot be produced from a cell and/or animal having a genome into which the excision toolbox (700(b)) is inserted.

The excision mechanism of the excision toolbox (800(b)) provided in the present disclosure is substantially the same as the above-described toolbox (700(b)) and thus the detailed explanation is omitted.

2-1-2. Excision Mechanism of Excision Toolbox Having Construction in which Polynucleotide Encoding Recombinase can be Expressed Under Particular Conditions The present disclosure provides an explanation on the excision mechanism of excision toolbox in which the expression of a recombinase is controlled by the inducible promoter and the tissue-specific promoter described above. For the convenience of explanation, hereinafter, the inducible promoter is assumed to be a promoter which can be operated at a low temperature condition that may occur during the cell replication step, and the tissue-specific promoter is assumed to be a promoter that can be operated in a reproductive tissue.

Hereinafter, the mechanism by which the excision toolbox (900(b)) is excised from the genome in a cell replication step is described.

During the cell replication step, a low temperature condition may be applied to the cell having a genome into which the above excision toolbox (900(b)) is inserted. At a low temperature condition, the inducible promoter (908) can be operated, and a first recombinase can be expressed in the cell by the operation of the inducible promoter (908).

The first recombinase expressed within the cell can interact with the recombinase recognition site (RRS), which constitutes a polynucleotide encoding an RSR (904) present in the excision toolbox (900(b)). In this case, the stop codon can be excised from the polynucleotide encoding the RSR (904), and the transcription and/or translation of the polynucleotide encoding the transposase (905) may occur. That is, the transposase can be expressed within the cell by the excision of the stop codon.

The expressed transposase can interact with a first ITR sequence (901) and a second ITR sequence (906), which are present in the genome of the cell. In this case, the excision toolbox (900(b)) can be excised from the genome of the cell.

Accordingly, when cell replication is attempted using a cell having a genome into which the excision toolbox (900(b)) is inserted, the excision toolbox (900(b)) can be excised from the genome of the cell. In this case, a replicated cell having the genome into which the excision toolbox (900(b)) is inserted cannot be produced.

Then, the mechanism by which the excision toolbox (900(b)) is excised from the genome in a reproductive tissue is described.

In the above-described reproductive tissue having a genome into which the excision toolbox (900(b)) is inserted, the tissue-specific promoter (910) can be operated, and a second recombinase can be expressed in the tissue by the operation of the tissue-specific promoter (910).

The second recombinase expressed in the reproductive tissue can interact with the recombinase recognition site which constitutes the polynucleotide encoding an RSR (904) present in the excision toolbox (900(b)). In this case, the stop codon can be excised from the polynucleotide encoding the RSR (904). The transposase can be expressed within the cell by the excision of the stop codon.

The expressed transposase can interact with the first ITR sequence (901) and the second ITR sequence (906) which are present in the genome of the cell. In this case, the excision toolbox (900(b)) can be excised from the genome of the reproductive tissue.

That is, the excision toolbox (900(b)) can be excised in the genome of a reproductive tissue. Accordingly, a gamete having the genome into which the excision toolbox 900(b) is inserted cannot be produced from a cell and/or animal having a genome into which the excision toolbox (900(b)) is inserted.

2-2. Excision Mechanism of Part in which Gene Editing has Occurred

Hereinafter, a mechanism by which a donor polynucleotide, which is knocked in on a genome, is excised from the genome by the transposase expressed from an excision toolbox is described.

According to the previous disclosure, it was assumed that the excision toolbox includes a polynucleotide encoding an RNA-guided endonuclease, and the knockin of the donor polynucleotide may be due to gene editing using the RNA-guided endonuclease expressed from the excision toolbox.

The mechanism by which a transposase is expressed from the excision toolbox under particular conditions has been described above, and thus the specific explanation on the mechanism of the expression of a transposase is omitted herein.

The donor polynucleotide which is knocked in to the genome by gene editing can be excised from the genome by the transposase expressed from the excision toolbox.

For example, when the donor polynucleotide is knocked in to the inside of the excision toolbox, the donor polynucleotide can be excised from the genome by excising the excision toolbox by the transposase expressed from the excision toolbox.

In another example, when the donor polynucleotide is knocked in to the inside of a toolbox other than the excision toolbox, the donor polynucleotide can be excised from the genome in the case where the donor polynucleotide has an ITR sequence, which can interact with the transposase expressed from the excision toolbox, at the 5' and 3' end of the donor polynucleotide.

In still another example, even when the donor polynucleotide is knocked in to an endo-polynucleotide, which is not a toolbox, the donor polynucleotide can be excised from the genome in the case where the donor polynucleotide has an ITR sequence, which can interact with the transposase expressed from the excision toolbox, at the 5' and 3' end of the donor polynucleotide.

3. Utilization of Excision Toolbox

Hereinafter, cases where the construction of toolbox needs to be changed to an excision toolbox are described. That is, the aspect of utilization of the excision toolbox is described.

For the convenience of explanation, hereinafter, it is assumed that a polynucleotide encoding an RNA-guided endonuclease is included to a toolbox.

In the case where a skilled person in the art, who has produced cells having a genome into which the toolbox is inserted, sells cells and/or animals having a genome into which the toolbox is inserted to a third party, the third party who has purchased the cells and/or animals from the skilled person in the art can obtain the RNA-guided endonuclease expressed from the cells and/or animals. In this case, the acquisition of the RNA-guided endonuclease expressed from the cells and/or animals by the third party can be considered as a legitimate benefit.

Furthermore, when the skilled person in the art sells the cells and/or animals having a genome, in which a donor polynucleotide is knocked in to the genome of the cell using the toolbox, the third party who has purchased the cells and/or animals can obtain the donor RNA and/or protein from the cells and/or animals. The donor RNA and/or protein is one which is expressed by the transcription and/or translation of the donor polynucleotide. In this case, the acquisition of the donor RNA and/or protein from the cells and/or animals purchased by the third party can be considered as a legitimate benefit.

In addition to the acquisition of the RNA-guided endonuclease, donor RNA and/or donor protein expressed from the cells and/or animals, any third party who has purchased the cells and/or animals may have an illegitimate benefit using the purchased cells and/or animals.

For example, an example that any third party who has purchased the cells having a genome into which the toolbox is inserted may have an illegitimate additional benefit may include cases where the third party is involved in a large-scale production or sales of the cells having a genome into which the toolbox and/or donor polynucleotide is inserted, by replication of the cells.

In another example, an example that any third party who has purchased gametes having a genome into which the toolbox is inserted may have an illegitimate additional benefit may include cases where the third party is involved in the production of individuals having a genome into which the toolbox and/or donor polynucleotide is inserted, by in vitro fertilization using the gametes.

In still another example, an example that any third party who has purchased animals having a genome into which the toolbox is inserted may have an illegitimate additional benefit may include cases where the third party is involved in the production or sales of gametes having a genome into which the toolbox and/or donor polynucleotide is inserted, by using the animal.

In still another example, an example that any third party who has purchased animals having a genome into which the toolbox is inserted may have an illegitimate additional benefit may include cases where the third party is involved in the production or sales of offspring having a genome into which the toolbox and/or donor polynucleotide is inserted, by using the animal.

As described above, as a safeguard measure to prevent any third party who has purchased the cells and/or animals from having an illegitimate additional benefit, it is possible that a skilled person in the art can sell, to a third party, the cells and/or animals having a genome into which the polynucleotide encoding an RNA-guided endonuclease is inserted, after changing the construction of the toolbox to the construction of the excision toolbox.

Hereinafter, the mechanism and effects thereof in cases where the construction of the toolbox has been changed to the construction of the excision toolbox are described.

For the convenience of explanation, hereinafter, only the excision mechanism and effects of the excision toolbox are described, but this can also be applied to the donor polynucleotide in the same manner.

In the case where a skilled person in the art sells the cells and/or animals having a genome into which the excision toolbox is inserted, if any third party who has purchased the cells and/or animals attempts to have an illegitimate additional benefit as described above, the excision toolbox may be excised from the genome of the cells and/or animals.

For example, if any third party, who has purchased the cells having a genome into which the excision toolbox is inserted, attempts to replicate the cells, the inducible promoter included in the excision toolbox can be operated and then a transposase can be expressed, and as a result, the excision toolbox can be excised from the genome of the cell.

In another example, in the case where any third party, who has purchased animals having a genome into which the excision toolbox is inserted, attempts to produce gametes using the animals, a transposase can be expressed in the tissue by the activity of the tissue-specific promoter therein, and as a result, gametes in which the excision toolbox is excised can be produced.

In still another example, in the case where any third party, who has purchased animals having a genome into which the excision toolbox is inserted, attempts to produce offspring using the animals, a transposase can be expressed in a reproductive tissue by the activity of the tissue-specific promoter therein, and as a result, offspring in which the excision toolbox is excised can be produced.

That is, to prevent any third party, who has purchased the cells and/or animals having a genome into which a polynucleotide encoding an RNA-guided endonuclease is inserted, from having an illegitimate additional benefit, a skilled person in the art can change the construction of the toolbox to the construction of the excision toolbox.

[Experimental Example 1] Preparation of Transgenic Embryo Having Genome in which Target Protein Gene is Inserted Using Somatic Cell Nuclear Transfer The present inventors have conducted the following experiment so as to insert the target protein gene into the bovine genome.

To visually confirm the insertion of the target protein gene, the present inventors selected a fluorescent protein gene as the target protein and conducted the experiment, and prepared a toolbox including the fluorescent protein gene and prepared a bovine fertilized egg including the toolbox prepared by the SCNT method.

1. Preparation of Toolbox Vector Including Target Protein Gene

To prepare a final expression vector including a toolbox in which a green fluorescent protein gene and a red fluorescent protein gene are included, the green fluorescent protein and the red fluorescent protein gene were amplified using the Gateway PCR cloning (MultiSite Gateway ProPlus, Invitrogen, 12537100, Life Technologies, Carlsbad, CA, USA).

The PCR primers used for the amplification of the green fluorescent protein gene and the red fluorescent protein gene are shown in Table 2 below.

In the present specification, the sequence number is expressed as SEQ ID NO.

TABLE 2

| Primer Type | SEQ Name | SEQ ID NO | Sequence |
|---|---|---|---|
| GFP-Forward | pr_GFP_F_1 | SEQ ID NO: 1 | GgggacaagtttgtacaaaaaagcaggcttcACCATGGCCAGCAAAGGAGAAGAACTT |
| GFP-Reverse | pr_GFP_R_1 | SEQ ID NO: 2 | GgggaccactttgtacaagaaagctgggtcTTATTTGTAGAGCTCATCCATGCC |
| RFP-Forward | pr_RFP_F_1 | SEQ ID NO: 3 | GgggacaagtttgtacaaaaaagcaggcttcACCATGGATAGCACTGAGAACGTCAT |
| RFP-Reverse | pr_RFP_R_1 | SEQ ID NO: 4 | ggggaccactttgtacaagaaagctgggtcCTACTGGAACAGGTGGTGGC |

The present inventors prepared a final expression vector using the amplified green fluorescent protein gene and/or red fluorescent protein gene.

Figure 24:
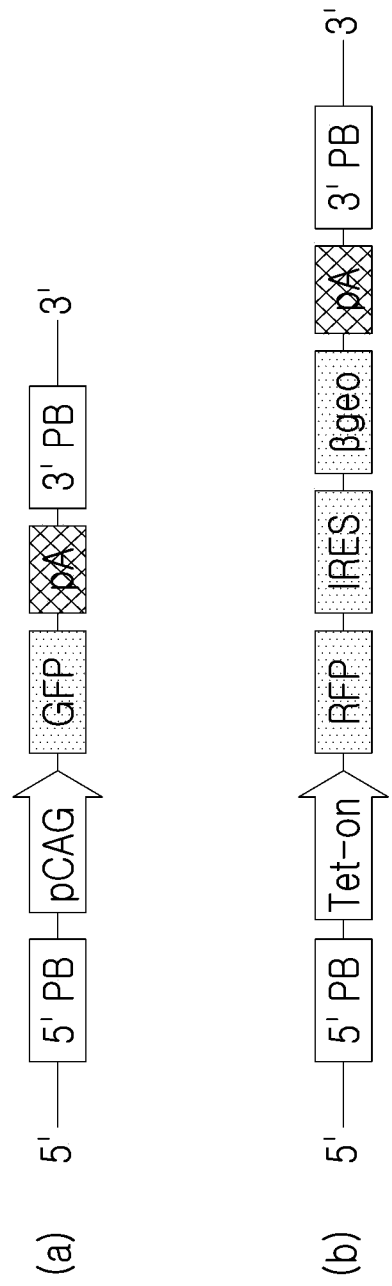
FIG. 24 illustrates part of a vector in which a gene encoding green fluorescent protein (green fluorescent protein gene) is included and part of a vector in which a gene encoding red fluorescent protein (red fluorescent protein gene) is included.

FIG. 24(a) illustrates part of the final expression vector for the expression of the green fluorescent protein and FIG. 24(b) illustrates part of the final expression vector for the expression of the red fluorescent protein.

For the preparation of the final expression vector, the pDonor (Invitrogen) was used as the entry vector, and the PB-CA vector (with a p-CCAGG promoter) and the PB-TET vector (with a Tet-on promoter) were used as the destination vector.

The piggyBac (PB) sequences used in this Experimental Example are shown in Table 3 below.

TABLE 3

| Transposon Type | SEQ Name | SEQ ID NO | Sequence |
|---|---|---|---|
| 5' PB | tp_PB_1 | SEQ ID NO: 5 | TTAACCCTAGAAAGATAGTCTGCGTAAAATTGACGCATGCATTCTTGAAATATTGCTCTCTCTTTCTAAATAGCGCGAATCCGTCGCTGTGCATTTAGGACATCTCAGTCGCCGCTTGGAGCTCCCGTGAGGCGTGCTTGTCAATGCGGTAAGTGTCACTGATTTTGAACTATAACGACCGCGTGAGTCAAAATGACGCATGATTATCTTTTACGTGACTTTTAAGATTTAACTCATACGATAATTATATTGTTATTTCATGTTCTACTTACGTGATAACTTATTATATATATATTTTCTTGTTATAGATATC |
| 3' PB | tp_PB_2 | SEQ ID NO: 6 | TTTGTTACTTTATAGAAGAAATTTTGAGTTTTTGTTTTTTTTTAATAAATAAATAAACATAAATAAATTGTTTGTTGAATTTATTATTAGTATGTAAGTGTAAATATAATAAAACTTAATATCTATTCAAATTAATAAATAAACCTCGATATACAGACCGATAAAACACATGCGTCAATTTTACGCATGATTATCTTTAACGTACGTCACAATATGATTATCTTTCTAGGGTTAA |

2. Preparation of Cloned Embryo (SCNT)

2-1. Isolation of Bovine Cells

The present inventors isolated fibroblasts from a bovine fetus so as to insert a toolbox including a target protein gene into the genome.

The bovine fetal tissue on the 45th day of gestation was minced using a surgical blade and dissociated at 37° C. for 1 hour using Dulbecco's modified Eagle's medium (DMEM, Invitrogen, Carlsbad, CA, USA) to which 25% (w/v) trypsin and 1 mM EDTA (Invitrogen) were added.

Trypsin-treated cells were centrifuged at 1,500 rpm for 2 min, washed once with DPBS without $Ca^{2+}$ and $Mg^{2+}$, and seeded into a 100-mm plastic culture dish.

The seeded cells were cultured in DMEM medium, to which 10% (v/v) FBS, 1 mM glutamine, 25 mM $NaHCO_3$, 1% (v/v) minimum essential medium (MEM) were added, at 39° C. under the conditions of humidified atmosphere of 5% $CO_2$ and 95% air for 6 to 8 days.

After unattached cells and a chunk of slices were removed from the seeded cells, the attached cells were cultured to have a confluency with each other in the culture dish, and cultured further at intervals of 4 to 6 days by trypsinization for 5 min using 0.1% trypsin and 0.02% EDTA. The cultured cells were dispensed to 3 new culture dishes for further subculture and then stored in freezing medium in liquid nitrogen at −196° C.

2-2. Toolbox Vector Transfection

The present inventors thawed the cells which were stored by the above method, cultured for 3 to 4 days, and recovered fibroblasts from the single layer using trypsin, and prepared donor cells for SCNT using the recovered fibroblasts.

Before about 18 to 24 hours for transfection, recovered fibroblasts were dispensed into 6-well plates. When the cells reached about 50-60% confluency, transfection proceeded to the fibroblasts according to the known manufacturer's method.

The plasmid vector (PB-CA-GFP) containing a green fluorescent protein gene, and pCy43 vector (transposase expression vector, Sanger Institute, Hinxton, UK) were transfected into the recovered fibroblasts, and then a donor cell in which a green fluorescent protein is expressed (hereinafter, GFP donor cell) was prepared.

Additionally, the plasmid vector (PB-TET-RFP) containing a red fluorescent protein gene, and pCy43 vector (transposase expression vector, Sanger Institute, Hinxton, UK) were transfected into the recovered fibroblasts, and then a donor cell in which a red fluorescent protein is expressed (hereinafter, RFP donor cell) was prepared.

The pCy43 vector was used for the transposition of PB-CA-GFP or PB-TET-RFP.

The expression of a green fluorescent protein was confirmed in the GFP donor cell prepared by the above method.

Figure 25:
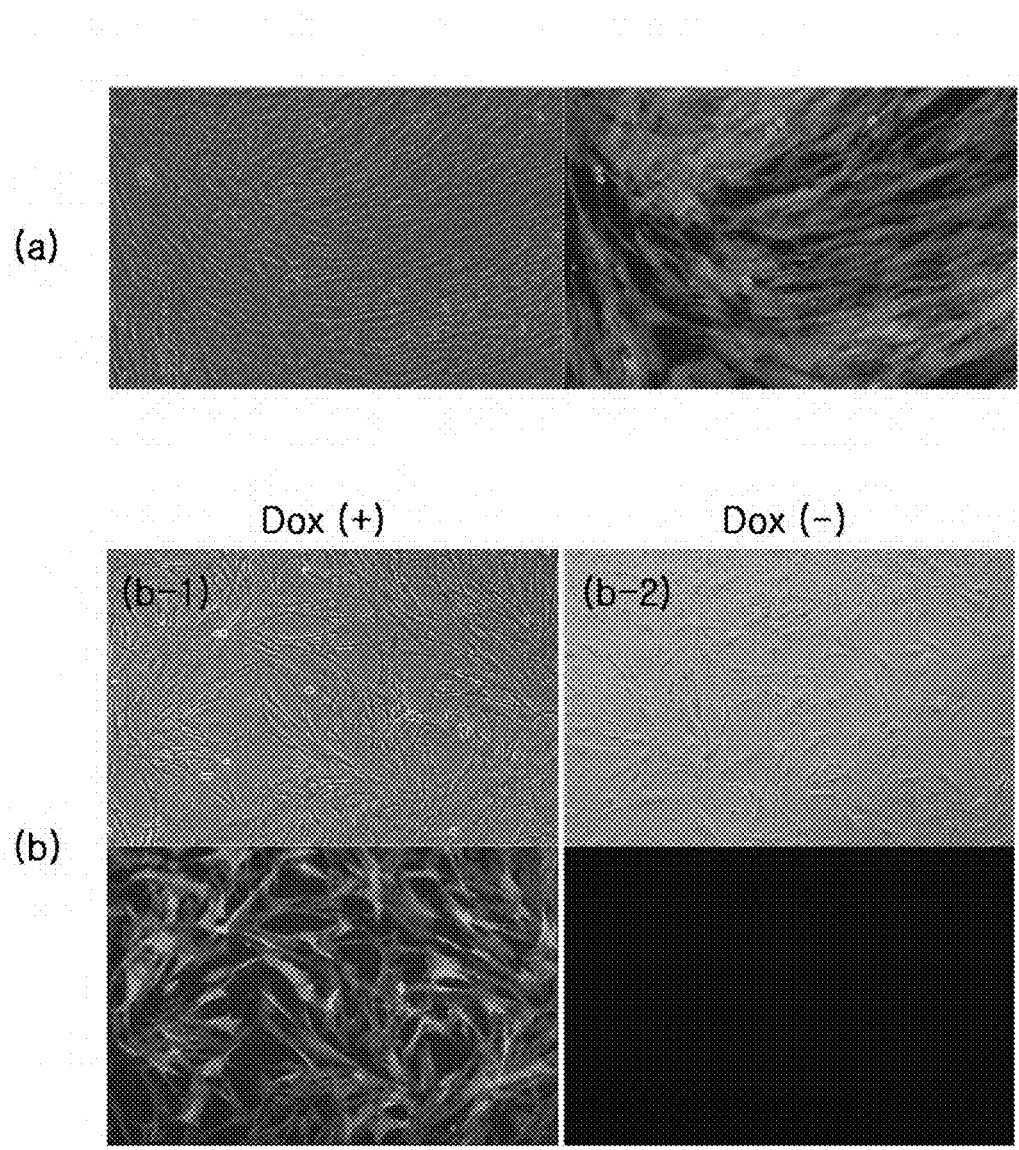
FIG. 25 shows images illustrating the expression of a fluorescent protein in a donor cell having a genome, into which a toolbox including a gene encoding fluorescent protein (fluorescent protein gene) is inserted.

FIG. 25(a) shows the expression of a green fluorescent protein in the GFP donor cell (see FIG. 25(a), left: visible light condition, right: fluorescent light condition).

Additionally, when the RFP donor cells prepared by the above method were treated with doxycycline (2 mg/mL) and neomycin (1 mg/mL), the expression of the red fluorescent protein was confirmed, and the disappearance of RFP expression was confirmed on the $8^{th}$ day after removal of doxycycline.

FIG. 25(b) shows the expression of a red fluorescent protein when the RFP donor cells were treated with doxycycline and neomycin (see FIG. 25(b) (b-1), top: visible light condition, bottom: fluorescent light condition), and shows the disappearance of RFP expression on the $8^{th}$ day after removal of doxycycline (see FIG. 25(b) (b-2), top: visible light condition, bottom: fluorescent light condition).

From the above results, it was confirmed that the expression timing of the red fluorescent protein can be controlled by doxycycline treatment when the Tet-on promoter is used.

In other words, it was confirmed that when an inducible promoter (e.g., Tet-on promoter) is used as an expression control element, the inducible promoter can be operated through the treatment with the conditions or material that can activate the inducible promoter (e.g. doxycycline) and that the transcription and/or translation of the target protein can be controlled by the operation of the inducible promoter in a timely manner.

Through the confirmation of the presence of the expression of a fluorescent protein, donor cells having a genome into which the target protein gene was inserted were selected, and transgenic embryos were produced by somatic cell nuclear transfer (SCNT) using the selected donor cells 2-3. Preparation of Cloned Embryo Using Donor Cell (SCNT)

The nucleus of each of the GFP donor cells or RFP donor cells prepared by the above method was transferred into each enucleated oocyte (enucleated ovum), electrically fused, activated by ionomycin for 4 min, and then cultured in 6-DMAP for 4 hours.

The cloned embryo which can express a green fluorescent protein (hereinafter, GFP cloned embryo) or cloned embryo which can express a red fluorescent protein (hereinafter, RFP cloned embryo) obtained by the electric fusion as described above was cultured in an incubator (39° C., 5% $CO_2$) in a 25 μL microdrop of chemically defined medium overlaid with mineral oil for 7 to 8 days. The chemically defined medium was prepared by the conventionally known method.

2-4. Confirmation of Toolbox Insertion Including Target Protein Gene 2-4-1. PCR, RT-PCR Results To confirm whether the green fluorescent protein gene and the red fluorescent protein gene were inserted into the genome of the bovine transgenic embryos produced by the above method (GFP cloned embryo and RFP cloned embryo) and to detect the presence/absence of mRNA expression therein, DNA PCR and RT-PCR (Eppendorf Vapo Protect Mastercycler, Eppendorf, Germany) were conducted.

For DNA PCR, genome DNA was extracted from the blood or cells of a transgenic cow using the DNA extraction kit (DNeasy Blood & Tissue kit 69506, Qiagen, Limburg, Netherlands).

For RT-PCR, total RNA was extracted using the RNA extraction kit (Easy spin total RNA extraction kit, Cat. 17221, iNtRON, Sungnam, Korea), and cDNA was synthesized using the cDNA synthesis kit (RNA to cDNA EcoDry ⓒ Premix Kit, PT5153-2, Clontech, California, US) for cDNA synthesis. For cDNA synthesis, 1 μg of total RNA was used.

The primers used for PCR are shown in Table 4 below.

TABLE 4

| Primer Type | SEQ Name | SEQ ID NO | Sequence |
|---|---|---|---|
| GFP-Forward | pr_GFP_F_2 | SEQ ID NO: 7 | CACATGAAGCAGCACGACTT |
| GFP-Reverse | pr_GFP_R_2 | SEQ ID NO: 8 | AGTTCACCTTGATGCCGTTC |
| RFP-Forward | pr_RFP_F_2 | SEQ ID NO: 9 | CCCCGTAATGCAGAAGAAGA |
| RFP-Reverse | pr_RFP_R_2 | SEQ ID NO: 10 | GGTGATGTCCAGCTTGGAGT |
| GAPDH-Forward | pr_GAPDH_F_1 | SEQ ID NO: 11 | GGCGTGAACCACGAGAAGTA |
| GAPDH-Reverse | pr_GAPDH_R_1 | SEQ ID NO: 12 | CCCTCCACGATGCCAAAGT |

Figure 26:
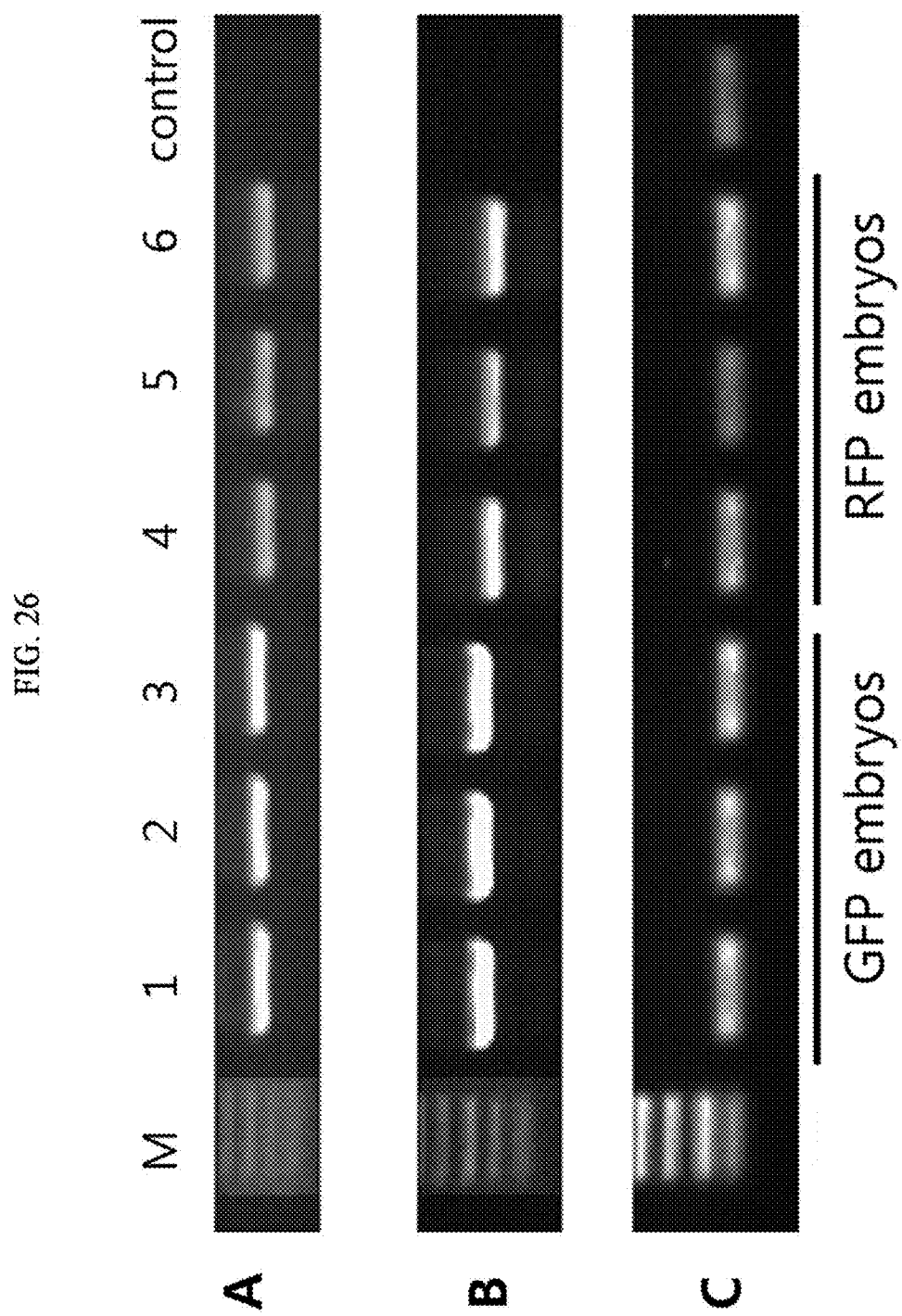
FIG. 26 shows images illustrating the result of RT-PCR, which shows the presence/absence of mRNA expression of a green fluorescent protein gene or a red fluorescent protein gene in a cloned embryo; and the result of DNA PCR, which confirms the insertion of the green fluorescent protein gene or the red fluorescent protein gene in the genome of a cloned embryo.

FIG. 26 shows the results of RT-PCR and DNA PCR of the transgenic embryos (GFP cloned embryo and RFP cloned embryo) (A: PCR result using genome DNA as a template, B: PCR result using cDNA as a template, C: GAPDH mRNA expression via RT-PCR, M: molecular marker, control: non-transformation embryo).

2-4-2. Confirmation of Fluorescent Protein Expression in Embryo

The expression of GFP or RFP without mosaicism was visually confirmed in the transgenic embryo (GFP cloned embryo and RFP cloned embryo).

Figure 27:
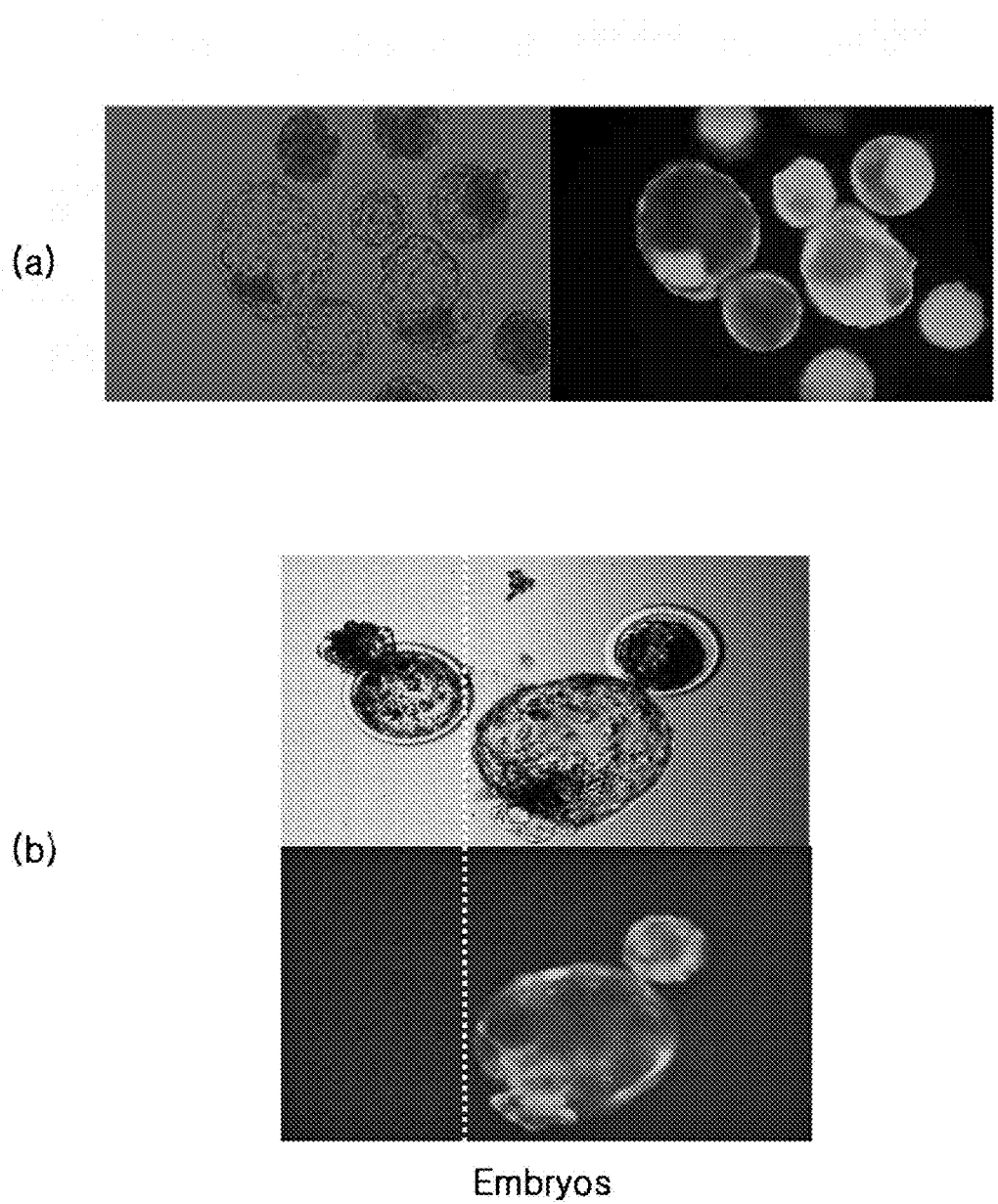
FIG. 27 shows images illustrating the expression of a fluorescent protein in a cloned embryo having a genome, into which a toolbox including a fluorescent protein gene is inserted.

FIG. 27(a) shows the expression of a green fluorescent protein in a GFP cloned embryo (left: visible light condition, right: fluorescent light condition).

FIG. 27(b) shows the results when the 7-day-old RFP cloned embryo was treated with doxycycline and then cultured two more days. When a transformed embryo was treated with doxycycline, the expression of a red fluorescent protein was confirmed (see FIG. 27(b); right of the dashed line), whereas when an non-transformed embryo was treated with doxycycline, the expression of a red fluorescent protein was not confirmed (see FIG. 27(b); left of the dashed line).

From this experiment, it was confirmed that cells and/or embryos having a genome into which a toolbox including a target protein gene for transformation is inserted can survive without any particular danger.

[Experimental Example 2] Preparation of Transgenic Cow Having Genome into which Target Protein Gene is Inserted Via Microinjection The present inventors conducted the following experiment so as to insert a target protein gene into the bovine genome.

As described above, for visual confirmation of the insertion of the target protein gene, the present inventors conducted the experiment by selecting a fluorescent protein gene as the target protein, and prepared a toolbox including the fluorescent protein gene, and thereby prepared a bovine fertilized egg which includes a toolbox prepared via a microinjection (MI) method, and transplanted the fertilized egg into the uterus of a surrogate mother thereby preparing a transgenic cow having a genome into which the fluorescent protein gene is inserted.

1. Preparation of Toolbox Vector Including Target Protein Gene

To prepare a final expression vector including a toolbox in which a yellow fluorescent protein gene, a green fluorescent protein gene, and a red fluorescent protein gene are included, the yellow fluorescent protein gene, green fluorescent protein gene, and red fluorescent protein gene were amplified using the Gateway PCR cloning (MultiSite Gateway ProPlus, Invitrogen, 12537100, Life Technologies, Carlsbad, CA, USA).

The primers used for the amplification of the yellow fluorescent protein gene, green fluorescent protein gene, and red fluorescent protein gene were purchased from the Addgene (addgene.org, Plasmid #34879).

Figure 28:
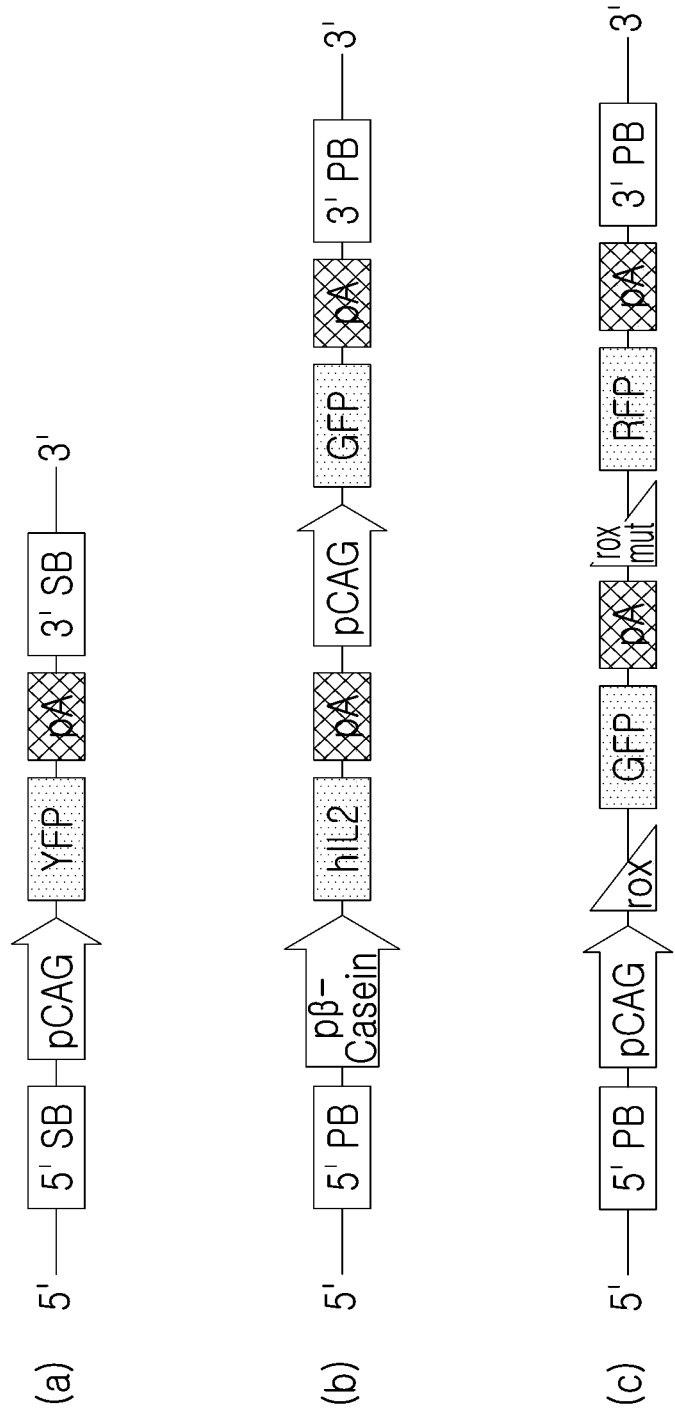
FIG. 28 illustrates partial constitution of several vectors in which each vector includes a fluorescent protein gene.

A final expression vector including a toolbox in which a yellow fluorescent protein gene is included (hereinafter, YFP vector) was prepared using the amplified gene. FIG. 28(a) illustrates part of the YFP vector.

Additionally, the cDNAs of β-casein promoter and human Interleukin 2 (hIL2) were amplified using the Gateway PCR cloning (MultiSite Gateway ProPlus, Invitrogen, 12537100, Life Technologies, Carlsbad, CA, USA). These cDNAs were inserted into PB-GFP by infusion cloning (In fusion HD cloning kit, Iontech, 639644, California, USA) and thereby the final expression vector including the toolbox (5'PB-β-casein promoter-hIL2-pA-pCAG-GFP-Pa-3'PB construction) that includes the GFP and hIL2 gene (hereinafter, GFP-hIL2 vector) was prepared. FIG. 28(b) illustrates part of the GFP-hIL2 vector.

Furthermore, the Rox-GFP-polyA-rox and the red fluorescent protein gene were amplified by the Gateway PCR cloning (MultiSite Gateway ProPlus, Invitrogen, 12537100, Life Technologies, Carlsbad, CA, USA), and a final expression vector (hereinafter, GFP-RFP vector) including the toolbox (5'PB-pCAG-rox-GFP-pA-rox-RFP-pA-3'PB construction) that includes the Rox-GFP-polyA-rox and the green fluorescent protein gene was prepared using the amplified Rox-GFP-polyA-rox and the red fluorescent protein gene. FIG. 28(c) illustrates part of the GFP-RFP vector.

The sleeping beauty (SB) sequences used in this experiment are shown in Table 5 below.

TABLE 5

| Transposon Type | SEQ Name | SEQ ID NO | Sequence |
| --- | --- | --- | --- |
| 5' SB | tp_SB_1 | SEQ ID NO: 13 | atacagttgaagtcggaagtttacatacacttaagttgga gtcattaaaactcgtttttcaactactccacaaatttcttgtt aacaaacaatagtttggcaagtcagttaggacatctact ttgtgcatgacacaagtcatttttccaacaattgtttacaga cagattatttcacttataattcactgtatcacaattccagtg ggtcagaagtttacatacactaagttgactgtgcctttaaa cagcttggaaaattccagaaaatgatgtcatggctttaga agct |
| 3' SB | tp_SB_2 | SEQ ID NO: 14 | gtggaaggctactcgaaatgtttgacccaagttaaacaa tttaaaggcaatgctaccaaatactaattgagtgtatgtaa acttctgacccactgggaatgtgatgaaagaaataaaag ctgaaatgaatcattctctctactattattctgatatttcacat tcttaaaataaagtggtgatcctaactgacctaagacagg gaattttactaggattaaatgtcaggaattgtgaaaaagt gagtttaaatgtatttggctaaggtgtatgtaaacttccga cttcaactgtatagggatcctctagctaga |

2. Preparation of Embryo (MI)

2-1. Ovum Collection and In Vitro Maturation (IVM)

Bovine ovaries collected in saline (35° C.) were transferred from the slaughterhouse to the laboratory within 2 hours. Cumulus-oocyte complexes (COCs) were sucked using an 18 gauge needle attached to a disposable syringe (10 mL) from 2-8 mm hair follicles.

COCs which have an evenly-granulated cytoplasm and are surrounded with cumulus cells of 3 or more layers were selected from the sucked COCs.

The selected COCs were washed 3 times with HEPES-buffered tissue culture medium-199 (TCM-199; Invitrogen, Carlsbad, CA, USA) supplemented with 10% FBS, 2 mM NaHCO$_3$(Sigma-Aldrich Corp., St. Louis, MO, USA) and 1% penicillin-streptomycin (v/v).

The selected COCs were cultured in 4 well-dishes (30-40 oocytes per well; Falcon, Becton-Dickinson Ltd., Plymouth, UK) at 39° C. and 5% CO$_2$ for 22 hours, and the medium used was TCM-199 (450 μL) supplemented with 10% FBS, 0.005 AU/ml FSH (Antrin, Teikoku, Japan), 100 μM Cysteamine (Sigma-Aldrich), and 1 μg/mL 17β-estradiol (Sigma-Aldrich).

2-2. Sperm Collection, In Vitro Fertilization (IVF) and In Vitro Culture of Embryos (IVC)

Sperms were isolated from the thawed bovine semen by centrifugation and the centrifugation was conducted in a Percoll discontinuous gradient (45-90%) at 1,500 rpm for 15 min.

Percoll solution 45% was prepared using 90% Percoll (Nutricell, Campinas, SP, Brazil) (1 mL) and capacitation-TALP (Nutricell) (1 mL).

The sperm pellet obtained by centrifugation was washed twice with capacitation-TALP (Nutricell) at 1,500 rpm for 5 min.

The sperms with active motility obtained from the sperm pellet were used for the fertilization with mature ova (24-hour IVM).

Ova and $1\text{-}2\times10^6$ sperms/mL were fertilized for 18 hours under the conditions of 39° C. and 5% $CO_2$ humidity in 30 μL microdrops of IVF-TALP medium (Nutricell) overlaid with mineral oil.

Presumptive zygotes were cultured in a culture medium overlaid with mineral oil (Sigma-Aldrich), and the culture conditions were 5% $O_2$, 5% $CO_2$ and 90% $N_2$ atmosphere at 39° C.

On the second day after the incubation, the cleavage rate of the zygote was recorded and the development of the embryo was monitored according to the steps of the International Embryo Transfer Society (IETS).

2-3. Microinjection (MI)

The above-described YFP vector, GFP-hIL2 vector and GFP-RFP vector (hereinafter, toolbox vector) and the transposase vector were microinjected into the cytoplasm of a fertilized egg, in which cumulus cells were removed, using the microinjector machine (Femtojet, Eppendorf, Germany).

The respective amount of the microinjected vector in the cytoplasm of the fertilized egg was 100 ng/mL (the ratio between the toolbox vector and transposase vector was 1:1).

The transposase vector (pCMV (CAT) T7-SB100X) for the sleeping beauty (SB) and the transposase vector (pCy43) for piggyBac (PB) were purchased from Addgene (addgene.org, Plasmid #34879) and provided by Sanger Institute (Hinxton, UK).

Seven days after vector microinjection, the embryos expressing a fluorescent protein were selected.

That is, using the above method, an embryo having a genome into which a toolbox including a yellow fluorescent protein gene is inserted (hereinafter, YFP embryo), an embryo having a genome into which a toolbox including a green fluorescent protein gene and hIL2 gene is inserted (hereinafter, GFP-hIL2 embryo), and an embryo having a genome into which a toolbox including rox-GFP-polyA-rox and a red fluorescent protein gene is inserted (hereinafter, GFP-RFP embryo) were produced.

3. Preparation of Transgenic Cow Having Genome in which Toolbox Including Target Protein Gene is Inserted 3-1. Preparation of Transgenic Cow The present inventors prepared a transgenic cow by transplanting the bovine embryo prepared by the above-described microinjection into the uterus of a surrogate mother.

The embryo which expresses a fluorescent protein was transferred into the uterine horn of a surrogate mother by the transcervical method in PBS supplemented with 20% FBS.

On the $45^{th}$ day of post estrus, the survival of the embryo and gestation were confirmed by rectal palpation and ultrasonography.

Figure 29:
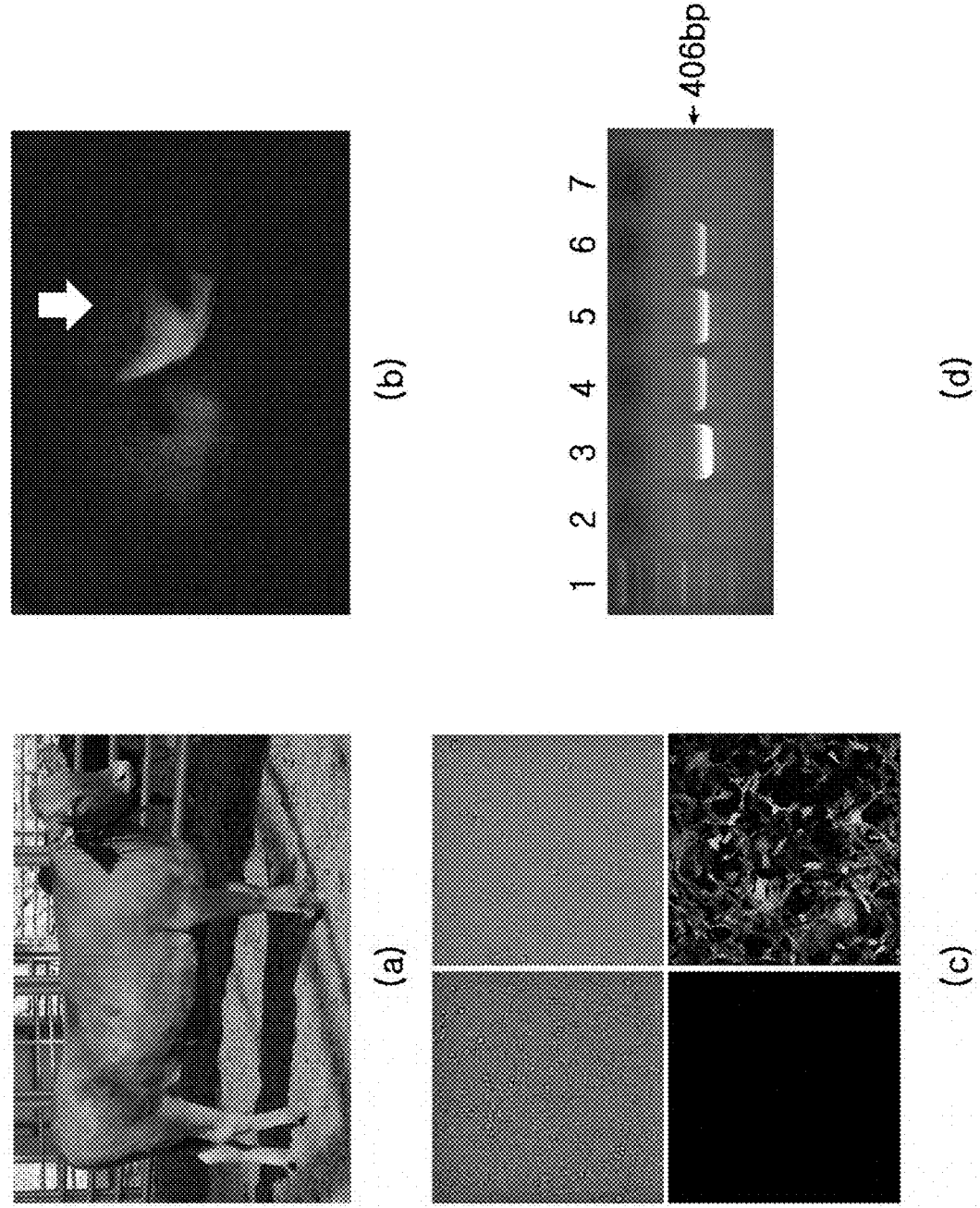
FIG. 29 shows images illustrating a transgenic cow having a genome into which a toolbox including a gene encoding yellow fluorescent protein (yellow fluorescent protein gene) is inserted, and the results confirming the expression of a yellow fluorescent protein in the transgenic cow.

3-2. Production of SNU-SB1 (Female) Individual and Confirmation of Presence/Absence of Toolbox Insertion Including Target Protein Gene An SNU-SB1 (female) was born from a surrogate mother into which a YFP embryo was transplanted by the above method. FIG. 29(*a*) shows the SNU-SB1.

The expression of a yellow fluorescent protein was confirmed in the nose of the SNU-SB1, and the expression of a yellow fluorescent protein was confirmed in the primary skin cell.

FIG. 29(*b*) shows the expression of a yellow fluorescent protein in the nose of the SNU-SB1, and FIG. 29(*c*) shows the expression of a yellow fluorescent protein in the primary skin cell of the SNU-SB1 (see FIG. 29(*c*), left row: skin cell of wild-type cow, right row: skin cell of transgenic cow, top: visible light condition, bottom: fluorescent condition).

Furthermore, the insertion of the yellow fluorescent protein gene was confirmed by DNA PCR. FIG. 29(*d*) shows the results confirming the insertion of the yellow fluorescent protein gene via DNA PCR (see FIG. 29(*d*), 1: molecular marker, 2: wild-type cow, 3: positive control group, 4: blood of transgenic cow, 5: ear tissue of transgenic cow, 6: placenta of transgenic cow, 7: negative control group).

The DNA extraction method for DNA PCR has been described above and thus detailed explanation is omitted.

3-3. Production of SNU-PB2 (Female) Individual and Confirmation of Presence/Absence of Toolbox Insertion Including Target Protein Gene An SNU-PB2 (female) was born from a surrogate mother into which a GFP-hIL2 embryo was transplanted by the above method.

The expression of a green fluorescent protein was confirmed in the eyes, nose, etc. of the SNU-PB2, and the expression of a green fluorescent protein was also confirmed in the primary skin cells of the SNU-PB2.

FIG. 30(*a*) shows the expression of a green fluorescent protein in the eyes and nose of the SNU-PB2, and FIG. 30(*b*) shows the expression of a green fluorescent protein in the primary skin cells of the SNU-PB2 (see FIG. 30(*b*), left: visible light condition, right: fluorescent condition).

Furthermore, the insertion of the green fluorescent protein gene, which is a gene included in the GFP-hIL2 vector, into a genome was confirmed via DNA PCR (Eppendorf Vapo Protect Mastercycler, Eppendorf, Germany).

FIG. 30(*c*) shows the results confirming the insertion of a green fluorescent protein gene via DNA PCR (see FIG. 30(*c*), 1: molecular marker, 2: wild-type cow, 3: blood of transgenic cow, 4: positive control group, 5: negative control group).

Additionally, the insertion of a green fluorescent protein gene in the genome and the mRNA expression were confirmed via RT-PCR (Eppendorf Vapo Protect Mastercycler, Eppendorf, Germany) using bovine primary cells.

FIG. 30(*d*) shows the results confirming the insertion of a green fluorescent protein gene via RT-PCR (see FIG. 30(*d*), 1: cDNA of wild-type cow, 2: cDNA of transgenic cow, 3: negative control group).

DNA and RNA extraction method for DNA PCR and RT-PCR have been described above and thus the specific explanations thereon are omitted herein.

From the above results, it was confirmed that the gene included in the GFP-hIL2 vector was inserted into the genome of the SNU-PB2.

Figure 31:
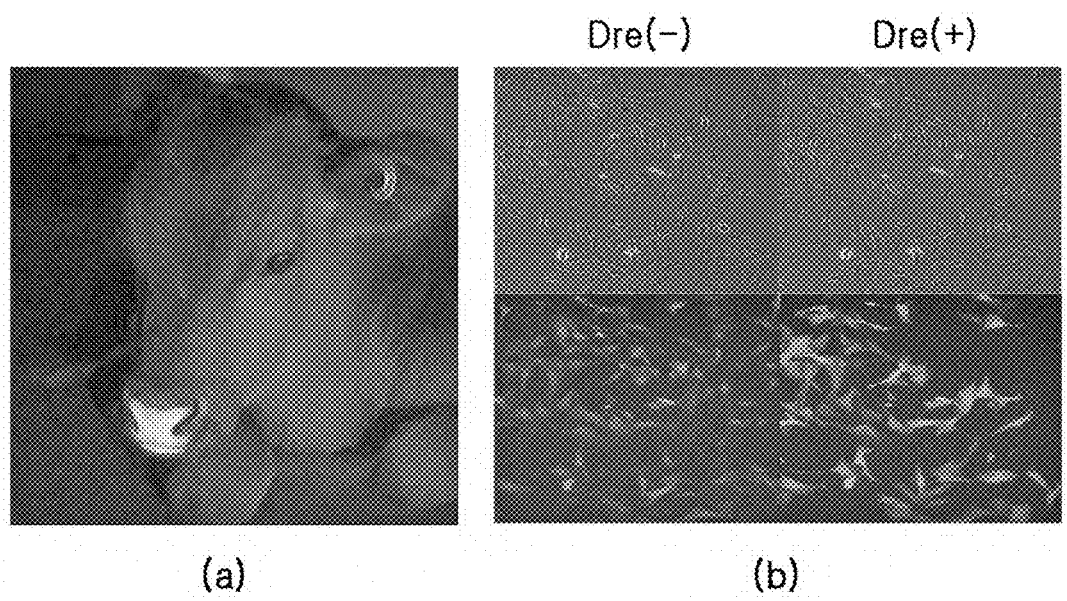
FIG. 31 shows images illustrating a transgenic cow having a genome into which a toolbox, which includes an expression control element, a green fluorescent protein gene, and a red fluorescent protein gene, is inserted; and the results of confirming the expression of a red fluorescent protein when the transgenic cow is treated with a material that affects the expression control element.

3-4. Production of SNU-PB1 (Male) Individual and Confirmation of Presence/Absence of Toolbox Insertion Including Target Protein Gene An SNU-PB1 (male) was born from a surrogate mother into which a GFP-RFP embryo was transplanted by the above method. FIG. 31(*a*) shows the expression of a green fluorescent protein in the SNU-PB1.

The expression of a green fluorescent protein was observed before Dre recombinase was transfected into the primary skin cells, which were isolated from the SNU-PB1 and cultured.

After the transfection of Dre recombinase in the form of an mRNA into the primary skin cells, which were isolated from the SNU-PB1 and cultured, the expression of a red fluorescent protein was observed in the cell.

FIG. 31(b) shows the results confirming the expression of a green fluorescent protein and the expression of a red fluorescent protein in the primary skin cells, which were isolated from the SNU-PB1 and cultured (see FIG. 31(b), top: visible light condition, bottom: fluorescent condition, left: before transfection with Dre recombinase, right: after transfection with Dre recombinase).

Figure 32:
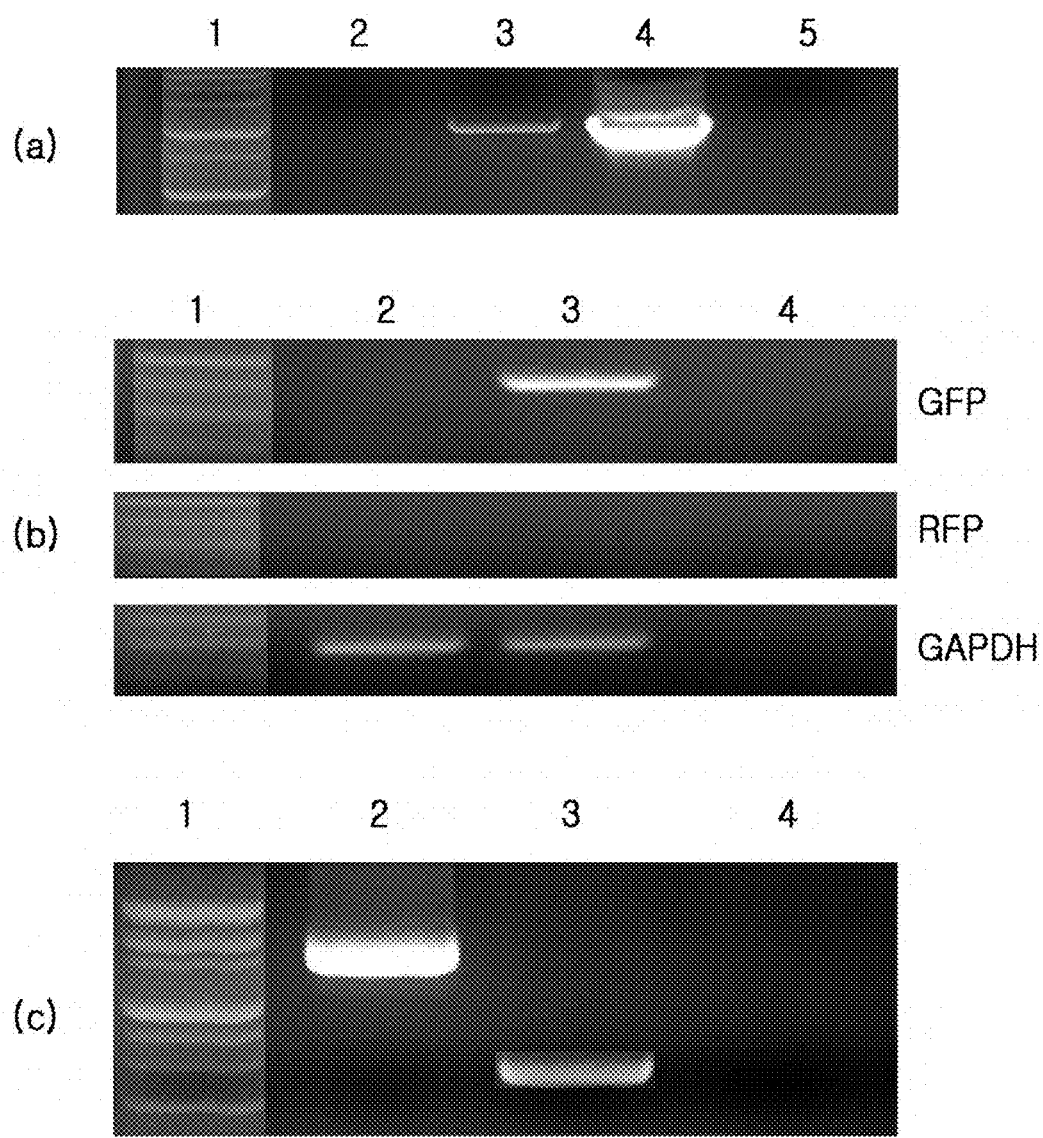
FIG. 32 shows images illustrating the results of DNA PCR and RT-PCR confirming the insertion and the transcription of a green fluorescent protein gene in a transgenic cow having a genome into which a toolbox, which includes an expression control element, a green fluorescent protein gene, and a red fluorescent protein gene, is inserted, and the results of DNA PCR confirming that the green fluorescent protein gene is removed and only the red fluorescent protein gene is present according to the treatment with a material that affects the expression control element in the transgenic cow.

Furthermore, before transfection with Dre recombinase, the insertion of a green fluorescent protein gene in the genome and the mRNA expression were confirmed by DNA PCR and RT-PCR (see FIG. 32(a) and FIG. 32(b)). FIG. 32(a) shows the results of DNA PCR before transfection with Dre recombinase (see FIG. 32(a), 1: molecular marker, 2: wild-type cow, 3: blood of transgenic cow, 4: positive control group (green fluorescent protein gene), 5: negative group). FIG. 32(b) shows RT-PCR results before transfection with Dre recombinase (see FIG. 32(b), 1: molecular marker, 2: wild-type cow, 3: transgenic cow, 4: negative group).

Additionally, it was confirmed that the green fluorescent protein gene was excised from the genome after transfection with Dre recombinase. FIG. 32(c) shows the DNA PCR results after transfection with Dre recombinase (see FIG. 32(c), 1: molecular marker, 2: before transfection with Dre, 3: after transfection with Dre, 4: negative group).

DNA and RNA extraction method for DNA PCR and RT-PCR have been described above and thus the specific explanations thereon are omitted herein.

From the above results, the present inventors have confirmed that a desired type of a target protein can be expressed by controlling in a timely fashion by providing a recombinase to a cell or animal having a genome into which the recombinase recognition site (RRS) is inserted.

4. Production of Transgenic Offspring Cow Having Genome into which Toolbox Including Target Protein Gene is Inserted 4-1. Transgenic Offspring Cow 4-1-1. SNU-F1-1 Cow An offspring cow (SNU-F1-1) was born by natural breeding between a female cow (SNU-SB1) and a male cow (SNU-PB1).

FIG. 33(a) shows SNU-F1-1, which is an offspring cow, and SNU-SB1, which is a parent cow (see FIG. 33(a), left arrow: SNU-F1-1, right arrow: SNU-SB1).

The present inventors have visually confirmed that a green fluorescent protein is expressed in the primary skin cells of SNU-F1-1, which is an offspring cow, and have visually confirmed that a red fluorescent protein is expressed after treatment with Dre recombinase.

FIG. 33(b) shows that a green fluorescent protein is expressed in the primary skin cells of SNU-F1-1 before treatment with Dre recombinase, and that a red fluorescent protein is expressed after treatment with Dre recombinase (top: before treatment with Dre, bottom: after treatment with Dre).

Furthermore, it was confirmed via DNA PCR analysis that PB-CAG promoter-Rox-GFP-Rox-RFP-PB, which is a construction of the GFP-RFP vector, is inserted into the genome of SNU-F1-1.

Figure 34:
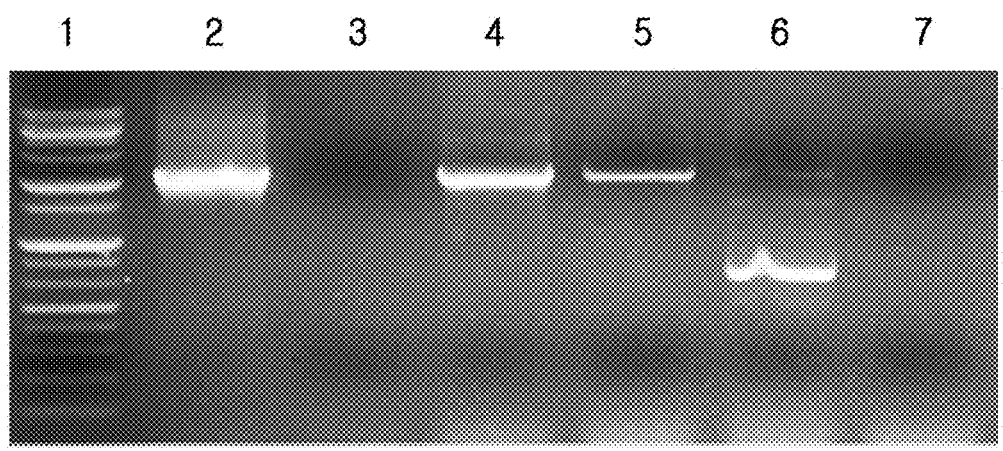
FIG. 34 shows an image illustrating the analysis results of DNA PCR confirming the presence of a fluorescent protein gene within the genome of an offspring cow having a genome into which a toolbox including a gene encoding fluorescent protein is inserted.

FIG. 34 shows DNA PCR analysis results of SNU-F1-1 (see FIG. 34, 1: molecular marker, 2: positive control group (GFP-RFP vector), 3: DNA obtained from a wild-type cow, 4: DNA obtained from blood of SNU-PB1, 5: DNA obtained from blood of SNU-F1-1, 6: DNA obtained by treating Dre recombinase on cells of SNU-F1-1, 7: negative control group (nuclease-free water)). DNA extraction method for DNA PCR has been described above and thus the specific explanation thereon is omitted herein.

Additionally, the present inventors have analyzed the DNA sequence of an offspring cow (SNU-F1-1), and from the analysis results, have confirmed that the toolbox including the PB-CAG promoter-Rox-GFP-Rox-RFP-PB, which is inserted into the genome of the male cow (SNU-PB1), is inserted into the genome of the offspring cow (SNU-F1-1). The insertion locus of the toolbox will be described later.

4-1-2. SNU-F1-2 Cow

The female cow (SNU-PB2) became pregnant with SNU-F1-2 by natural breeding between a female cow (SNU-PB2) and a male cow (SNU-PB1). The female cow (SNU-PB2), during pregnancy, was attacked by a different cow and injured, and thus the female cow (SNU-PB2) was euthanized.

The present inventors have visually confirmed that a green fluorescent protein is expressed in fetal fibroblasts obtained from the SNU-F1-2 fetus.

Figure 35:
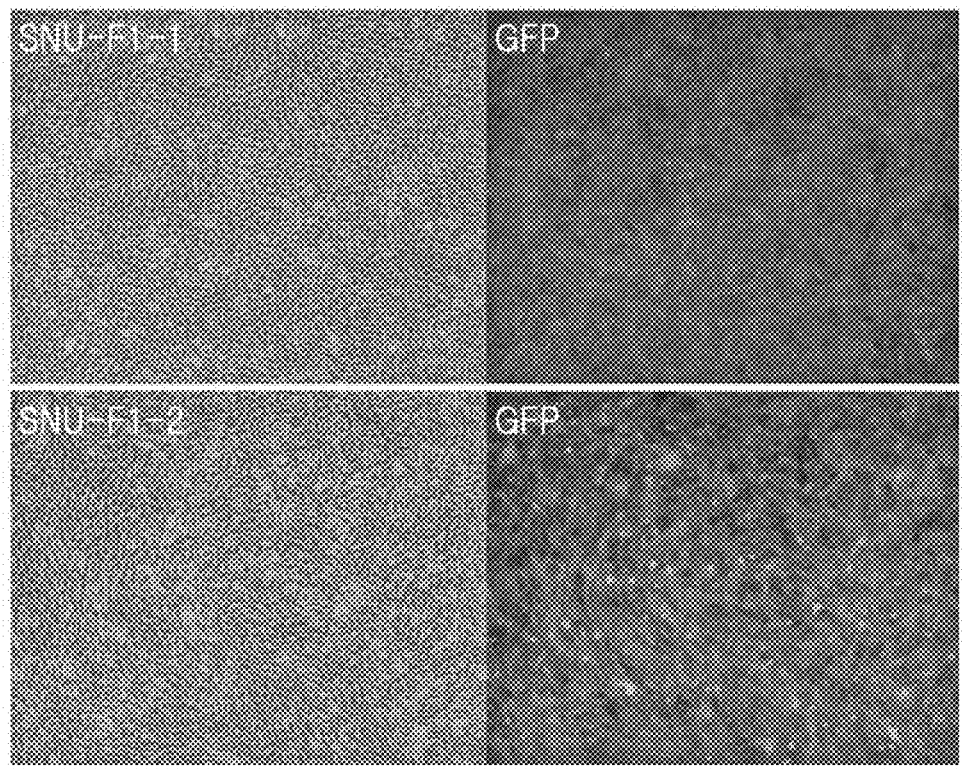
FIG. 35 shows images illustrating the differences in expression level of a fluorescent protein according to the number of toolboxes including a green fluorescent protein gene, which are inserted into the genome.

FIG. 35 shows that a green fluorescent protein is expressed in the fibroblasts of SNU-F1-2 fetus (see FIG. 35 below, left: visible light condition, right: fluorescent condition).

Additionally, through the DNA sequence analysis of the SNU-F1-2 fetus, the present inventors have confirmed that the toolbox including PB-beta-casein promoter-hIL2-pA-CAG promoter-GFP-pA-PB, which is inserted into the genome of the female cow (SNU-PB2), was also delivered into the genome of the fetus SNU-F1-2. The insertion locus of the toolbox will be described later.

Through this experiment, it was confirmed that animals having a genome into which the target protein gene for transfection is inserted can survive without health problems and produce healthy offspring.

Additionally, through these results, it was confirmed that the toolbox included in the F0 generation transgenic bovine genome can be transmitted to F1 generation.

4-2. Female Cow Milk

To demonstrate that the protein expressed from the gene inserted into a genome can be included in the female cow milk, the present inventors analyzed milk of a female cow in which a toolbox with the same construction as the toolbox inserted into the genome of the SNU-PB2 (a toolbox with the construction of 5'PB-β-casein promoter-hIL2-pA-pCAG-GFP-Pa-3'PB) is inserted.

As a result of the analysis of the milk of the female cow having a genome into which a toolbox including a fluorescent protein gene is inserted using a confocal microscope, it was visually confirmed that a green fluorescent protein is expressed in the female cow milk.

Figure 36:
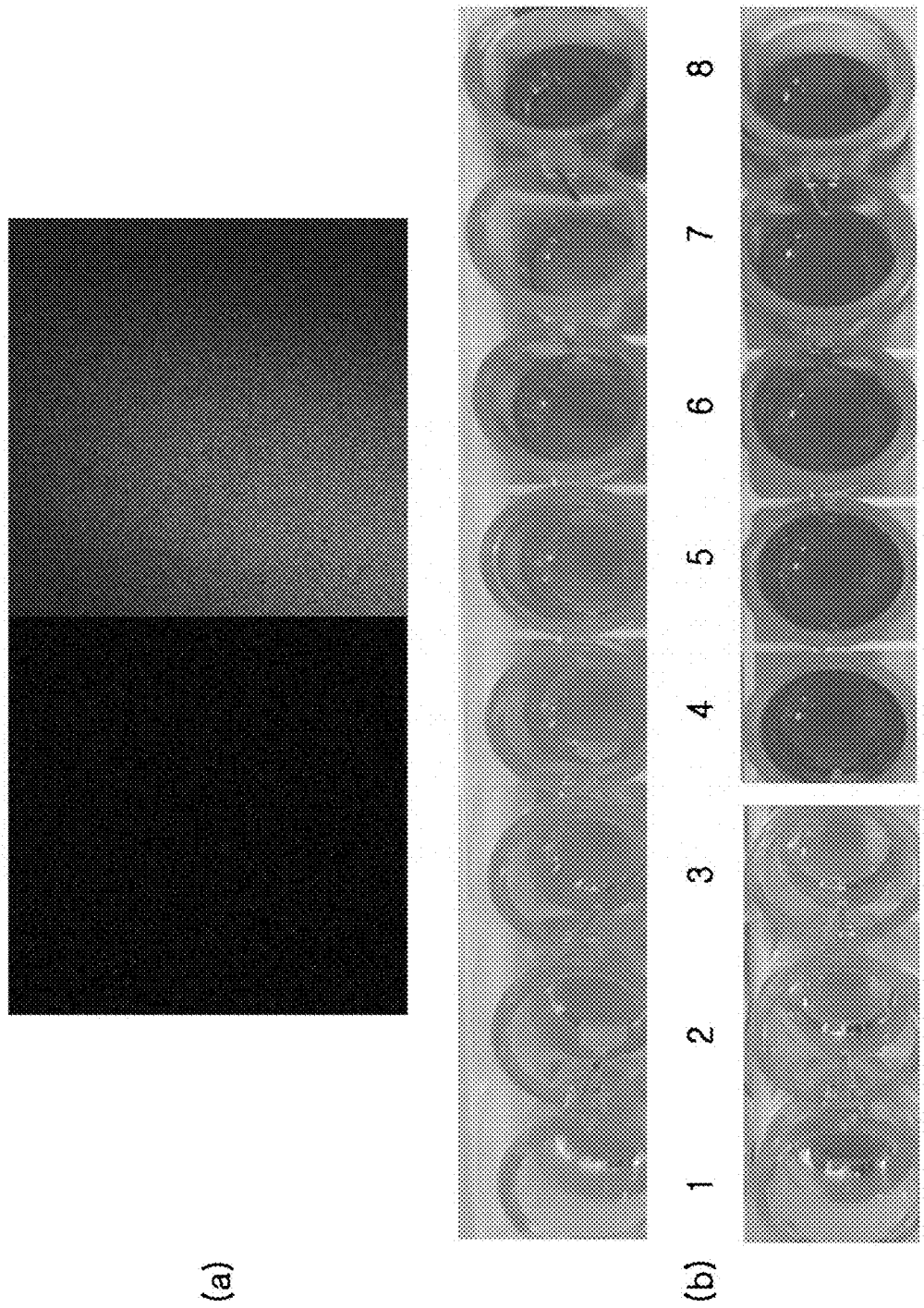
FIG. 36 shows images illustrating the visual results and ELISA results confirming the expression of a green fluorescent protein in milk of a cow, which has a genome into which a toolbox including a green fluorescent protein gene is inserted.

FIG. 36(a) shows the results confirming the presence/absence of expression of a fluorescent protein in cow milk using a confocal microscope (see FIG. 36(a), left: wild-type cow milk, right: milk of transgenic cow inserted with toolbox).

Additionally, it was confirmed by ELISA that human interleukin (hIL) expressed by the toolbox component is included in the female cow milk.

FIG. 36(b) shows the results confirming via ELISA that human interleukin is included in the milk (see FIG. 36(b), top: ELISA control, bottom: 1 to 3; wild-type cow milk, 4 to 8; milk of transgenic cow inserted with toolbox).

It was confirmed that even when an offspring cow intakes milk, in which a green fluorescent protein and human interleukin (hIL) are included, the offspring cow can survive without health problems.

From this experiment, it was confirmed that proteins expressed through transcription and translation of an exo-polynucleotide may be included in the milk of a transgenic female cow. That is, it was confirmed that a transgenic cow can be utilized as a bioreactor.

5. Insertion Locus in Genome at which Target Protein Gene can be Inserted

The present inventors have confirmed, through sequence analysis, the insertion loci at which the toolbox including a target protein gene (e.g. fluorescent protein gene) can be inserted in the genome of the F0 transgenic cow and offspring cow.

DNA samples were prepared for sequence analysis and DNA samples were extracted from blood or the primary cells according to the manufacturer's protocol using a DNA extraction kit. The quality of genomic DNA (O.D. 260/280 ratio is 1.8-2.0 and O.D. 260/230 ratio greater than 1.6) and the amount (1 μg) for the preparation of a library were confirmed using the Qubit fluorometer dsDNA analysis kit (Invitrogen, CA) and Infinite F200 Pro NanoQuant (TECAN, Mannedorf).

To prepare a library for mass sequence analysis, the genome DNA purified from the samples of F0 transgenic cow (SNU-SB1, SNU-PB1 and SNU-PB2) and offspring cows (SNU-F1-1 and SNU-F1-2) was randomly cleaved using the Covaris S2 Ultrasonicator, and thereby DNA fragments with an average size of 350 bp were obtained. A DNA sequencing library was prepared using TruSeq DNA PCR-Free Sample Preparation Kit (from Illumina (San Diego, CA, USA)), and the library was prepared according to the manufacturer's protocol.

The size and quality of the final library were evaluated by the Agilent High Sensitivity DNA kit (AgilentTechnologies, Santa Clara).

Sequencing was performed in Illumina HiSeq 2500 using the TruSeq Paired End Cluster Kit v3 and the TruSeq SBS Kit v3-HS (FC-401-3001), and the image analysis was performed using the HiSeq control software (ver. 2.2.58).

Remaining reads were performed using BWA ver. 0.7.5a., and *Bos taurus* genome (UMD 3.1, http://asia.ensembl.org/Bos_taurus/Info/Annotation) and target protein gene sequences were simultaneously mapped.

The insertion locus of the target protein gene was analyzed using the mapping data BAM (aligned format) formed by BWA.

BWA means that, as determined by the Smith-Waterman-like scoring scheme, part of the nucleotides can be omitted (hereinafter, soft-clipped) in the extreme of the read.

The insertion locus was deduced by confirming the mapped pattern of the Soft-Clipped sequence.

Furthermore, Delly softwarers were applied in parallel to assess changes in genome structure as an index of target protein gene insertion.

Finally, the candidate insertion locus was manually checked using the IGV software.

The copy number variations (CNVs) were confirmed by the Control-FREEC software. This software is used to calculate a multiple of the region of interest.

5-1. Insertion Locus in Parent Generation Transgenic Cow Genome at which Target Protein Gene can be Inserted Hereinafter, insertion sites in the parent generation transgenic cow genome confirmed by sequence analysis at which a toolbox including a target protein gene is inserted are described.

Table 6 below discloses insertion loci at which a toolbox is inserted into the genome of SNU-SB-1.

Table 7 below discloses insertion loci at which a toolbox is inserted into the genome of SNU-PB-1.

Table 8 below discloses insertion loci at which a toolbox is inserted into the genome of SNU-PB-2.

The locus numbers described in Tables 6 to 10 below indicate artificially numbered locations in the chromosome where toolboxes are inserted.

As described above, the locus of a toolbox can be specified by one or more of the following two: an endogenous gene located closest to the 5' end of the toolbox based on the toolbox (hereinafter, 5' gene); and an endogenous gene located closest to the 3' end of the toolbox based on the toolbox (hereinafter, 3' gene).

For example, locus numbers 4-1 and 21-1 in Table 6 below are different loci present in the bovine genome.

In another example, locus numbers 6-1 and 6-2 in Table 7 below are different loci present in the bovine genome.

TABLE 6

| Bovine Genome Chromosome | Locus No. | 5' Gene | 3' Gene |
|---|---|---|---|
| 4 | 4-1 | MIS184 | HUNK |
| 21 | 21-1 | TRPM1 | APBA2 |
| 26 | 26-1 | MKI67 | EBF3 |

TABLE 7

| Bovine Genome Chromosome | Locus No. | 5' Gene | 3' Gene |
|---|---|---|---|
| 1 | 1-1 | MIS184 | HUNK |
| 2 | 2-1 | SLC38A11 | COBLL1 |
| 3 | 3-1 | GBP5 | GBP4 |
| 4 | 4-2 | TSGA13 | MKLN1 |
| 5 | 5-1 | ATXN7L3B | CAPS2 |
| 6 | 6-1 | DKK2 | GIMD1 |
|   | 6-2 | PLAC8 | COQ2 |
| 7 | 7-1 | ERAP2 | LNPEP |
| 14 | 14-1 | CSMD3 | CSMD3 |
| 17 | 17-1 | ORAI1 | RNF34 |
| 22 | 22-1 | bta-mir-2370 | DENND6A |
| 25 | 25-1 | AUTS2 | ENSBTAG00000047342 |
| 26 | 26-2 | EMX2 | RAB11FIP2 |
| X | X-1 | WWC3 | DDX3Y |

TABLE 8

| Bovine Genome Chromosome | Locus No. | 5' Gene | 3' Gene |
|---|---|---|---|
| 3 | 3-2 | PEX19 | PEA15 |
|   | 3-3 | PDE4B | OB-R |
| 5 | 5-2 | TMEM5 | AVPR1A |
|   | 5-3 | XRCC6BP1 | CTDSP2 |
|   | 5-4 | MPST | KCTD17 |
| 6 | 6-3 | LCORL | SLIT2 |
| 7 | 7-2 | C7H5orf30 | NUDT12 |
| 9 | 9-1 | STXBP5 | SAMD5 |
| 10 | 10-1 | ALDH6A1 | VSX2 |
| 11 | 11-1 | PTP | LRRTM4 |
|   | 11-2 | PSMD13 | — |
| 15 | 15-1 | SMAP | INSC |
| 18 | 18-1 | HSD17B2 | CDH13 |
| X | X-2 | ARAF | SYN1 |
|   | X-3 | PBDC1 | MAGEE2 |

5-2. Insertion Locus in Offspring Cow Genome at which Target Protein Gene can be Inserted 5-2-1. Comparison of Insertion Loci of Target Protein Gene Inserted in Parent Generation Transgenic Cow Genome and Offspring Cow Genome Hereinafter, insertion sites, where a toolbox including a target protein gene is inserted into the parent generation transgenic cow genome, and insertion sites, where a toolbox including a target protein gene is inserted into the offspring cow genome, confirmed by sequence analysis were compared.

Table 9 below discloses insertion loci at which the toolboxes are inserted into the genome of SNU-F1-1.

TABLE 9

| Bovine Genome Chromosome | Locus No. | 5' Gene | 3'Gene |
| --- | --- | --- | --- |
| 4 | 4-2 | TSGA13 | MKLN1 |
|  | 4-4 | ENSBTAG00000001198.5 | ENSBTAG00000046257.1 |
| 6 | 6-1 | DKK2 | GIMD1 |

As a result of sequence analysis using skin fibroblasts of an offspring cow, it was confirmed that the insertion locus at which a toolbox is inserted into the genome of SNU-F1-1, an offspring cow, overlaps in part with the insertion locus at which a toolbox is inserted into the genome of the parent generation cow (SNU-PB1, male) (see Tables 7 and 9).

Table 10 below discloses the insertion loci at which toolboxes are inserted into the genome of SNU-F1-2.

TABLE 10

| Bovine Genome Chromosome | Locus No. | 5' Gene | 3' Gene |
| --- | --- | --- | --- |
| 1 | 1-2 | ENSBTAG00000025847.3 | ENSBTAG00000011051.5 |
| 3 | 3-4 | PDE4B | LEPR |
| 4 | 4-3 | NPVF | C7orf31 |
| 10 | 10-1 | ALDH6A1 | VSX2 |
| 12 | 12-1 | ENSBTAG00000010680.5 | U2 |
| X | X-3 | PBDC1 | MAGEE2 |

As a result of sequence analysis using fetal fibroblasts of SNU-F1-2, an offspring cow, it was confirmed that the insertion locus at which a toolbox is inserted into the genome of SNU-F1-2, an offspring cow, overlaps in part with the insertion locus at which a toolbox is inserted into the genome of the parent generation cow (SNU-PB2, female) (see Tables 8 and 10).

As described above, through the sequence analysis, it was confirmed that at least one insertion locus at which a target protein gene is inserted into the parent generation animal genome can be transmitted intactly to the animal genome of an offspring generation and present.

5-2-2. Correlation Between Number of Target Protein Genes Inserted into Genome and Expression Level of Target Protein The present inventors have analyzed SNU-F1-1 and SNU-F1-2 and thereby examined the correlation between the expression levels of target proteins and the number of target protein genes inserted into the genome of the cell. This was confirmed by measuring the intensities of fluorescence in the skin fibroblasts of SNU-F1-1 and the fibroblasts derived from SNU-F1-2 fetus.

By the measurement of fluorescence intensity, it was confirmed that the expression level of the fluorescent protein in the fibroblasts derived from SNU-F1-2 fetus was about 2.2-fold higher than that of the SNU-F1-1 fibroblasts (see FIG. 35, top: SNU-F1-1, bottom: SNU-F1-2, left: visible light condition, right: fluorescent condition).

For quantification of fluorescence intensity of SNU-F1-1 and SNU-F1-2 samples, the cell images of the same size and density were obtained using the ImageJ (v1.50, NIH).

From the results that while the target protein gene is inserted into 6 insertion sites in the genome of SNU-F1-2, the target protein gene is inserted into 3 insertion sites in the genome of SNU-F1-1, it was confirmed that the expression level of the target protein gene (a transformed protein expressed by a gene inserted from the outside) in a transgenic bovine cell is correlated to the copy number of the genes inserted from the outside.

[Experimental Example 3] Gene Editing Having Target Protein Gene Inserted into Genome as Target Site The present inventors performed experiments demonstrating that gene editing can be performed having, as a target, the target protein gene artificially inserted into the bovine genome by the above method.

That is, by the experimental results below, the enablement of gene editing even in the "artificial editing site" artificially inserted into the genome can be supported.

To more effectively confirming that gene editing can occur in a target protein gene which is artificially inserted into the genome, the present inventors conducted the following experiment using cells having a genome into which a green fluorescent protein gene is inserted as the target protein gene.

1. Knockout of Target Protein Gene 1-1. Isolation of Fibroblasts Having Genome into which Green Fluorescent Protein Gene is Inserted To confirm that the target protein gene inserted from outside can be knocked out, the present inventors isolated fibroblasts having a genome into which a green fluorescent protein gene is inserted (hereinafter, GFP fibroblast) from the tissue of a transformed embryo having a genome into which a green fluorescent protein gene is inserted.

For the isolation of GFP fibroblasts, a fetus was collected from a surrogate mother into which a GFP embryo was transplanted, and the collection of the fetus was proceeded on the 40$^{th}$ day of pregnancy of the surrogate mother.

The skin of the collected fetus was subjected to enzyme digestion by collagenase, and then primary fibroblasts were attached to culture dishes.

The primary fibroblasts were expanded by a culture medium (DMEM (Gibco, Carlsbad, CA, USA), 15% FBS (Gibco), 100 mM beta-mercaptoethanol (Sigma), 1% NEAA (Sigma), and 1% penicillin/streptomycin (Gibco)) in the culture dishes.

The expression of a green fluorescent protein in the isolated fibroblasts was confirmed by a fluorescence microscope (Nikon, Tokyo, Japan).

1-2. CRISPR/Cas9 Vector Transfection Targeting Target Protein Gene

To knockout the green fluorescent protein gene inserted into the GFP fibroblast genome isolated by the above-described method, a modified CRISPR/Cas9 system using a single guide RNA (sgRNA) was used.

To knockout the green fluorescent protein gene, the sgRNA expression vector having the U6 promoter and the Cas9 expression vector having the CMV promoter were prepared.

Figure 37:
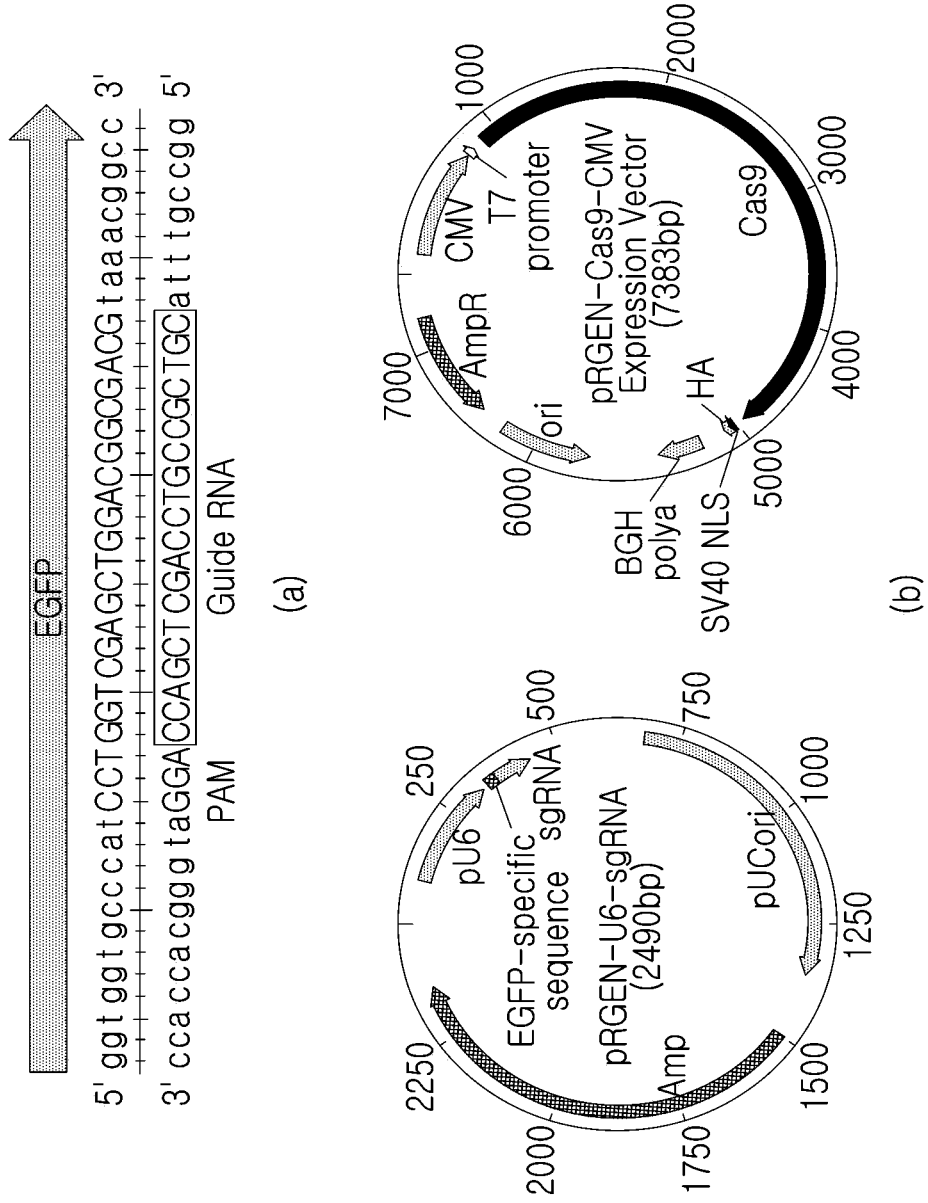
FIG. 37 shows schematic diagrams illustrating sgRNA expression vector and Cas9 expression vector to knockout a green fluorescent protein gene inserted into a genome of a cell.

FIG. 37(a) illustrates a designed sgRNA for specifically targeting a green fluorescent protein gene.

FIG. 37(b) illustrates a sgRNA expression vector and a Cas9 expression vector (left: sgRNA expression vector, right: Cas9 expression vector).

The sgRNA expression vector and the Cas9 protein expression vector (total 10 g, 1:3 ratio) were transfected to fibroblasts isolated by the above method. The transfected fibroblasts were cultured further in an incubator (38° C., 5% $CO_2$) for 10 days.

1-3. Confirmation of Expression of Fluorescent Protein and Indel for Knockout-Confirmation The sgRNA expression vector and Cas9 expression vector were transfected to the fibroblasts isolated by the above method and then the excision of the expression of a green fluorescent protein was confirmed by a fluorescence microscope.

Figure 38:
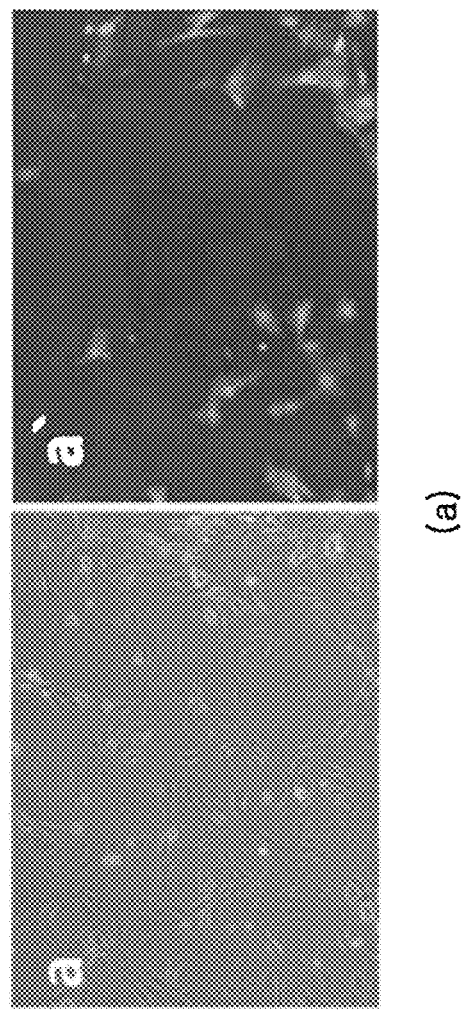
FIG. 38 shows images illustrating the visual results that a green fluorescent protein is not expressed and the results confirming the indels of a green fluorescent protein gene, after transfection of a sgRNA expression vector and a Cas9 expression vector into a bovine fibroblast, which has a genome into which a toolbox including a fluorescent protein gene is inserted.

FIG. 38(a) shows the results confirming that the green fluorescent protein was not expressed after the sgRNA expression vector and the Cas9 expression vector were transfected to the fibroblasts having a genome into which the green fluorescent protein gene was inserted (see FIG. 38(a), a: visible light condition, a': fluorescent condition).

That is, it was confirmed that the green fluorescent protein gene was knocked out after the transfection of the sgRNA expression vector and the Cas9 expression vector.

Additionally, the present inventors isolated whole genomic DNA from the fibroblast including a green fluorescent protein negative colony and confirmed the indel of a green fluorescent protein gene as a target site by PCR amplification.

The isolation of whole genomic DNA was performed using the G-Spin™ Total DNA Extraction Mini Kit (iNtRON, Seoul, Republic of Korea).

A 575 bp fragment including the target site was amplified by primers so as to identify the indel of the target site by PCR amplification. The primers are shown in Table 11 below.

FIG. 38(b) shows the indel that occurred in the green fluorescent protein gene.

Through this experiment, it was confirmed that the guide nucleic acid provided from outside can cause knockout of a specific gene in the bovine genome and that the cow can survive even if a knockout occurs in a specific gene in the bovine genome.

2. Knockin of Donor Polynucleotide

The present inventors conducted an experiment in which a donor polynucleotide was knocked in using a green fluorescent protein gene, inserted in a transgenic bovine genome produced by the above method, as a target gene.

Primary cells were obtained from a transgenic cow (e.g. SNU-PB2) produced by the above method, plasmid vectors were transfected to the primary cells through Nucleofactor technology (Neon, Invitrogen; program #16).

As the plasmid vector, i) a sgRNA expression vector having the U6 promoter (Toolgen, Seoul, Republic of Korea, GFP gene targeting), ii) a CRISPR/Cas9 expression vector having the CMV promoter, and iii) a donor DNA (puromycin resistance gene) expression vector were used.

The transfected primary cells were cultured with 4 μg/mL puromycin (GIBCO) for 3 days. After exchanging with fresh culture media, the primary cells were cultured further for 10 more days.

As a result, it was confirmed that, in the case of primary cells transfected with the sgRNA expression vector (Toolgen, Seoul, Republic of Korea), CRISPR/Cas9 expression vector, and donor DNA (puromycin resistance gene) expression vector, colonies survived even when puromycin was treated.

Figure 39:
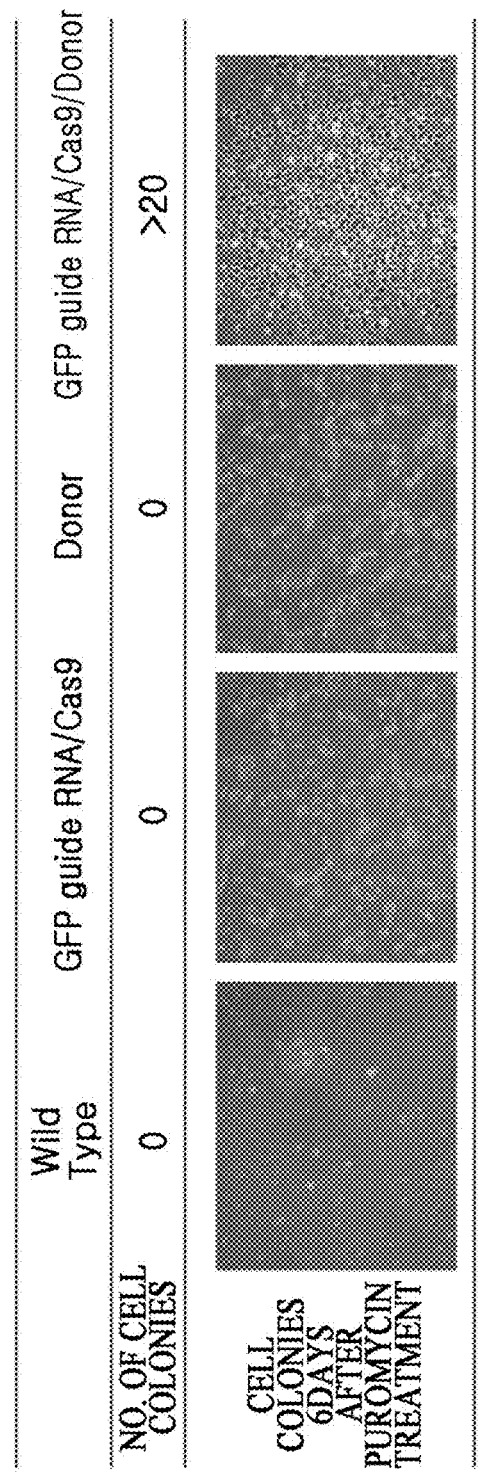
FIG. 39 shows images illustrating the results that donor DNA is knocked in, in the case where primary cells having a genome into which a toolbox including a green fluorescent protein gene is inserted was transfected with gRNA capable of targeting the gene encoding green fluorescent protein, Cas9, and donor DNA (puromycin resistance gene).

FIG. 39 shows that when primary cells having a genome into which a green fluorescent protein gene is inserted, are transfected with gRNA, Cas9, and donor DNA (puromycin resistance gene), which can bind to the green fluorescent protein gene, the primary cells have puromycin resistance.

Additionally, it was confirmed that, in the case of primary cells transfected with the sgRNA expression vector (Toolgen, Seoul, Republic of Korea), CRISPR/Cas9 expression vector, and donor DNA (puromycin resistance gene) expression vector, which target a green fluorescent protein, the green fluorescent protein is no longer expressed.

Figure 40:
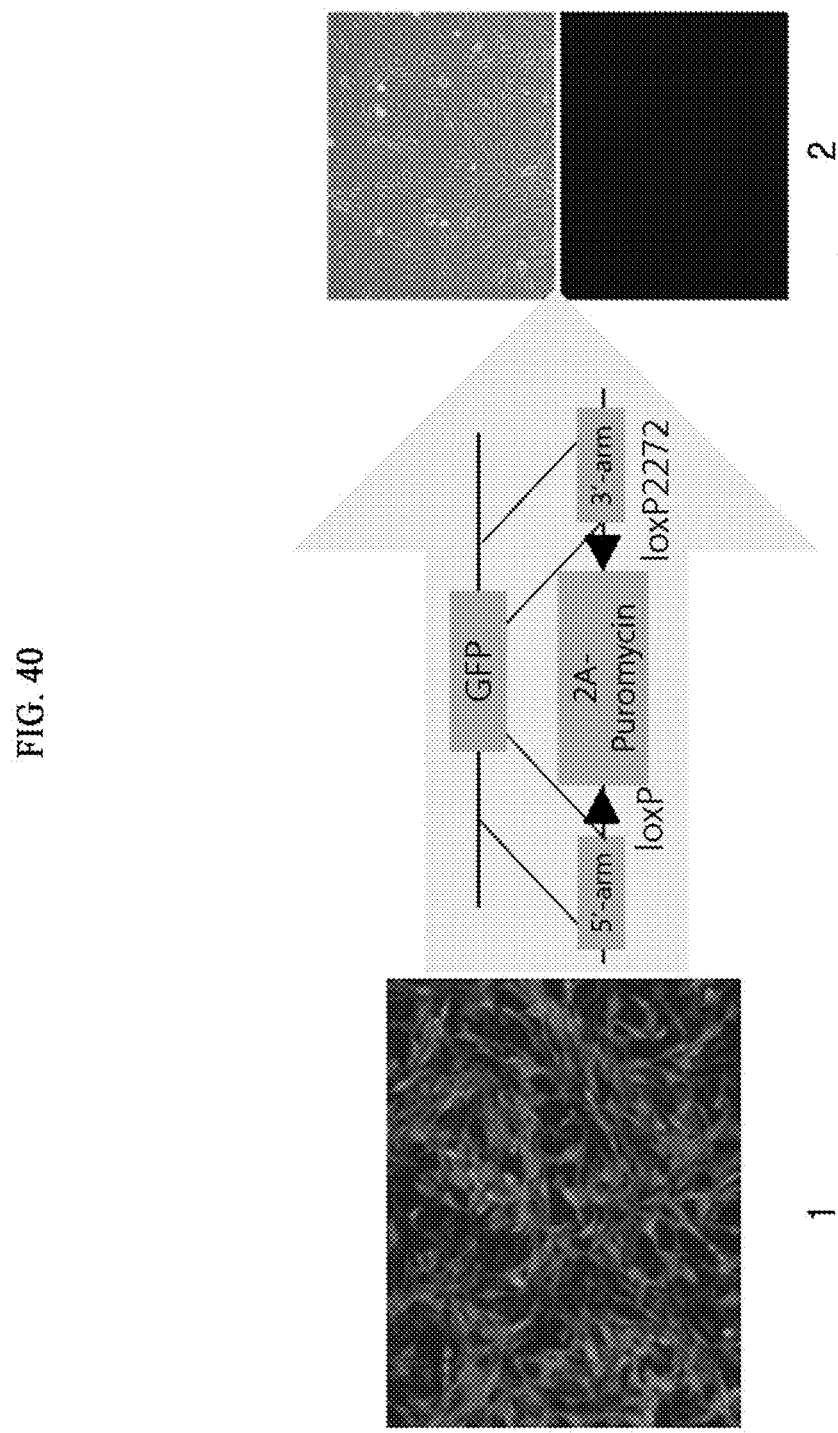
FIG. 40 shows images illustrating that a green fluorescent protein is not expressed in primary cells which were transfected with sgRNA expression vector, CRISPR/Cas9 expression vector and donor DNA (puromycin resistance gene) expression vector, which target the green fluorescent protein.

FIG. 40 shows that the green fluorescent protein is not expressed in the primary cells transfected with the sgRNA expression vector, CRISPR/Cas9 expression vector, and donor DNA (puromycin resistance gene) expression vector, which target a green fluorescent protein (see FIG. 40, 1: before transfection, 2: after transfection).

From the above results of i) results of survival of colonies and ii) non-expression of a green fluorescent protein, it was confirmed that the CRISPR/Cas system using sgRNA and CRISPR/Cas9 is operated in the primary cells of SNU-PB-2.

Furthermore, the present inventors performed an experiment to knockin the donor polynucleotide (including a red fluorescent protein gene) using the green fluorescent protein

TABLE 11

| PCR Primer | SEQ Name | SEQ ID NO | Sequence |
| --- | --- | --- | --- |
| Forward | in_pr_GFP_F1 | SEQ ID NO: 15 | GGACTTCCTTTGTCCCAAATCT |
| Reverse | in_pr_GFP_R1 | SEQ ID NO: 16 | TAGCGGCTGAAGCACTGC | gene (GFP gene), which is inserted into the genome of the above-described offspring cow (SNU-F1-1), as a target gene.

As in the above method, the primary cells of SNU-F1-1 were obtained, and i) sgRNA expression vector having the U6 promoter (Toolgen, Seoul, Republic of Korea, GFP gene targeting), ii) CRISPR/Cas9 expression vector having the CMV promoter, and iii) donor DNA (including a red fluorescent protein gene) expression vector were transfected into the primary cells via Nucleofactor technology (Neon, Invitrogen; program #16).

Figure 41:
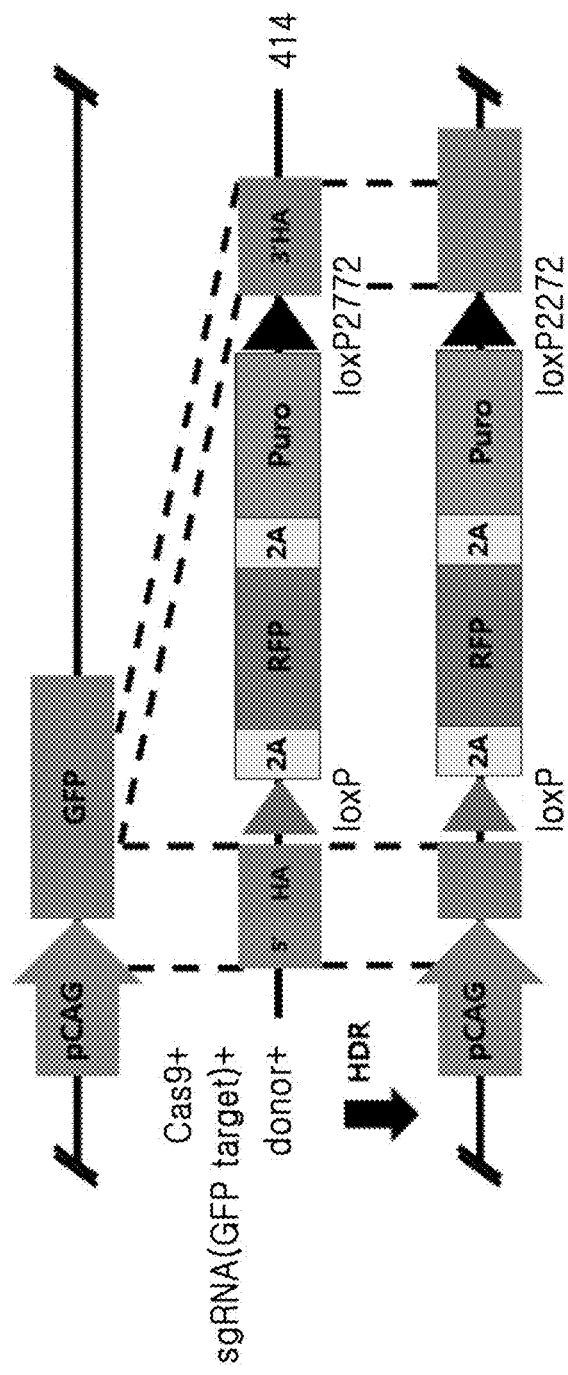

FIG. 41 illustrates a process in which the donor polynucleotide (414) is knocked in to the green fluorescent protein gene present in the genome of primary cells.

Figure 42:
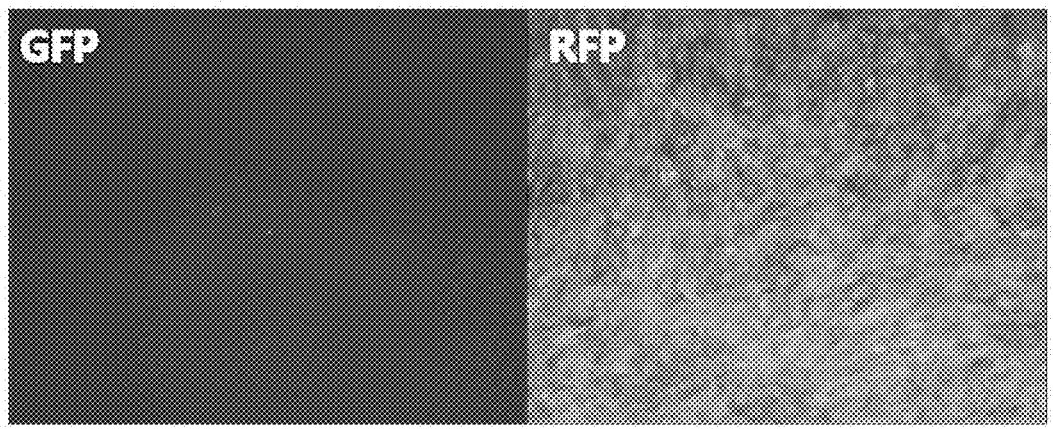
FIG. 42 shows images illustrating that a red fluorescent protein gene, which targets a green fluorescent protein gene in bovine primary cells having a genome into which a green fluorescent protein gene is inserted, is knocked in and then expressed.

In the case of primary cells transfected with sgRNA expression vector (Toolgen, Seoul, Republic of Korea), CRISPR/Cas9 expression vector, and donor DNA (including a red fluorescent protein gene) expression vector, it was confirmed that the green fluorescent protein is no longer expressed and that the red fluorescent protein is expressed (see FIG. 42).

FIG. 42 shows that a green fluorescent protein gene is knocked out in primary cells having a genome into which the green fluorescent protein gene is inserted, and after the knockin of a red fluorescent protein gene, the red fluorescent protein gene is expressed therein.

From the above results of i) the non-expression of a green fluorescent protein and ii) the expression of a red fluorescent protein, it was confirmed that the CRISPR/Cas system using sgRNA and CRISPR/Cas9 can operate even in the primary cells of the offspring cow.

From this experiment, it was confirmed that a donor polynucleotide can be knocked in by having the artificial editing site inserted from the outside as a target site.

Additionally, it was confirmed from this experiment that the cells can survive even when the donor polynucleotide is knocked in to the target site present in the genome of the cell.

Furthermore, it was confirmed from this experiment that in the case where the donor polynucleotide is knocked in using a fluorescent protein gene as a target gene, cells in which the $(n+1)^{th}$ gene editing has occurred can be selected using a cell having a genome into which a fluorescent protein gene is inserted (cells in which the $n^{th}$ gene editing has occurred; n is a natural number of 1 or greater), taking advantage of the fact that the fluorescence signal of the cell provided to the outside becomes weaker due to non-expression of a fluorescent protein.

[Experimental Example 4] Transgenic Cow in which RNA-Guided Endonuclease is Expressed 1. Preparation of Transgenic Cow in which RNA-Guided Endonuclease is Expressed The present inventors performed the following experiment so as to prepare a transgenic cow in which an RNA-guided endonuclease is expressed (hereinafter, spCas9 cow).

1-1. Preparation of Vector

A spCas9 cDNA (presented by Toolgen) including a puromycin resistance gene and a red fluorescent protein gene (RFP gene) were cloned by PCR.

Additionally, NCBI database-based Fat-1 DNA was synthesized and Fat-1 gene was cloned along with the EF1alpha promoter.

The Cas9-Puro-RFP, EF1 alpha, and fat-1 DNAs were inserted into the piggyBac transposon expression vector (PB transposon expression vector), and thereby the final expression vector (hereinafter, spCas9 vector; PB-CAG-Cas9-RFP-EF1-fat1) was prepared.

FIG. 43(a) illustrates part of the spCas9 vector.

The piggyBac (PB) sequences used in this Experimental Example are the same as those shown in Table 3 above.

1-2. Preparation of Embryo (MI)

Since the method of integrating the spCas9 gene into the bovine genome and the experimental conditions thereof are the same as those for inserting the target protein gene and the experimental conditions thereof, the method for preparing an embryo having a genome into which the spCas9 gene is inserted will be briefly described.

As described above, bovine ova were collected by separating COCs from the ovary followed by washing, and the sperms were collected by separating from bovine semen by centrifugation.

After removing cumulus cells from the fertilized egg obtained by in vitro fertilization between the collected ova and sperms, the spCas9 vector and the transposase vector were microinjected into the cytoplasm (each at 50 ng/mL, 1:1 ratio) using the microinjector machine (Femtojet, Eppendorf, Germany). The transposase vector (pCy43) was provided by Sanger Institute (Hinxton, UK).

In the microinjected embryo, a red fluorescent protein was expressed.

FIG. 43(b) shows that a red fluorescent protein was expressed in the embryo into which the spCas9 vector is microinjected.

Since the spCas9 vector includes a red fluorescent protein gene (see FIG. 43(a)), it was confirmed by the result of expression of a red fluorescent protein that the spCas9 gene was inserted into the genome of the embryo into which the vector was microinjected.

1-3. Preparation of Transgenic Cow 1-3-1. Transgenic Cow

Since the method of transplanting the transformed embryo into the uterus of a surrogate mother and the experimental conditions thereof have been described above, the method of producing the spCas9 cow (F0) is briefly described below.

The embryo produced by the above method was transplanted into the uterus of a surrogate mother, on the $45^{th}$ day of post estrus, a total of 4 surrogate mothers were found to be pregnant as confirmed by rectal palpation and ultrasonography.

After the pregnancy period, four spCas9 cows (F0) were born. FIG. 43(c) shows SNU-Cas9-2 (F0).

Table 12 below discloses the sex and age of transgenic cows.

TABLE 12

| Name | RFP Expression Ratio | Sex | Age |
|---|---|---|---|
| SNU-Cas9-1 (F0) | 58.3% | Female | 5 Months |
| SNU-Cas9-2 (F0) | 33.7% | Male | 23 Months |
| SNU-Cas9-3 (F0) | 87.0% | Male | 6 Months |
| SNU-Cas9-4 (F0) | 74.8% | Female | 24 Months |

For the blood analysis of the spCas9 cows, whole blood samples (5 mL) were taken from the jugular vein. A portion of the collected samples (1 mL) was used for Complete Blood Count (CBC) (Hemavet 950, Drew Scientific, USA) and the rest of the samples were used for serum chemistry analysis (BS-400, Mindray, China). All values of CBC and serum analysis confirmed by blood analysis were in the reference range and it was confirmed that there was no health problem of the spCas9 cows even when Cas9 was expressed.

The present inventors obtained ova from SNU-Cas9-4 (female) and obtained sperms from the SNU-Cas9-2 (male).

To obtain the sperms, semen was collected from an 18-month-old male transgenic cattle, using an artificial vagina (Fujihira Industry, Tokyo, Japan) containing hot water at 50-55° C., and the collected sperms were immediately transferred to and frozen in a freezer.

The semen was diluted at a 50%:50% ratio using the OPTIXcell (IVM technologies, France) and maintained at room temperature for 10 min. Then, the diluted semen was diluted again at a 50%:50% ratio, and the concentration of the sperms was maintained at $5.0 \times 10^7$/mL at 4° C. for 2 hours.

The concentrated sperms were put into 500 µL of semen straw (IMV technologies, France) and sealed with straw powder (Fujihira Industry, Tokyo, Japan). The straw was frozen at 5.0 cm above the liquid nitrogen surface for 30 min and then thrown into a liquid nitrogen tank.

An offspring having a genome into which the spCas9 gene was inserted was produced by natural breeding between an SNU-Cas9-2 (male) and an SNU-Cas9-4 (female), while securing gametes therefrom.

1-3-2. Confirmation of Polynucleotide Encoding RNA-Guided Endonuclease Insertion in Transgenic Cow Genome 1-3-2-1. Confirmation of Fluorescent Protein Expression Primary cells were isolated and cultured from the ear skin tissue of the spCas9 cow in order to determine whether the fluorescent protein was expressed in cells of spCas9 cow.

For isolation of the primary cells, the ear skin tissue was separated by a biopsy punch to a diameter of 0.5 mm. The tissues were washed 3 or more times with PBS containing 1% penicillin/streptomycin and cut as small as possible with a surgical blade. The excised tissues were incubated with collagenase type IV (Gibco) in HBSS at 37° C. for 16 hours.

After one week, the growth of skin fibroblasts was observed and the culture dish was re-filled with a fresh culture medium (DMEM supplemented with 10% FBS, 1% NEAA, 100 mM beta-mercaptoethanol, 1% P/S).

After the primary cells became confluent, some cells were stored in a freezer and some cells were observed by a fluorescence microscope without cryopreservation.

FIG. 44(a) shows the expression of a red fluorescent protein in primary cells of spCas9 cow.

Additionally, the expression ratio of the red fluorescent protein was confirmed in each spCas9 cow, and this was done by counting 3 times in total and calculating the ratio of cells in which the red fluorescent protein was expressed in 100 cells. The expression ratio of a red fluorescent protein of each spCas9 cow is shown in Table 12 above.

Since the spCas9 vector is designed to include the red fluorescent protein gene, it can be predicted from the above results that the spCas9 gene has been inserted into the spCas9 bovine genome.

However, the present inventors conducted DNA PCR and RT-PCR for more accurate confirmation of spCas9 and Fat1 gene insertion, and spCas9 and Fat1 expression in each spCas9 bovine genome 1-3-2-2. DNA PCR and RT-PCR Results Genome DNA was extracted from cultured cells using the DNA extract kit (DNeasy Blood&Tissue kit 69506, Qiagen, Limburg, Netherlands), and PCR (Eppendorf Vapo Protect Mastercycler, Eppendorf, Germany) was performed using the extracted DNA along with PCR primers specific to spCas9 and Fat1.

The primers for DNA PCR and RT-PCR are shown in Table 13 below.

TABLE 13

| Primer Type | SEQ Name | SEQ ID NO | Sequence |
|---|---|---|---|
| spCas9-Forward | pr_spCas9_F1 | SEQ ID NO: 17 | GACAAGAAGTACAGCATCGG |
| spCas9-Reverse | pr_spCas9_R1 | SEQ ID NO: 18 | CAACCAGCTGTTCGAGGAGA |
| Fat1-Forward | pr_Fat1_F_1 | SEQ ID NO: 19 | AAACACGAAACAGGCGACCA |
| Fat1-Reverse | pr_Fat1_R_1 | SEQ ID NO: 20 | TTTGTCGTTGGCCACGATTG |
| GAPDH-Forward | pr_GAPDH_F_2 | SEQ ID NO: 21 | GGCGTGAACCACGAGAAGTA |
| GAPDH-Reverse | pr_GAPDH_R_2 | SEQ ID NO: 22 | CCCTCCACGATGCCAAAGT |

The PCR product was loaded on a 1% agarose gel with a DNA marker. As a result, it was confirmed by DNA PCR and RT-PCR that the spCas9 gene was inserted into the spCas9 bovine genome.

FIG. 44(b) shows the DNA PCR results using the spCas9 cow (M: molecular marker, 1: SNU-Cas9-1(F0), 2: SNU-Cas9-2(F0), 3: SNU-Cas9-3(F0), 4: SNU-Cas9-4(F0), 5: wild-type cow, (+): positive control (spCas9 DNAs), (−): negative control group DNAs).

FIG. 44(c) shows the RT-PCR results using the spCas9 cow (M: molecular marker, 1: SNU-Cas9-1(F0), 2: SNU-Cas9-2(F0), 3: SNU-Cas9-3(F0), 4: SNU-Cas9-4(F0), 5: wild-type cow, (−): negative control group DNAs).

1-3-2-3. Sequence Analysis (Locus at which Polynucleotide Encoding RNA-Guided Endonuclease can be Inserted)

Furthermore, the present inventors have confirmed the insertion of spCas9 gene by sequence analysis of spCas9 cow (F0).

The results of sequence analysis are shown in Table 14 below.

TABLE 14

| Bovine Genome Chromosome | Locus No. | 5' Gene | 3' Gene |
|---|---|---|---|
| 1 | 1-3 | KCNAB1 | GMPS |
|   | 1-4 | CHAF1B | PIGP |
| 2 | 2-2 | HNRNPR | LUZP1 |
| 7 | 7-3 | MRPL22 | HAVCR1 |
| 8 | 8-1 | STMN4 | CHRNA2 |
| 14 | 14-2 | TGS1 | LYN |
| 16 | 16-1 | H3F3C | TFB2M |
| 18 | 18-2 | CLIP3 | OVOL3 |
| X | X-4 | MGC134232 | PHKA2 |

Furthermore, it was confirmed that the spCas9 gene can be inserted at the location of SEQ ID GJ059944.1 in addition to the locus described in the Table above.

From this experiment, it was confirmed that cow can survive even if spCas9 is continuously expressed in a transgenic cow and/or transformed cell having a genome into which a polynucleotide encoding spCas9 is inserted.

1-3-3. Confirmation of Changes in Expression Level of Essential Gene of Transgenic Cow RNA sequencing (RNA-seq) analysis was performed to confirm whether spCas9 and Fat1, which are expressed in spCas9 transgenic cow (F0), affect the expression of the essential gene.

For RNA-seq analysis, RNA was extracted from the primary cells of spCas9 transgenic cow.

RNA quality was assessed by rRNA band integrity analysis in an Agilent RNA 6000 nano kit (Agilent Technologies, CA, USA).

Prior to the construction of a cDNA library, 2 μg of total RNA and magnetic beads with an oligo (dT) were used to enrich poly(A) mRNA.

Subsequently, the purified mRNA was then broken into short fragments and double stranded cDNA was synthesized immediately.

The synthesized cDNA was added to end-repair and poly(A) and ligated with a sequencing adapter using the TruSeq Stranded mRNA sample preparation kit (Illumina, CA, USA).

Suitable fragments, which were automatically purified by the BluePippin 2% agarose gel cassette (Sage Science, MA, USA), were selected as templates for PCR amplification.

The size and quality of the final library were assessed by electrophoresis using the Agilent High Sensitivity DNA kit (Agilent Technologies, CA), and the fragments were found to be in a range of 350-450 bp.

The constructed library was sequenced by the Illumina HiSeq2500 sequencer (Illumina, CA, USA).

The low-quality readings identified by the sequencing results were filtered by the manufacturer's script. The filtered readings were mapped to the human reference genome (Ensembl release 72, Flicek P. et al., 2013) using the aligner STAR v.2.3.0e (Dobin et al. 2013).

Gene expression levels were measured by Cufflinks v2.1.1 (Trapnell C. et al., 2010) using the gene annotation database of Ensembl release 72.

The non-coding gene region was removed with the mask option. To increase the accuracy of the measurements, multiple readout correction and fragbias-correction options were applied, and all other options were set to default values.

For differential expression analysis, gene level count data were generated using the HTSeq-count v0.5.4p3 (Anders S. et al. 2014) tool with the "-m intersection-nonempty" option and -r option, taking both sequences into account. Based on the calculated read count data, DEG was identified using an R package called TCC (Sun J. et al., 2013). To compare the tag count data, the TCC package applied a robust normalization strategy, and the normalization factor was calculated using the iterative DEGES/edgeR method. Using the p.adjust function of the R package with default parameters set, the Q value was calculated based on the p value. Differentially expressed genes were found to have a qvalue threshold of less than 0.05.

The Gene Ontology (GO) database classifies genes according to three categories of biological processes (BP), cell components (CC), and molecular functions (MF), and predicts the functions of selected genes.

To characterize the genes identified in the DEG analysis, a GO-based trend test was performed using the Fisher's exact test (Fisher R. A., 1922). P-values <0.001 were considered statistically significant.

RNA-seq analysis by the above method confirmed that the essential gene was not included in the list of genes with altered expression levels. That is, it was confirmed that the essential gene is not affected by the expression of spCas9.

The following Table 15 discloses 10 genes with a large change in expression level in the cells of spCas9 transgenic cow (the top 5 genes with an increased expression level and the top 5 genes with a decreased expression level).

TABLE 15

| Gene Access Number | Gene | P Value | Fold Change | |
|---|---|---|---|---|
| ENSBTAG00000021211 | DPT | 0.0009 | 5.42 | ↑ |
| ENSBTAG00000000745 | AQP1 | 0.0026 | 3.63 | ↑ |
| ENSBTAG00000007740 | BMK | 0.0001 | 3.63 | ↑ |
| ENSBTAG00000012623 | NDP | 0.0008 | 3.56 | ↑ |
| ENSBTAG00000002123 | MYO3A | 0.0001 | 3.38 | ↑ |
| ENSBTAG00000014132 | SNED1 | 0.0009 | −5.16 | ↓ |
| ENSBTAG00000015441 | ACTB | 0.0001 | −4.45 | ↓ |
| ENSBTAG00000005353 | DES | 0.0001 | −4.41 | ↓ |
| ENSBTAG00000025210 | COL4A2 | 0.0001 | −4.39 | ↓ |
| ENSBTAG00000012849 | COL4A1 | 0.0001 | −4.16 | ↓ |

1-4. Preparation of Offspring Cow of Transgenic Cow
1-4-1. Offspring Cow of Transgenic Cow
1-4-1-1. Production of Offspring Cow by In Vitro Fertilization (IVF)

Ova were obtained from the slaughterhouse-derived or living bovine ovary, and ova to which cumulus cells were well-attached were selected by microscopic examination.

The selected ova were matured for 22 hours in tissue culture medium (TCM199) (18-Nakseongdae R & D center). The tissue culture medium is supplemented with 10% serum and estrogen, epithelial growth factor, and 1% antibiotic for use.

The ova matured for 22 hours were fertilized with sperms of frozen-thawed spCas9 cow (F0). About 16 hours after fertilization, the cumulus cells were removed and the fertilized embryo was assessed under a microscope.

Among the evaluated embryos, viable embryos were transferred to in vitro culture media. The culture medium used was serum-free (Islam et al., Theriogenology, 2011).

The selected embryos were incubated in stage 1 medium for about 4 days and in stage 2 medium for an additional 3 days. Then, the development of blastocysts was evaluated.

Among the developed embryos, embryos in which red fluorescent protein was expressed were identified. The present inventors confirmed that the embryos in which the red fluorescent protein was expressed were the embryos in which Cas9 was expressed, and the embryos in which the red fluorescent protein was expressed were selected and transplanted into a surrogate mother. This led to the production of a calf (F1) expressing spCas9.

1-4-1-2. Production of Offspring Cow Via Natural Breeding and Somatic Cell Nuclear Transfer A calf (F1) expressing spCas9 was born by natural breeding between spCas9 female cow (F0) and spCas9 male cow (F0).

To increase the number of calves (F1) expressing spCas9, the somatic cell nuclear transfer method may be used in addition to in vitro fertilization methods. Hereinafter, the somatic cell nuclear transfer method will be described.

After the ova obtained from the slaughterhouse were cultured for about 20 to 24 hours, the cumulus cells were physically removed with an enzyme (hyaluronidase), and the first polar body and nucleus were removed with a micropipette.

Additionally, ear skin fibroblasts of calf (F1) expressing spCas9 were cultured up to 100% in culture medium.

The enucleated ovum fused with the ear skin fibroblast of the cultured calf (F1) through the electrical shock method.

Fused embryos were activated through calcium and 6-DMAP. After activation, live cloned embryos were cultured on serum-free medium described above.

1-4-2. Confirmation of Changes in Expression Level of Essential Gene of Transgenic Offspring Cow As a result of RNA-seq analysis of a transgenic offspring cow produced by the above-described method, it was confirmed that the essential gene was not included in the list of genes with altered expression levels. That is, the expression of spCas9 does not affect the essential gene even in the case of a transgenic offspring cow.

Figure 45:
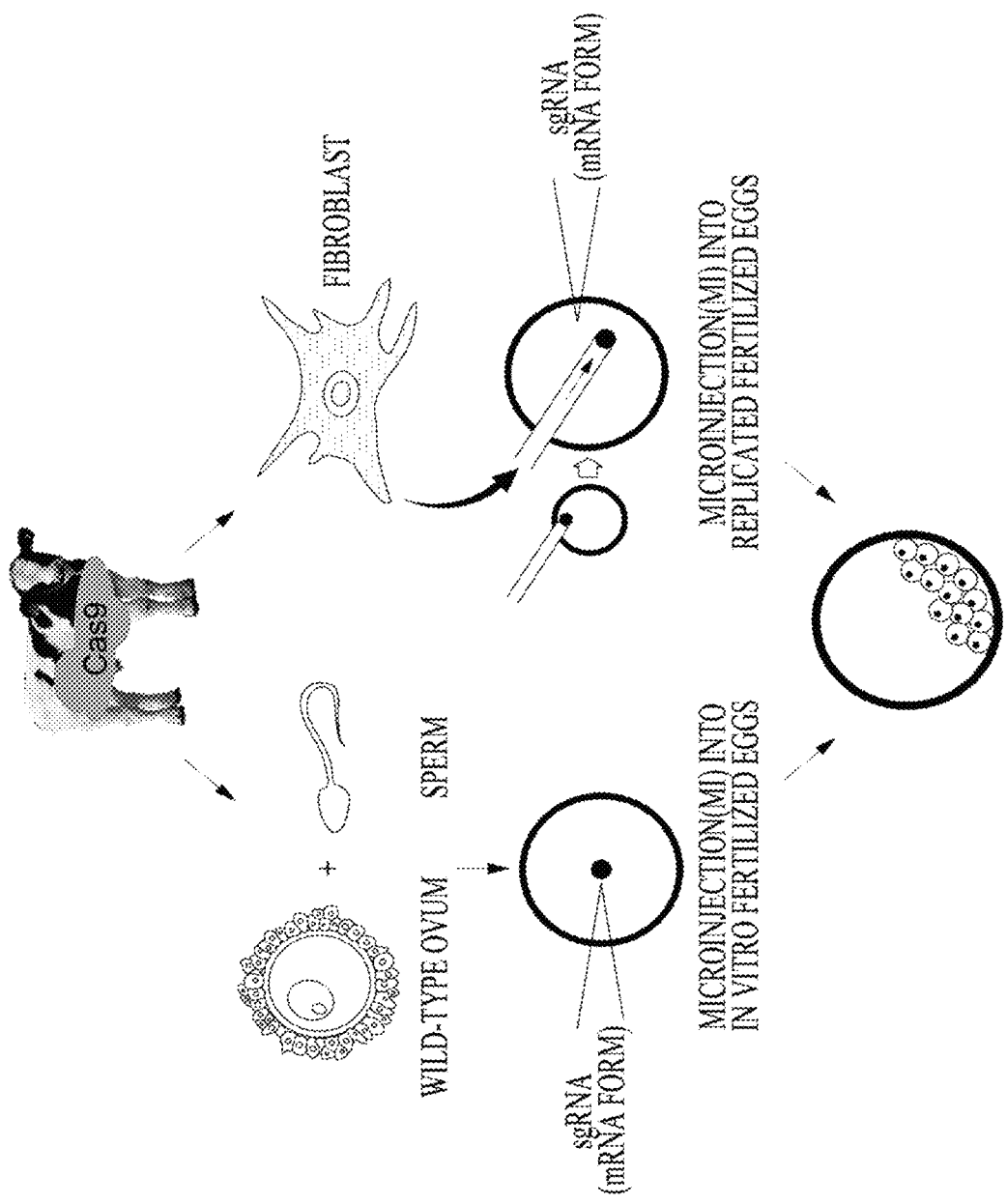
FIG. 45 shows a schematic diagram illustrating a process of knocking out a target gene using a cow having a genome into which Cas9 gene is inserted.

2. Second Gene Editing Using RNA-Guided Endonuclease Expressed in Transgenic Cow-Knockout The present inventors conducted an experiment to confirm whether knockout of a target gene can be effectively induced in somatic cells and fertilized eggs derived from the above-described transgenic cow (spCas9 cow) that expresses the RNA-guided endonuclease. FIG. 45 illustrates a method for knockout of a target gene in the genome of a cell of spCas9 cow.

To confirm the presence/absence of Cas9 activity in the cells of the spCas9 transgenic cow, a plasmid vector capable of expressing sgRNAs for various target genes was synthesized using the protocol of the website (rgenome.net).

The method for preparing a plasmid vector capable of expressing sgRNAs has been described above, and thus a detailed explanation is omitted.

Table 16 below shows sgRNA sequences for various target genes (PRNP gene, Beta-lactoglobulin (BLG) gene, Retinoblastoma 1 (Rb1) gene, Nanog gene, TP53 gene, IFNT gene, and beta-casein (BCN) gene).

2-1. Knockout in Somatic Cell

The present inventors have conducted the T7 endonuclease 1 assay (T7E1 assay) using DNA PCR (Eppendorf Vapo Protect Mastercycler, Eppendorf, Germany) well known to a skilled person in the art, so as to confirm that spCas9 can be expressed in the somatic cell of spCas9 cow (F0) and knockout of the target gene can occur.

A plasmid vector capable of expressing each of the above-described sgRNAs was transfected into fibroblasts isolated from the spCas9a transgenic cow, and the transfected primary cells were further cultured for 10 days in an incubator at 38° C. and 5% $CO_2$.

After 48 hours, the cultured cells were harvested and genomic DNA of each cell was extracted from each of the transfected cells using the DNA extract kit (DNeasy Blood & Tissue kit 69506, Qiagen, Limburg, the Netherlands).

Each extracted DNA was placed in a PCR tube, and 10 μL of buffer was added using the Direct PCR lysis kit and 0.5 μL of proteinase K was additionally added thereto.

The PCR tubes including the respective DNAs were treated in a PCR machine at 56° C. for 180 min, treated at 85° C. for 15 min, and then subjected to PCR after adding a PRNP forward primer and a PRNP reverse primer thereto. After PCR, 10-15 μL of the PCR product was obtained.

The PCR product was mixed with 0.2 μL of the T7 endonuclease I (T7E1 enzyme) and 2 μL of the buffer (final volume 20 μL), and reacted at 37° C. for about 30 min. The reaction products were subjected to electrophoresis.

As a result of the electrophoresis, it was confirmed that mutations occurred in all of the above-described target genes (PRNP gene, beta-lactoglobulin (BLG) gene, retinoblastoma 1 (Rb1) gene, Nanog gene, TP53 gene, and beta-casein (BCN) gene) present in the primary cell.

Figure 46:
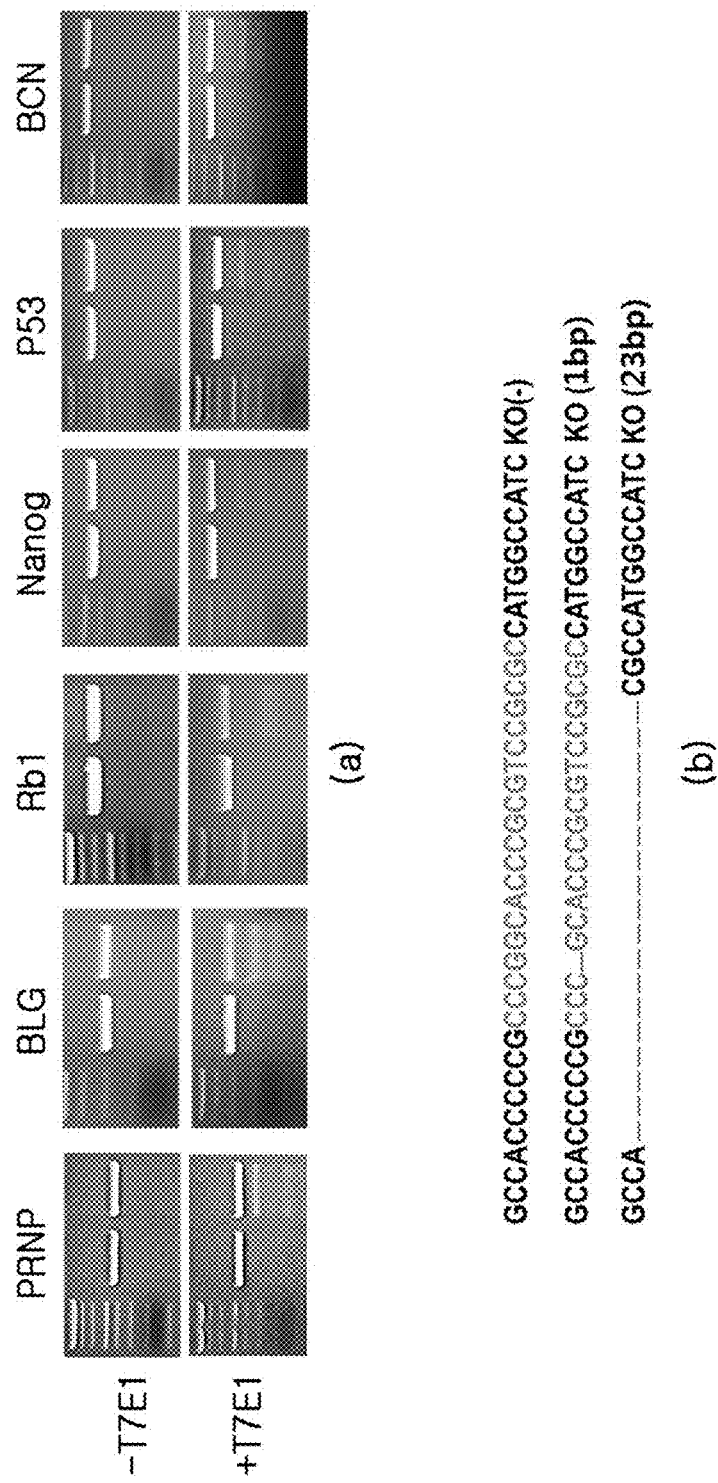
FIG. 46 shows images illustrating the knockout results of PRNP gene, beta-lactoglobulin (BLG) gene, retinoblastoma 1 (Rb1) gene, nanog gene, p53 gene, and beta-casein (BCN) gene, using a cow having a genome into which spCas9 gene is inserted.

FIG. 46(a) shows the results of electrophoresis, after the treatment of the T7E1 on the DNA PCR product, in PRNP gene, beta-lactoglobulin (BLG) gene, retinoblastoma 1 (Rb1) gene, Nanog gene, TP53 gene, and beta-casein (BCN) gene in spCas9 bovine fibroblasts.

Table 17 below discloses primers for DNA PCR for identifying the indel of each target gene.

TABLE 16

| sgRNA Type | SEQ Name | SEQ ID NO | Sequence |
| --- | --- | --- | --- |
| PRNP gene-targeting sgRNA | gn_PRNP_1 | SEQ ID NO: 23 | AAAAACCAACATGAAGCATGTGG |
| BLG gene-targeting sgRNA | gn_BLG_1 | SEQ ID NO: 24 | CCCCCTGAGAGTGTATGTGGAGG |
| Rb1 gene-targeting sgRNA | gn_Rb1_1 | SEQ ID NO: 25 | TGACCTCGCCTTGGTGTTCGAGG |
| Nanog gene-targeting sgRNA | gn_Nanog_1 | SEQ ID NO: 26 | ACCACTGTCCCCGTCTGTGGAGG |
| TP53 gene-targeting sgRNA | gn_TP53_1 | SEQ ID NO: 27 | GCGCGGACGCGGGTGCCGGGCG G |
| IFNT gene-targeting sgRNA | gn_IFNT_1 | SEQ ID NO: 28 | AGTGGAGAGTCTGTTCATTTGGG |
| BCN gene-targeting sgRNA | gn_BCN_1 | SEQ ID NO: 29 | TTGCAAGGGCCAGAGCCACCAGG |

TABLE 17

| Target Gene | Primer Type | SEQ Name | SEQ ID NO | Sequence |
| --- | --- | --- | --- | --- |
| PRNP gene | Forward | in_pr_PRNP_F_1 | SEQ ID NO: 30 | GCAAGAAGCGACCAAAACCT |
|  | Reverse | in_pr_PRNP_R_1 | SEQ ID NO: 31 | GGTGCATGTTTTCACGATAG |
| BLG gene | Forward | in_pr_BLG_F_1 | SEQ ID NO: 32 | TTAAAGGCCGTGTCTCCAGT |
|  | Reverse | in_pr_BLG_R_1 | SEQ ID NO: 33 | GAAAGCCCTGGATAAGCAGC |
| Rb1 gene | Forward | in_pr_Rb1_F_1 | SEQ ID NO: 34 | CCCCCACCAACTGAGTAGAA |
|  | Reverse | in_pr_Rb1_R_1 | SEQ ID NO: 35 | GATTCCAGAATGAGGGAGCT |
| Nanog gene | Forward | in_pr_Nanog_F_1 | SEQ ID NO: 36 | ACCTACCATCTCGCTCTGAG |
|  | Reverse | in_pr_Nanog_R_1 | SEQ ID NO: 37 | ACCAAGAATCGAACCCAGGC |
| TP53 gene | Forward | in_pr_TP53_F_1 | SEQ ID NO: 38 | CTTCAGCCTTTGCCTTTTTG |
|  | Reverse | in_pr_TP53_R_1 | SEQ ID NO: 39 | TTCCGGTCGTCCAAATACTC |
| IFNT gene | Forward | in_pr_IFNT_F_1 | SEQ ID NO: 40 | TCTTCCCCATGGCTTTTGTG |
|  | Reverse | in_pr_IFNT_R_1 | SEQ ID NO: 41 | TGGAGATGATAAGAGCCCTC |
| BCN gene | Forward | in_pr_BCN_F_1 | SEQ ID NO: 42 | TGGCTGGCAGTGAAACATTA |
|  | Reverse | in_pr_BCN_R_1 | SEQ ID NO: 43 | AGGGATTGATGGTACAGATGG |

Additionally, it was confirmed that the target gene, PRNP gene, was knocked out through the sequence analysis. FIG. 46(b) shows the indel of PRNP gene of the spCas9 cow through the sequence analysis.

Through this experiment, it was confirmed that spCas9 can be expressed in the somatic cell of a spCas9 cow, and knockout of a target gene can be induced by the operation of the CRISPR/Cas9 system in the somatic cell.

2-2. Knockout in F1 Fertilized Egg Produced by In Vitro Fertilization

The present inventors conducted the following experiment so as to confirm that spCas9 can be expressed in a fertilized egg which is produced by in vitro fertilization using the gamete of a spCas9 cow and knockout of a target gene can occur by the expressed spCas9.

2-2-1. Production of Fertilized Egg Expressing RNA-Guided Endonuclease

Sperms obtained from SNU-Cas9-2 and wild-type ova were fertilized to produce fertilized eggs (and/or embryos). The method of obtaining gametes from a cow and in vitro fertilization methods have been described above and thus detailed explanation is omitted.

In vitro fertilized egg (and/or embryo) was cultured in a chemically defined culture medium for 7 days. After 7 days, some blastocysts were observed to express a red fluorescent protein (without mosaicism) under a fluorescence microscope (Nikon, Tokyo, Japan)

Figure 47:
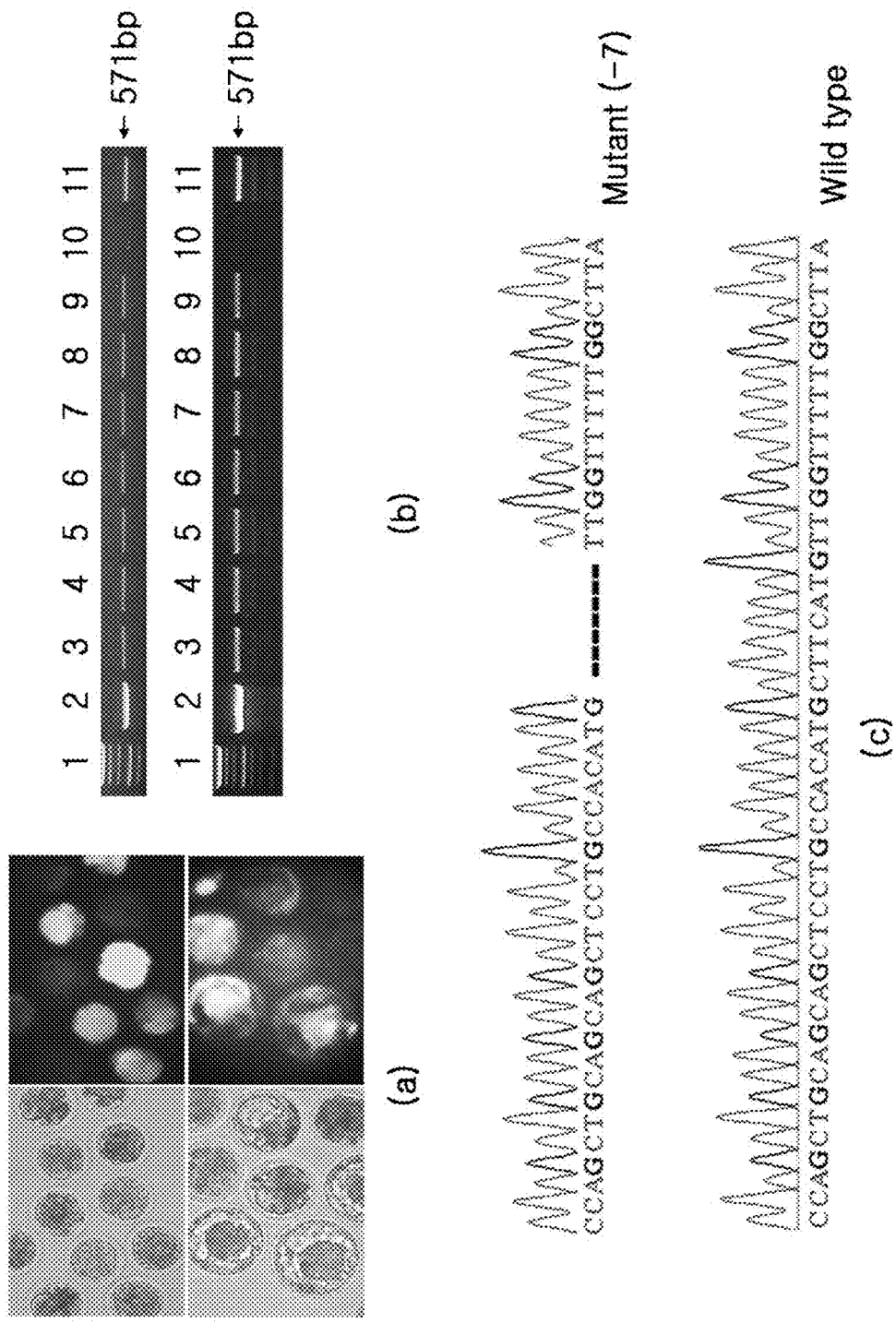
FIG. 47 shows images illustrating the results of electrophoresis and sequence analysis confirming the knockout of PRNP gene, after injection of a guide nucleic acid targeting PRNP gene into blastocysts that were prepared using bovine gametes having a genome into which spCas9 gene is inserted.

FIG. 47(a) shows the expression of a red fluorescent protein in morula embryo and blastocysts, which were produced using a spCas9 cow (see FIG. 47(a), (a-1): morula embryo in visible light condition, (a-1'): morula embryo in fluorescent condition, (a-2) blastocysts in visible light condition, (a-2') blastocysts in fluorescent condition).

That is, the insertion of the spCas9 gene into the genome of the spCas9 fertilized egg was visually confirmed.

2-2-2. Results of Microinjection of sgRNA Vector to Blastocysts

The sgRNA in the form of mRNA capable of specifically binding to the PRNP gene was microinjected into the blastocysts produced by in vitro fertilization using the sperms of the above-described SNU-Cas9-2. Since the microinjection method has been described above, detailed explanation is omitted.

The indel of PRNP gene was confirmed via DNA PCR (Eppendorf Vapo Protect Mastercycler, Eppendorf, Germany).

The PRNP primers used for DNA PCR analysis (forward primer—SEQ ID NO: 30, reverse primer—SEQ ID NO: 31) are as disclosed in Table 17.

The DNA PCR analysis method to confirm specific indel is as described below.

The sgRNA was microinjected into blastocysts obtained by in vitro fertilization and DNA extracted from 8 finally selected blastocysts was transferred into each PCR tube. Using a Direct PCR lysis kit, 10 µL buffer was added and 0.5 µL proteinase K was additionally added.

The PCR tubes were treated in a PCR machine at 56° C. for 180 min, treated at 85° C. for 15 min, and then subjected to PCR after adding a PRNP forward primer and a PRNP reverse primer thereto. After PCR, 10-15 µL of the PCR product was obtained.

The PCR product was mixed with 0.2 µL of the T7 endonuclease I (T7E1 enzyme) and 2 µL of the buffer (final volume 20 µL), and reacted at 37° C. for about 30 min. The reaction products were subjected to electrophoresis.

As a result of electrophoresis, the indel occurrence was confirmed in the PRNP gene of DNA extracted from each blastocyst.

FIG. 47(b) confirms the indel occurrence in the PRNP gene by the T7E1 treatment, after microinjection of the sgRNA (which targets PRNP gene) into the blastocysts produced by in vitro fertilization (see FIG. 47(b), top: (−)T7E1, bottom: (+)T7E1, 1: marker gene, 2-9: blastocysts to which the sgRNA was microinjected, 10: wild-type fertilized egg, 11: PRNP gene).

Additionally, the indel of PRNP gene was confirmed by genome sequence analysis of blastocysts.

FIG. 47(c) shows the indel results of PRNP gene through sequence analysis of the blastocysts, after microinjection of the sgRNA (which targets PRNP gene) into the blastocysts produced by in vitro fertilization.

Through some experiments described above, it was confirmed that spCas9 can be expressed in the fertilized egg produced using the gamete of a spCas9 cow and that the knockout of a target gene can be induced by the expressed spCas9.

2-3. Knockout in Cell of Offspring Cow Produced by Natural Breeding

To confirm that Cas9 is also expressed in cells of a calf born by natural breeding of spCas9 cows, the present inventors isolated the primary cells of the calf and performed the following experiment.

Figure 48:
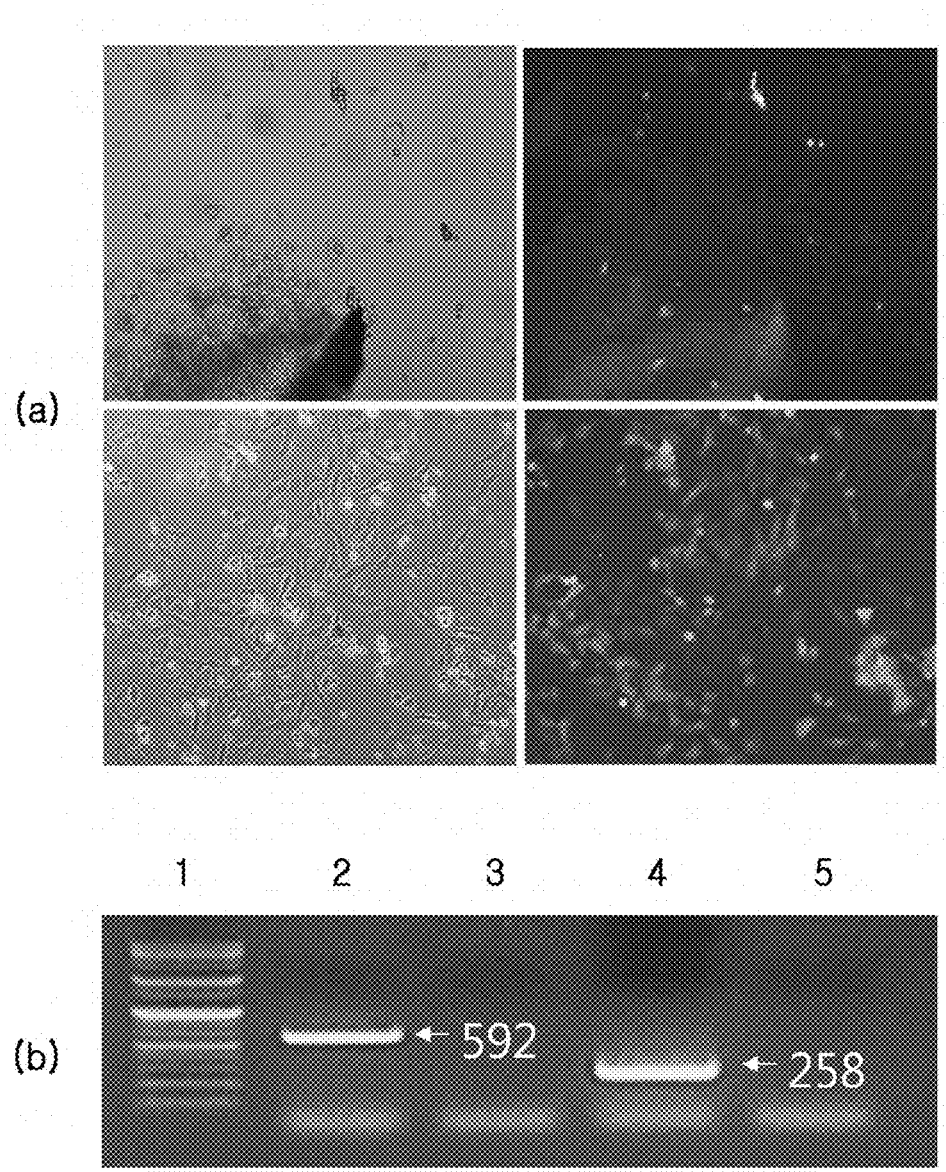
FIG. 48 shows images illustrating that a red fluorescent protein is expressed in primary cells of an offspring cow obtained by natural breeding of cows having a genome into which spCas9 gene is inserted; and the insertion of spCas9 gene and Fat1 gene into the offspring bovine genome by DNA PCR.

A calf (SNU-Cas9-F1) was born by natural breeding between an SNU-Cas9-4 (female) and an SNU-Cas9-2 (male), and primary cells were isolated from the SNU-Cas9-F1 calf. FIG. 48(a) shows that a red fluorescent protein is uniformly expressed in the primary cells.

DNA was extracted from the primary cells by the DNA extraction kit (DNeasy Blood & Tissue kit 69506, Qiagen, Limburg, Netherlands), and DNA PCR was performed using the extracted DNA, and the DNA PCR results with regard to Cas9 and Fat1 were shown to be positive.

FIG. 48(b) shows the DNA PCR results obtained using the primary cells of the SNU-Cas9-F1 calf (see FIG. 48(b), 1: size marker, 2: spCas9 gene, 3: negative control group, 4: Fat1 gene, 4: negative control group).

Through these results, it was confirmed that primary cells of SNU-Cas9-F1 include a transform gene of F0 generation.

Furthermore, the present inventors conducted an experiment in which a sgRNA was transfected into the primary cells of the calf to confirm that knockout of a target gene could also occur in cells of the calf (F1) born by natural breeding of spCas9 cows.

Specifically, DNA was extracted from primary cells transfected with a sgRNA that can specifically bind to PRNP gene, and the extracted DNA was loaded into each PCR tube.

Using a Direct PCR lysis kit, 10 μL buffer was added and 0.5 μL proteinase K was additionally added.

The PCR tubes were treated in a PCR machine at 56° C. for 180 min, treated at 85° C. for 15 min, and then subjected to PCR after adding a PRNP forward primer and a PRNP reverse primer thereto. After PCR, 10-15 μL of the PCR product was obtained.

The PCR product was mixed with 0.5-1 μL of the T7 endonuclease I and 2 μL of the buffer (final volume 20 μL), and reacted at 37° C. for about 30 min. The reaction products were subjected to electrophoresis.

As a result of electrophoresis, the indel occurrence in PRNP gene was confirmed.

Figure 49:
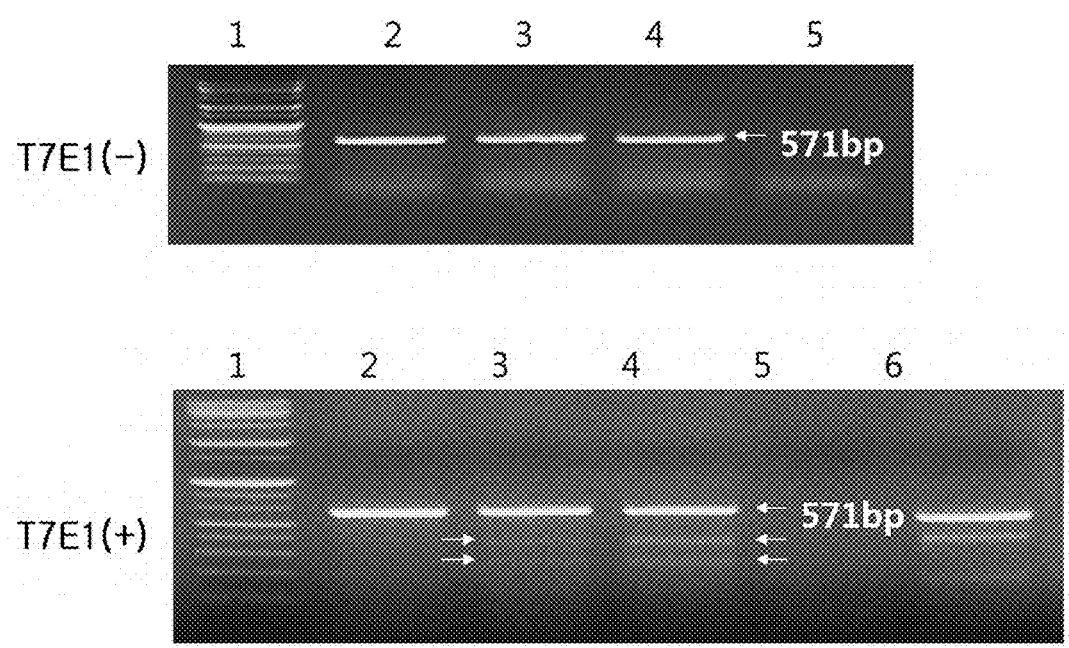
FIG. 49 shows images illustrating the results of electrophoresis confirming the indels of PRNP gene, after the transfection of sgRNA targeting the PRNP gene into primary cells of a transgenic cow having a genome into which spCas9 gene is inserted.

FIG. 49 shows the results confirming the indel of PRNP gene via DNA PCR of primary cells of SNU-Cas9-F1, which were transfected with the sgRNA that targets PRNP gene (see FIG. 49, 1: size marker, 2: wild-type cow, 3: SNU-Cas9-2 cow, 4: SNU-Cas9-F1, 5: negative control group, 6: positive control group (PRNP gene)).

The PRNP primers used for DNA PCR analysis for identification of mutation in the PRNP gene are as disclosed in Table 17.

Through this experiment, the germline transmission of a transgene to offspring and the fertility of a transgenic female cow were confirmed.

Additionally, through this experiment, it was confirmed that spCas9 can be expressed in a transgenic offspring and that the expressed spCas9 can form a complex with a guide nucleic acid provided in cells or animals and thereby knock-out the target gene.

Depending on the type of the target gene, various effects can be seen. For example, when the PRNP gene is used as the target gene as in this experiment, a cow having resistance to mad cow disease can be produced.

In another example, when β-lactoglobulin gene is used as a target gene as in this experiment, allergen-free milk can be obtained.

That is, the transgenic cow in which spCas9 can be expressed can be used for milk protein engineering.

3. Second Gene Editing Using RNA-Guided Endonuclease Expressed in Transgenic Cow-Knockin The present inventors obtained primary cells from a bovine fetus having spCas9-2A-GFP so as to confirm that knockin can effectively occur in cells derived from the above-described transgenic cow (spCas9 cow) (F0), in which the RNA-guided endonuclease is expressed.

GFP expression was observed in the obtained spCas9-2A-GFP cells, and an experiment to knock in the mcherry gene with the GFP location as a target was performed.

Specifically, the knockin experiment was performed using two different methods, that is, 1) HITI (3-2. vector injection into the cell for HITI) and 2) HDR (3-3. vector injection into the cell for HDR), in cells where Cas9 is expressed.

3-1. Vector Construction

Two types of donor vectors were prepared for the experiments of HDR knockin and HITI knockin.

FIG. 50(a) illustrates part of a donor vector for HITI.

The donor vector for HITI may have a constitution in which a first target site is included at 5' end of a donor polynucleotide to knock in, and a second target site is included at 3' end of the donor polynucleotide. The sequence of the donor vector for HITI is the same as SEQ ID NO: 44 (SEQ Name: HITI_RFP donor_1). The first target site and the second target site can be bound to sgRNAs, which can specifically bind to GFP gene, and may be cleaved by an engineered nuclease.

FIG. 50(b) illustrates part of a donor vector for HDR.

Figure 50:
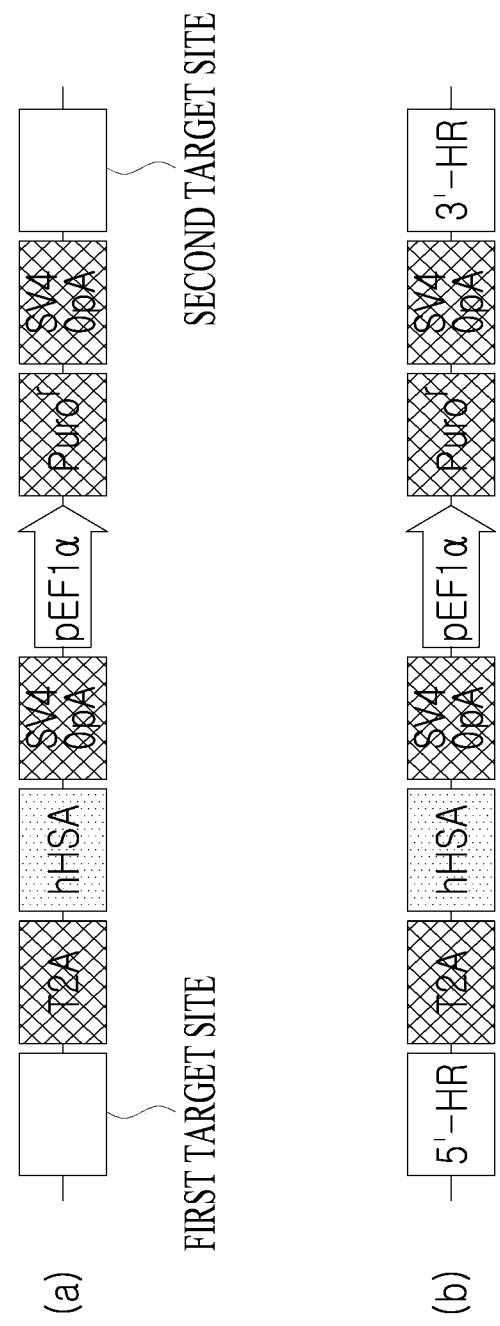
FIG. 50 shows schematic diagrams illustrating part of a donor polynucleotide vector for HDR and a donor polynucleotide vector for HITI.

The donor vector for HDR may have a constitution in which a first homology nucleotide sequence (5'-HR described in FIG. 50(b)) is included at 5' end of a donor polynucleotide to knock in, and a second homology nucleotide sequence (3'-HR described in FIG. 50 (b)) is included at 3' end of the donor polynucleotide. The first homology nucleotide sequence and the second homology nucleotide sequence are the same as part of the sequences included in the bovine albumin gene.

The sequence of the donor vector for HDR is the same as SEQ ID NO: 45 (SEQ Name: HDR_RFP donor_1).

Figure 58:
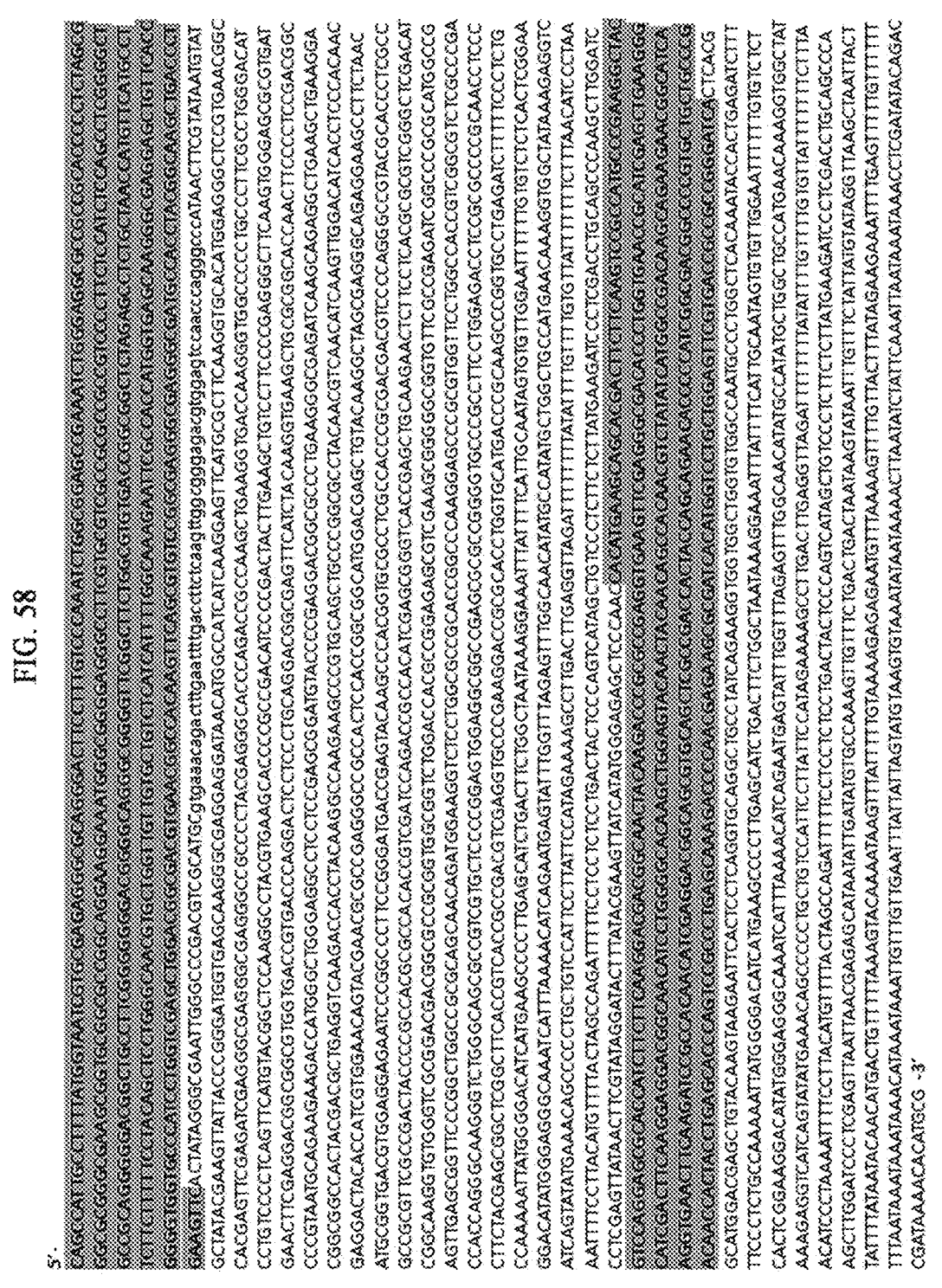

The first homology nucleotide sequence in the donor vector for HDR used in this experiment is the same as the nucleotide sequence from the $1^{st}$ to the $532^{nd}$ of SEQ ID NO: 45; and the second homology nucleotide sequence is the same as the nucleotide sequence from the 2,585$^{th}$ to the 3,044$^{th}$ of SEQ ID NO: 45. FIG. 58 illustrates the sequence of the donor vector for HDR (SEQ ID NO: 45), and the highlighted portion of the entire sequence represents the first homology nucleotide sequence and the second homology nucleotide sequence.

3-2. Vector Injection into Cell for HITI

Primary cells obtained from the spCas9 cow (F0) were isolated and cultured by the above-described method. The cultured primary cells of the spCas9 cow (F0) were isolated by trypsin. The isolated cells (1×10$^5$ to 3×10$^5$) were transfected with a sgRNA (1 μg), that can specifically bind to GFP by electroporation method, and a donor vector (1 μg) for HITI. The transfection was induced using a Neon instrument and program 16 included in the instrument was applied as the condition of the transfection. Twelve hours after transfection, the cells were exchanged with a fresh medium, and the cells in which mcherry gene is knocked in were confirmed using antibiotics and selection markers.

FIG. 51(*a*) shows the DNA PCR results confirming the knockin of the mcherry gene; in which lane 1 represents marker gene; lane 2 represents genomic DNA of spCas9 cow (control group), lane 3 represents cells transfected with donor vector for HITI; and lane 4 represents negative control group. The forward primer sequence for the DNA PCR is SEQ ID NO: 46 (SEQ Name: HITI_pr_RFP_F_1) and the reverse primer sequence for the DNA PCR is SEQ ID NO: 47 (SEQ Name: HITI_pr_RFP_R_1).

FIG. 51(*b*) shows the results confirming the expression of mcherry in the primary cells of the spCas9 cow, in which the primary cells are transfected with the donor vector for HITI.

3-3. Vector Injection into Cell for HDR

Primary cells obtained from spCas9 cow (F0) were isolated and cultured in the same manner as in the above-described method.

The isolated cells (1×10$^5$ to 3×10$^5$) were transfected with a sgRNA (1 μg), that can specifically bind to GFP gene by electroporation method, and a donor vector (1 μg) for HDR. The transfection was induced using a Neon instrument and, program 16 included in the instrument was applied as the condition of the transfection. Twelve hours after transfection, the cells were exchanged with a fresh medium, and the cells in which mcherry gene is knocked in were confirmed using antibiotics and selection markers.

FIG. 52(*a*) shows the DNA PCR results confirming the knockin of the mcherry gene; in which lane 1 represents marker gene; lane 2 represents genomic DNA of spCas9 cow (control group), lane 3 represents cells transfected with donor vector for HDR; and lane 4 represents negative control group. The forward primer sequence for the DNA PCR is SEQ ID NO: 48 (SEQ Name: HDR_pr_RFP_F_1) and the reverse primer sequence for the DNA PCR is SEQ ID NO: 49 (SEQ Name: HDR_pr_RFP_R_1).

FIG. 52(*b*) shows the results confirming the expression of mcherry in the primary cells of spCas9 cow, in which the primary cells are transfected with the donor vector for HDR.

Through this experiment, it was confirmed that spCas9 can be expressed in cells of a transgenic cow and that the expressed spCas9 can form a complex with the guide nucleic acid provided in the cells and thereby knock in the donor polynucleotide at the target gene.

Depending on the type of the target gene, various effects may be seen. For example, when β-casein gene is used as a target gene, various proteins can be expressed in the milk of a transgenic cow depending on the type of the donor polynucleotide.

3-4. Somatic Cell Nuclear Transfer Using spCas9 Primary Cell in which Donor is Knocked in The present inventors performed the somatic cell nuclear transfer using the primary cells prepared by the above-described HDR and HITI methods. The description of the somatic cell nuclear transfer method has been described above, and thus detailed explanation is omitted It was confirmed that embryos in which mcherry was expressed through the somatic cell nuclear transfer were obtained.

Figure 53:
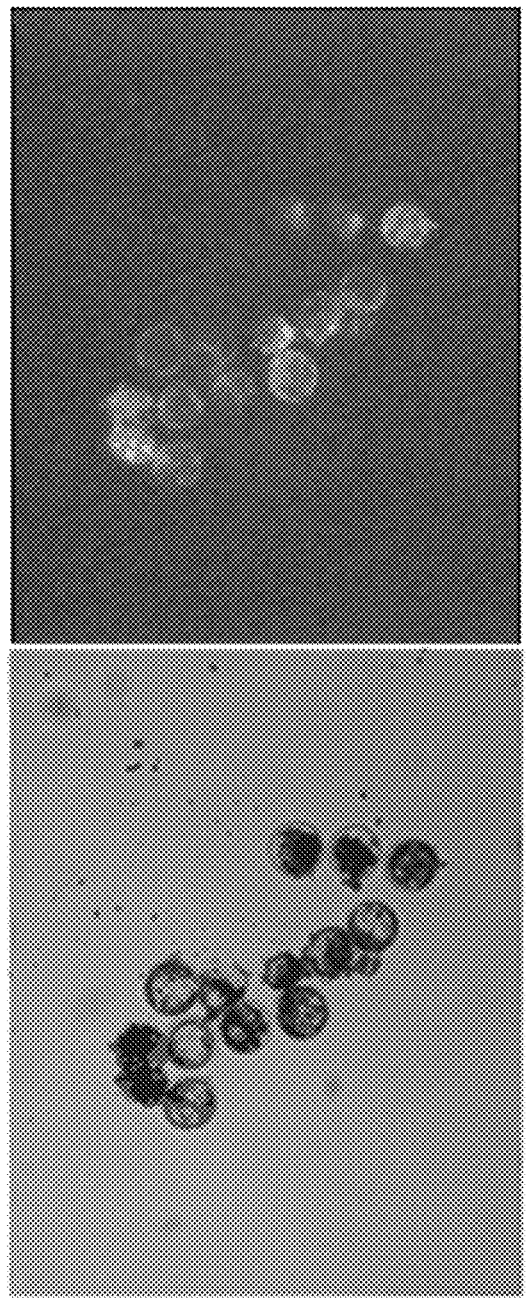

FIG. 53 shows the expression of mcherry in an embryo which is produced through the somatic cell nuclear transfer using the primary cells of spCas9 cow having a genome in which mcherry gene is knocked in.

Since the experiment which is the same as the above-described experimental method can be performed using a donor vector which includes a different gene, various types of cells in which the gene encoding the target protein is knocked in can be accurately prepared. This can be used for a large-scale production of cows that express target proteins.

[Experimental Example 5] Transgenic Cow which Expresses RNA-Guided Endonuclease and Guide Nucleic Acid 1. Preparation of Vector which Includes Polynucleotide Encoding RNA-Guided Endonuclease and Polynucleotide Encoding Guide Nucleic Acid A final expression vector (hereinafter, spCas9-sgRNA vector) was prepared using the amplified spCas9 gene, a sgRNA which targets beta-lactoglobulin gene (BLG gene), and a red fluorescent protein gene.

Figure 54:
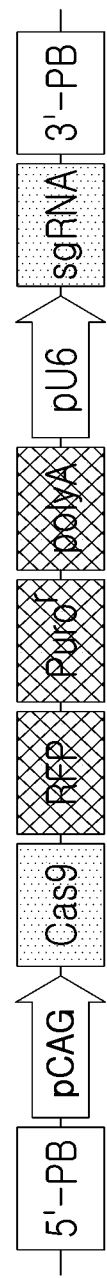
FIG. 54 shows a schematic diagram illustrating part of the final expression vector for enabling the expression of spCas9 and sgRNA.

FIG. 54 illustrates part of the final expression vector for expressing a spCas9 and a sgRNA.

The sequence of sgRNA included in the final expression vector is the same as SEQ ID NO: 24 disclosed in Table 16.

2. Preparation of Embryo (MI)

Since the method for integrating a toolbox into a bovine genome and the experimental conditions thereof are the same as those for integrating the above-described target protein gene and the experimental conditions thereof, the method for preparing an embryo having a genome into which the spCas9 and the sgRNA are inserted will be described briefly.

As described above, bovine ova were collected by separating COCs from the ovary followed by washing, and the sperms were collected by separating from bovine semen by centrifugation.

After removing cumulus cells from the fertilized egg obtained by in vitro fertilization between the collected ova and sperms, the above-described spCas9-sgRNA vector and the transposase vector were microinjected into the cytoplasm (spCas9-sgRNA vector and transposase each at 50 ng/mL, 1:1 ratio) using the microinjector machine (Femtojet, Eppendorf, Germany).

The expression of a red fluorescent protein was visually confirmed in the embryo (spCas9-sgRNA embryo) produced after microinjection, and a transgenic cow was prepared using the embryo.

3. Preparation of Transgenic Cow 3-1. Transgenic Cow

Since the method for transplanting a transformed embryo into the uterus of a surrogate mother and the experimental conditions thereof are described above, hereinafter, a method for producing a transgenic cow will be briefly described.

The spCas9-sgRNA embryo produced by the above method was transplanted into the uterus of a surrogate mother, on the 45$^{th}$ day of post estrus, the survival of the embryo and gestation of the surrogate mother were confirmed by rectal palpation and ultrasonography.

A transgenic cow (SNU-Cas9-BLG-KO-1(male)) having a genome into which the spCas9 gene and the sgRNA are inserted was born from the surrogate mother, and sperms were obtained from the SNU-Cas9-BLG-KO-1(male).

3-2. Confirmation of Presence/Absence of Insertion of Polynucleotide Encoding RNA-Guided Endonuclease and Polynucleotide Encoding Guide Nucleic Acid into Transgenic Bovine Genome 3-2-1. Confirmation of Fluorescent Protein Expression Primary cells were isolated from the skin tissue of SNU-Cas9-BLG-KO-1 (male) by the above-described primary cell isolation method and the expression of a red fluorescent protein was confirmed from the primary cells.

FIG. 55(*a*) shows the expression of a red fluorescent protein in the primary cells of SNU-Cas9-BLG-KO-1 (see FIG. 55(*a*), left: visible light condition, right: fluorescent condition).

The spCas9-sgRNA vector was designed to include a red fluorescent protein gene, and from the above results, it was visually confirmed that polynucleotides encoding the spCas9 gene and the sgRNA were inserted into the genome of SNU-Cas9-BLG-KO-1 (male).

3-2-2. DNA PCR and RT-PCR Results

The presence/absence of insertion of polynucleotides encoding spCas9 gene and sgRNA into the genome of SNU-Cas9-BLG-KO-1 (male) was confirmed using DNA PCR and RT-PCR (Eppendorf Vapo Protect Mastercycler, Eppendorf, Germany). The primers used to perform DNA PCR and RT-PCR are as shown in Table 18 below.

TABLE 18

| Primer Type | SEQ Name | SEQ ID NO | Sequence |
| --- | --- | --- | --- |
| spCas9-Forward | pr_spCas9_F_2 | SEQ ID NO: 50 | gacaagaagtacagcatcgg |
| spCas9-Reverse | pr_spCas9_R_2 | SEQ ID NO: 51 | caaccagctgttcgaggaga |
| GAPDH-Forward | pr_GAPDH_F_3 | SEQ ID NO: 52 | GGCGTGAACCACGAGAAGTA |
| GAPDH-Reverse | pr_GAPDH_R_3 | SEQ ID NO: 53 | CCCTCCACGATGCCAAAGT |

Since DNA PCR and RT-PCR methods have been described above, the detailed description thereof is omitted.

3-2-3. Confirmation of Indel in Beta-Lactoglobulin

Whole genomic DNA was isolated from fibroblasts of the SNU-Cas9-BLG-KO-1 (male) by the G-Spin™ Total DNA Extraction Mini Kit (iNtRON, Seoul, Republic of Korea).

Mutation in β-lactoglobulin gene was confirmed by fluorescent PCR (fPCR) using the isolated whole genomic DNA.

FIG. 55(*b*) shows the results confirming the knockout of beta-lactoglobulin gene in the fibroblasts of the SNU-Cas9-BLG-KO-1 using fPCR (see FIG. 55(*b*), left: wild-type bovine fibroblast, right: fibroblasts in which BLG is knocked out).

The primers for confirming the mutation in beta-lactoglobulin gene are as disclosed in Table 19 below.

TABLE 19

| Primer Type | SEQ Name | SEQ ID NO | Sequence |
| --- | --- | --- | --- |
| Forward primer | in_pr_BLG_F_1 | SEQ ID NO: 54 | TTAAAGGCCGTGTCTCCAGT |
| Reverse primer | in_pr_BLG_R_1 | SEQ ID NO: 55 | GAAAGCCCTGGATAAGCAGC |

Through this experiment, it was confirmed that in the case of a transgenic cow in which both spCas9 and a guide nucleic acid can be expressed, the target gene including a sequence which is the same as or complementary to one region of the guide nucleic acid can be knocked out although no additional treatment is applied.

Additionally, it was confirmed that a transformed cell, a transgenic embryo and/or a transgenic animal can survive even though the target gene is knocked out.

Various effects may appear according to the type of the target gene. In particular, in the case where beta-lactoglobulin (BLG) gene is used as a target gene as in this experiment, allergen-free milk can be obtained. That is, a transgenic cow in which spCas9 and/or a guide nucleic acid can be expressed can be utilized in milk protein engineering.

Furthermore, it was confirmed that the transformed cell, transgenic embryo, and/or transgenic animal can survive even when spCas9 and a guide nucleic acid are continuously expressed.

[Experimental Example 6] Transgenic Cow in which Expression of RNA-Guided Endonuclease is Controlled by Expression Control Element The present inventors prepared a bovine primary cell in which the expression of the component of an engineered nuclease can be controlled, and confirmed that gene editing can be controlled in the bovine primary cell 1. Preparation of Vector A vector for producing the primary cells of a cow in which the expression of the component of an engineered nuclease can be controlled was prepared.

The vector in which the expression of an RNA-guided endonuclease can be controlled is described referring to FIG. 56.

The vector includes [loxP-green fluorescent protein gene-polyA-loxP] at the 5' end direction of spCas9 DNA (presented by Toolgen). The expression of Cas9 does not occur until the [loxP-green fluorescent protein gene-polyA-loxP] is excised.

The sgRNA disclosed in FIG. 56 has TP53 gene as a target gene and the sequence of the sgRNA is the same as SEQ ID NO: 27 (GCGCGGACGCGGGTGCCGGGCGG).

2. Preparation of Bovine Cell in which Expression of RNA-Guided Endonuclease can be Controlled The present inventors isolated fibroblasts from a wild-type cow so as to produce a bovine cell in which expression of an RNA-guided endonuclease can be controlled.

Since the method for isolating bovine fibroblast has been described above in Experimental Example 1, the detailed explanation is omitted.

The isolated fibroblasts were dispensed into 6-well plates. When the cells reached about 50-60% confluency, the above-described vector which can control the expression of the RNA-guided endonuclease (see FIG. 56(a)) (hereinafter, expression controllable vector) was transfected.

The expression of a green fluorescent protein was confirmed in the bovine cell transfected with an expression controllable vector, and the bovine cells in which the expression of a green fluorescent protein was confirmed were selected.

Since the green fluorescent protein gene is included within the expression controllable vector, the bovine cells in which the green fluorescent protein is expressed are bovine cells where the expression of an RNA-guided endonuclease can be controlled (hereinafter, expression controllable cell).

3. Results of T7E1 Assay in Transformed Cell

With regard to the expression controllable cell prepared by the above-described method, in order to confirm that gene editing can occur only when Cre recombinase (a material that affects the expression control element) is treated on the expression controllable cell, the present inventors treated the expression controllable cells with Cre recombinase. Then, DNA PCR and T7E1 assay were performed with regard to the expression controllable cells treated with Cre recombinase and the expression controllable cells not treated with Cre recombinase.

DNA was extracted from the expression controllable cells not treated with the Cre recombinase and then the extracted DNA (sample 1) was transferred into a PCR tube. Additionally, DNA was extracted from the expression controllable cells treated with the Cre recombinase and then the extracted DNA (sample 2) was transferred into a PCR tube.

Furthermore, distilled water without DNA as a negative control group was loaded into a PCR tube.

As a positive control group, DNA was extracted from primary cells of a cow having a genome, into which polynucleotides encoding spCas9 DNA and sgRNA were inserted, transfected with a vector that does not include [loxP-green fluorescent protein gene-polyA-loxP2772] (i.e., an expression control element) (see FIG. 56(b)), and then the extracted DNA (positive control group) was transferred into a PCR tube.

Using a Direct PCR lysis kit, 10 µL buffer was added to each of the PCR tubes containing the sample 1, sample 2, sample of negative control group, and sample of positive control group, and then, 0.5 µL proteinase K was additionally added to each of the PCR tubes.

Each of the PCR tubes was treated in a PCR machine at 56° C. for 180 min, treated at 85° C. for 15 min, and then subjected to PCR after adding a PRNP forward primer and a PRNP reverse primer thereto. After PCR, 10-15 µL each of the PCR products was obtained.

Each of the PCR products was mixed with 0.5-1 µL of the T7 endonuclease I and 2 µL of the buffer (final volume 20 µL), and reacted at 37° C. for about 30 min. The reaction products were subjected to electrophoresis.

As a result, it was confirmed that an indel occurred in a target gene when the Cre recombinase was treated on the expression controllable cells.

Figure 57:
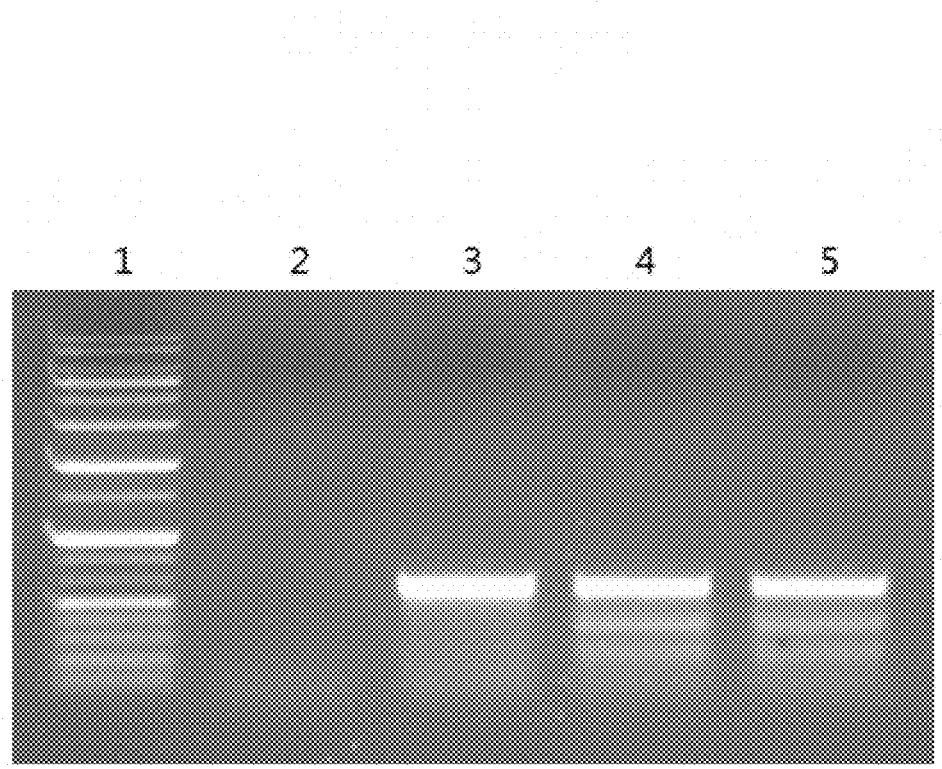
FIG. 57 shows an image illustrating the results confirming, by DNA PCR, the presence/absence of indels of a target gene according to the presence/absence of treatment of Cre recombinase to cells, in which the expression of RNA-guided endonuclease can be controlled.

FIG. 57 shows the DNA PCR results confirming indels of a target gene in expression controllable cells not treated with Cre recombinase and expression controllable cells treated with Cre recombinase (see FIG. 57, 1: size marker, 2: negative control group, 3: expression controllable cell not treated with Cre recombinase, 4: expression controllable cell treated with Cre recombinase, 5: positive control group).

Through this experiment, the present inventors confirmed that gene editing can be controlled to be achieved at the desired time when a cow or cells of the cow having a genome into which an expression control element that can control the expression of components of an engineered nuclease is inserted is used.

REFERENCE NUMERAL 100, 320, 340: toolbox
101, 107, 201, 207, 322, 329, 343, 349, 361, 367, 371, 379, 701, 705, 801, 808, 901, 906: ITR sequence
102, 103, 132, 363, 373: polynucleotide encoding RNA-guided endonuclease
104, 105, 134, 365, 375, 377: polynucleotide encoding guide nucleic acid

110: polynucleotide encoding components of engineered nuclease
130, 130(a), 130(b): expression control element
202, 203, 204, 205, 206: polynucleotide having PAM sequence
210, 220, 230, 240: chromosome
231, 420, 430: target site
232, 232(a), 232(b), 423, 433: donor polynucleotide
401: fertilized egg
403, 405, 407, 409, 411, 413, 415, 417: embryo
704, 706, 804, 807, 905: polynucleotide encoding transposase
700(b), 800(b): excision toolbox
909, 911: polynucleotide encoding recombinase

INDUSTRIAL APPLICABILITY

When a transgenic animal having a genome into which a gene encoding a gene editing tool is inserted is used, animals in which genes are knocked in or knocked out can be more efficiently prepared.

For example, a transgenic animal having a genome into which a gene encoding a target protein has been inserted can be prepared using a gene editing tool expressed in the transgenic animal. In this case, the transgenic animal can be utilized as a bioreactor.

In another example, a transgenic animal having a genome in which a specific gene is knocked out can be prepared using a gene editing tool expressed in the transgenic animal. In this case, the transgenic animal may be used as a disease animal model or breed improvement animal, in particular, when the transgenic animal is a large animal, the transgenic animal may have better industrial applicability when used as a bioreactor for producing a target protein or when used as a disease animal model.

Furthermore, a transgenic cell, an embryo, and an animal which have a genome into which a gene encoding a gene editing tool has been inserted can be used as a platform technology.

For example, since a transgenic cell, an embryo, and an animal which have a genome into which a gene encoding a gene editing tool has been inserted can be used to knock in various types of genes, the transgenic cell, the embryo and the animal can be used to produce a variety of target proteins.

SEQUENCE LISTING FREE TEXT

SEQ ID NO: 1 to SEQ ID NO: 4, SEQ ID NO: 7 to SEQ ID NO: 12, SEQ ID NO: 15, SEQ ID NO: 16 to SEQ ID NO: 22, SEQ ID NO: 30 to SEQ ID NO: 43, SEQ ID NO: 46 to SEQ ID NO: 55 show primer sequences.

SEQ ID NO: 5, SEQ ID NO: 6, SEQ ID NO: 13, and SEQ ID NO: 14 show the sequence of a transposon gene.

SEQ ID NO: 23 to SEQ ID NO: 29 show the sequence of a guide nucleic acid.

SEQ ID NO: 45 to SEQ ID NO: 46 show the sequence of a donor vector.

What is claimed is:

1. A transgenic bovine animal comprising a plurality of cells having a genome comprising a polynucleotide comprising:
   a first Inverted Terminal Repeat (ITR) sequence, a sequence encoding a Cas9 protein, and a second ITR sequence,
   wherein the sequence encoding the Cas9 protein is located between the first ITR sequence in a 5' direction and the second ITR sequence in a 3' direction,
   wherein the polynucleotide is located on at least one locus selected from:
   a locus located between KCNAB 1 gene and GMPS gene;
   a locus located between CHAFIB gene and PIGP gene;
   a locus located between HNRNPR gene and LUZP1 gene;
   a locus located between MRPL22 gene and HAVCR1 gene;
   a locus located between STMN4 gene and CHRNA2 gene;
   a locus located between TGS1 gene and LYN gene;
   a locus located between H3F3C gene and TFB2M gene;
   a locus located between CLIP3 gene and OVOL3 gene; and
   a locus located between MGC134232 gene and PHKA2 gene,
   wherein the plurality of cells express the Cas9 protein such that the transgenic bovine animal expresses the Cas9 protein.

2. The transgenic bovine animal of claim 1, wherein the genome of the plurality of cells further comprises a toolbox comprising a polynucleotide encoding one selected from a guide RNA, a marker, an albumin, interleukin-2, erythropoietin, and insulin,
   wherein the toolbox is located at a locus different from the locus where the polynucleotide encoding the Cas9 protein is located.

3. The transgenic bovine animal of claim 2, wherein the toolbox comprises the polynucleotide encoding the guide RNA,
   wherein the guide RNA is capable of forming a complex with the Cas9 protein expressed in the plurality of cells of the transgenic bovine animal.

4. The transgenic bovine animal of claim 1, wherein the Cas9 protein is a *Streptococcus pyogenes* derived Cas9 protein (SpCas9 protein) or mutant thereof.

5. The transgenic bovine animal of claim 1, wherein the transgenic bovine animal has a germline cell comprising the polynucleotide.

6. A transgenic bovine animal embryo comprising a plurality of cells having a genome comprising a polynucleotide comprising:
   a first ITR sequence, a sequence encoding a Cas9 protein, and a second ITR sequence,
   wherein the sequence encoding the Cas9 protein is located between the first ITR sequence in a 5' direction and the second ITR sequence in a 3' direction,
   wherein the polynucleotide is located on at least one locus selected from:
   a locus located between KCNAB 1 gene and GMPS gene;
   a locus located between CHAFIB gene and PIGP gene;
   a locus located between HNRNPR gene and LUZP1 gene;
   a locus located between MRPL22 gene and HAVCR1 gene;
   a locus located between STMN4 gene and CHRNA2 gene;
   a locus located between TGS 1 gene and LYN gene;
   a locus located between H3F3C gene and TFB2M gene;
   a locus located between CLIP3 gene and OVOL3 gene; and a locus located between MGC134232 gene and PHKA2 gene,
   wherein the plurality of cells express the Cas9 protein such that the transgenic bovine embryo expresses the Cas9 protein.

7. The transgenic bovine animal embryo of claim 6, wherein the genome of the plurality of cells further comprises a toolbox comprising a polynucleotide encoding one selected from a guide RNA, a marker an albumin interleukin-2 erythropoietin, and insulin,
   wherein the toolbox is located at a locus different from the locus where the polynucleotide encoding the Cas9 protein is located.

8. The transgenic bovine animal embryo of claim 6, wherein the toolbox comprises the polynucleotide encoding the guide RNA,
   wherein the guide RNA is capable of forming a complex with the Cas9 protein expressed in the plurality of cells of the transgenic bovine animal.

9. The transgenic bovine animal embryo of claim 6, wherein the Cas9 protein is a *Streptococcus pyogenes* derived Cas9 protein (SpCas9 protein) or mutant thereof.

* * * * *